US011130794B2

(12) United States Patent
Tornoee et al.

(10) Patent No.: US 11,130,794 B2
(45) Date of Patent: Sep. 28, 2021

(54) BIFUNCTIONAL COMPOUNDS

(71) Applicant: Novo Nordisk A/S, Bagsvaerd (DK)

(72) Inventors: Christian Wenzel Tornoee, Lyngby (DK); Anne Louise Bank Kodal, Koebenhavn N (DK); Steffen Reedtz-Runge, Bikeroed (DK); Lennart Lykke, Koebenhavn V (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/632,007

(22) PCT Filed: Jul. 19, 2018

(86) PCT No.: PCT/EP2018/069610
§ 371 (c)(1),
(2) Date: Jan. 17, 2020

(87) PCT Pub. No.: WO2019/016306
PCT Pub. Date: Jan. 24, 2019

(65) Prior Publication Data
US 2020/0231645 A1  Jul. 23, 2020

(30) Foreign Application Priority Data
Jul. 19, 2017 (EP) ..................................... 17182010

(51) Int. Cl.
| C07K 19/00 | (2006.01) |
| A61K 38/17 | (2006.01) |
| A61K 38/26 | (2006.01) |
| A61K 47/64 | (2017.01) |
| A61K 47/65 | (2017.01) |
| C07K 14/605 | (2006.01) |
| C07K 14/485 | (2006.01) |
| A61K 38/00 | (2006.01) |

(52) U.S. Cl.
CPC .......... *C07K 14/605* (2013.01); *A61K 38/177* (2013.01); *A61K 38/26* (2013.01); *A61K 47/6425* (2017.08); *A61K 47/65* (2017.08); *C07K 14/485* (2013.01); *A61K 38/00* (2013.01); *C07K 2319/00* (2013.01); *C07K 2319/32* (2013.01)

(58) Field of Classification Search
CPC .... A61K 38/22; A61K 38/26; A61K 38/1709; A61K 38/177; A61K 47/64; A61K 47/6425; A61K 47/65; C07K 14/435; C07K 14/575; C07K 14/605; C07K 14/705; C07K 2319/32; C07K 2319/33; C07K 2319/74
See application file for complete search history.

(56) References Cited

U.S. PATENT DOCUMENTS

| 8,541,368 | B2 | 9/2013 | Lau et al. |
| 8,557,771 | B2 | 10/2013 | Fan et al. |
| 8,673,850 | B2 | 3/2014 | Seidah et al. |
| 9,745,359 | B2 | 8/2017 | Qin |
| 10,822,385 | B2 | 11/2020 | Chen et al. |
| 2014/0212431 | A1 | 7/2014 | Kirchhofer et al. |
| 2014/0357838 | A1 | 12/2014 | Madsen et al. |
| 2019/0016768 | A1 | 1/2019 | Chen et al. |
| 2020/0165313 | A1 | 5/2020 | Lau et al. |
| 2020/0407409 | A1 | 12/2020 | Chen et al. |

FOREIGN PATENT DOCUMENTS

| CN | 102153652 A | 8/2011 |
| CN | 104093735 A | 10/2014 |
| CN | 104558198 A | 4/2015 |
| CN | 105367884 A | 3/2016 |
| EP | 2296694 A2 | 3/2011 |
| JP | 2010535849 A | 11/2010 |
| JP | 2014510516 A | 5/2014 |
| RU | 2528735 C2 | 9/2014 |
| WO | 2007018619 A2 | 2/2007 |
| WO | 2007022123 A2 | 2/2007 |
| WO | 2009022006 | 2/2009 |
| WO | 2009131740 | 10/2009 |
| WO | 2010029513 | 3/2010 |
| WO | 2011020319 A1 | 2/2011 |
| WO | 2012110422 | 8/2012 |
| WO | 12177741 A1 | 12/2012 |
| WO | 13049234 A2 | 4/2013 |
| WO | 2013170636 A1 | 11/2013 |
| WO | 2014031420 A1 | 2/2014 |
| WO | 2014037373 A1 | 3/2014 |
| WO | 2014170496 A1 | 10/2014 |
| WO | 15051214 A1 | 4/2015 |
| WO | 2015/127273 A1 | 8/2015 |
| WO | 2015185640 A1 | 12/2015 |
| WO | 2016147162 A1 | 9/2016 |

(Continued)

OTHER PUBLICATIONS

Lau Jesper et al.,"Discovery of the Once-Weekly Glucagon-Lik Peptide-1(GLP-1) Analogue Semaglutide," Journal of Medicinal Chemistry, 2015, vol. 58, No. 18, pp. 7370-7380.

(Continued)

*Primary Examiner* — Jeffrey E. Russel
(74) *Attorney, Agent, or Firm* — Jianjie Hu

(57) ABSTRACT

The application discloses compounds useful in treatment of diabetes, weight loss and/or reduction of cardiovascular risks. The compounds are bi-functional and therefore suitable as a simple treatment for patients that may benefit from treatment with both a GLP-1 receptor agonist and a PCSK9 inhibitor.

25 Claims, No Drawings
Specification includes a Sequence Listing.

(56) References Cited

FOREIGN PATENT DOCUMENTS

WO      2017121850 A1     7/2017

OTHER PUBLICATIONS

Scheen Andre J. "Dulaglutide for the treatment of type 2 diabetes," Expert Opinion on Biological Therapy, 2017, vol. 17, No. 4, pp. 485-496.

Shan et. al., PCSK9 binds to multiple receptors and can be functionally inhibited by an EGF-A peptide, Biochemical and Biophysical Research Communications, 2008, vol. 375, pp. 69-73.

Trevaskis et al., "MEDI4166: A PCSK9 Ab-GLP-1 Fusion Molecule that Elicits Robust Antidiabetic and Antihyperlipidemic Effects in Rodents and Nonhuman Primates," Diabetologia, Aug. 2016, vol. 59, Suppl 1, pp. S528-S529.

Trevaskis et al., "MEDI4166: A PCSK9 Ab-GLP-1 Fusion Molecule that Elicits Robust Antidiabetic and Antihyperlipidemic Effects in Rodents and Nonhuman Primates," American Diabetes Association, Late Breaking Abstracts, Jun. 2016, vol. 65, Suppl 1A, 35-LB, pp. LB9.

Zhang et al., "Calcium-Independent Inhibition of PCSK9 by Affinity-Improved Variants of the LDL Receptor EGF(A) Domain," Journal of Molecular Biology, 2012, vol. 422, No. 5, pp. 685-696.

Boswell et al, Global Defects in the Expression and Function of the Low Density; Lipoprotein Receptor (LDLR) Associated With Two Familial; Hypercholesterolemia Mutations Resulting in Misfolding of The; LDLR Epidermal Growth Factor-AB Pair, vol. 279, No. 29, Issue of Jul. 16, pp. 30611-30621, 2004.

Burgeron et al., "Proprotein Convertase Subtilisin/Kexin Type 9 Inhibition a New Therapeutic Mechanism for Reducing Cardiovascular Disease Risk," Circulation, 2015, vol. 132, No. 17, pp. 1648-1666.

Gu et al., Characterization of the Rose of EGF-A of Low Density Lipoprotein Receptor in PCSK9 Binding, The Journal of Lipid Research, 2013, vol. 54, No. 12, pp. 3345-3357.

Lim et al., "Site-Specific Fatty Acid-Conjugation to Prolong Protein Half-Lifein Vivo," Journal of Controlled Release, 2013, vol. 170, No. 2, pp. 219-225.

Schroeder et al., Design and Synthesis of Truncated EGF-A Peptides That Restore LDL-R Recycling in the Presence of PCSK9 In Vitro, Chemistry & Biology 21, 284-294, ; Feb. 20, 2014.

Shan et al., "PCSK9 Binds to Multiple Receptors and Can Be Functionally Inhibited by an EGF-A Peptide," Biochemical and Biophysical Research Communications, 2008, vol. 375, No. 1, pp. 69-73.

Zhang et al, Identification of a Small Peptide That Inhibits PCSK9 Protein Binding to the Low Density Lipoprotein Receptor, The Journal of Biological Chemistry vol. 289, No. 2, pp. 342-955, Jan. 10, 2014.

Zhang et al., Calcium-Independent Inhibition of PCSK9 by; Affinity-Improved Variants of the LDL Receptor EGF(A) Domain, J. Mol. Biol. (2012) 422, 685-696.

Avanti et al., "A New Strategy to Stabilize Oxytocin in Aqueous Solutions: I. The effects of Divaltent Metal Ions and Citrate Buffer," The AAPS Journal, 2011, vol. 13, No. 2, pp. 284-290.

Avanti et al., "A New Strategy to Stabilize Oxytocin in Aqueous Solutions: II. Suppression of Cystein-Mediated Intermolecular Reactions by Combination of Divalent Metal Ions and Citrate," Molecular Pharmaceutics, 2012, vol. 9, No. 3, pp. 554-562.

B. Chen et al., "Influence of Calcium Ions on the Structure and Stability of Recombinant Human Deoxyribonuclease I in the Aqueous and Lyophilized States," Journal of Pharmaceutical Sciences, 1999, vol. 88, No. 4, pp. 477-482.

M.C. Manning et al., "Stability of Protein Pharmaceuticals: An Update," Pharmaceutical Research, 2010, vol. 27, No. 4, pp. 544-575.

N.D. Kurniawan et al., "NMR Structure and Backbone Dynamics of a Concatemer of Epidermal Growth Factor Homology Modules of the Human Low-Density Lipoprotein Receptor," Journal of Molecular Biology, 2001, vol. 311, pp. 341-356.

Schroeder et al., "Design and Synthesis of Truncated EGF-A Peptides that Restore LDL-R Recycling in the Presence of PCSK9 In Vitro," Chemistry and Biology, 2014, vol. 21, pp. 284-294.

Wakankar et al., "Formulation Considerations for Proteins Susceptible to Asparagine Deamidation and Aspartate Isomerization," Journal of Pharmaceutical Sciences, 2006, vol. 95, No. 11, pp. 2321-2336.

Wang Yu et al., "Advances in Research on Modification of Protein and Peptide Drugs with Fatty Acids," Progress in Pharmaceutical Sciences, Dec. 2015, vol. 39, No. 9, pp. 651-658.

SEQUENCE LISTING

```
<160> NUMBER OF SEQ ID NOS: 388

<210> SEQ ID NO 1
<211> LENGTH: 40
<212> TYPE: PRT
<213> ORGANISM: Homo sapiens

<400> SEQUENCE: 1

Gly Thr Asn Glu Cys Leu Asp Asn Asn Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic sequence

<400> SEQUENCE: 2

Gly Thr Asn Glu Cys Leu Ala Asn Leu Gly Gly Cys Ser His Ile Cys
1               5                   10                  15

Arg Lys Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic sequence

<400> SEQUENCE: 3

Gly Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 4
<211> LENGTH: 41
<212> TYPE: PRT
<213> ORGANISM: Artificial Sequence
<220> FEATURE:
<223> OTHER INFORMATION: Synthetic sequence
```

```
<400> SEQUENCE: 4

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic

<400> SEQUENCE: 5

Gly Thr Asn Glu Cys Leu Asp Pro Leu Gly Gly Cys Ser His Ile Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic sequence

<400> SEQUENCE: 6

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 7
<211> LENGTH: 40
<212> TYPE: PRT
<213> ORGANISM: Artificial Sequence
<220> FEATURE:
<223> OTHER INFORMATION: Synthetic sequence

<400> SEQUENCE: 7

Gly Thr Asn Glu Cys Leu Lys Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic sequence

<400> SEQUENCE: 8
```

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Lys Cys Glu
        35                  40

<210> SEQ ID NO 9
<211> LENGTH: 41
<212> TYPE: PRT
<213> ORGANISM: Artificial Sequence
<220> FEATURE:
<223> OTHER INFORMATION: Synthetic

<400> SEQUENCE: 9

Asn Thr Asn Glu Cys Leu Asp Asn Leu Gly Gly Cys Ser His Ile Cys
1               5                   10                  15

Arg Asp Leu Asp Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 10
<211> LENGTH: 41
<212> TYPE: PRT
<213> ORGANISM: Artificial Sequence
<220> FEATURE:
<223> OTHER INFORMATION: Synthetic sequence

<400> SEQUENCE: 10

Asn Thr Asn Glu Cys Leu Asp Asn Leu Gly Gly Cys Ser His Val Cys
1               5                   10                  15

Arg Asp Leu Asp Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 11
<211> LENGTH: 40
<212> TYPE: PRT
<213> ORGANISM: Artificial Sequence
<220> FEATURE:
<223> OTHER INFORMATION: Synthetic sequence

<400> SEQUENCE: 11

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 12
<211> LENGTH: 40
<212> TYPE: PRT
<213> ORGANISM: Artificial Sequence
<220> FEATURE:
<223> OTHER INFORMATION: Synthetic sequence

<400> SEQUENCE: 12

Lys Thr Asn Glu Cys Leu Asp Asn Leu Gly Gly Cys Ser His Val Cys
1               5                   10                  15

-continued

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 13
<211> LENGTH: 41
<212> TYPE: PRT
<213> ORGANISM: Artificial Sequence
<220> FEATURE:
<223> OTHER INFORMATION: Synthetic sequence

<400> SEQUENCE: 13

Lys Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic sequence

<400> SEQUENCE: 14

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Lys His Arg Cys Glu
        35                  40

<210> SEQ ID NO 15
<211> LENGTH: 41
<212> TYPE: PRT
<213> ORGANISM: Artificial Sequence
<220> FEATURE:
<223> OTHER INFORMATION: Synthetic sequence

<400> SEQUENCE: 15

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Lys Lys
        35                  40

<210> SEQ ID NO 16
<211> LENGTH: 41
<212> TYPE: PRT
<213> ORGANISM: Artificial Sequence
<220> FEATURE:
<223> OTHER INFORMATION: Synthetic sequence

<400> SEQUENCE: 16

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

```
Leu Val Ala Gln Arg Lys Cys Glu Lys
        35                  40

<210> SEQ ID NO 17
<211> LENGTH: 41
<212> TYPE: PRT
<213> ORGANISM: Artificial Sequence
<220> FEATURE:
<223> OTHER INFORMATION: Synthetic sequence

<400> SEQUENCE: 17

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Glu Lys
        35                  40

<210> SEQ ID NO 18
<211> LENGTH: 41
<212> TYPE: PRT
<213> ORGANISM: Artificial Sequence
<220> FEATURE:
<223> OTHER INFORMATION: Synthetic sequence

<400> SEQUENCE: 18

Gly Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 19
<211> LENGTH: 41
<212> TYPE: PRT
<213> ORGANISM: Artificial Sequence
<220> FEATURE:
<223> OTHER INFORMATION: Synthetic sequence

<400> SEQUENCE: 19

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Lys
        35                  40

<210> SEQ ID NO 20
<211> LENGTH: 40
<212> TYPE: PRT
<213> ORGANISM: Artificial Sequence
<220> FEATURE:
<223> OTHER INFORMATION: Synthetic

<400> SEQUENCE: 20

Gly Thr Asp Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Lys
        35                  40
```

```
<210> SEQ ID NO 21
<211> LENGTH: 40
<212> TYPE: PRT
<213> ORGANISM: Artificial Sequence
<220> FEATURE:
<223> OTHER INFORMATION: Synthetic sequence

<400> SEQUENCE: 21

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Glu
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic sequence

<400> SEQUENCE: 22

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
            20                  25                  30

Leu Val Ala Gln Arg Arg Cys Glu
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic sequence

<400> SEQUENCE: 23

Gly Thr Asn Glu Cys Leu Asp Asn Leu Gly Gly Cys Ser His Val Cys
1               5                   10                  15

Arg Asp Leu Gln Ile Gly Tyr Glu Cys Leu Cys Pro Asp Gly Phe Gln
            20                  25                  30

Leu Val Ala Gln Arg Arg Cys Glu
        35                  40

<210> SEQ ID NO 24
<211> LENGTH: 40
<212> TYPE: PRT
<213> ORGANISM: Artificial Sequence
<220> FEATURE:
<223> OTHER INFORMATION: Synthetic sequence

<400> SEQUENCE: 24

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Lys
        35                  40

<210> SEQ ID NO 25
<211> LENGTH: 40
```

```
<212> TYPE: PRT
<213> ORGANISM: Artificial Sequence
<220> FEATURE:
<223> OTHER INFORMATION: Synthetic sequence

<400> SEQUENCE: 25

Lys Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 26
<211> LENGTH: 40
<212> TYPE: PRT
<213> ORGANISM: Artificial Sequence
<220> FEATURE:
<223> OTHER INFORMATION: Synthetic sequence

<400> SEQUENCE: 26

Gly Thr Asn Glu Cys Leu Asp His Leu Gly Gly Cys Ser His Ile Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic sequence

<400> SEQUENCE: 27

Gly Thr Asn Glu Cys Leu Asp Lys Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 28
<211> LENGTH: 40
<212> TYPE: PRT
<213> ORGANISM: Artificial Sequence
<220> FEATURE:
<223> OTHER INFORMATION: Synthetic sequence

<400> SEQUENCE: 28

Lys Lys Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 29
<211> LENGTH: 40
<212> TYPE: PRT
<213> ORGANISM: Artificial Sequence
<220> FEATURE:
```

<223> OTHER INFORMATION: Synthetic sequence

<400> SEQUENCE: 29

Lys Thr Asn Glu Cys Leu Asp Asn Leu Gly Gly Cys Ser His Val Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 30
<211> LENGTH: 40
<212> TYPE: PRT
<213> ORGANISM: Artificial Sequence
<220> FEATURE:
<223> OTHER INFORMATION: Synthetic sequence

<400> SEQUENCE: 30

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic sequence

<400> SEQUENCE: 31

Gly Thr Asn Glu Cys Leu Asp Asn Leu Gly Gly Cys Ser His Val Cys
1               5                   10                  15

Arg Asp Leu Glu Ile Gly Tyr Glu Cys Lys Cys Pro Asp Gly Phe Gln
            20                  25                  30

Leu Val Ala Gln Arg Arg Cys Glu
        35                  40

<210> SEQ ID NO 32
<211> LENGTH: 41
<212> TYPE: PRT
<213> ORGANISM: Artificial Sequence
<220> FEATURE:
<223> OTHER INFORMATION: Synthetic sequence

<400> SEQUENCE: 32

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic sequence

<400> SEQUENCE: 33

```
Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Lys Ala Gln Arg Arg Cys Glu
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic sequence

<400> SEQUENCE: 34

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Lys Val Ala Gln Arg Arg Cys Glu
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic sequence

<400> SEQUENCE: 35

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Lys Gln
            20                  25                  30

Leu Val Ala Gln Arg Arg Cys Glu
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic sequence

<400> SEQUENCE: 36

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Lys Phe Gln
            20                  25                  30

Leu Val Ala Gln Arg Arg Cys Glu
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthetic sequence

<400> SEQUENCE: 37

Gly Thr Asn Glu Cys Leu Asp Asn Leu Gly Gly Cys Ser His Val Cys
1               5                   10                  15
```

Arg Asp Leu Glu Ile Gly Tyr Glu Cys Leu Cys Lys Asp Gly Phe Gln
            20                  25                  30

Leu Val Ala Gln Arg Arg Cys Glu
        35                  40

<210> SEQ ID NO 38
<211> LENGTH: 40
<212> TYPE: PRT
<213> ORGANISM: Artificial Sequence
<220> FEATURE:
<223> OTHER INFORMATION: Synthetic sequence

<400> SEQUENCE: 38

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Lys Arg Cys Glu
        35                  40

<210> SEQ ID NO 39
<211> LENGTH: 40
<212> TYPE: PRT
<213> ORGANISM: Artificial Sequence
<220> FEATURE:
<223> OTHER INFORMATION: Synthetic sequence

<400> SEQUENCE: 39

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic sequence

<400> SEQUENCE: 40

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Lys Arg Arg Cys Glu
        35                  40

<210> SEQ ID NO 41
<211> LENGTH: 40
<212> TYPE: PRT
<213> ORGANISM: Artificial Sequence
<220> FEATURE:
<223> OTHER INFORMATION: Synthetic sequence

<400> SEQUENCE: 41

Gly Thr Asn Glu Cys Leu Asp Asn Leu Gly Gly Cys Ser His Val Cys
1               5                   10                  15

Arg Asp Leu Glu Ile Gly Tyr Lys Cys Leu Cys Pro Asp Gly Phe Gln
            20                  25                  30

```
Leu Val Ala Gln Arg Arg Cys Glu
        35                  40

<210> SEQ ID NO 42
<211> LENGTH: 40
<212> TYPE: PRT
<213> ORGANISM: Artificial Sequence
<220> FEATURE:
<223> OTHER INFORMATION: Synthetic sequence

<400> SEQUENCE: 42

Gly Thr Asn Glu Cys Leu Asp Asn Leu Gly Gly Cys Ser His Val Cys
1               5                   10                  15

Arg Asp Leu Glu Ile Gly Lys Glu Cys Leu Cys Pro Asp Gly Phe Gln
            20                  25                  30

Leu Val Ala Gln Arg Arg Cys Glu
        35                  40

<210> SEQ ID NO 43
<211> LENGTH: 41
<212> TYPE: PRT
<213> ORGANISM: Artificial Sequence
<220> FEATURE:
<223> OTHER INFORMATION: Synthetic sequence

<400> SEQUENCE: 43

Gly Thr Asn Glu Cys Leu Asp His Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 44
<211> LENGTH: 40
<212> TYPE: PRT
<213> ORGANISM: Artificial Sequence
<220> FEATURE:
<223> OTHER INFORMATION: Synthetic sequence

<400> SEQUENCE: 44

Gly Thr Asn Glu Cys Leu Asp Asn Leu Gly Gly Cys Ser His Val Cys
1               5                   10                  15

Arg Asp Leu Glu Ile Lys Tyr Glu Cys Leu Cys Pro Asp Gly Phe Gln
            20                  25                  30

Leu Val Ala Gln Arg Arg Cys Glu
        35                  40

<210> SEQ ID NO 45
<211> LENGTH: 40
<212> TYPE: PRT
<213> ORGANISM: Artificial Sequence
<220> FEATURE:
<223> OTHER INFORMATION: Synthetic sequence

<400> SEQUENCE: 45

Gly Thr Asn Glu Cys Leu Asp Asn Leu Gly Gly Cys Ser His Val Cys
1               5                   10                  15

Arg Asp Lys Glu Ile Gly Tyr Glu Cys Leu Cys Pro Asp Gly Phe Gln
            20                  25                  30

Leu Val Ala Gln Arg Arg Cys Glu
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Synthetic sequence

<400> SEQUENCE: 46

Gly Thr Asn Glu Cys Leu Asp Asn Leu Gly Gly Cys Ser His Lys Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 47
<211> LENGTH: 41
<212> TYPE: PRT
<213> ORGANISM: Artificial Sequence
<220> FEATURE:
<223> OTHER INFORMATION: Synthetic sequence

<400> SEQUENCE: 47

Gly Thr Asn Glu Cys Leu Asp Asn Leu Gly Gly Cys Ser His Val Cys
1               5                   10                  15

Ser Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 48
<211> LENGTH: 41
<212> TYPE: PRT
<213> ORGANISM: Artificial Sequence
<220> FEATURE:
<223> OTHER INFORMATION: Synthetic sequence

<400> SEQUENCE: 48

Gly Thr Asn Glu Cys Leu Asp Asn Leu Gly Gly Cys Ser His Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 49
<211> LENGTH: 40
<212> TYPE: PRT
<213> ORGANISM: Artificial Sequence
<220> FEATURE:
<223> OTHER INFORMATION: Synthetic sequence

<400> SEQUENCE: 49

Gly Thr Asn Glu Cys Leu Asp Asn Leu Gly Gly Cys Ser Tyr Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 50

```
<211> LENGTH: 40
<212> TYPE: PRT
<213> ORGANISM: Artificial Sequence
<220> FEATURE:
<223> OTHER INFORMATION: Synthetic sequence

<400> SEQUENCE: 50

Asn Thr Asn Glu Cys Leu Asp Asn Leu Gly Gly Cys Ser His Val Cys
1               5                   10                  15

Ser Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 51
<211> LENGTH: 40
<212> TYPE: PRT
<213> ORGANISM: Artificial Sequence
<220> FEATURE:
<223> OTHER INFORMATION: Synthetic sequence

<400> SEQUENCE: 51

Gly Thr Asn Glu Cys Leu Asp Asn Leu Gly Gly Cys Ser Lys Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic sequence

<400> SEQUENCE: 52

Gly Thr Asn Glu Cys Leu Asp Asn Leu Gly Gly Cys Lys His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 53
<211> LENGTH: 40
<212> TYPE: PRT
<213> ORGANISM: Artificial Sequence
<220> FEATURE:
<223> OTHER INFORMATION: Synthetic sequence

<400> SEQUENCE: 53

Gly Thr Asn Glu Cys Leu Asp Asn Leu Gly Lys Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 54
<211> LENGTH: 40
<212> TYPE: PRT
<213> ORGANISM: Artificial Sequence
```

<220> FEATURE:
<223> OTHER INFORMATION: Synthetic sequence

<400> SEQUENCE: 54

Gly Thr Asn Glu Cys Leu Asp Asn Leu Lys Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 55
<211> LENGTH: 41
<212> TYPE: PRT
<213> ORGANISM: Artificial Sequence
<220> FEATURE:
<223> OTHER INFORMATION: Synthetic sequence

<400> SEQUENCE: 55

Asn Thr Asn Glu Cys Leu Asp His Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Synthetic sequence

<400> SEQUENCE: 56

Gly Thr Asn Glu Cys Leu Asp Asn Lys Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 57
<211> LENGTH: 40
<212> TYPE: PRT
<213> ORGANISM: Artificial Sequence
<220> FEATURE:
<223> OTHER INFORMATION: Synthetic sequence

<400> SEQUENCE: 57

Gly Thr Asn Glu Cys Lys Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 58
<211> LENGTH: 41
<212> TYPE: PRT
<213> ORGANISM: Artificial Sequence
<220> FEATURE:
<223> OTHER INFORMATION: Synthetic sequence -continued

```
<400> SEQUENCE: 58

Asn Thr Asn Glu Cys Leu Asp Asn Leu Gly Gly Cys Ser His Val Cys
1               5                   10                  15

Arg Asp Leu Arg Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic sequence

<400> SEQUENCE: 59

Gly Thr Asn Glu Cys Leu Asp Asn Leu Gly Gly Cys Ser His Ile Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Lys
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic sequence

<400> SEQUENCE: 60

Gly Thr Asn Glu Cys Leu Asp Asn Leu Gly Gly Cys Ser Tyr Val Cys
1               5                   10                  15

Asn Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic sequence

<400> SEQUENCE: 61

Gly Thr Asn Glu Cys Leu Asp Asn Leu Gly Gly Cys Ser His Ile Cys
1               5                   10                  15

Asn Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic sequence

<400> SEQUENCE: 62

Gly Thr Asn Glu Cys Leu Asp His Leu Gly Gly Cys Ser His Val Cys
```

```
                1               5                      10                     15
Arg Asp Leu Lys Ile Gly Tyr Glu Cys Leu Cys Pro Asp Gly Phe Gln
                20                      25                     30

Leu Val Ala Gln Arg Arg Cys Glu
        35                      40

<210> SEQ ID NO 63
<211> LENGTH: 40
<212> TYPE: PRT
<213> ORGANISM: Artificial Sequence
<220> FEATURE:
<223> OTHER INFORMATION: Synthetic sequence

<400> SEQUENCE: 63

Gly Thr Asn Lys Cys Leu Asp Asn Leu Gly Gly Cys Ser His Val Cys
1               5                      10                     15

Arg Asp Leu Glu Ile Gly Tyr Glu Cys Leu Cys Pro Asp Gly Phe Gln
                20                      25                     30

Leu Val Ala Gln Arg Arg Cys Glu
        35                      40

<210> SEQ ID NO 64
<211> LENGTH: 40
<212> TYPE: PRT
<213> ORGANISM: Artificial Sequence
<220> FEATURE:
<223> OTHER INFORMATION: Synthetic sequence

<400> SEQUENCE: 64

Gly Lys Asn Glu Cys Leu Asp Asn Leu Gly Gly Cys Ser His Val Cys
1               5                      10                     15

Arg Asp Leu Glu Ile Gly Tyr Glu Cys Leu Cys Pro Asp Gly Phe Gln
                20                      25                     30

Leu Val Ala Gln Arg Arg Cys Glu
        35                      40

<210> SEQ ID NO 65
<211> LENGTH: 41
<212> TYPE: PRT
<213> ORGANISM: Artificial Sequence
<220> FEATURE:
<223> OTHER INFORMATION: Synthetic sequence

<400> SEQUENCE: 65

Lys Gly Thr Asn Glu Cys Leu Asp Asn Leu Gly Gly Cys Ser His Val
1               5                      10                     15

Cys Arg Asp Leu Glu Ile Gly Tyr Glu Cys Leu Cys Pro Asp Gly Phe
                20                      25                     30

Gln Leu Val Ala Gln Arg Arg Cys Glu
        35                      40

<210> SEQ ID NO 66
<211> LENGTH: 39
<212> TYPE: PRT
<213> ORGANISM: Artificial Sequence
<220> FEATURE:
<223> OTHER INFORMATION: Synthetic sequence

<400> SEQUENCE: 66

Gly Asn Glu Cys Leu Asp Asn Leu Gly Gly Cys Ser His Val Cys Arg
1               5                      10                     15

Asp Leu Glu Ile Gly Tyr Glu Cys Leu Cys Pro Asp Gly Phe Gln Leu
                20                      25                     30
```

```
Val Ala Lys Arg Arg Cys Glu
        35

<210> SEQ ID NO 67
<211> LENGTH: 41
<212> TYPE: PRT
<213> ORGANISM: Artificial Sequence
<220> FEATURE:
<223> OTHER INFORMATION: Synthetic sequence

<400> SEQUENCE: 67

Gly Thr Asn Glu Cys Leu Asp Asn Leu Gly Gly Cys Ser Asp Val Cys
1               5                  10                  15

Arg Asp Leu Glu Ile Gly Tyr Glu Cys Leu Cys Pro Asp Gly Phe Gly
            20                  25                  30

Leu Val Ala Gln Arg Arg Cys Glu Lys
        35                  40

<210> SEQ ID NO 68
<211> LENGTH: 41
<212> TYPE: PRT
<213> ORGANISM: Artificial Sequence
<220> FEATURE:
<223> OTHER INFORMATION: Synthetic sequence

<400> SEQUENCE: 68

Gly Thr Asn Glu Cys Leu Asp Asn Leu Gly Gly Cys Ser Asp Val Cys
1               5                  10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 69
<211> LENGTH: 41
<212> TYPE: PRT
<213> ORGANISM: Artificial Sequence
<220> FEATURE:
<223> OTHER INFORMATION: Synthetic sequence

<400> SEQUENCE: 69

Gly Thr Asn Glu Cys Leu Asp His Leu Gly Gly Cys Ser His Val Cys
1               5                  10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic sequence

<400> SEQUENCE: 70

Gly Thr Asn Glu Cys Leu Asp Asn Leu Gly Gly Cys Ser His Val Cys
1               5                  10                  15

Arg Asp Leu Glu Lys Gly Tyr Glu Cys Leu Cys Pro Asp Gly Phe Gln
            20                  25                  30

Leu Val Ala Lys Arg Arg Cys Glu
        35                  40
```

<210> SEQ ID NO 71
<211> LENGTH: 40
<212> TYPE: PRT
<213> ORGANISM: Artificial Sequence
<220> FEATURE:
<223> OTHER INFORMATION: Synthetic sequence

<400> SEQUENCE: 71

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Lys
                20                  25                  30

Leu Val Ala Gln Arg Arg Cys Glu
            35                  40

<210> SEQ ID NO 72
<211> LENGTH: 41
<212> TYPE: PRT
<213> ORGANISM: Artificial Sequence
<220> FEATURE:
<223> OTHER INFORMATION: Synthetic sequence

<400> SEQUENCE: 72

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
                20                  25                  30

Leu Val Ala Gln Arg Arg Cys Glu Lys
            35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic sequence

<400> SEQUENCE: 73

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Lys Gly Phe Gln
                20                  25                  30

Leu Val Ala Gln Arg Arg Cys Glu
            35                  40

<210> SEQ ID NO 74
<211> LENGTH: 40
<212> TYPE: PRT
<213> ORGANISM: Artificial Sequence
<220> FEATURE:
<223> OTHER INFORMATION: Synthetic sequence

<400> SEQUENCE: 74

Thr Asn Glu Cys Leu Asp His Leu Gly Gly Cys Ser His Val Cys Arg
1               5                   10                  15

Asp Leu Glu Lys Gly Tyr Glu Cys Leu Cys Pro Asp Gly Phe Gln Leu
                20                  25                  30

Val Ala Gln Arg Arg Cys Glu Lys
            35                  40

<210> SEQ ID NO 75

```
<211> LENGTH: 41
<212> TYPE: PRT
<213> ORGANISM: Artificial Sequence
<220> FEATURE:
<223> OTHER INFORMATION: Synthetic sequence

<400> SEQUENCE: 75

Ala Gly Thr Asn Glu Cys Leu Asp Asn Leu Gly Gly Cys Ser His Val
1               5                   10                  15

Cys Arg Asp Leu Glu Lys Gly Tyr Glu Cys Leu Cys Pro Asp Gly Phe
                20                  25                  30

Gln Leu Val Ala Gln Arg Arg Cys Glu
        35                  40

<210> SEQ ID NO 76
<211> LENGTH: 39
<212> TYPE: PRT
<213> ORGANISM: Artificial Sequence
<220> FEATURE:
<223> OTHER INFORMATION: Synthetic sequence

<400> SEQUENCE: 76

Thr Asn Glu Cys Leu Asp Asn Leu Gly Gly Cys Ser His Val Cys Arg
1               5                   10                  15

Asp Leu Glu Lys Gly Tyr Glu Cys Leu Cys Pro Asp Gly Phe Gln Leu
                20                  25                  30

Val Ala Gln Arg Arg Cys Glu
        35

<210> SEQ ID NO 77
<211> LENGTH: 40
<212> TYPE: PRT
<213> ORGANISM: Artificial Sequence
<220> FEATURE:
<223> OTHER INFORMATION: Synthetic sequence

<400> SEQUENCE: 77

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Asp Gly Phe Gln
                20                  25                  30

Leu Val Ala Gln Arg Arg Cys Lys
        35                  40

<210> SEQ ID NO 78
<211> LENGTH: 41
<212> TYPE: PRT
<213> ORGANISM: Artificial Sequence
<220> FEATURE:
<223> OTHER INFORMATION: Synthetic sequence

<400> SEQUENCE: 78

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
                20                  25                  30

Leu Val Ala Lys Arg Arg Cys Glu Lys
        35                  40

<210> SEQ ID NO 79
<211> LENGTH: 40
<212> TYPE: PRT
<213> ORGANISM: Artificial Sequence
```

```
<220> FEATURE:
<223> OTHER INFORMATION: Synthetic sequence

<400> SEQUENCE: 79

Gly Thr Asn Glu Cys Leu Ala Asn Leu Gly Gly Cys Ser His Ile Cys
1               5                   10                  15

Arg Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 80
<211> LENGTH: 40
<212> TYPE: PRT
<213> ORGANISM: Artificial Sequence
<220> FEATURE:
<223> OTHER INFORMATION: GTNECLDNLG GCSHVCRKLK IGYECLCPDG FQLVAQRRCE

<400> SEQUENCE: 80

Gly Thr Asn Glu Cys Leu Asp Asn Leu Gly Gly Cys Ser His Val Cys
1               5                   10                  15

Arg Lys Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 81
<211> LENGTH: 40
<212> TYPE: PRT
<213> ORGANISM: Artificial Sequence
<220> FEATURE:
<223> OTHER INFORMATION: Synthetic sequence

<400> SEQUENCE: 81

Gly Thr Asn Glu Cys Leu Asp Asn Leu Gly Gly Cys Ser His Val Cys
1               5                   10                  15

Asn Asp Leu Lys Ile Gly Tyr Glu Cys Leu Cys Pro Asp Gly Phe Gln
            20                  25                  30

Leu Val Ala Gln Arg Arg Cys Glu
        35                  40

<210> SEQ ID NO 82
<211> LENGTH: 41
<212> TYPE: PRT
<213> ORGANISM: Artificial Sequence
<220> FEATURE:
<223> OTHER INFORMATION: synthetic

<400> SEQUENCE: 82

Gly Thr Asn Glu Cys Leu Asp His Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 83
<211> LENGTH: 39
<212> TYPE: PRT
<213> ORGANISM: Artificial Sequence
<220> FEATURE:
<223> OTHER INFORMATION: synthetic
```

```
<400> SEQUENCE: 83

Asn Glu Cys Leu Asp His Leu Gly Gly Cys Ser His Val Cys Arg Asp
1               5                   10                  15

Leu Glu Lys Gly Tyr Glu Cys Leu Cys Pro Asp Gly Phe Gln Leu Val
            20                  25                  30

Ala Gln Arg Arg Cys Glu Lys
        35

<210> SEQ ID NO 84
<211> LENGTH: 41
<212> TYPE: PRT
<213> ORGANISM: Artificial Sequence
<220> FEATURE:
<223> OTHER INFORMATION: synthetic

<400> SEQUENCE: 84

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Glu Lys
        35                  40

<210> SEQ ID NO 85
<211> LENGTH: 41
<212> TYPE: PRT
<213> ORGANISM: Artificial Sequence
<220> FEATURE:
<223> OTHER INFORMATION: synthetic

<400> SEQUENCE: 85

Gly Thr Asn Glu Cys Leu Asp Asn Leu Gly Gly Cys Ser Tyr Val Cys
1               5                   10                  15

Asn Asp Leu Glu Ile Gly Tyr Glu Cys Leu Cys Pro Asp Gly Phe Lys
            20                  25                  30

Leu Val Ala Gln Arg Arg Cys Glu Lys
        35                  40

<210> SEQ ID NO 86
<211> LENGTH: 41
<212> TYPE: PRT
<213> ORGANISM: Artificial Sequence
<220> FEATURE:
<223> OTHER INFORMATION: synthetic

<400> SEQUENCE: 86

Gly Thr Asn Glu Cys Leu Asp His Leu Gly Gly Cys Ser His Val Cys
1               5                   10                  15

Arg Asp Leu Glu Ile Lys Tyr Glu Cys Leu Cys Pro Asp Gly Phe Gln
            20                  25                  30

Leu Val Ala Gln Arg Arg Cys Glu Lys
        35                  40

<210> SEQ ID NO 87
<211> LENGTH: 41
<212> TYPE: PRT
<213> ORGANISM: Artificial Sequence
<220> FEATURE:
<223> OTHER INFORMATION: synthetic

<400> SEQUENCE: 87

Gly Trp Asn Glu Cys Leu Asp Asn Leu Gly Gly Cys Ser His Val Cys
```

```
                1               5                   10                  15
Arg Asp Leu Glu Ile Gly Tyr Glu Cys Leu Cys Pro Asp Gly Phe Gln
                20                  25                  30

Leu Val Ala Gln Arg Arg Cys Glu Lys
        35                  40

<210> SEQ ID NO 88
<211> LENGTH: 40
<212> TYPE: PRT
<213> ORGANISM: Artificial Sequence
<220> FEATURE:
<223> OTHER INFORMATION: synthetic

<400> SEQUENCE: 88

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
                20                  25                  30

Leu Val Ala Lys Arg Arg Cys Glu
        35                  40

<210> SEQ ID NO 89
<211> LENGTH: 40
<212> TYPE: PRT
<213> ORGANISM: Artificial Sequence
<220> FEATURE:
<223> OTHER INFORMATION: synthetic

<400> SEQUENCE: 89

Gly Thr Asn Glu Cys Leu Asp Asn Leu Gly Gly Cys Ser His Val Cys
1               5                   10                  15

Lys Asp Leu Glu Lys Gly Tyr Glu Cys Leu Cys Pro Asp Gly Phe Gln
                20                  25                  30

Leu Val Ala Gln Arg Arg Cys Glu
        35                  40

<210> SEQ ID NO 90
<211> LENGTH: 40
<212> TYPE: PRT
<213> ORGANISM: Artificial Sequence
<220> FEATURE:
<223> OTHER INFORMATION: synthetic

<400> SEQUENCE: 90

Thr Asn Glu Cys Leu Asp Asn Leu Gly Gly Cys Ser His Val Cys Arg
1               5                   10                  15

Asp Leu Glu Ile Gly Tyr Glu Cys Leu Cys Pro Asp Gly Phe Gln Leu
                20                  25                  30

Val Ala Gln Arg Arg Cys Glu Lys
        35                  40

<210> SEQ ID NO 91
<211> LENGTH: 40
<212> TYPE: PRT
<213> ORGANISM: Artificial Sequence
<220> FEATURE:
<223> OTHER INFORMATION: synthetic

<400> SEQUENCE: 91

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Lys
```

```
            20                  25                  30

Leu Val Ala Lys Arg Arg Cys Glu
        35                  40

<210> SEQ ID NO 92
<211> LENGTH: 42
<212> TYPE: PRT
<213> ORGANISM: Artificial Sequence
<220> FEATURE:
<223> OTHER INFORMATION: synthetic

<400> SEQUENCE: 92

Ala Gly Thr Asn Glu Cys Leu Asp Asn Leu Gly Gly Cys Ser His Val
1               5                   10                  15

Cys Arg Asp Leu Glu Ile Gly Tyr Glu Cys Leu Cys Pro Asp Gly Phe
            20                  25                  30

Gln Leu Val Ala Gln Arg Arg Cys Glu Lys
        35                  40

<210> SEQ ID NO 93
<211> LENGTH: 41
<212> TYPE: PRT
<213> ORGANISM: Artificial Sequence
<220> FEATURE:
<223> OTHER INFORMATION: synthetic

<400> SEQUENCE: 93

Gly Thr Asn Glu Cys Leu Asp Asn Leu Gly Gly Cys Ser Tyr Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Glu Lys
        35                  40

<210> SEQ ID NO 94
<211> LENGTH: 40
<212> TYPE: PRT
<213> ORGANISM: Artificial Sequence
<220> FEATURE:
<223> OTHER INFORMATION: synthetic

<400> SEQUENCE: 94

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Gln
            20                  25                  30

Leu Val Ala Gln Arg Arg Cys Lys
        35                  40

<210> SEQ ID NO 95
<211> LENGTH: 40
<212> TYPE: PRT
<213> ORGANISM: Artificial Sequence
<220> FEATURE:
<223> OTHER INFORMATION: synthetic

<400> SEQUENCE: 95

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Lys Gly Phe Gln
            20                  25                  30

Leu Val Ala Gln Arg Arg Cys Lys
```

35                  40

<210> SEQ ID NO 96
<211> LENGTH: 40
<212> TYPE: PRT
<213> ORGANISM: Artificial Sequence
<220> FEATURE:
<223> OTHER INFORMATION: synthetic

<400> SEQUENCE: 96

Gly Thr Asn Glu Cys Leu Asp His Leu Gly Gly Cys Ser His Val Cys
1               5                   10                  15

Arg Asp Leu Glu Lys Gly Tyr Glu Cys Leu Cys Pro Asp Gly Phe Gln
            20                  25                  30

Leu Val Ala Gln Arg Arg Cys Lys
        35                  40

<210> SEQ ID NO 97
<211> LENGTH: 40
<212> TYPE: PRT
<213> ORGANISM: Artificial Sequence
<220> FEATURE:
<223> OTHER INFORMATION: synthetic

<400> SEQUENCE: 97

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Lys
        35                  40

<210> SEQ ID NO 98
<211> LENGTH: 41
<212> TYPE: PRT
<213> ORGANISM: Artificial Sequence
<220> FEATURE:
<223> OTHER INFORMATION: synthetic

<400> SEQUENCE: 98

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Glu Lys
        35                  40

<210> SEQ ID NO 99
<211> LENGTH: 40
<212> TYPE: PRT
<213> ORGANISM: Artificial Sequence
<220> FEATURE:
<223> OTHER INFORMATION: synthetic

<400> SEQUENCE: 99

Gly Thr Asn Glu Cys Leu Asp Asn Leu Gly Gly Cys Ser His Val Cys
1               5                   10                  15

Arg Asp Leu Glu Lys Lys Tyr Glu Cys Leu Cys Pro Asp Gly Phe Gln
            20                  25                  30

Leu Val Ala Gln Arg Arg Cys Glu
        35                  40

-continued

```
<210> SEQ ID NO 100
<211> LENGTH: 40
<212> TYPE: PRT
<213> ORGANISM: Artificial Sequence
<220> FEATURE:
<223> OTHER INFORMATION: synthetic

<400> SEQUENCE: 100

Gly Thr Asn Glu Cys Leu Asp Asn Leu Gly Gly Cys Ser His Val Cys
1               5                   10                  15

Arg Asp Leu Lys Lys Gly Tyr Glu Cys Leu Cys Pro Asp Gly Phe Gln
            20                  25                  30

Leu Val Ala Gln Arg Arg Cys Glu
        35                  40

<210> SEQ ID NO 101
<211> LENGTH: 40
<212> TYPE: PRT
<213> ORGANISM: Artificial Sequence
<220> FEATURE:
<223> OTHER INFORMATION: synthetic

<400> SEQUENCE: 101

Gly Thr Asn Glu Cys Leu Asp Asn Leu Gly Gly Cys Ser His Val Cys
1               5                   10                  15

Arg Asp Leu Lys Ile Lys Tyr Glu Cys Leu Cys Pro Asp Gly Phe Gln
            20                  25                  30

Leu Val Ala Gln Arg Arg Cys Glu
        35                  40

<210> SEQ ID NO 102
<211> LENGTH: 40
<212> TYPE: PRT
<213> ORGANISM: Artificial Sequence
<220> FEATURE:
<223> OTHER INFORMATION: synthetic

<400> SEQUENCE: 102

Gly Thr Asn Glu Cys Leu Asp Asn Leu Gly Gly Cys Ser His Val Cys
1               5                   10                  15

Arg Asp Lys Glu Lys Gly Tyr Glu Cys Leu Cys Pro Asp Gly Phe Gln
            20                  25                  30

Leu Val Ala Gln Arg Arg Cys Glu
        35                  40

<210> SEQ ID NO 103
<211> LENGTH: 41
<212> TYPE: PRT
<213> ORGANISM: Artificial Sequence
<220> FEATURE:
<223> OTHER INFORMATION: synthetic

<400> SEQUENCE: 103

Gly Thr Asn Glu Cys Leu Asp His Leu Gly Gly Cys Ser His Val Cys
1               5                   10                  15

Arg Asp Leu Glu Lys Gly Tyr Glu Cys Leu Cys Pro Glu Gly Phe Gln
            20                  25                  30

Leu Val Ala Gln Arg Arg Cys Glu Lys
        35                  40

<210> SEQ ID NO 104
<211> LENGTH: 41
<212> TYPE: PRT
```

<213> ORGANISM: Artificial Sequence
<220> FEATURE:
<223> OTHER INFORMATION: synthetic

<400> SEQUENCE: 104

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Lys Arg Arg Cys Glu Lys
        35                  40

<210> SEQ ID NO 105
<211> LENGTH: 41
<212> TYPE: PRT
<213> ORGANISM: Artificial Sequence
<220> FEATURE:
<223> OTHER INFORMATION: synthetic

<400> SEQUENCE: 105

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Lys
            20                  25                  30

Leu Val Ala Gln Arg Arg Cys Glu Lys
        35                  40

<210> SEQ ID NO 106
<211> LENGTH: 40
<212> TYPE: PRT
<213> ORGANISM: Artificial Sequence
<220> FEATURE:
<223> OTHER INFORMATION: Synthetic

<400> SEQUENCE: 106

Gly Thr Asn Glu Cys Leu Asp Asn Leu Gly Gly Cys Ser His Val Cys
1               5                   10                  15

Lys Asp Leu Glu Ile Gly Tyr Glu Cys Leu Cys Pro Asp Gly Phe Lys
            20                  25                  30

Leu Val Ala Gln Arg Arg Cys Glu
        35                  40

<210> SEQ ID NO 107
<211> LENGTH: 40
<212> TYPE: PRT
<213> ORGANISM: Artificial Sequence
<220> FEATURE:
<223> OTHER INFORMATION: Synthetic

<400> SEQUENCE: 107

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Asp Gly Phe Gln
            20                  25                  30

Leu Val Ala Gln Arg Arg Cys Glu
        35                  40

<210> SEQ ID NO 108
<211> LENGTH: 40
<212> TYPE: PRT
<213> ORGANISM: Artificial Sequence
<220> FEATURE:
<223> OTHER INFORMATION: Synthetic

<400> SEQUENCE: 108

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 109
<211> LENGTH: 40
<212> TYPE: PRT
<213> ORGANISM: Artificial Sequence
<220> FEATURE:
<223> OTHER INFORMATION: Synthetic

<400> SEQUENCE: 109

Gly Thr Asn Glu Cys Leu Asp Asn Leu Gly Gly Cys Ser His Ile Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 110
<211> LENGTH: 40
<212> TYPE: PRT
<213> ORGANISM: Artificial Sequence
<220> FEATURE:
<223> OTHER INFORMATION: Synthetic

<400> SEQUENCE: 110

Gly Thr Asn Glu Cys Leu Asp Asn Leu Gly Gly Cys Ser Tyr Val Cys
1               5                   10                  15

Asn Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 111
<211> LENGTH: 40
<212> TYPE: PRT
<213> ORGANISM: Artificial Sequence
<220> FEATURE:
<223> OTHER INFORMATION: Synthetic

<400> SEQUENCE: 111

Gly Thr Asn Glu Cys Leu Asp His Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu
        35                  40

<210> SEQ ID NO 112
<211> LENGTH: 40
<212> TYPE: PRT
<213> ORGANISM: Artificial Sequence
<220> FEATURE:
<223> OTHER INFORMATION: Synthetic

<400> SEQUENCE: 112

Gly Thr Asn Glu Cys Leu Asp Asn Leu Gly Gly Cys Ser His Val Cys
1               5                   10                  15

Arg Asp Leu Glu Lys Gly Tyr Glu Cys Leu Cys Pro Glu Gly Phe Gln
                20                  25                  30

Leu Val Ala Gln Arg Arg Cys Glu
        35                  40

<210> SEQ ID NO 113
<211> LENGTH: 40
<212> TYPE: PRT
<213> ORGANISM: Artificial Sequence
<220> FEATURE:
<223> OTHER INFORMATION: Synthetic

<400> SEQUENCE: 113

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Lys
                20                  25                  30

Leu Val Ala Gln Arg Arg Cys Glu
        35                  40

<210> SEQ ID NO 114
<211> LENGTH: 40
<212> TYPE: PRT
<213> ORGANISM: Artificial Sequence
<220> FEATURE:
<223> OTHER INFORMATION: Synthetic

<400> SEQUENCE: 114

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
                20                  25                  30

Leu Val Ala Lys Arg Arg Cys Glu
        35                  40

<210> SEQ ID NO 115
<211> LENGTH: 4
<212> TYPE: PRT
<213> ORGANISM: Artificial Sequence
<220> FEATURE:
<223> OTHER INFORMATION: Synthetic

<400> SEQUENCE: 115

Gly Gln Ala Pro
1

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Gln Ala Pro Gly Gln Ala Pro
1               5

<210> SEQ ID NO 117
<211> LENGTH: 12
<212> TYPE: PRT
<213> ORGANISM: Artificial Sequence
<220> FEATURE:

<223> OTHER INFORMATION: Synthetic

<400> SEQUENCE: 117

Gly Gln Ala Pro Gly Gln Ala Pro Gly Gln Ala Pro
1               5                   10

<210> SEQ ID NO 118
<211> LENGTH: 24
<212> TYPE: PRT
<213> ORGANISM: Artificial Sequence
<220> FEATURE:
<223> OTHER INFORMATION: Synthetic

<400> SEQUENCE: 118

Gly Gln Ala Pro Gly Gln Ala Pro Gly Gln Ala Pro Gly Gln Ala Pro
1               5                   10                  15

Gly Gln Ala Pro Gly Gln Ala Pro
            20

<210> SEQ ID NO 119
<211> LENGTH: 40
<212> TYPE: PRT
<213> ORGANISM: Artificial Sequence
<220> FEATURE:
<223> OTHER INFORMATION: Synthetic

<400> SEQUENCE: 119

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro
        35                  40

<210> SEQ ID NO 120
<211> LENGTH: 80
<212> TYPE: PRT
<213> ORGANISM: Artificial Sequence
<220> FEATURE:
<223> OTHER INFORMATION: Synthetic

<400> SEQUENCE: 120

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro Gly Gln Ala Pro
    50                  55                  60

Gly Gln Ala Pro Gly Gln Ala Pro Gly Gln Ala Pro Gly Gln Ala Pro
65                  70                  75                  80

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Lys Gln Ala Pro Gly Gln Ala Pro
1               5

```
<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Gly Lys Ala Pro Gly Gln Ala Pro
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

Gly Gln Lys Pro Gly Gln Ala Pro
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Gln Ala Lys Gly Gln Ala Pro
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic

<400> SEQUENCE: 125

Gly Gln Ala Pro Lys Gln Ala Pro
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Gly Gln Ala Pro Gly Lys Ala Pro
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Gly Gln Ala Pro Gly Gln Lys Pro
1               5
```

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Gly Gln Ala Pro Gly Gln Ala Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

Gly Ala Pro Ser Gly Ala Pro Ser
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Gly Ser Gly Ser Gly Ser Gly Ser
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic

<400> SEQUENCE: 131

Gly Glu Gly Ser Gly Glu Gly Ser
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Gly Gly Gly Gly Gly Gly Gly
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

Gly Lys Gly Gly Gly Gly Gly Gly
1               5

-continued

```
<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Gly Gly Gly Gly Ser Gly Gly Gly Gly Ser
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Gly Gly Gly Gly Gly Gly Glu Ser
1               5

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Gly Gly Gly Gly Gly Gly Gly Gly Glu Ser
1               5                   10

<210> SEQ ID NO 137
<211> LENGTH: 31
<212> TYPE: PRT
<213> ORGANISM: Homo sapiens

<400> SEQUENCE: 137

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 138

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Synthetic
```

```
<220> FEATURE:
<221> NAME/KEY: MOD_RES
<222> LOCATION: (2)..(2)
<223> OTHER INFORMATION: Aib

<400> SEQUENCE: 139

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Synthetic

<400> SEQUENCE: 140

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 141
<211> LENGTH: 31
<212> TYPE: PRT
<213> ORGANISM: Artificial Sequence
<220> FEATURE:
<223> OTHER INFORMATION: Synthetic

<400> SEQUENCE: 141

His Trp Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 142

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Gln Gly Arg Gly
            20                  25                  30

<210> SEQ ID NO 143
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 143
```

His Xaa Glu Gly Thr Phe Thr Ser Asp Val Ser Ser Tyr Leu Glu Gly
1               5                   10                  15

Gln Ala Ala Lys Glu Phe Ile Ala Trp
            20                  25

<210> SEQ ID NO 144
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 144

His Xaa Glu Gly Thr Phe Thr Ser Asp Val Ser Ser Tyr Leu Glu Gly
1               5                   10                  15

Gln Ala Ala Lys Glu Phe Ile Ala Trp Leu
            20                  25

<210> SEQ ID NO 145
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 145

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val
            20                  25

<210> SEQ ID NO 146
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 146

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg
            20                  25

<210> SEQ ID NO 147
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 147

His Xaa Glu Gly Thr Lys Thr Ser Asp Val Ser Ser Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 148
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 148

His Xaa Glu Gly Thr Phe Thr Ser Asp Val Ser Ser Tyr Leu Lys Gly
1               5                   10                  15

Gln Ala Ala Arg Glu Phe Ile Ala Trp Leu Val Arg Gly Arg Gly
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 149

His Xaa Glu Gly Thr Phe Thr Ser Asp Val Ser Ser Tyr Leu Glu Gly
1               5                   10                  15

Gln Lys Ala Arg Glu Phe Ile Ala Trp Leu Val Arg Gly Arg Gly
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 150

His Xaa Glu Gly Thr Phe Thr Ser Asp Val Ser Ser Tyr Leu Glu Gly
1               5                   10                  15

Gln Ala Lys Arg Glu Phe Ile Ala Trp Leu Val Arg Gly Arg Gly
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 151

His Xaa Glu Gly Thr Phe Thr Ser Asp Val Ser Ser Tyr Leu Glu Gly
1               5                   10                  15

Gln Ala Ala Arg Lys Phe Ile Ala Trp Leu Val Arg Gly Arg Gly
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 152

His Xaa Glu Gly Thr Phe Thr Ser Asp Val Ser Ser Tyr Leu Glu Gly
1               5                   10                  15

Gln Ala Ala Arg Glu Phe Ile Ala Lys Leu Val Arg Gly Arg Gly
            20                  25                  30

<210> SEQ ID NO 153
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 153

His Xaa Glu Gly Thr Phe Thr Ser Asp Val Ser Ser Tyr Leu Glu Gly
1               5                   10                  15

Gln Ala Ala Arg Glu Phe Ile Ala Trp Lys Val Arg Gly Arg Gly
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 154

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly
            20                  25                  30

<210> SEQ ID NO 155
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 155

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly
            20                  25                  30

<210> SEQ ID NO 156
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 156

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 157

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly
            20                  25                  30

<210> SEQ ID NO 158
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 158

His Xaa Glu Gly Thr Phe Thr Ser Asp Val Ser Ser Tyr Leu Glu Gly
1               5                   10                  15

Gln Val Ala Lys Glu Phe Ile Ala Trp Leu Val Arg Gly Arg Gly
            20                  25                  30

<210> SEQ ID NO 159
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)

<223> OTHER INFORMATION: Aib

<400> SEQUENCE: 159

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly
            20                  25                  30

<210> SEQ ID NO 160
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 160

His Xaa Glu Gly Thr Phe Thr Ser Asp Val Ser Ser Tyr Leu Glu Gly
1               5                   10                  15

Gln Ala Val Lys Glu Phe Ile Ala Trp Leu Val Arg Gly Arg Gly
            20                  25                  30

<210> SEQ ID NO 161
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 161

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly
            20                  25                  30

<210> SEQ ID NO 162
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 162

His Xaa Glu Gly Thr Phe Thr Ser Asp Val Ser Ser Tyr Leu Glu Gly
1               5                   10                  15

Gln Ala Ala Lys Glu Phe Ala Ala Trp Leu Val Arg Gly Arg Gly
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (2)..(2)
<223> OTHER INFORMATION: Aib

<400> SEQUENCE: 163

His Xaa Glu Gly Thr Phe Thr Ser Asp Val Ser Ser Tyr Leu Glu Gly
1               5                   10                  15

Gln Ala Ala Lys Glu Phe Val Ala Trp Leu Val Arg Gly Arg Gly
            20                  25                  30

<210> SEQ ID NO 164
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 164

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly
            20                  25                  30

<210> SEQ ID NO 165
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 165

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 166

His Xaa Glu Gly Thr Phe Thr Ser Asp Val Ser Ser Tyr Leu Glu Gly
1               5                   10                  15

Gln Ala Ala Lys Glu Phe Ile Ala Trp Ala Val Arg Gly Arg Gly
            20                  25                  30

<210> SEQ ID NO 167
<211> LENGTH: 31
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (2)..(2)
<223> OTHER INFORMATION: Aib

<400> SEQUENCE: 167

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly
            20                  25                  30

<210> SEQ ID NO 168
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 168

His Xaa Glu Gly Thr Phe Thr Ser Asp Val Ser Ser Tyr Leu Glu Gly
1               5                   10                  15

Gln Ala Ala Lys Glu Phe Ile Ala Trp Ile Val Arg Gly Arg Gly
            20                  25                  30

<210> SEQ ID NO 169
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 169

His Xaa Glu Gly Thr Phe Thr Ser Asp Val Ser Ser Tyr Leu Glu Gly
1               5                   10                  15

Gln Ala Ala Lys Glu Phe Ile Ala Trp Thr Val Arg Gly Arg Gly
            20                  25                  30

<210> SEQ ID NO 170
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 170

His Xaa Glu Gly Thr Phe Thr Ser Asp Val Ser Ser Tyr Leu Glu Gly
1               5                   10                  15

Gln Ala Ala Lys Glu Phe Ile Ala Trp Val Val Arg Gly Arg Gly
            20                  25                  30

<210> SEQ ID NO 171
<211> LENGTH: 31
<212> TYPE: PRT
<213> ORGANISM: Artificial Sequence
<220> FEATURE:
<223> OTHER INFORMATION: Synthetic
```

<220> FEATURE:
<221> NAME/KEY: MOD_RES
<222> LOCATION: (2)..(2)
<223> OTHER INFORMATION: Aib

<400> SEQUENCE: 171

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly
            20                  25                  30

<210> SEQ ID NO 172
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 172

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Ile Arg Gly Arg Gly
            20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 173

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Leu Arg Gly Arg Gly
            20                  25                  30

<210> SEQ ID NO 174
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 174

His Xaa Glu Gly Thr Phe Thr Ser Asp Val Ser Ser Tyr Leu Lys Gly
1               5                   10                  15

Gln Ala Ala Lys Glu Phe Ile Ala Trp Leu Val Arg Gly Arg Gly
            20                  25                  30

<210> SEQ ID NO 175
<211> LENGTH: 31
<212> TYPE: PRT
<213> ORGANISM: Artificial Sequence
<220> FEATURE:

<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 175

His Xaa Glu Gly Thr Phe Thr Ser Asp Val Ser Ser Tyr Leu Glu Gly
1               5                   10                  15
Lys Ala Ala Lys Glu Phe Ile Ala Trp Leu Val Arg Gly Arg Gly
            20                  25                  30

<210> SEQ ID NO 176
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 176

His Xaa Glu Gly Thr Phe Thr Ser Asp Val Ser Ser Tyr Leu Glu Gly
1               5                   10                  15
Gln Lys Ala Lys Glu Phe Ile Ala Trp Leu Val Arg Gly Arg Gly
            20                  25                  30

<210> SEQ ID NO 177
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 177

His Xaa Glu Gly Thr Phe Thr Ser Asp Val Ser Ser Tyr Leu Glu Gly
1               5                   10                  15
Gln Ala Lys Lys Glu Phe Ile Ala Trp Leu Val Arg Gly Arg Gly
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 178

His Xaa Glu Gly Thr Phe Thr Ser Asp Val Ser Ser Tyr Leu Glu Gly
1               5                   10                  15
Gln Ala Ala Lys Lys Phe Ile Ala Trp Leu Val Arg Gly Arg Gly
            20                  25                  30

<210> SEQ ID NO 179
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 179

His Xaa Glu Gly Thr Phe Thr Ser Asp Val Ser Ser Tyr Leu Glu Gly
1               5                   10                  15

Gln Ala Ala Lys Glu Phe Ile Lys Trp Leu Val Arg Gly Arg Gly
            20                  25                  30

<210> SEQ ID NO 180
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 180

His Xaa Glu Gly Thr Phe Thr Ser Asp Val Ser Ser Tyr Leu Glu Gly
1               5                   10                  15

Gln Ala Ala Lys Glu Phe Ile Ala Lys Leu Val Arg Gly Arg Gly
            20                  25                  30

<210> SEQ ID NO 181
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 181

His Xaa Glu Gly Thr Phe Thr Ser Asp Val Ser Ser Tyr Leu Glu Gly
1               5                   10                  15

Gln Ala Ala Lys Glu Phe Ile Ala Trp Lys Val Arg Gly Arg Gly
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 182

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Lys Arg Gly Arg Gly
            20                  25                  30

<210> SEQ ID NO 183
<211> LENGTH: 31
<212> TYPE: PRT

<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 183

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly
            20                  25                  30

<210> SEQ ID NO 184
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 184

His Xaa Glu Gly Thr Phe Thr Ser Asp Val Ser Ser Tyr Leu Glu Gly
1               5                   10                  15

Lys Ala Ala Arg Glu Phe Ile Ala Trp Leu Val Arg Gly Arg Gly
            20                  25                  30

<210> SEQ ID NO 185
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 185

His Xaa Glu Gly Thr Phe Thr Ser Asp Val Ser Ser Tyr Leu Glu Gly
1               5                   10                  15

Gln Ala Ala Arg Glu Phe Ile Lys Trp Leu Val Arg Gly Arg Gly
            20                  25                  30

<210> SEQ ID NO 186
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 186

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Lys Arg Gly Arg Gly
            20                  25                  30

<210> SEQ ID NO 187
<211> LENGTH: 31

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: wherein X is A, G, W or Aib
<220> FEATURE:
<221> NAME/KEY: VARIANT
<222> LOCATION: (6)..(6)
<223> OTHER INFORMATION: wherein X is F or K
<220> FEATURE:
<221> NAME/KEY: VARIANT
<222> LOCATION: (15)..(15)
<223> OTHER INFORMATION: wherein X is E, G or K
<220> FEATURE:
<221> NAME/KEY: VARIANT
<222> LOCATION: (17)..(17)
<223> OTHER INFORMATION: wherein X is Q, G or K
<220> FEATURE:
<221> NAME/KEY: VARIANT
<222> LOCATION: (18)..(18)
<223> OTHER INFORMATION: wherein X is A, G, V or K
<220> FEATURE:
<221> NAME/KEY: VARIANT
<222> LOCATION: (19)..(19)
<223> OTHER INFORMATION: wherein X is A, G, V or K
<220> FEATURE:
<221> NAME/KEY: VARIANT
<222> LOCATION: (20)..(20)
<223> OTHER INFORMATION: wherein X is K or R
<220> FEATURE:
<221> NAME/KEY: VARIANT
<222> LOCATION: (21)..(21)
<223> OTHER INFORMATION: wherein X is E, G or K
<220> FEATURE:
<221> NAME/KEY: VARIANT
<222> LOCATION: (23)..(23)
<223> OTHER INFORMATION: wherein X is I, A or V
<220> FEATURE:
<221> NAME/KEY: VARIANT
<222> LOCATION: (24)..(24)
<223> OTHER INFORMATION: wherein X is A, G or K
<220> FEATURE:
<221> NAME/KEY: VARIANT
<222> LOCATION: (25)..(25)
<223> OTHER INFORMATION: wherein X is W, G or K
<220> FEATURE:
<221> NAME/KEY: VARIANT
<222> LOCATION: (26)..(26)
<223> OTHER INFORMATION: wherein X is L, G, T, V, I or K
<220> FEATURE:
<221> NAME/KEY: VARIANT
<222> LOCATION: (27)..(27)
<223> OTHER INFORMATION: wherein X is V, G, I, L, K or absent
<220> FEATURE:
<221> NAME/KEY: VARIANT
<222> LOCATION: (28)..(28)
<223> OTHER INFORMATION: wherein X is K, R, Q or absent
<220> FEATURE:
<221> NAME/KEY: VARIANT
<222> LOCATION: (29)..(29)
<223> OTHER INFORMATION: wherein X is G or absent
<220> FEATURE:
<221> NAME/KEY: VARIANT
<222> LOCATION: (30)..(30)
<223> OTHER INFORMATION: wherein X is R, K or absent
<220> FEATURE:
<221> NAME/KEY: VARIANT
<222> LOCATION: (31)..(31)
<223> OTHER INFORMATION: wherein X is G or is absent

<400> SEQUENCE: 187

His Xaa Glu Gly Thr Xaa Thr Ser Asp Val Ser Ser Tyr Leu Xaa Gly
 1               5                  10                  15

Xaa Xaa Xaa Xaa Xaa Phe Xaa Xaa Xaa Xaa Xaa Xaa Xaa Xaa Xaa
```

-continued

```
                20                  25                  30
```

<210> SEQ ID NO 188
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 188

```
His Xaa Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75
```

<210> SEQ ID NO 189
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 189

```
His Xaa Glu Gly Thr Phe Thr Ser Asp Val Ser Ser Tyr Leu Glu Gly
1               5                  10                  15

Gln Ala Ala Lys Glu Phe Ile Ala Trp Leu Val Arg Gly Arg Gly Gly
            20                  25                  30

Gln Ala Pro Gly Thr Asn Glu Cys Leu Asp Asn Leu Gly Gly Cys Ser
        35                  40                  45

His Val Cys Arg Asp Leu Glu Ile Gly Tyr Glu Cys Leu Cys Pro Glu
    50                  55                  60

Gly Phe Gln Leu Val Ala Gln Arg Arg Cys Glu
65                  70                  75
```

<210> SEQ ID NO 190
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 190

```
His Xaa Glu Gly Thr Phe Thr Ser Asp Val Ser Ser Tyr Leu Glu Gly
1               5                  10                  15

Gln Ala Ala Lys Glu Phe Ile Ala Trp Leu Val Arg Gly Arg Gly Gly
            20                  25                  30
```

Gln Ala Pro Gly Gln Ala Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Glu Gly Phe Gln Leu Val Ala Gln Arg Arg Cys Glu Lys
65                  70                  75                  80

<210> SEQ ID NO 191
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 191

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
             20                  25                  30

Gln Ala Pro Gly Gln Ala Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Lys Gly Phe Gln Leu Val Ala Gln Arg Arg Cys Glu
65                  70                  75

<210> SEQ ID NO 192
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 192

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
             20                  25                  30

Gln Ala Pro Gly Gln Ala Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Asp Gly Phe Gln Leu Val Ala Gln Arg Arg Cys Glu
65                  70                  75

<210> SEQ ID NO 193
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 193

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 194
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 194

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Ile Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 195
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 195

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser Tyr Val Cys Asn Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 196
<211> LENGTH: 79

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 196

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp His Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 197
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 197

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 198
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 198

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
```

Leu Cys Pro Glu Gly Phe Lys Leu Val Ala Gln Arg Arg Cys Glu
65                  70                  75

<210> SEQ ID NO 199
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 199

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 200
<211> LENGTH: 83
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 200

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Gln Ala Pro Gly Thr Asn Glu Cys
        35                  40                  45

Leu Asp Asn Leu Gly Gly Cys Ser His Val Cys Arg Asp Leu Glu Ile
    50                  55                  60

Gly Tyr Glu Cys Leu Cys Pro Glu Gly Phe Gln Leu Val Ala Gln Arg
65                  70                  75                  80

Arg Cys Glu

<210> SEQ ID NO 201
<211> LENGTH: 95
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 201

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Gln Ala Pro Gly Gln Ala Pro Gly
        35                  40                  45

Gln Ala Pro Gly Gln Ala Pro Gly Thr Asn Glu Cys Leu Asp Asn Leu
50                  55                  60

Gly Gly Cys Ser His Val Cys Arg Asp Leu Glu Ile Gly Tyr Glu Cys
65                  70                  75                  80

Leu Cys Pro Glu Gly Phe Gln Leu Val Ala Gln Arg Arg Cys Glu
            85                  90                  95

<210> SEQ ID NO 202
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 202

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Gln Ala Pro Gly Gln Ala Pro Gly
        35                  40                  45

Gln Ala Pro Gly Gln Ala Pro Gly Gln Ala Pro Gly Gln Ala Pro Gly
    50                  55                  60

Gln Ala Pro Gly Gln Ala Pro Gly Thr Asn Glu Cys Leu Asp Asn Leu
65                  70                  75                  80

Gly Gly Cys Ser His Val Cys Arg Asp Leu Glu Ile Gly Tyr Glu Cys
                85                  90                  95

Leu Cys Pro Glu Gly Phe Gln Leu Val Ala Gln Arg Arg Cys Glu
            100                 105                 110

<210> SEQ ID NO 203
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 203

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Gln Ala Pro Gly Gln Ala Pro Gly
        35                  40                  45

Gln Ala Pro Gly Gln Ala Pro Gly Gln Ala Pro Gly Gln Ala Pro Gly
    50                  55                  60

Gln Ala Pro Gly Gln Ala Pro Gly Gln Ala Pro Gly Gln Ala Pro Gly
65                  70                  75                  80

Gln Ala Pro Gly Gln Ala Pro Gly Gln Ala Pro Gly Gln Ala Pro Gly
                85                  90                  95

Gln Ala Pro Gly Gln Ala Pro Gly Gln Ala Pro Gly Gln Ala Pro Gly
                100                 105                 110

Thr Asn Glu Cys Leu Asp Asn Leu Gly Gly Cys Ser His Val Cys Arg
            115                 120                 125

Asp Leu Glu Ile Gly Tyr Glu Cys Leu Cys Pro Glu Gly Phe Gln Leu
        130                 135                 140

Val Ala Gln Arg Arg Cys Glu
145                 150

<210> SEQ ID NO 204
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 204

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 205
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 205

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Lys Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 206
<211> LENGTH: 79

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 206

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 207
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 207

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 208
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 208

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
```

Leu Cys Pro Glu Gly Phe Gln Leu Val Ala Gln Arg Arg Cys Glu
65                  70                  75

<210> SEQ ID NO 209
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 209

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 210

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 211
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 211

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 212
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 212

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Ala Pro Ser Gly Ala Pro Ser Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 213
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 213

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Ser Gly Ser Gly Ser Gly Ser Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 214
<211> LENGTH: 79
<212> TYPE: PRT
<213> ORGANISM: Artificial Sequence
<220> FEATURE:
<223> OTHER INFORMATION: Synthetic
<220> FEATURE:

```
<221> NAME/KEY: MOD_RES
<222> LOCATION: (2)..(2)
<223> OTHER INFORMATION: Aib

<400> SEQUENCE: 214

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Glu Gly Ser Gly Glu Gly Ser Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 215
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 215

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gly Gly Gly Gly Gly Gly Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 216
<211> LENGTH: 81
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 216

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gly Gly Gly Ser Gly Gly Gly Gly Ser Gly Thr Asn Glu Cys Leu Asp
        35                  40                  45

Asn Leu Gly Gly Cys Ser His Val Cys Arg Asp Leu Glu Ile Gly Tyr
    50                  55                  60

Glu Cys Leu Cys Pro Glu Gly Phe Gln Leu Val Ala Gln Arg Arg Cys
65                  70                  75                  80
```

Glu

<210> SEQ ID NO 217
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 217

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gly Gly Gly Gly Gly Glu Ser Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 218
<211> LENGTH: 81
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 218

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gly Gly Gly Gly Gly Gly Gly Glu Ser Gly Thr Asn Glu Cys Leu Asp
        35                  40                  45

Asn Leu Gly Gly Cys Ser His Val Cys Arg Asp Leu Glu Ile Gly Tyr
    50                  55                  60

Glu Cys Leu Cys Pro Glu Gly Phe Gln Leu Val Ala Gln Arg Arg Cys
65                  70                  75                  80

Glu

<210> SEQ ID NO 219
<211> LENGTH: 79
<212> TYPE: PRT
<213> ORGANISM: Artificial Sequence
<220> FEATURE:
<223> OTHER INFORMATION: Synthetic

<400> SEQUENCE: 219

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu

```
                35                  40                  45
Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
65                  70                  75

<210> SEQ ID NO 220
<211> LENGTH: 79
<212> TYPE: PRT
<213> ORGANISM: Artificial Sequence
<220> FEATURE:
<223> OTHER INFORMATION: Synthetic

<400> SEQUENCE: 220

His Trp Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 221
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 221

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Gln Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 222
<211> LENGTH: 73
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 222

His Xaa Glu Gly Thr Phe Thr Ser Asp Val Ser Ser Tyr Leu Glu Gly
1               5                   10                  15
```

```
Gln Ala Ala Lys Glu Phe Ile Ala Trp Gly Gln Ala Pro Gly Gln Ala
            20                  25                  30

Pro Gly Thr Asn Glu Cys Leu Asp Asn Leu Gly Gly Cys Ser His Val
        35                  40                  45

Cys Arg Asp Leu Glu Ile Gly Tyr Glu Cys Leu Cys Pro Glu Gly Phe
50                  55                  60

Gln Leu Val Ala Gln Arg Arg Cys Glu
65                  70
```

<210> SEQ ID NO 223
<211> LENGTH: 74
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 223

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Gln Ala Pro Gly Gln
            20                  25                  30

Ala Pro Gly Thr Asn Glu Cys Leu Asp Asn Leu Gly Gly Cys Ser His
        35                  40                  45

Val Cys Arg Asp Leu Glu Ile Gly Tyr Glu Cys Leu Cys Pro Glu Gly
    50                  55                  60

Phe Gln Leu Val Ala Gln Arg Arg Cys Glu
65                  70
```

<210> SEQ ID NO 224
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 224

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Gly Gln Ala Pro Gly
            20                  25                  30

Gln Ala Pro Gly Thr Asn Glu Cys Leu Asp Asn Leu Gly Gly Cys Ser
        35                  40                  45

His Val Cys Arg Asp Leu Glu Ile Gly Tyr Glu Cys Leu Cys Pro Glu
    50                  55                  60

Gly Phe Gln Leu Val Ala Gln Arg Arg Cys Glu
65                  70                  75
```

<210> SEQ ID NO 225
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 225

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Gln Ala Pro
            20                  25                  30

Gly Gln Ala Pro Gly Thr Asn Glu Cys Leu Asp Asn Leu Gly Gly Cys
        35                  40                  45

Ser His Val Cys Arg Asp Leu Glu Ile Gly Tyr Glu Cys Leu Cys Pro
    50                  55                  60

Glu Gly Phe Gln Leu Val Ala Gln Arg Arg Cys Glu
65                  70                  75

<210> SEQ ID NO 226
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 226

His Xaa Glu Gly Thr Lys Thr Ser Asp Val Ser Ser Tyr Leu Glu Gly
1               5                   10                  15

Gln Ala Ala Arg Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 227
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 227

His Xaa Glu Gly Thr Phe Thr Ser Asp Val Ser Ser Tyr Leu Lys Gly
1               5                   10                  15

Gln Ala Ala Arg Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

```
<210> SEQ ID NO 228
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 228

His Xaa Glu Gly Thr Phe Thr Ser Asp Val Ser Ser Tyr Leu Glu Gly
1               5                   10                  15

Gln Lys Ala Arg Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 229
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 229

His Xaa Glu Gly Thr Phe Thr Ser Asp Val Ser Ser Tyr Leu Glu Gly
1               5                   10                  15

Gln Ala Lys Arg Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 230
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 230

His Xaa Glu Gly Thr Phe Thr Ser Asp Val Ser Ser Tyr Leu Glu Gly
1               5                   10                  15

Gln Ala Ala Arg Lys Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45
```

```
Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
 65                  70                  75
```

<210> SEQ ID NO 231
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 231

```
His Xaa Glu Gly Thr Phe Thr Ser Asp Val Ser Ser Tyr Leu Glu Gly
 1               5                  10                  15

Gln Ala Ala Arg Glu Phe Ile Ala Lys Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
 65                  70                  75
```

<210> SEQ ID NO 232
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 232

```
His Xaa Glu Gly Thr Phe Thr Ser Asp Val Ser Ser Tyr Leu Glu Gly
 1               5                  10                  15

Gln Ala Ala Arg Glu Phe Ile Ala Trp Lys Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
 65                  70                  75
```

<210> SEQ ID NO 233
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 233

```
His Xaa Glu Gly Thr Phe Thr Ser Asp Val Ser Ser Tyr Leu Gly Gly
1               5                   10                  15

Gln Ala Ala Arg Glu Phe Ile Ala Trp Leu Val Arg Gly Lys Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75
```

<210> SEQ ID NO 234
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 234

```
His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80
```

<210> SEQ ID NO 235
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 235

```
His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65                  70                  75
```

<210> SEQ ID NO 236
<211> LENGTH: 79
<212> TYPE: PRT
<213> ORGANISM: Artificial Sequence
<220> FEATURE:

```
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 236

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 237
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 237

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 238
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 238

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
```

```
                65                  70                  75

<210> SEQ ID NO 239
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 239

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 240
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 240

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 241
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 241

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30
```

```
Lys Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 242
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 242

```
His Xaa Glu Gly Thr Phe Thr Ser Asp Val Ser Ser Tyr Leu Gly Gly
 1               5                  10                  15

Gln Ala Ala Lys Glu Phe Ile Ala Trp Leu Val Arg Gly Arg Gly Gly
        20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 243
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 243

```
His Xaa Glu Gly Thr Phe Thr Ser Asp Val Ser Ser Tyr Leu Gly Gly
 1               5                  10                  15

Gln Ala Ala Lys Glu Phe Ile Ala Trp Leu Val Arg Gly Arg Gly Gly
        20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 244
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 244

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 245
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 245

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 246
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 246

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 247
<211> LENGTH: 79

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 247

His Xaa Glu Gly Thr Phe Thr Ser Asp Val Ser Ser Tyr Leu Gly Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 248
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 248

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 249
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 249

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
```

Leu Cys Pro Lys Gly Phe Gln Leu Val Ala Gln Arg Arg Cys Glu
65                  70                  75

<210> SEQ ID NO 250
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 250

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 251
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 251

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Lys Gly Tyr Glu Cys
        50                  55                  60

Leu Cys Pro Glu Gly Phe Gln Leu Val Ala Gln Arg Arg Cys Glu
65                  70                  75

<210> SEQ ID NO 252
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 252

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Lys Leu Val Ala Gln Arg Arg Cys Glu
65                  70                  75

<210> SEQ ID NO 253
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 253

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Lys Arg Arg Cys Glu
65                  70                  75

<210> SEQ ID NO 254
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 254

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 255
<211> LENGTH: 79
<212> TYPE: PRT
<213> ORGANISM: Artificial Sequence
<220> FEATURE:
<223> OTHER INFORMATION: Synthetic
<220> FEATURE:

```
<221> NAME/KEY: MOD_RES
<222> LOCATION: (2)..(2)
<223> OTHER INFORMATION: Aib

<400> SEQUENCE: 255
```

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Lys Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

```
<210> SEQ ID NO 256
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 256
```

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Lys Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

```
<210> SEQ ID NO 257
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 257
```

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Lys Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 258
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 258

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 259
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 259

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 260
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 260

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu 35                  40                  45

Gly Gly Cys Ser His Val Cys Arg Asp Leu Glu Ile Gly Tyr Glu Cys
         50                  55                  60

Leu Cys Pro Glu Gly Phe Gln Leu Val Ala Gln Arg Arg Cys Glu
65                  70                  75

<210> SEQ ID NO 261
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 261

His Xaa Glu Gly Thr Phe Thr Ser Asp Val Ser Ser Tyr Leu Glu Gly
1               5                   10                  15

Gly Ala Ala Lys Glu Phe Ile Ala Trp Leu Val Arg Gly Arg Gly Gly
                20                  25                  30

Gln Ala Pro Gly Gln Ala Lys Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 262
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 262

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu Lys
65                  70                  75                  80

<210> SEQ ID NO 263
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 263

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65              70                  75

<210> SEQ ID NO 264
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 264

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65              70                  75

<210> SEQ ID NO 265
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 265

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65              70                  75

<210> SEQ ID NO 266
<211> LENGTH: 79
<212> TYPE: PRT
<213> ORGANISM: Artificial Sequence

```
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 266

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
65                  70                  75

<210> SEQ ID NO 267
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 267

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 268
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 268

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60
```

Leu Cys Pro Glu Gly Phe Gln Leu Val Ala Gln Arg Arg Cys Glu
65                  70                  75

<210> SEQ ID NO 269
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 269

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Lys Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 270
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 270

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 271
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 271

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly

```
                    20                  25                  30
Gln Ala Lys Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 272
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 272

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 273
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 273

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 274
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
```

<223> OTHER INFORMATION: Aib

<400> SEQUENCE: 274

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 275
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 275

His Xaa Glu Gly Thr Phe Thr Ser Asp Val Ser Ser Tyr Leu Glu Gly
1               5                   10                  15

Gln Gly Ala Lys Glu Phe Ile Ala Trp Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 276
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 276

His Xaa Glu Gly Thr Phe Thr Ser Asp Val Ser Ser Tyr Leu Glu Gly
1               5                   10                  15

Gln Val Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 277

```
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 277

His Xaa Glu Gly Thr Phe Thr Ser Asp Val Ser Ser Tyr Leu Glu Gly
 1               5                  10                  15

Gln Ala Gly Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 278
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 278

His Xaa Glu Gly Thr Phe Thr Ser Asp Val Ser Ser Tyr Leu Glu Gly
 1               5                  10                  15

Gln Ala Gly Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65                  70                  75

<210> SEQ ID NO 279
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 279

His Xaa Glu Gly Thr Phe Thr Ser Asp Val Ser Ser Tyr Leu Glu Gly
 1               5                  10                  15

Gln Ala Gly Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45
```

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
65                  70                  75

<210> SEQ ID NO 280
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 280

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 281
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 281

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
65                  70                  75

<210> SEQ ID NO 282
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 282

His Xaa Glu Gly Thr Phe Thr Ser Asp Val Ser Ser Tyr Leu Glu Gly

-continued

```
                1               5                   10                  15
Gln Ala Gly Lys Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Lys Arg Arg Cys Glu
65                  70                  75

<210> SEQ ID NO 283
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 283

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Lys
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 284
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 284

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
                20                  25                  30

Lys Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 285
<211> LENGTH: 79
<212> TYPE: PRT
<213> ORGANISM: Artificial Sequence
<220> FEATURE:
<223> OTHER INFORMATION: Synthetic
```

```
<220> FEATURE:
<221> NAME/KEY: MOD_RES
<222> LOCATION: (2)..(2)
<223> OTHER INFORMATION: Aib

<400> SEQUENCE: 285

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 286
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 286

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 287
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 287

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75
```

<210> SEQ ID NO 288
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 288

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 289
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 289

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 290
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 290

His Xaa Glu Gly Thr Phe Thr Ser Asp Val Ser Ser Tyr Leu Glu Gly
1               5                   10                  15

Gln Ala Gly Lys Glu Phe Ile Ala Trp Leu Val Arg Gly Arg Gly Gly
            20                  25                  30

Gln Ala Pro Gly Gln Ala Lys Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75

<210> SEQ ID NO 291
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 291

His Xaa Glu Gly Thr Phe Thr Ser Asp Val Ser Ser Tyr Leu Glu Gly
 1               5                  10                  15

Gln Ala Val Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75

<210> SEQ ID NO 292
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 292

His Xaa Glu Gly Thr Phe Thr Ser Asp Val Ser Ser Tyr Leu Glu Gly
 1               5                  10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu Lys
 65                  70                  75                  80

<210> SEQ ID NO 293
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 293

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Lys Gly Phe Gln Leu Val Ala Gln Arg Arg Cys Glu
65                  70                  75

<210> SEQ ID NO 294
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 294

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 295
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 295

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
50                  55                  60

Leu Cys Pro Glu Gly Phe Gln Leu Val Ala Gln Arg Arg Cys Glu
65                  70                  75

<210> SEQ ID NO 296
<211> LENGTH: 79
<212> TYPE: PRT

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 296

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
65                  70                  75

<210> SEQ ID NO 297
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 297

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 298
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 298

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60
```

Leu Cys Pro Glu Gly Phe Gln Leu Val Ala Gln Arg Arg Cys Glu
65                  70                  75

<210> SEQ ID NO 299
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 299

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
                20                  25                  30

Lys Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 300
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 300

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
                20                  25                  30

Gln Lys Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 301
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 301

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 302
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 302

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 303
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 303

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 304
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (2)..(2)
<223> OTHER INFORMATION: Aib

<400> SEQUENCE: 304
```

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

```
<210> SEQ ID NO 305
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 305
```

His Xaa Glu Gly Thr Phe Thr Ser Asp Val Ser Ser Tyr Leu Glu Gly
1               5                   10                  15

Gln Ala Ala Lys Gly Phe Ile Ala Trp Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

```
<210> SEQ ID NO 306
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 306
```

His Xaa Glu Gly Thr Phe Thr Ser Asp Val Ser Ser Tyr Leu Glu Gly
1               5                   10                  15

Gln Ala Ala Lys Glu Phe Ala Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

```
<210> SEQ ID NO 307
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 307

His Xaa Glu Gly Thr Phe Thr Ser Asp Val Ser Ser Tyr Leu Glu Gly
1               5                   10                  15

Gln Ala Ala Lys Glu Phe Val Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 308
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 308

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 309
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 309

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45
```

Gly Gly Cys Ser His Val Cys Arg Asp Leu Glu Ile Gly Tyr Glu Cys
            50                  55                  60

Leu Cys Pro Lys Gly Phe Gln Leu Val Ala Gln Arg Arg Cys Glu
65                  70                  75

<210> SEQ ID NO 310
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 310

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 311
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 311

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 312
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 312

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
65                  70                  75

<210> SEQ ID NO 313
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 313

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 314
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 314

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 315
<211> LENGTH: 79
<212> TYPE: PRT
<213> ORGANISM: Artificial Sequence
<220> FEATURE:

```
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 315

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Lys Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 316
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 316

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 317
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 317

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
```

65     70     75

<210> SEQ ID NO 318
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 318

His Xaa Glu Gly Thr Phe Thr Ser Asp Val Ser Ser Tyr Leu Glu Gly
1     5     10     15

Gln Ala Ala Lys Glu Phe Ile Gly Trp Leu Val Arg Gly Arg Gly Gly
    20     25     30

Gln Ala Pro Lys Gln Ala Pro Gly Thr Asn Glu Cys Leu Asp Asn Leu
  35     40     45

Gly Gly Cys Ser His Val Cys Arg Asp Leu Glu Ile Gly Tyr Glu Cys
50     55     60

Leu Cys Pro Glu Gly Phe Gln Leu Val Ala Gln Arg Arg Cys Glu
65     70     75

<210> SEQ ID NO 319
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 319

His Xaa Glu Gly Thr Phe Thr Ser Asp Val Ser Ser Tyr Leu Glu Gly
1     5     10     15

Gln Ala Ala Lys Glu Phe Ile Gly Trp Leu Val Arg Gly Arg Gly Gly
    20     25     30

Gln Ala Pro Gly Lys Ala Pro Gly Thr Asn Glu Cys Leu Asp Asn Leu
  35     40     45

Gly Gly Cys Ser His Val Cys Arg Asp Leu Glu Ile Gly Tyr Glu Cys
50     55     60

Leu Cys Pro Glu Gly Phe Gln Leu Val Ala Gln Arg Arg Cys Glu
65     70     75

<210> SEQ ID NO 320
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 320

His Xaa Glu Gly Thr Phe Thr Ser Asp Val Ser Ser Tyr Leu Glu Gly
1     5     10     15

Gln Ala Ala Lys Glu Phe Ile Gly Trp Leu Val Arg Gly Arg Gly Gly
    20     25     30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 321
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 321

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 322
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 322

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 323
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 323

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65                  70                  75

<210> SEQ ID NO 324
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 324

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 325
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 325

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 326
<211> LENGTH: 79

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 326

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Lys Leu Val Ala Gln Arg Arg Cys Glu
65                  70                  75

<210> SEQ ID NO 327
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 327

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 328
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 328

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
```

```
                    50                  55                  60

Leu Cys Pro Glu Gly Phe Gln Leu Val Ala Gln Arg Arg Cys Glu
 65                  70                  75
```

<210> SEQ ID NO 329
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 329

```
His Xaa Glu Gly Thr Phe Thr Ser Asp Val Ser Ser Tyr Leu Glu Gly
 1               5                  10                  15

Gln Ala Ala Lys Glu Phe Ile Ala Gly Leu Val Arg Gly Arg Gly Gly
                20                  25                  30

Lys Ala Pro Gly Gln Ala Pro Gly Thr Asn Glu Cys Leu Asp Asn Leu
             35                  40                  45

Gly Gly Cys Ser His Val Cys Arg Asp Leu Glu Ile Gly Tyr Glu Cys
         50                  55                  60

Leu Cys Pro Glu Gly Phe Gln Leu Val Ala Gln Arg Arg Cys Glu
 65                  70                  75
```

<210> SEQ ID NO 330
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 330

```
His Xaa Glu Gly Thr Phe Thr Ser Asp Val Ser Ser Tyr Leu Glu Gly
 1               5                  10                  15

Gln Ala Ala Lys Glu Phe Ile Ala Gly Leu Val Arg Gly Arg Gly Gly
                20                  25                  30

Gln Lys Pro Gly Gln Ala Pro Gly Thr Asn Glu Cys Leu Asp Asn Leu
             35                  40                  45

Gly Gly Cys Ser His Val Cys Arg Asp Leu Glu Ile Gly Tyr Glu Cys
         50                  55                  60

Leu Cys Pro Glu Gly Phe Gln Leu Val Ala Gln Arg Arg Cys Glu
 65                  70                  75
```

<210> SEQ ID NO 331
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 331

```
His Xaa Glu Gly Thr Phe Thr Ser Asp Val Ser Ser Tyr Leu Glu Gly
 1               5                  10                  15
```

```
Gln Ala Ala Lys Glu Phe Ile Ala Gly Leu Val Arg Gly Arg Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
65                  70                  75

<210> SEQ ID NO 332
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 332

His Xaa Glu Gly Thr Phe Thr Ser Asp Val Ser Ser Tyr Leu Glu Gly
1               5                  10                  15

Gln Ala Ala Lys Glu Phe Ile Ala Gly Leu Val Arg Gly Arg Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
65                  70                  75

<210> SEQ ID NO 333
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 333

His Xaa Glu Gly Thr Phe Thr Ser Asp Val Ser Ser Tyr Leu Glu Gly
1               5                  10                  15

Gln Ala Ala Lys Glu Phe Ile Ala Gly Leu Val Arg Gly Arg Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
65                  70                  75

<210> SEQ ID NO 334
<211> LENGTH: 79
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (2)..(2)
<223> OTHER INFORMATION: Aib

<400> SEQUENCE: 334

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 335
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 335

His Xaa Glu Gly Thr Phe Thr Ser Asp Val Ser Ser Tyr Leu Glu Gly
1               5                   10                  15

Gln Ala Ala Lys Glu Phe Ile Ala Gly Leu Val Arg Gly Arg Gly Gly
            20                  25                  30

Gln Ala Pro Gly Gln Ala Lys Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75

<210> SEQ ID NO 336
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 336

His Xaa Glu Gly Thr Phe Thr Ser Asp Val Ser Ser Tyr Leu Glu Gly
1               5                   10                  15

Gln Ala Ala Lys Glu Phe Ile Ala Trp Ala Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
50                  55                  60

Leu Cys Pro Glu Gly Phe Gln Leu Val Ala Gln Arg Arg Cys Glu
65                  70                  75
```

<210> SEQ ID NO 337
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 337

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 338
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 338

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65                  70                  75

<210> SEQ ID NO 339
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 339

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Pro Gly Gln Ala Pro Gly Thr Asn Glu Cys Leu Asp Asn Leu

```
                35                  40                  45
Gly Gly Cys Ser His Val Cys Arg Asp Leu Glu Ile Gly Tyr Glu Cys
         50                  55                  60

Leu Cys Pro Glu Gly Phe Gln Leu Val Ala Gln Arg Arg Cys Glu
 65                  70                  75
```

<210> SEQ ID NO 340
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 340

```
His Xaa Glu Gly Thr Phe Thr Ser Asp Val Ser Ser Tyr Leu Glu Gly
 1               5                  10                  15

Gln Ala Ala Lys Glu Phe Ile Ala Trp Gly Val Arg Gly Arg Gly Gly
             20                  25                  30

Gln Ala Pro Gly Gln Ala Pro Gly Thr Asn Glu Cys Leu Asp Asn Leu
         35                  40                  45

Gly Gly Cys Ser His Val Cys Arg Asp Leu Glu Lys Gly Tyr Glu Cys
     50                  55                  60

Leu Cys Pro Glu Gly Phe Gln Leu Val Ala Gln Arg Arg Cys Glu
 65                  70                  75
```

<210> SEQ ID NO 341
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 341

```
His Xaa Glu Gly Thr Phe Thr Ser Asp Val Ser Ser Tyr Leu Glu Gly
 1               5                  10                  15

Gln Ala Ala Lys Glu Phe Ile Ala Trp Gly Val Arg Gly Arg Gly Gly
             20                  25                  30

Gln Ala Pro Gly Gln Ala Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Glu Gly Phe Lys Leu Val Ala Gln Arg Arg Cys Glu
 65                  70                  75
```

<210> SEQ ID NO 342
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 342

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 343
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 343

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 344
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 344

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Lys Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 345
<211> LENGTH: 79
<212> TYPE: PRT
<213> ORGANISM: Artificial Sequence

```
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 345

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Lys Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 346
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 346

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Lys Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 347
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 347

His Xaa Glu Gly Thr Phe Thr Ser Asp Val Ser Ser Tyr Leu Glu Gly
1               5                   10                  15

Gln Ala Ala Lys Glu Phe Ile Ala Trp Gly Val Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60
```

```
Leu Cys Pro Glu Gly Phe Gln Leu Val Ala Gln Arg Arg Cys Glu
 65                  70                  75
```

<210> SEQ ID NO 348
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 348

```
His Xaa Glu Gly Thr Phe Thr Ser Asp Val Ser Ser Tyr Leu Glu Gly
  1               5                  10                  15

Gln Ala Ala Lys Glu Phe Ile Ala Trp Gly Val Arg Gly Arg Gly Gly
             20                  25                  30

Gln Ala Pro Gly Lys Ala Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Glu Gly Phe Gln Leu Val Ala Gln Arg Arg Cys Glu
 65                  70                  75
```

<210> SEQ ID NO 349
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 349

```
His Xaa Glu Gly Thr Phe Thr Ser Asp Val Ser Ser Tyr Leu Glu Gly
  1               5                  10                  15

Gln Ala Ala Lys Glu Phe Ile Ala Trp Gly Val Arg Gly Arg Gly Gly
             20                  25                  30

Gln Ala Pro Gly Gln Lys Pro Gly Thr Asn Glu Cys Leu Asp Asn Leu
         35                  40                  45

Gly Gly Cys Ser His Val Cys Arg Asp Leu Glu Ile Gly Tyr Glu Cys
     50                  55                  60

Leu Cys Pro Glu Gly Phe Gln Leu Val Ala Gln Arg Arg Cys Glu
 65                  70                  75
```

<210> SEQ ID NO 350
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 350

```
His Xaa Glu Gly Thr Phe Thr Ser Asp Val Ser Ser Tyr Leu Glu Gly
  1               5                  10                  15

Gln Ala Ala Lys Glu Phe Ile Ala Trp Gly Val Arg Gly Arg Gly Gly
```

20                  25                  30

Gln Ala Pro Gly Gln Ala Lys Gly Thr Asn Glu Cys Leu Asp Asn Leu
                35                  40                  45

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
65                  70                  75

<210> SEQ ID NO 351
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 351

His Xaa Glu Gly Thr Phe Thr Ser Asp Val Ser Ser Tyr Leu Glu Gly
1               5                   10                  15

Gln Ala Ala Lys Glu Phe Ile Ala Trp Ile Val Arg Gly Arg Gly Gly
                20                  25                  30

Gln Ala Pro Gly Gln Ala Pro Gly Thr Asn Glu Cys Leu Asp Asn Leu
                35                  40                  45

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
65                  70                  75

<210> SEQ ID NO 352
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 352

His Xaa Glu Gly Thr Phe Thr Ser Asp Val Ser Ser Tyr Leu Glu Gly
1               5                   10                  15

Gln Ala Ala Lys Glu Phe Ile Ala Trp Thr Val Arg Gly Arg Gly Gly
                20                  25                  30

Gln Ala Pro Gly Gln Ala Pro Gly Thr Asn Glu Cys Leu Asp Asn Leu
                35                  40                  45

Gly Gly Cys Ser His Val Cys Arg Asp Leu Glu Ile Gly Tyr Glu Cys
            50                  55                  60

Leu Cys Pro Glu Gly Phe Gln Leu Val Ala Gln Arg Arg Cys Glu
65                  70                  75

<210> SEQ ID NO 353
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)

-continued

<223> OTHER INFORMATION: Aib

<400> SEQUENCE: 353

His Xaa Glu Gly Thr Phe Thr Ser Asp Val Ser Ser Tyr Leu Glu Gly
1               5                   10                  15

Gln Ala Ala Lys Glu Phe Ile Ala Trp Val Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 354
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 354

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu Lys
65                  70                  75                  80

<210> SEQ ID NO 355
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 355

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Lys Gly Phe Gln Leu Val Ala Gln Arg Arg Cys Glu
65                  70                  75

<210> SEQ ID NO 356

```
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 356

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 357
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 357

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Lys Gly Tyr Glu Cys
    50                  55                  60

Leu Cys Pro Glu Gly Phe Gln Leu Val Ala Gln Arg Arg Cys Glu
65                  70                  75

<210> SEQ ID NO 358
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 358

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45
```

Gly Gly Cys Ser His Val Cys Arg Asp Leu Glu Ile Gly Tyr Glu Cys
            50                  55                  60

Leu Cys Pro Glu Gly Phe Lys Leu Val Ala Gln Arg Arg Cys Glu
65                  70                  75

<210> SEQ ID NO 359
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 359

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Lys Arg Arg Cys Glu
65                  70                  75

<210> SEQ ID NO 360
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 360

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Lys
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 361
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 361

His Xaa Glu Gly Thr Phe Thr Ser Asp Val Ser Ser Tyr Leu Glu Gly

```
                1               5                  10                  15
Gln Ala Ala Lys Glu Phe Ile Ala Trp Leu Gly Arg Gly Arg Gly Gly
            20                  25                  30
Lys Ala Pro Gly Gln Ala Pro Gly Thr Asn Glu Cys Leu Asp Asn Leu
        35                  40                  45
Gly Gly Cys Ser His Val Cys Arg Asp Leu Glu Ile Gly Tyr Glu Cys
    50                  55                  60
Leu Cys Pro Glu Gly Phe Gln Leu Val Ala Gln Arg Arg Cys Glu
65                  70                  75

<210> SEQ ID NO 362
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 362

His Xaa Glu Gly Thr Phe Thr Ser Asp Val Ser Ser Tyr Leu Glu Gly
1               5                   10                  15
Gln Ala Ala Lys Glu Phe Ile Ala Trp Leu Gly Arg Gly Arg Gly Gly
            20                  25                  30
Gln Lys Pro Gly Gln Ala Pro Gly Thr Asn Glu Cys Leu Asp Asn Leu
        35                  40                  45
Gly Gly Cys Ser His Val Cys Arg Asp Leu Glu Ile Gly Tyr Glu Cys
    50                  55                  60
Leu Cys Pro Glu Gly Phe Gln Leu Val Ala Gln Arg Arg Cys Glu
65                  70                  75

<210> SEQ ID NO 363
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 363

His Xaa Glu Gly Thr Phe Thr Ser Asp Val Ser Ser Tyr Leu Glu Gly
1               5                   10                  15
Gln Ala Ala Lys Glu Phe Ile Ala Trp Leu Gly Arg Gly Arg Gly Gly
            20                  25                  30
Gln Ala Lys Gly Gln Ala Pro Gly Thr Asn Glu Cys Leu Asp Asn Leu
        35                  40                  45
Gly Gly Cys Ser His Val Cys Arg Asp Leu Glu Ile Gly Tyr Glu Cys
    50                  55                  60
Leu Cys Pro Glu Gly Phe Gln Leu Val Ala Gln Arg Arg Cys Glu
65                  70                  75

<210> SEQ ID NO 364
<211> LENGTH: 79
<212> TYPE: PRT
<213> ORGANISM: Artificial Sequence
<220> FEATURE:
<223> OTHER INFORMATION: Synthetic
```

```
<220> FEATURE:
<221> NAME/KEY: MOD_RES
<222> LOCATION: (2)..(2)
<223> OTHER INFORMATION: Aib

<400> SEQUENCE: 364

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Lys Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 365
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 365

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Lys Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 366
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 366

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
            20                  25                  30

Gln Ala Pro Gly Gln Lys Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75
```

<210> SEQ ID NO 367
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 367

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Gly Arg Gly Arg Gly Gly
                20                  25                  30

Gln Ala Pro Gly Gln Ala Lys Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 368
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 368

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Ile Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 369
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 369

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Leu Arg Gly Arg Gly Gly
                20                  25                  30

```
Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 370
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 370

```
His Xaa Glu Gly Thr Phe Thr Ser Asp Val Ser Ser Tyr Leu Lys Gly
 1               5                  10                  15

Gln Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 371
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 371

```
His Xaa Glu Gly Thr Phe Thr Ser Asp Val Ser Ser Tyr Leu Glu Gly
 1               5                  10                  15

Lys Ala Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
 50                  55                  60

Leu Cys Pro Glu Gly Phe Gln Leu Val Ala Gln Arg Arg Cys Glu
 65                  70                  75
```

<210> SEQ ID NO 372
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 372

His Xaa Glu Gly Thr Phe Thr Ser Asp Val Ser Ser Tyr Leu Glu Gly
1               5                   10                  15

Gln Lys Ala Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 373
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 373

His Xaa Glu Gly Thr Phe Thr Ser Asp Val Ser Ser Tyr Leu Glu Gly
1               5                   10                  15

Gln Ala Lys Lys Glu Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 374
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 374

His Xaa Glu Gly Thr Phe Thr Ser Asp Val Ser Ser Tyr Leu Glu Gly
1               5                   10                  15

Gln Ala Ala Lys Lys Phe Ile Ala Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 375
<211> LENGTH: 79
<212> TYPE: PRT

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 375

His Xaa Glu Gly Thr Phe Thr Ser Asp Val Ser Ser Tyr Leu Glu Gly
1               5                   10                  15

Gln Ala Ala Lys Glu Phe Ile Lys Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 376
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 376

His Xaa Glu Gly Thr Phe Thr Ser Asp Val Ser Ser Tyr Leu Glu Gly
1               5                   10                  15

Gln Ala Ala Lys Glu Phe Ile Ala Lys Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 377
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 377

His Xaa Glu Gly Thr Phe Thr Ser Asp Val Ser Ser Tyr Leu Glu Gly
1               5                   10                  15

Gln Ala Ala Lys Glu Phe Ile Ala Trp Lys Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60
```

```
Leu Cys Pro Glu Gly Phe Gln Leu Val Ala Gln Arg Arg Cys Glu
65                  70                  75
```

<210> SEQ ID NO 378
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 378

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Lys Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75
```

<210> SEQ ID NO 379
<211> LENGTH: 80
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 379

```
His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu Lys
65                  70                  75                  80
```

<210> SEQ ID NO 380
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 380

```
His Xaa Glu Gly Thr Phe Thr Ser Asp Val Ser Ser Tyr Leu Glu Gly
1               5                   10                  15
```

Gln Ala Ala Arg Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Lys Gly Tyr Glu Cys
        50                  55                  60

Leu Cys Pro Lys Gly Phe Gln Leu Val Ala Gln Arg Arg Cys Glu
65                  70                  75

<210> SEQ ID NO 381
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 381

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Gly
                20                  25                  30

Lys Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 382
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 382

His Xaa Glu Gly Thr Phe Thr Ser Asp Val Ser Ser Tyr Leu Glu Gly
1               5                   10                  15

Lys Ala Ala Arg Glu Phe Ile Ala Trp Leu Val Arg Gly Arg Gly Gly
                20                  25                  30

Gln Ala Pro Gly Gln Ala Pro Gly Thr Asn Glu Cys Leu Asp Asn Leu
            35                  40                  45

Gly Gly Cys Ser His Val Cys Arg Asp Leu Glu Ile Gly Tyr Glu Cys
        50                  55                  60

Leu Cys Pro Glu Gly Phe Gln Leu Val Ala Gln Arg Arg Cys Glu
65                  70                  75

<210> SEQ ID NO 383
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (2)..(2)
<223> OTHER INFORMATION: Aib

<400> SEQUENCE: 383

His Xaa Glu Gly Thr Phe Thr Ser Asp Val Ser Ser Tyr Leu Glu Gly
1               5                   10                  15

Gln Ala Ala Arg Glu Phe Ile Lys Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 384
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 384

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Lys Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Glu Gly Phe Gln Leu Val Ala Gln Arg Arg Cys Glu
65                  70                  75

<210> SEQ ID NO 385
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: GTNECLDNLGGCSHVCRDLEIGYECLCPEGFQLVAQRRCEGQAPGQAPHXEGTFTS
        DVSSYLEGQAAKEFIAWLVKGRG
<222> LOCATION: (50)..(50)
<223> OTHER INFORMATION: Aib
<220> FEATURE:
<221> NAME/KEY: MOD_RES
<222> LOCATION: (50)..(50)
<223> OTHER INFORMATION: Aib

<400> SEQUENCE: 385

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Gln Ala Pro Gly Gln Ala Pro
        35                  40                  45

His Xaa Glu Gly Thr Phe Thr Ser Asp Val Ser Ser Tyr Leu Glu Gly
    50                  55                  60
```

Gln Ala Ala Lys Glu Phe Ile Ala Trp Leu Val Lys Gly Arg Gly
65                  70                  75

<210> SEQ ID NO 386
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (50)..(50)
<223> OTHER INFORMATION: Aib

<400> SEQUENCE: 386

Gly Thr Asn Glu Cys Leu Asp Asn Leu Gly Gly Cys Ser His Val Cys
1               5                   10                  15

Arg Asp Leu Glu Ile Gly Tyr Glu Cys Leu Cys Pro Glu Gly Phe Gln
            20                  25                  30

Leu Val Ala Gln Arg Arg Cys Glu Gly Gln Ala Pro Gly Gln Ala Pro
        35                  40                  45

His Xaa Glu Gly Thr Phe Thr Ser Asp Val Ser Ser Tyr Leu Glu Gly
    50                  55                  60

Gln Ala Ala Lys Glu Phe Ile Ala Trp Leu Val Arg Gly Arg Gly
65                  70                  75

<210> SEQ ID NO 387
<211> LENGTH: 79
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)

<400> SEQUENCE: 387

His Xaa Glu Gly Thr Phe Thr Ser Asp Val Ser Ser Tyr Leu Glu Gly
1               5                   10                  15

Gln Ala Ala Lys Glu Phe Ile Gly Trp Leu Val Arg Gly Arg Gly Gly
            20                  25                  30

Gln Ala Pro Gly Gln Ala Pro Gly Thr Asn Glu Cys Leu Asp Asn Leu
        35                  40                  45

Gly Gly Cys Ser His Val Cys Arg Asp Leu Glu Ile Gly Tyr Glu Cys
    50                  55                  60

Leu Cys Pro Asp Gly Phe Gln Leu Val Ala Gln Arg Arg Cys Glu
65                  70                  75

<210> SEQ ID NO 388
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (2)..(2)
<223> OTHER INFORMATION: Aib

<400> SEQUENCE: 388

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Gly
            20                  25                  30

Gln Ala Pro Gly Gln Ala Pro Gly Gln Ala Pro Gly Gln Ala Pro Gly
        35                  40                  45

Gln Ala Pro Gly Gln Ala Pro Gly Gln Ala Pro Gly Gln Ala Pro Gly
    50                  55                  60

Gln Ala Pro Gly Gln Ala Pro Gly Thr Asn Glu Cys Leu Asp Asn Leu
65                  70                  75                  80

Gly Gly Cys Ser His Val Cys Arg Asp Leu Glu Ile Gly Tyr Glu Cys
                85                  90                  95

Leu Cys Pro Asp Gly Phe Gln Leu Val Ala Gln Arg Arg Cys Glu
            100                 105                 110
```

BIFUNCTIONAL COMPOUNDS

CROSS-REFERENCE TO RELATED APPLICATIONS

This application is a 35 U.S.C. § 371 National Stage application of International Application PCT/EP2018/069610 (WO 2019/016306), filed Jul. 19, 2018, which claims priority to European Patent Application 17182010.3, filed Jul. 19, 2017.

TECHNICAL FIELD OF THE INVENTION

The present invention relates to bi-functional compounds which inhibits PCSK9 and stimulates the GLP-1 receptor and their pharmaceutical use.

BACKGROUND

High LDL-C(Low Density Lipoprotein cholesterol) levels and dyslipidaemia are well-recognised drivers of cardiovascular disease.

Statins have been approved for the treatment of dyslipidemia for 25 years. This class has demonstrated substantial and consistent reduction of cardiovascular events with an acceptable safety profile. The best-selling statin, atorvastatin (LIPITOR™) was the world's best-selling drug of all time, with more than $125 billion in sales from 1996 to 2012.

Despite the availability and widespread use of statins and other lipid lowering agents, many patients do not reach their target LDL-C levels and remain at high risk for developing cardiovascular disease. PCSK9 (Proprotein Convertase Subtilisin/Kexin type 9) promotes hepatic LDL-R (LDL receptor) degradation, thereby reducing hepatic LDL-R surface expression and consequently clearance of LDL particles. Conversely, blocking PCSK9 increase the clearance of LDL-C as well as other atherogenic lipoproteins. Indeed, LDL receptors contribute to the clearance of atherogenic lipoproteins other than LDL, such as intermediate-density lipoproteins and remnant particles. Increased intermediate-density lipoproteins and remnant particle clearance may have therapeutic benefits beyond that provided by LDL reduction.

Statins increase the expression of both LDL-R and PCSK9 via the SREBP2 transcription factor. The increased expression of PCSK9 may diminish the effect of statins on LDL-C clearance from the circulation. By inhibiting the binding of PCSK9 to the LDL-R and thereby preventing LDL-R degradation the efficacy of statins is enhanced. Taken together, PCSK9 inhibition offers a novel approach to lipid management.

The EGF(A) (Epidermal Growth Factor-like domain A) sequence (40 amino acids) of the LDL-R (LDL-R-(293-332)) is well recognized as the site for PCSK9 binding. The isolated wild-type EGF(A) peptide has been shown to inhibit the binding of PCSK9 to the LDL-R with an $IC_{50}$ in the low μM range (Biochemical and Biophysical Research Communications 375 (2008) 69-73). This poor potency will prevent a practical pharmaceutical use of the EGF(A) peptide. Furthermore, the half-life of such peptides would be expected to be too short to be of therapeutic use.

WO2012177741 and J. Mol. Biol. (2012) 422, 685-696 disclose analogues of the EGF(A) and Fc-Fusion thereof.

Two anti-PCSK9 antibodies, alirocumab/PRALUENT® and evolocumab/REPATHA®, have recently been approved for the treatment of high LDL-C levels. These are administered by 1 ml subcutaneous injections every two weeks.

In WO 2015/127273 the fusion of an anti-PCSK9 antibody and a GLP-1 agonist is explored seeking to combine the functionalities of GLP-1 and the anti-PCSK9 antibody.

Multiple treatments are available for treatment of diabetes and cardiovascular diseases, but combination of multiple individual drugs are not always attractive and a single molecule addressing both disease states would be desirable to improve treatment, such as efficacy, compliance and convenience.

SUMMARY

The present invention relates to EGF(A) analogues with the ability to inhibit PCSK9 binding to LDL-R and thereby reducing LDL cholesterol. Such molecules may be combined with GLP-1 receptor agonists forming bi-functional molecules providing further treatment options, addressing both diabetes and cardiovascular diseases by one drug. The invention in an aspect relates to a compound comprising a GLP-1 agonist and a PCSK9 inhibitor.

An aspect of the invention relates to a compound comprising a GLP-1 analogue and an EGF(A) analogue, wherein
  i. said GLP-1 analogue is an analogue of GLP-1(7-37) identified by SEQ ID No: 137 and
  ii. said EGF(A) analogue is an analogue of the EGF(A) domain of LDL-R (293-332) identified by SEQ ID No:1.

Such compounds may in an embodiment comprise a fusion polypeptide comprising the two analogues optionally linked by a spacer peptide inserted between the two analogues. The compounds may further comprise a half-life extending moiety, which may be referred to as a substituent attached to an amino acid residue of one of the GLP-1 analogue, the EGF(A) analogue or the spacer. In one embodiment the compound comprise one or two substituents attached to different amino acid residues of the fusion polypeptide.

In further aspects the invention relates to a pharmaceutical composition comprising a compound of the invention as well as medical use of compounds of the invention.

DESCRIPTION

The present invention relates to bi-functional compounds stimulating the GLP-1 receptor and inhibiting PCSK9. In order to prepare compounds of pharmaceutical relevance modification to the wild-type peptides is required both in order to improve functionality and to enable convenient administration.

An aspect of the invention relates to compound comprising a GLP-1 receptor agonist and a PCSK9 inhibitor. Several GLP-1 receptor agonists are known in the art and may be combined with various PCSK9 inhibitors. As described herein the GLP-1 receptor agonist may be analogues of human GLP-1(7-37) (SEQ ID No: 137) or such as Extendin 4 and analogues hereof also known to function as a GLP-1 receptor agonist.

PCSK9 inhibitors are known in the form of antibodies, while the present application is primarily concerned with PCSK9 inhibitors in the form of analogues of the EGF(A) domain of LDL-R (293-332) (SEQ ID NO: 1).

An aspect of the invention relates to a compound comprising a GLP-1 analogue and an EGF(A) analogue, wherein said GLP-1 analogue is an analogue of GLP-1(7-37) (SEQ ID No: 137) and said EGF(A) analogue is an analogue of the EGF(A) domain of LDL-R (293-332) (SEQ ID NO: 1).

The term "compound" is used herein to refer to a molecular entity, and "compounds" may thus have different structural elements besides the minimum element defined for each compound or group of compounds. It follows that a compound may be a polypeptide or a derivative thereof, as long as the compound comprises the defined structural and/or functional elements.

The term "compound" is also meant to cover pharmaceutically relevant forms hereof, i.e. the invention relates to a compound as defined herein or a pharmaceutically acceptable salt, amide, or ester thereof.

The term "peptide" or "polypeptide", as e.g. used in the context of the invention, refers to a compound which comprises a series of amino acids interconnected by amide (or peptide) bonds. In a particular embodiment the peptide consists of amino acids interconnected by peptide bonds.

The terms "fusion" and "fused" are used in relation to polypeptides comprising two individually defined peptide sequences which are connected by a peptide bond or by a peptide spacer (also connected by peptide bonds). A fusion polypeptide is thus a continuous stretch of amino acid residues connected by peptide bonds.

The term "analogue" generally refers to a peptide, the sequence of which has one or more amino acid changes when compared to a reference amino acid sequence. Analogues "comprising" certain specified changes may comprise further changes, when compared to their reference sequence. In particular embodiments, an analogue "has" or "comprises" specified changes. In other particular embodiments, an analogue "consists of" the changes. When the term "consists" or "consisting" is used in relation to an analogue e.g. an analogue consists or consisting of a group of specified amino acid substitutions, it should be understood that the specified amino acid substitutions are the only amino acid substitutions in the analogue. In contrast an analogue "comprising" a group of specified amino acid substitutions may have additional substitutions. An "analogue" may also include amino acid elongations in the N-terminal and/or C-terminal positions and/or truncations in the N-terminal and/or C-terminal positions.

In general amino acid residues may be identified by their full name, their one-letter code, and/or their three-letter code. These three ways are fully equivalent.

Amino acids are molecules containing an amino group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid, or 2-aminoisobutyric acid), norleucine, norvaline as well as the D-isomers of the proteinogenic amino acids.

In what follows, each amino acid of the peptides of the invention for which the optical isomer is not stated is to be understood to mean the L-isomer (unless otherwise specified).

GLP-1 Analogue

The present invention relates to compounds comprising a glucagon-like peptide 1 (GLP-1) analogue. The term "GLP-1 analogue" as used herein refers to an analogue (or variant) of the human glucagon-like peptide-1 (GLP-1(7-37)), the sequence of which is included in the sequence listing as SEQ ID NO: 137. The peptide having the sequence of SEQ ID NO: 137 may also be designated "native" or wild-type GLP-1.

The numbering of amino acid residues (such as "position 8") in the GLP-1 analogues of the invention follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue. In native GLP-1 the C-terminal amino acid residue is Gly, with number 37.

The numbering is done differently in the sequence listing, where the first amino acid residue of SEQ ID NO: 137 (His) is assigned no. 1, and the last (Gly) no. 31. However, herein we follow the established numbering practice in the art, as explained above.

GLP-1 analogues are known in the art and several GLP-1 analogues are supplied to the market for treatment of type 2 diabetes and obesity. GLP-1 analogues are, as described above, variants of the wt human GLP-1 sequence and thus comprise one or more amino acid substitution, deletion and/or addition compared to SEQ ID NO. 137.

Each of the GLP-1 analogues may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 137).

These changes may represent, independently, one or more amino acid substitutions, additions, and/or deletions.

The following is a non-limiting example of suitable analogue nomenclature. The GLP-1 analogue incorporated as GLP-1 analogue #2 (SEQ ID NO: 139) and included in compound #1, may be referred to as (8Aib, 34R)GLP-1(7-37).

When this analogue is aligned with native GLP-1, the amino acid at the position in the analogue which corresponds, according to the alignment, to position 8 in native GLP-1 is Aib and the amino acid at the position in the analogue which corresponds to position 34 in native GLP-1 is R, while all other amino acids in this analogue are identical to the corresponding amino acid in native GLP-1.

Analogues "comprising" certain specified changes may comprise further changes, when compared to wt GLP-1 (SEQ ID NO: 137). In contrast the term "consisting" is used to refer to particular embodiment, where the analogue only has the specified changes i.e. there are no further changes in the GLP-1 analogue when compared to wt GLP-1 (SEQ ID NO: 137). By refereeing back to the example above the GLP-1 analogue #2 (SEQ ID NO: 139) may be said to be a GLP-1 analogue wherein the substitutions consist of 8Aib and 34R, or for short at GLP-1 analogue consisting of 8Aib and 34R.

The expressions "a position equivalent to" or "corresponding position" is used herein to characterise the site of change in a variant GLP-1(7-37) sequence by reference to a reference sequence such as native GLP-1(7-37) (SEQ ID NO: 137). Equivalent or corresponding positions, as well as the number of changes, are easily deduced, e.g. by simple handwriting and visual inspection; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below of native GLP-1 of SEQ ID NO: 137 and the analogue thereof identified by SEQ ID NO: 139:

```
#========================================
# Aligned_sequences: 2
# 1: SEQ_ID_NO_137
# 2: SEQ_ID_NO_139
# Matrix: EBLOSUM62
# Gap_penalty: 10.0
# Extend_penalty: 0.5

# Length: 31
# Identity:        29/31 (93.5%)
# Similarity:      30/31 (96.8%)
# Gaps:             0/31 ( 0.0%)
# Score: 154.0
#========================================

SEQ_ID_NO_137   1 HAEGTFTSDVSSYLEGQAAKEFIAWLVKGRG 31
                  |.||||||||||||||||||||||||||.|||
SEQ_ID_NO_139   1 HXEGTFTSDVSSYLEGQAAKEFIAWLVRGRG 31
```

When 6 is added to the position numbers shown in this alignment (e.g. to "1" and "31" in SEQ ID NO 137) one gets the position numbering as used herein. For example, in wt GLP-1 (which is identical to SEQ ID NO: 137), the N-terminal amino acid (H) has position number 7, and the C-terminal amino acid (G) has number 37. Regarding GLP-1 analogue #2 (SEQ ID NO 139), the N-terminal amino acid (H) has number 7 and the C-terminal amino acid (G) has number 37 as for wt GLP-1 while residues 2 and 28 are substituted and numbered 8 and 34 respectively.

In case specific amino acid residues or the like with no one-letter codon (such as 2-Amino-2-methylpropanoic acid (Aib) are included in the sequence these may, for alignment purposes, be replaced with, e.g., X. If desired, X can later be manually corrected.

The following are non-limiting examples of what can be inferred from the above alignment:

As an example it can be inferred that sequence 2 has 2 amino acid changes as compared to sequence 1 (namely at all those positions where a full stop ("."), a colon (":"), or a horizontal hyphen ("-") is shown in the alignment).

In what follows, all amino acids of the GLP-1 analogue of the invention for which the optical isomer is not stated is to be understood to mean the L-isomer (unless otherwise specified).

In one embodiment the GLP-1 analogue of the invention is an analogue of GLP-1(7-37) consisting of 26 to 36 amino acid residues.

In one embodiment GLP-1 analogue has at most 10 amino acid substitutions compared to human GLP-1(7-37). In further embodiments GLP-1 analogue has at most 8, such as at most 7, 6, 5, 4, 3 or 2 amino acid substitutions compared to human GLP-1(7-37.)

A wealth of GLP-1 analogues has previously been described as well as their function as GLP-1 receptor agonists.

The wt GLP-1 peptide of SEQ ID NO: 137 comprise two Lys residues in positions 26 and 34. As seen herein below the Lys residues are particular relevant when compounds comprising a substituent attached via Lys residues are to be prepared.

In one embodiment the GLP-1 analogue according to the invention comprises zero, one or two Lys residues. In one embodiment the GLP-1 analogue comprises one or two Lys residues which are selected from the wt Lys residues and Lys residues introduced to the GLP-1 analogue by amino acid substitution. A Lys residue introduced by amino acid substitution may be referred to as an additional Lys residue. In one embodiment the GLP-1 analogue comprises an additional Lys residue. An additional Lys may be introduced in various positions in the GLP-1 analogue, such as in one or more positions selected from position 12, 21, 23, 24, 25, 27, 30, 31, 32, 33 and 36K. In one embodiment the GLP-1 analogue comprises an additional Lys selected from the group of: 12K, 21K, 23K, 24K, 25K, 27K, 30K, 31K, 32K, 33K and 36K.

In one embodiment the GLP-1 analogue comprises one or two Lys residue selected from the group consisting of: 12K, 21K, 23K, 24K, 25K, 26K, 27K, 30K, 31K, 32K, 33K, 34K and 36K.

In one embodiment the GLP-1 analogue comprises one or two Lys residue selected from the group consisting of: 21K, 23K, 24K, 25K, 26K, 27K, 30K, 31K, 32K, 33K and 34K.

In one embodiment the GLP-1 analogue comprises exactly two Lys residue selected from the group consisting of: 12K, 21K, 23K, 24K, 25K, 26K, 27K, 30K, 31K, 32K, 33K, 34K and 36K.

In one embodiment the GLP-1 analogue comprises exactly two Lys residue selected from the group consisting of: 21K, 23K, 24K, 25K, 26K, 27K, 30K, 31K, 32K, 33K and 34K.

In one embodiment the GLP-1 analogue comprises exactly two Lys residues selected from the pairs of:
a) 21K and 26K
b) 23K and 26K
c) 24K and 26K
d) 25K and 26K
e) 27K and 26K
f) 30K and 26K
g) 31K and 26K
h) 32K and 26K
i) 33K and 26K
j) 34K and 26K In one embodiment the GLP-1 analogue comprises the Lys residues 26K and 34K.

In one embodiment the GLP-1 analogue comprises exactly one Lys residue selected from: 12K, 21K, 23K, 24K, 25K, 26K, 27K, 30K, 31K, 32K, 33K, 34K and 36K.

In one embodiment the GLP-1 analogue comprises exactly one Lys residue selected from: 21K, 23K, 24K, 25K, 26K, 27K, 30K, 31K, 32K, 33K and 34K.

In one embodiment the GLP-1 analogue comprises exactly one Lys residue selected from: 21K, 23K, 24K, 25K, 26K 27K 30K.

In one embodiment the GLP-1 analogue comprises exactly one Lys residue which is 26K.

In one embodiment the GLP-1 analogue comprises a substitution or deletion of one or both of 26K and 34K. In one embodiment the GLP-1 analogue does not comprise 26K. In one embodiment the GLP-1 analogue comprises a deletion of 26K. In one embodiment the GLP-1 analogue comprises an amino acid substitution of 26K. In one embodiment the GLP-1 analogue comprises 26R.

In one embodiment the GLP-1 analogue does not comprise 34K. In one embodiment the GLP-1 analogue comprises a deletion of 34K. In one embodiment the GLP-1 analogue comprises an amino acid substitution of 34K. In one embodiment the GLP-1 analogue comprises 34R or 34Q.

As mentioned above the GLP-1 analogue according to the invention is similar in length to wt GLP-1. In one embodiment the GLP-1 analogue comprises at least 26, such as at least 28 or at least 30 amino acid residues. In one embodiment the GLP-1 analogue comprises at least 31, such as at least 32 or at least 33 amino acid residues In one embodiment the GLP-1 analogue has a deletion of 1-5 amino acids at the C-terminal. In one embodiment the GLP-1 analogue comprises a deletion of AA 35-37, AA 34-37 or AA 33-37.

In one embodiment the GLP-1 analogue comprises 33 L.

As mentioned above the GLP-1 analogue may comprise one or more amino acid substitutions compared to wt GLP-1, such as at most 5 amino acid substitutions, such as at most 4 amino acid substitutions, such as at most 3 amino acid substitutions.

In one embodiment the GLP-1 analogue has at least 75% identity, such as 80%, such as 85, such as 90 or even 95% identity to SEQ ID NO.:127 corresponding to up to 7, 6, 4, 3 and 1 amino acid substitutions relative to SEQ ID NO 1, respectively in case of no truncation.

In addition or in alternative to an additional Lys residues introduced by amino acid substitution the GLP-1 analogue may comprise one or more amino acid substitution, substituting a wt residue with a different amino acid residue.

In one embodiment the GLP-1 analogue comprises an amino acid substitution of 8A, such as a substitution of 8A to 8G or 8W, which may also be referred to as A8G and A8W.

In one embodiment the GLP-1 analogue comprises an amino acid substitution of 8A, such as a substitution of 8A to a non-proteogenic amino acid residue, such as Aib.

In one embodiment the GLP-1 analogue comprises an amino acid substitution of 8A to G, W or the non-proteogenic amino acid residue Aib.

In one embodiment the GLP-1 analogue comprises one or more amino acid substitutions selected from amino acid substitutions in position 8, 12, 21, 23, 24, 25, 26, 27, 29, 30, 31, 32, 33, 34 and 36.

In one embodiment the GLP-1 analogue comprises one or more amino acid substitutions selected from amino acid substitutions in position 8, 21, 23, 24, 25, 26, 27, 29, 30, 31, 32, 33 and 34.

In one embodiment the GLP-1 analogue comprises one or more amino acid substitutions selected from amino acid substitutions in position 8, 21, 23, 24, 25, 27, 29, 30, 31, 32 or 33. In one embodiment the wt amino acid residue in position 8, 21, 23, 24, 25, 27, 29, 30, 31, 32 or 33 is substituted by a G, V, A, T, L or I residues.

In one embodiment the GLP-1 analogue comprises substitutions of 8A and 34K.

In one embodiment the GLP-1 analogue comprises 8Aib and 34R. In one embodiment the GLP-1 analogue comprises 8Aib and 34R and a substitution in a position selected from the positions 21, 23, 24, 25, 27, 29, 30, 31, 32 and 33.

In one embodiment the GLP-1 analogue comprises 8Aib and 34R. In one embodiment the GLP-1 analogue comprises 8Aib and 34R and a substitution in a position selected from the positions 21, 23, 24, 25, 27, 29, 30, 31, 32 and 33, wherein the substitution in position 21, 23, 24, 25, 27, 29, 30, 31, 32 or 33 is a G, V, A, T, L or I residue.

In one embodiment the GLP-1 analogue comprises one or two Lys residues and a group of substitutions selected from:

| |
|---|
| a) 8Aib, 21G |
| b) 8Aib, 23G |
| c) 8Aib, 24G |
| d) 8Aib, 24V |
| e) 8Aib, 25G |
| f) 8Aib, 25V |
| g) 8Aib, 27G |
| h) 8Aib, 29A, |
| i) 8Aib, 29V |
| j) 8Aib, 30G |
| k) 8Aib, 31G |
| l) 8Aib, 32A |
| m) 8Aib, 32G |
| n) 8Aib, 32I |
| o) 8Aib, 32T |
| p) 8Aib, 32V |
| q) 8Aib, 33G |
| r) 8Aib, 33I and |
| s) 8Aib, 33L |
| t) 8Aib |

In one embodiment the GLP-1 analogue comprises one or two Lys residues and a group of substitutions selected from;

| |
|---|
| a) 8Aib, 21G |
| b) 8Aib, 23G |
| c) 8Aib, 24G |
| d) 8Aib, 24V |
| e) 8Aib, 25G |
| f) 8Aib, 25V |
| g) 8Aib, 27G |
| h) 8Aib, 29V |
| i) 8Aib, 30G |
| j) 8Aib, 31G |
| k) 8Aib, 32A |
| l) 8Aib, 32I |
| m) 8Aib, 32T |
| n) 8Aib, 32V |
| o) 8Aib, 33G |
| p) 8Aib, 33I and |
| q) 8Aib, 33L |
| r) 8Aib |

In one embodiment, such GLP-1 analogue comprises one or two Lys residues as described herein above, such as 26K and/or 34K, or such as 26K and/or a Lys introduced by substitution together with K34R.

In one embodiment, the GLP-1 analogue has the sequence defined by SEQ ID NO 187:H-$X_8$-E-G-T-$X_{12}$-T-S-D-V-S-S-Y-L-$X_{21}$-G-$X_{23}$-$X_{24}$-$X_{25}$-$X_{26}$-$X_{27}$-F-$X_{29}$-$X_{30}$-$X_{31}$-$X_{32}$-$X_{33}$-$X_{34}$-$X_{35}$-$X_{36}$-$X_{37}$ wherein $X_8$ is A, G, W or Aib,
$X_{12}$ F or K
$X_{21}$ is E, G or K
$X_{23}$ is Q, G or K
$X_{24}$ is A, G, V or K
$X_{25}$ is A, G, V or K
$X_{26}$ is K or R
$X_{27}$ is E, G or K
$X_{29}$ is I, A or V
$X_{30}$ is A, G or K
$X_{31}$ is W, G or K
$X_{32}$ is L, G, T, V, I or K
$X_{33}$ is V, G, I, L, K or absent
$X_{34}$ is K, R, Q or absent $X_{35}$ is G or absent $X_{36}$ is R, K or absent $X_{37}$ is G or is absent.

In one embodiment, the GLP-1 analogue has the sequence defined by SEQ ID NO 187:H-$X_8$-E-G-T-$X_{12}$-T-S-D-V-S-S-Y-L-$X_{21}$-G-$X_{23}$-$X_{24}$-$X_{25}$-$X_{26}$-$X_{27}$-F-$X_{29}$-$X_{30}$-$X_{31}$-$X_{32}$-$X_{33}$-$X_{34}$-$X_{35}$-$X_{36}$-$X_{37}$ wherein $X_8$ is A, G, W or Aib, $X_{12}$ F or K $X_{21}$ is E, G or K $X_{23}$ is Q, G or K $X_{24}$ is A, G, V or K $X_{25}$ is A, G, V or K $X_{26}$ is K or R $X_{27}$ is E, G or K $X_{29}$ is I or V $X_{30}$ is A, G or K $X_{31}$ is W, G or K $X_{32}$ is L, G, T, V, I or K $X_{33}$ is V, G, I, L, K or absent $X_{34}$ is K, R, Q or absent $X_{35}$ is G or absent $X_{36}$ is R, K or absent $X_{37}$ is G or is absent.

In one embodiment, the GLP-1 analogue has the sequence defined by SEQ ID NO 187:H-$X_8$-E-G-T-$X_{12}$-T-S-D-V-S-S-Y-L-$X_{21}$-G-$X_{23}$-$X_{24}$-$X_{25}$-$X_{26}$-$X_{27}$-F-$X_{29}$-$X_{30}$-$X_{31}$-$X_{32}$-$X_{33}$-$X_{34}$-$X_{35}$-$X_{36}$-$X_{37}$ wherein $X_8$ is A, G, W or Aib, $X_{12}$ F or K $X_{21}$ is E, G or K $X_{23}$ is Q, G or K $X_{24}$ is A, G, V or K $X_{25}$ is A, G, V or K $X_{26}$ is K or R $X_{27}$ is E, G or K $X_{29}$ is I, A or V $X_{30}$ is A, G or K $X_{31}$ is W, G or K $X_{32}$ is L, T, V, I or K $X_{33}$ is V, G, I, L, K or absent $X_{34}$ is K, R, Q or absent $X_{35}$ is G or absent $X_{36}$ is R, K or absent $X_{37}$ is G or is absent.

In one embodiment, the GLP-1 analogue has the sequence defined by SEQ ID NO 187:H-$X_8$-E-G-T-$X_{12}$-T-S-D-V-S-S-Y-L-$X_{21}$-G-$X_{23}$-$X_{24}$-$X_{25}$-$X_{26}$-$X_{27}$-F-$X_{29}$-$X_{30}$-$X_{31}$-$X_{32}$-$X_{33}$-$X_{34}$-$X_{35}$-$X_{36}$-$X_{37}$ wherein $X_8$ is A, G, W or Aib, $X_{12}$ F or K $X_{21}$ is E, G or K $X_{23}$ is Q, G or K $X_{24}$ is A, G, V or K $X_{25}$ is A, G, V or K $X_{26}$ is K or R $X_{27}$ is E, G or K $X_{29}$ is T or V $X_{30}$ is A, G or K $X_{31}$ is W, G or K $X_{32}$ is L, V, I or K $X_{33}$ is V, G, I, L, K or absent $X_{34}$ is K, R, Q or absent $X_{35}$ is G or absent $X_{36}$ is R, K or absent $X_{37}$ is G or is absent.

As seen, the Examples herein comprise more than 40 GLP-1 analogues which are also envisioned in the context of a compound comprising both a GLP-1 analogue and a EGF(A) analogue. These analogues are identified in the table below, wherein the amino acid changes compared to wt residues (as described herein above) are shown together with the Lys residue(s) present in the analogue.

| GLP-1 analogue # | GLP-1 analogues | Lys residues | SEQ ID |
|---|---|---|---|
|  | Wt | 26K, 34K | 137 |
| 1 | 8Aib | 26K, 34K | 138 |
| 2 | 8Aib, 34R | 26K | 139 |
| 3 | 8G, 34R | 26K | 140 |
| 4 | 8W, 34R | 26K | 141 |
| 5 | 8Aib, 34Q | 26K | 142 |
| 6 | 8Aib, des(32-37) | 26K | 143 |
| 7 | 8Aib, des(33-37) | 26K | 144 |
| 8 | 8Aib, des(34-37) | 26K | 145 |
| 9 | 8Aib, 34R, des(35-37) | 26K | 146 |
| 10 | 8Aib, 12K, 26R, 34R | 12K | 147 |
| 11 | 8Aib, 21K, 26R, 34R | 21K | 148 |
| 12 | 8Aib, 24K, 26R, 34R | 24K | 149 |
| 13 | 8Aib, 25K, 26R, 34R | 25K | 150 |
| 14 | 8Aib, 26R, 27K, 34R | 27K | 151 |
| 15 | 8Aib, 26R, 31K, 34R | 31K | 152 |
| 16 | 8Aib, 26R, 32K, 34R | 32K | 153 |
| 17 | 8Aib, 26R, 34R, 36K | 36K | 154 |
| 18 | 8Aib, 21G, 34R | 26K | 155 |
| 19 | 8Aib, 23G, 34R | 26K | 156 |
| 20 | 8Aib, 24G, 34R | 26K | 157 |
| 21 | 8Aib, 24V, 34R | 26K | 158 |
| 22 | 8Aib, 25G, 34R | 26K | 159 |
| 23 | 8Aib, 25V, 34R | 26K | 160 |
| 24 | 8Aib, 27G, 34R | 26K | 161 |
| 25 | 8Aib, 29A, 34R | 26K | 162 |
| 26 | 8Aib, 29V, 34R | 26K | 163 |
| 27 | 8Aib, 30G, 34R | 26K | 164 |
| 28 | 8Aib, 31G, 34R | 26K | 165 |
| 29 | 8Aib, 32A, 34R | 26K | 166 |
| 30 | 8Aib, 32G, 34R | 26K | 167 |
| 31 | 8Aib, 32I, 34R | 26K | 168 |
| 32 | 8Aib, 32T, 34R | 26K | 169 |
| 33 | 8Aib, 32V, 34R | 26K | 170 |
| 34 | 8Aib, 33G, 34R | 26K | 171 |
| 35 | 8Aib, 33I, 34R | 26K | 172 |
| 36 | 8Aib, 33L, 34R | 26K | 173 |
| 37 | 8Aib, 21K, 34R | 21K, 26K | 174 |
| 38 | 8Aib, 23K, 34R | 23K, 26K | 175 |
| 39 | 8Aib, 24K, 34R | 24K, 26K | 176 |
| 40 | 8Aib, 25K, 34R | 25K, 26K | 177 |
| 41 | 8Aib, 27K, 34R | 27K, 26K | 178 |
| 42 | 8Aib, 30K, 34R | 30K, 26K | 179 |
| 43 | 8Aib, 31K, 34R | 31K, 26K | 180 |
| 44 | 8Aib, 32K, 34R | 32K, 26K | 181 |
| 45 | 8Aib, 33K, 34R | 33K, 26K | 182 |
| 46 | 8Aib, 26R | — | 183 |
| 47 | 8Aib, 23K, 26R, 34R | 23K | 184 |
| 48 | 8Aib, 26R, 30K, 34R | 30K | 185 |
| 49 | 8Aib, 26R, 33K, 34R | 33K | 186 |
| 50 | H-X8-E-G-T-X12-T-S-D-V-S-S-Y-L-X21-G-X23-X24-X25-X26-X27-F-X29-X30-X31-X32-X33-X34-X35-X36-X37 | — | 187 |

In one embodiment the GLP-1 analogue comprises or consists of an analogue selected from the group of analogues defined by SEQ ID NO.: 138-186.

In one embodiment the GLP-1 analogue comprises or consists of an analogue selected from the group of analogues defined by SEQ ID NO.: 138-142 and 144-186.

In one embodiment the GLP-1 analogue comprises or consists of an analogue selected from the group of analogues defined by SEQ ID NO.: 138-142 and 144-166, 168, 169-186.

In one embodiment the GLP-1 analogue comprises or consists of an analogue selected from the group of analogues defined by SEQ ID NO.: 138-142 and 144-161, 163-166, 168, 169-186.

In one embodiment the GLP-1 analogue comprises or consists of an analogue selected from the group of analogues defined by SEQ ID NO.: 138-142 and 145-161, 163-166, 168, 169-186.

In one embodiment the GLP-1 analogue comprises or consists of an analogue selected from the group of analogues defined by SEQ ID NO.: 139 and 147-154.

In one embodiment the GLP-1 analogue comprises or consists of an analogue selected from the group of analogues defined by SEQ ID NO.: 138 and 174-182 and 184-186.

In one embodiment the GLP-1 analogue comprises or consists of an analogue selected from the group of analogues defined by SEQ ID NO.: 166-170.

In one embodiment the GLP-1 analogue comprises or consists of an analogue selected from the group of analogues defined by SEQ ID NO.: 163-166.

In one embodiment the GLP-1 analogue comprises or consists of an analogue defined by SEQ ID NO.: 164.

EGF(A) Analogue

The term "EGF(A) analogue" herein refers to a variant of the EGF(A) domain of LDL-R (293-332) (SEQ ID NO: 1). A similar nomenclature is applied to the EGF(A) analogues as was described for GLP-1 analogues herein above.

The terms "EGF(A) domain of the LDL-R", "LDL-R (293-332)", "native LDL-R (293-332), "EGF(A) (293-332)", "wild-type EGF(A)", "wt-EGF(A)" or "native EGF(A)" as used herein refer to a peptide consisting of the sequence SEQ ID NO: 1.

```
SEQ ID NO: 1 is:
Gly-Thr-Asn-Glu-Cys-Leu-Asp-Asn-Asn-Gly-Gly-Cys-

Ser-His-Val-Cys-Asn-Asp-Leu-Lys-Ile-Gly-Tyr-Glu-

Cys-Leu-Cys-Pro-Asp-Gly-Phe-Gln-Leu-Val-Ala-Gln-

Arg-Arg-Cys-Glu.
```

In this application the numbering of the amino acid residues follows the numbering for the EGF(A) domain of the LDL-R (LDL-R-(293-332)), wherein the first (N-terminal) amino acid residue is numbered or accorded position no. 293, and the subsequent amino acid residues towards the C-terminus are numbered 294, 295, 296 and so on, until the last (C-terminal) amino acid residue, which in the EGF(A) domain of the LDL-R is Glu with number 332.

The numbering is done differently in the sequence listing, where the first amino acid residue of SEQ ID NO: 1 (Gly) is assigned no. 1, and the last (Glu) no. 40. The same applies for the other sequences of the sequence listing, i.e. the N-terminal amino acid assigned is no. 1 irrespective of its positioning relative to 293Gly or 293 substituting amino acid residue by reference to LDL-R(293-332). However, herein the numbering of amino acid positions is with reference to LDL-R(293-332), as explained above.

The level of identity to SEQ ID NO.:1 can be calculated by determining the number of amino acids that are not changed relative to SEQ ID NO 1. SEQ ID NO: 1 consists of 40 amino acid residues and if three amino acid substitutions are introduced the level of identity is 37/40%=92.5%. If 5 amino acid residues are changed the level of identity is 87.5%. If the peptide is N-terminal or C-terminal elongated that part is usually not included in the comparison, whereas a deletion of one or more amino acids shortens the comparator. For instance, in the examples above, if the N-terminal amino acid is deleted the level of identity is slightly reduced to 36/39×100% and 34/39×100%, respectively. When discussing identity of the back-bone sequences of a derivative the amino acid residue of the substituent e.g. the residue to which the substituent is attached, also termed the amino acid residue of the substituent may be either a wild type (wt) or a substituted amino acid. If the amino acid residue of the substituent is a wild type residue, such as 312K this residue is included in the calculation of identity level, whereas a Lys in any other position from 293 to 332 would be an amino acid substitution and not included when calculated amino acid identity to SEQ ID NO.:1.

Each of the EGF(A) analogues of the invention may be described by reference to i) the number of the amino acid residue in the native EGF(A) (LDL-R(293-332)) which corresponds to the amino acid residue which is changed (i.e., the corresponding position in native LDL-R(293-332) EGF (A)), and to ii) the actual change.

In other words, the EGF(A) analogues may be described by reference to the native LDL-R(293-332) EGF(A) peptide, namely as a variant thereof in which a number of amino acid residues have been changed when compared to native LDL-R(293-332) EGF(A) (SEQ ID NO: 1). These changes may represent, independently, one or more amino acid substitutions.

The followings are non-limiting examples of suitable analogue nomenclature:

The EGF(A) analogue incorporated in example compound #1 of the derivatives comprising a GLP-1 analogue and an EGF(A) analogue herein, may be referred to as the following LDL-R(293-332) EGF(A) analogue: (301Leu, 309Arg, 312Glu, 321Glu) LDL-R(293-332) EGF(A), or (Leu301, Arg309, Glu312, Glu321)-LDL-R(293-332) EGF (A) or (301L,309R,312E,321E) LDL-R(293-332) or (L301, R309,E312,E321) LDL-R(293-332). This means that when this analogue is aligned with native LDL-R(293-332), it has i) a Leu at the position in the analogue which corresponds, according to the alignment, to position 301 in native LDL-R(293-332) EGF(A), ii) an Arg at the position in the analogue which corresponds to position 309 in native LDL-R(293-332) EGF(A), iii) a Glu at the position in the analogue which corresponds to position 312 in native LDL-R (293-332) EGF(A), iv) a Glu at the position in the analogue which corresponds to position 321 in native LDL-R(293-332) EGF(A).

The expressions "a position equivalent to" or "corresponding position" may be used to characterise the site of change in a variant LDL-R(293-332) EGF(A) sequence by reference to the reference sequence native LDL-R(293-332) EGF(A) (SEQ ID NO: 1).

Equivalent or corresponding positions, as well as the number of changes, are easily deduced, e.g. by simple calculation and/or a standard protein or peptide alignment program may be used, such as "align" which is based on a Needleman-Wunsch algorithm.

In one embodiment the EGF(A) analogue has 1-15 amino acid substitutions compared to SEQ ID NO.: 1. In one embodiments the EGF(A) analogue has 1-10 amino acid substitutions compared to SEQ ID NO.: 1. In one embodiments the EGF(A) analogue has 1-8 amino acid substitutions compared to SEQ ID NO.: 1, such as 1-7, 1-6, 1-5 amino acid substitutions compared to SEQ ID NO.: 1. In a particular embodiment, up to 7 amino acid substitutions may be present, for example up to 6, 5, 4, 3, 2 or 1 amino acid substitutions may be present in the EGF(A) analogue.

In one embodiment the EGF(A) analogue has at least 75% identity, such as 80%, such as 85, such as 90 or even 95% identity to SEQ ID NO.:1. In one embodiment wherein there is no deletion/truncation, this corresponds to up to 10, 8, 6, 4 and 2 amino acid substitutions relative to SEQ ID NO 1, respectively.

In one embodiment the EGF(A) analogue has at least 90% identity, such as 92%, such as 94, such as 96 or even 98% identity to SEQ ID NO.:1

In one embodiment the EGF(A) analogue comprises at least 35, such as 36, 37, 38, 39 or at least 40 amino acids. In a particular embodiment the EGF(A) analogue is composed of 36, such as 38 or 40 amino acids. In an additional particular embodiment the EGF(A) analogue consists of 35, 36, 37, 38, 39 or 40 amino acids.

In the presence of amino acid additions, referred to herein as N-terminal and C-terminal elongations, the EGF(A) analogue may comprise up to 60 amino acids. In a particular embodiment the EGF(A) analogue comprises 35-60, 38-55, 40-50, 40-45, 40-42 or 40-41 amino acids. In an embodiment, the EGF(A) analogue consists of 40 or 41 amino acid residues.

In one embodiment the EGF(A) analogue comprises the amino acid substitution of amino acid residue 301 from Asn to Leu, also described by Asn301Leu or simply 301Leu. In a specific embodiment, the EGF(A) analogue comprises the substitution 301Leu.

In addition or alternatively the EGF(A) analogue comprises the amino acid residues 297Cys, 304Cys, 308Cys, 317Cys, 319Cys and 331Cys. Those Cys residues are wild type residues which may be engaged in disulphide bridges, such as the disulphide bridges between 297Cys and 308Cys, between 304Cys and 317Cys and between 319Cys and 331Cys.

In one embodiment, the EGF(A) analogue comprises 301Leu and a number of further amino acid substitutions, as described below.

In one embodiment the EGF(A) analogue comprises 301Leu, 310Asp and an amino acid substitution of 312Lys.

In one embodiment, the EGF(A) analogue comprises 301Leu and 310Asp and wherein the analogue does not have a substitution of 299Asp to Glu, Val or His.

In one embodiment the EGF(A) analogue comprises 301Leu, 309Arg and 312Glu. In one embodiment the EGF(A) analogue comprises 301Leu, 309Arg, 312Glu and 321Glu.

In one embodiment the EGF(A) analogue comprises 301Leu and 309Arg with a proviso that the analogue does not have a substitution of 310Asp to 310Lys or In one embodiment the EGF(A) analogue comprises 301Leu and 309Arg with a proviso that the analogue does not have a substitution of 299Asp to Glu, Val or His.

In a further embodiment the EGF(A) analogue does not have any of the substitutions D310K, D310N, D310Q, D310Q, D310R and D310A or even any substitution of 310Asp.

In one embodiment the EGF(A) analogue comprises one, two, three or all four wild type residues: 295Asn, 296Glu, 298Leu and 302Gly.

In one embodiment the EGF(A) analogue comprises one, two, three, four or all five wild type residues: 295Asn, 296Glu, 298Leu, 302Gly and 310Asp.

In one embodiment the peptide has 295Asn.

In one embodiment the EGF(A) analogue has 296Glu. In one embodiment the EGF(A) analogue has 298Leu. In one embodiment the EGF(A) analogue has 302Gly. In one embodiment the EGF(A) analogue has 310Asp.

In one embodiment the EGF(A) analogue has two or more of 310Asp, 295Asn and 296Glu. In one embodiment the EGF(A) analogue has all three of 310Asp, 295Asn and 296Glu.

The EGF(A) analogue may comprise further amino acid substitutions as described herein. In one embodiment the analogue may further comprise one or more amino acid substitution in a position(s) selected from the group of positions: 293, 294, 296, 299, 300, 303, 305, 306, 309, 311, 312, 313, 314, 315, 316, 318, 320, 321, 322, 323, 324, 325, 326, 328, 329, 330 and 332.

In one embodiment the analogue may further comprise one or more amino acid substitution(s) in a position(s) selected from the group of positions: 293, 294, 299, 300, 303, 305, 306, 309, 311, 312, 313, 314, 316, 318, 321, 322, 323, 324, 325, 326, 328, 329, 330, 331 and 332.

In one embodiment the analogue may further comprise one or more amino acid substitution(s) in a position(s) selected from the 294, 299, 300, 303, 309, 312, 313, 314, 316, 318, 321, 322, 323, 324, 325, 326, 328, 329, 330 and 332.

In one embodiment the analogue may further comprise one or more amino acid substitution(s) in a position(s) selected from the 299, 300, 309, 313, 316, 318, 321, 322, 323, 324, 326, 328, 329, 330 and 332.

In one embodiment the analogue may further comprise one or further amino acid substitution(s) in a position(s) selected from the group of positions: 309, 312, 313, 321, 324, 328 and 332.

In a further embodiment the EGF(A) analogue comprise either the wt amino acid residue or a different residue i.e. an amino acid substitution, in certain specific positions in addition to the amino acid residues specified herein above.

In one such embodiment the EGF(A) analogue comprises the amino acid residue Gly(G) or Asn(N) in position 293.

In one such embodiment the EGF(A) analogue comprises the amino acid residue Trp (W), Thr(T) or Gly(G) in position 294.

In one such embodiment the EGF(A) analogue comprises the amino acid residue Asp(D), Gly(G), Pro(P), Arg(R), Lys(K), Ser(S), Thr(T), Asn(N), Gln(Q), Ala(A), Ile(I), Leu(L), Met(M), Phe(F), Tyr(Y) or Trp(W) in position 299.

In one such embodiment the EGF(A) analogue comprises the amino acid residue Asp(D), Gly(G), Pro (P), Arg(R), Lys(K), Ser(S), Thr(T), Asn(N), Gln(Q), Ala(A), Met(M), Phe(F), Tyr(Y) or Trp(W) in position 299.

In one such embodiment the EGF(A) analogue comprises the amino acid residue Asp(D), Ser (S), Arg(R), Leu (L), Ala (A), Lys(K) or Tyr(Y) in position 299.

In one such embodiment the EGF(A) analogue comprises the amino acid residue Asp(D) or Ala(A) in position 299.

In one such embodiment the EGF(A) analogue comprises the amino acid residue His(H) or Asn(N) in position 300.

In one such embodiment the EGF(A) analogue comprises the amino acid residue Val(V), Ser(S), Thr (T) or Ile (I) in position 307.

In one such embodiment the EGF(A) analogue comprises the amino acid residue Val(V) or Ile (I) in position 307.

In one such embodiment the EGF(A) analogue comprises Ser (S), Thr (T) or Ile (I) in position 307.

In one such embodiment the EGF(A) analogue comprises Ile (I) in position 307.

In one such embodiment the EGF(A) analogue comprises the amino acid residue Asn(N), Glu (E), His (H,) Arg (R), Ser (S) or Lys (K) in position 309.

In one such embodiment the EGF(A) analogue of the invention comprises the amino acid residue Asn(N), Arg (R), Ser (S) or Lys (K) in position 309.

In one such embodiment the EGF(A) analogue comprises the amino acid residue Asn(N), Arg (R) or Ser (S) in position 309.

In one such embodiment the EGF(A) analogue comprises the amino acid residue Asn(N) or Arg (R) in position 309.

In one such embodiment the EGF(A) analogue comprises the amino acid residue Lys(K) or Arg (R) in position 309.

The EGF(A) analogue may comprise several amino acid substitutions as described herein, such as one or more amino acid substitutions selected from the group of: 299Ala, 307Ile and 321Glu.

In further embodiments, the EGF(A) analogue comprises the amino acid residue Asp(D), Lys (K) or Glu(E) in position 321.

In further embodiments, the EGF(A) analogue comprises the amino acid residue Asp(D) or Glu(E) in position 321.

In further embodiments, the EGF(A) analogue comprises the amino acid residue Glu(E) in position 321.

In further embodiments, the EGF(A) analogue comprises the amino acid residue Gln (Q) or Gly (G) in position 324.

In further embodiments, the EGF(A) analogue comprises the amino acid residue Arg (R) or His (H) in position 329.

In further embodiments, the EGF(A) analogue does not have a substitution of 300Asn(N) to Pro(P).

The EGF(A) domain of LDL-R includes a Lysine in position 312 which may be useful for substitution as described herein. In embodiments where attachment of the substituent to 312 is not wanted 312Lys may be substituted by another amino acid as described herein.

In one embodiment the EGF(A) analogue comprises no Lys residue.

In one embodiment, Lys in position 312 is substituted by an amino acid residue selected from: Gly, Pro, Asp, Glu, Arg, His, Ser, Thr, Asn, Gln, Ala, Val, Ile, Leu, Met, Phe and Tyr. In one embodiment, Lys in position 312 is substituted by an amino acid residue selected from: Gly, Asp, Glu, Ser, Thr, Asn, Ala, Val, Ile, Leu, Phe and Tyr. In one embodiment, Lys in position 312 is substituted by an amino acid residue selected from: Asp, Glu, Thr, Asn, Ile, Leu, Phe and Tyr. In one embodiment, 312Lys is substituted by 312Asp, 312Glu, 312Thr, 312Asn, 312Ile or 312Phe. In one embodiment, 312Lys is substituted by 312Glu, 312Asp, 312Gln or 312Arg.

In one embodiment, 312Lys is substituted by 312Glu, 312Thr, 312Asn, 312Ile, 312Phe or 312Tyr. In one embodiment, 312Lys is substituted by 312Glu, 312Asn or 312Ile.

In one embodiment, 312Lys is substituted by 312Glu or 312Arg. In one embodiment 312Lys is substituted by 312Arg. In one embodiment, 312Lys is substituted by 312Glu.

To include an option for attaching the substituent in various positions (see further below), a Lys may be introduced by amino acid substitution of a wild type residue of SEQ ID NO.: 1 or by a peptide elongation of SEQ ID NO.: 1, such as a 292Lys or a 333Lys.

In cases where more than one substituent is desired one may be via 312Lys while the second is via a Lys introduced by peptide elongation or substitution in SEQ ID NO.: 1.

In one embodiment the EGF(A) analogue of SEQ ID NO: 1 comprises at least one Lys residue in a position selected from the group of: 292Lys, 293Lys, 294Lys, 296Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In one embodiment the EGF(A) analogue of SEQ ID NO: 1 comprises at least one Lys residue in a position selected from the group of: 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In one embodiment the EGF(A) analogue of SEQ ID NO: 1 comprises at least one Lys residue in a position selected from the group of: 292Lys, 293Lys, 294Lys, 300Lys, 303Lys, 305Lys, 306Lys, 309Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In one embodiment the EGF(A) analogue of SEQ ID NO: 1 comprises at least one Lys residue in a position selected from the group of: 292Lys, 293Lys, 294Lys, 300Lys, 303Lys, 305Lys, 306Lys, 311Lys, 312Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.

In one embodiment the EGF(A) analogue of SEQ ID NO: 1 comprises at least one Lys residue in a position selected from the group of: 292Lys, 293Lys, 294Lys, 300Lys, 303Lys, 305Lys, 306Lys, 311Lys, 313Lys, 314Lys, 316Lys, 318Lys, 322Lys, 323Lys, 324Lys, 325Lys, 326Lys, 327Lys, 328Lys, 329Lys, 330Lys, 332Lys and 333Lys.

In addition or alternatively, the EGF(A) analogue of the invention comprises at least one amino acid substitution selected from 292Lys, 293Lys, 294Lys, 295Lys, 296Lys, 298Lys, 299Lys, 301Lys, 302Lys, 303Lys, 305Lys, 306Lys, 307Lys, 309Lys, 310Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from:292Lys, 293Lys, 294Lys, 295Lys, 296Lys, 298Lys, 299Lys, 302Lys, 303Lys, 305Lys, 306Lys, 307Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 295Lys, 296Lys, 298Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 295Lys, 296Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue peptide of the invention comprises at least one amino acid substitution selected from 292Lys, 293Lys, 294Lys, 296Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 299Lys, 303Lys, 305Lys, 306Lys, 309Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 299Lys, 303Lys, 305Lys, 306Lys, 310Lys, 311Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 299Lys, 303Lys, 305Lys, 306Lys, 309Lys, 310Lys, 311Lys, 313Lys, 314Lys, 315Lys, 316Lys, 318Lys, 321Lys, 322Lys, 323Lys, 324Lys, 325Lys, 326Lys, 327Lys, 328Lys, 329Lys, 330Lys, 332Lys and 333Lys.

In a further embodiment, the EGF(A) analogue of the invention comprises at least one amino acid substitution selected from 292Lys, 293Lys, 294Lys, 303Lys, 305Lys, 306Lys, 310Lys, 311Lys, 313Lys, 314Lys, 315Lys, 316Lys, 318Lys, 321Lys, 322Lys, 323Lys, 324Lys, 325Lys, 326Lys, 327Lys, 328Lys, 329Lys, 330Lys, 332Lys and 333Lys. In one embodiment, the EGF(A) analogues of the invention do not comprise any of the following substitutions: 296K, 298K, 301K, 302K and 307K.

In one embodiment, the EGF(A) analogue comprises any of the following substitution: 296K, 298K, 301K, 302K, 307K and 310K.

In one embodiment, the EGF(A) analogue comprises any of the following substitution: 296K, 298K, 301K, 302K, 307K, and 295K.

In one embodiment, the EGF(A) analogue comprises any of the following substitution: 296K, 298K, 301K, 302K, 307K and 295D.

In a particular embodiment, the EGF(A) analogue comprises 1 or 2, of such Lys substitutions.

In addition or alternatively, the EGF(A) analogue may comprise 312Lys.

In one embodiment the EGF(A) analogue of the invention comprises two Lys residues. In one embodiment the EGF(A) analogue of the invention comprises two Lys residues selected from the pairs consisting of:

| |
|---|
| i. 293K and 294K |
| ii. 293K and 312K |
| iii. 293K and 333K |
| iv. 309K and 313K |
| v. 309K and 324K |
| vi. 309K and 328K |
| vii. 309K and 332K |
| viii. 309K and 333K |
| ix. 311K and 313K |
| x. 312K and 333K |
| xi. 312K and 313K |
| xii. 312K and 314K |
| xiii. 313K and 314K |
| xiv. 313K and 321K |
| xv. 313K and 324K |
| xvi. 313K and 328K |
| xvii. 313K and 332K |
| xviii. 313K and 333K |
| xix. 314K and 333K |
| xx. 321K and 332K |
| xxi. 321K and 333K |
| xxii. 324K and 333K |
| xxiii. 324K and 328K |
| xxiv. 328K and 333K |
| xxv. 330K and 333K and |
| xxvi. 332K and 333K. |

In a further embodiment the EGF(A) analogue comprises at least two amino acid substitutions identified by any of the groups I-XXIV shown below compared to SEQ ID NO.:1.

In a still further embodiment, the EGF(A) analogue consists of the amino acid substitutions identified by any of the groups I-XXIV as shown below.

In a further embodiment the EGF(A) analogue comprises at least two amino acid substitutions identified by any of the groups I-XVI shown below compared to SEQ ID NO.:1.

In a still further embodiment, the EGF(A) analogue consists of the amino acid substitutions identified by any of the groups I-XVI as shown below.

I. 301Leu and 309Arg
II. 301Leu, 309Arg, 312Glu
III. 301Leu, 307Ile and 309Arg
IV. 301Leu, 307Ile, 309Arg and 312Glu
V. 301Leu, 309Arg and 321Glu
VI. 301Leu, 309Arg, 321Glu and 312Glu
VII. 301Leu, 307Ile, 309Arg and 299Ala
VIII. 301Leu, 307Ile, 309Arg, 299Ala and 312Glu
IX. 301Leu and 309Arg and at least one Lys substitution
X. 301Leu, 309Arg, 312Glu and at least one Lys substitution
XI. 301Leu, 307Ile and 309Arg and at least one Lys substitution
XII. 301Leu, 307Ile, 309Arg and 312Glu and at least one Lys substitution
XIII 301Leu, 309Arg and 321Glu and at least one Lys substitution
XIV. 301Leu, 309Arg, 321Glu and 312Glu and at least one Lys substitution
XV. 301Leu, 307Ile, 309Arg and 299Ala and at least one Lys substitution or
XVI. 301Leu, 307Ile, 309Arg, 299Ala and 312Glu and at least one Lys substitution.

In one embodiment, the EGF(A) peptide analogue comprises or consists of the amino acid substitutions identified by any of
V. 301Leu, 309Arg and 321Glu
VI. 301Leu, 309Arg, 321Glu and 312Glu
XIII 301Leu, 309Arg, 312Glu and at least one Lys substitution or
XIV. 301Leu, 309Arg, 321Glu and 312Glu and at least one Lys substitution.

In a further embodiment the EGF(A) analogue comprises at least two amino acid substitutions identified by any of the groups XVII-XX shown below compared to SEQ ID NO.: 1.

In a still further embodiment, the EGF(A) analogue consists of at the amino acid substitutions identified by any of the groups XVII-XX as shown below compared to SEQ ID NO.: 1.

XVII. 301Leu and 309Lys
XVIII. 301Leu, 309Lys and 312Glu
XIX. 301Leu and 309Lys and at least one further Lys substitution XX. 301Leu, 309Lys and 312Glu and at least one further Lys substitution.

In a further embodiment the EGF(A) analogue according to the invention comprises at least two amino acid substitutions identified by any of the groups XXI-XXIV shown below compared to SEQ ID NO.: 1.

In a still further embodiment, the EGF(A) analogue of the invention consists of the amino acid substitution identified by any of the groups XXI-XXIV as shown below compared to SEQ ID NO.: 1.

XXI. 301Leu and 307Ile,

XXII. 301Leu, 307Ile and 312Glu

XXIII. 301Leu and 307Ile and at least one further Lys substitution and

XXIV. 301Leu, 3307Ile and 312Glu and at least one further Lys substitution.

In further specific embodiments the EGF(A) analogue comprises or consists of anyone of the amino acid sequences identified by SEQ ID 1 to 114.

In one embodiment the EGF(A) analogue comprises or consists of anyone of the amino acid sequences identified by SEQ ID NO.: 2-114.

In one embodiment the EGF(A) analogue comprises or consists of anyone of the amino acid sequences identified by SEQ ID NO.: 2-47 and 49-114.

In one embodiment the EGF(A) analogue comprises or consists of anyone of the amino acid sequences identified by anyone of the amino acid sequences SEQ ID NO.: 2-44, 46, 47 and 49-114.

In one embodiment the EGF(A) analogue comprises or consists of anyone of the amino acid sequences identified by of SEQ ID NO.: 2-44, 46, 47, 49-53, 55, 58-114.

In one embodiment the EGF(A) analogue comprises or consists of anyone of the amino acid sequences identified by SEQ ID NO.: 2-4, 6-44, 46, 47, 49-53, 55, 58-114.

In one embodiment the EGF(A) analogue comprises or consists of anyone of the amino acid sequences identified by SEQ ID NO.: 2-4, 6-19, 21-44, 46, 47, 49-53, 55, 58-114.

In one embodiment the EGF(A) analogue comprises or consists of anyone of the amino acid sequences identified by SEQ ID NO.: 19, 21, 73, 107, 108, 109, 110, 111, 112, 113, 114.

In one embodiment the EGF(A) analogue as described above comprises no Lys residues and the EGF(A) analogue thus comprises or consists of anyone of the amino acid sequences identified by SEQ ID NO.: 5, 6, 23, 26, 49, 50, 107-111.

In one embodiment the EGF(A) analogue comprises or consists of anyone of the amino acid sequences identified by SEQ ID NO.: 5, 6, 23, 26, 49, 50 or 107.

In one preferred embodiment the EGF(A) analogue comprises both a mutation of the 312K residue, the 321D residue and no Lys residue, such as where the EGF(A) analogue comprises or consists of anyone of the amino acid sequences identified by SEQ ID NO.: 108, 109, 110 or 111.

In one embodiment the EGF(A) analogue comprises or consists of the amino acid sequences identified by SEQ ID NO.:108.

The examples herein provide various EGF(A) analogues which are include in the table below including information on amino acid substitutions, Lys residues and the SEQ ID NO.

| EGF(A) analogue # | Sequence modifications | Lys residues | SEQ ID: NO |
|---|---|---|---|
| — | WT - EGF(A) | | 1 |
| 1. | 299A, 301L, 307I, 309R, 310K | 310K, 312K | 2 |
| 2. | 301L, 309R | 312K | 3 |
| 3. | 301L, 309R, 312E, 333K | 333K | 4 |
| 4. | 300P, 301L, 307I, 309R, 312E | None | 5 |
| 5. | 301L, 309R, 312E | None | 6 |
| 6. | 299K, 301L, 309R, 312E | 299K | 7 |
| 7. | 301L, 309R, 312E, 330K | 330K | 8 |
| 8. | 293N, 301L, 307I, 309R, 312D, 333K | 312K, 333K | 9 |
| 9. | 293N, 301L, 309R, 312D, 333K | 333K | 10 |
| 10. | 301L, 309R, 312E, 332K | 332K | 11 |
| 11. | 293K, 301L, 309R, 312E | 293K | 12 |
| 12. | 293K, 301L, 309R, 312E, 333K | 293K, 333K | 13 |
| 13. | 301L, 309R, 312E, 328K, 329H | 328K, | 14 |
| 14. | 301L, 309R, 312E, 332K, 333K | 332K, 333K | 15 |
| 15. | 301L, 309R, 312E, 330K, 333K | 330K, 333K | 16 |
| 16. | 301L, 309R, 312E, 321K, 333K | 321K, 333K | 17 |
| 17. | 301L, 309R, 333K | 333K | 18 |
| 18. | 301L, 309R, 312E, 321E, 333K | 333K | 19 |
| 19. | 295D, 301L, 309R, 312E, 332K | 332K | 20 |
| 20. | 301L, 309R, 312E, 321K | 321K | 21 |
| 21. | 301L, 309R, 312E, 324K | 324K | 22 |
| 22. | 301L, 309R, 312Q | None | 23 |
| 23. | 301L, 309R, 312E, 321E, 332K | 332K | 24 |
| 24. | 293K, 301L, 309R, 312E, 321E | 293K | 25 |
| 25. | 300H, 301L, 307I, 309R, 312E | None | 26 |
| 26. | 300K, 301L, 309R, 312E | 300K | 27 |
| 27. | 293K, 294K, 301L, 309R, 312E | 293K | 28 |
| 28. | 293K, 301L, 309R | 293K, 312K | 29 |
| 29. | 301L, 309K, 312E | 309K | 30 |
| 30. | 301L, 309R, 312E, 318K | 318K | 31 |
| 31. | 301L, 309R, 312E, 313K, 333K | 313K, 333K | 32 |
| 32. | 301L, 309R, 312E, 326K | 326K | 33 |
| 33. | 301L, 309R, 312E, 325K | 325K | 34 |
| 34. | 301L, 309R, 312E, 323K | 323K | 35 |
| 35. | 301L, 309R, 312E, 322K | 322K | 36 |
| 36. | 301L, 309R, 312E, 320K | 320K | 37 |
| 37. | 301L, 309R, 312E, 329K | 329K | 38 |
| 38. | 301L, 309R, 312E, 313K | 313K | 39 |
| 39. | 301L, 309R, 312E, 328K | 328K | 40 |
| 40. | 301L, 309R, 312E, 316K | 316K | 41 |
| 41. | 301L, 309R, 312E, 315K | 315K | 42 |
| 42. | 300H, 301L, 309R, 312R, 333K | 333K | 43 |
| 43. | 301L, 309R, 312E, 314K | 314K | 44 |
| 44. | 301L, 309R, 311K, 312E | 311K | 45 |
| 45. | 301L, 307K, 309R, 312E | 307K | 46 |
| 46. | 301L, 309S, 312R, 333K | 333K | 47 |
| 47. | 301L, 309S, 312E, 333K | 333K | 48 |
| 48. | 301L, 306Y, 309S, 312E | None | 49 |
| 49. | 293N, 301L, 309S, 312E | None | 50 |
| 50. | 301L, 306K, 309R, 312E | 306K | 51 |
| 51. | 301L, 305K, 309R, 312E | 305K | 52 |
| 52. | 301L, 303K, 309R, 312E | 303K | 53 |
| 53. | 301L, 302K, 309R, 312E | 302K | 54 |
| 54. | 293N, 300H, 301L, 309R, 312R, 333K | 333K | 55 |
| 55. | 301K, 309R, 312E | 301K | 56 |
| 56. | 298K, 301L, 309R, 312E | 298K | 57 |
| 57. | 293N, 301L, 309R, 312R, 333K | 333K | 58 |
| 58. | 301L, 307I, 332K | 312K, 332K | 59 |
| 59. | 301L, 306Y, 312E, 332K | 332K | 60 |
| 60. | 301L, 307I, 312E, 332K | 332K | 61 |
| 61. | 300H, 301L, 309R | 312K | 62 |
| 62. | 296K, 301L, 309R, 312E | 296K | 63 |
| 63. | 294K, 301L, 309R, 312E | 294K | 64 |
| 64. | 292K, 301L, 309R, 312E | 292K | 65 |
| 65. | des293, 294G, 301L, 309R, 312E, 328K | 328K | 66 |
| 66. | 301L, 306D, 309R, 312E, 324G, 333K | 333K | 67 |
| 67. | 301L, 306D, 309R, 312E, 333K | 333K | 68 |
| 68. | 300H, 301L, 309R, 312E, 313K, 333K | 313K, 333K | 69 |
| 69. | 301L, 309R, 312E, 313K, 328K | 313K, 328K | 70 |
| 70. | 301L, 309R, 312E, 313K, 324K | 313K, 324K | 71 |
| 71. | 301L, 309R, 312E, 324K, 333K | 324K, 333K | 72 |
| 72. | 301L, 309R, 312E, 313K, 321K | 313K, 321K | 73 |

-continued

| EGF(A) analogue # | Sequence modifications | Lys residues | SEQ ID: NO |
|---|---|---|---|
| 73. | des293, 300H, 301L, 309R, 312E, 313K, 333K | 313K, 333K | 74 |
| 74. | 292A, 301L, 309R, 312E, 313K | 313K | 75 |
| 75. | des293, 301L, 309R, 312E, 313K | 313K | 76 |
| 76. | 301L, 309R, 312E, 313K, 332K | 313K, 332K | 77 |
| 77. | 301L, 309R, 312E, 328K, 333K | 328K, 333K | 78 |
| 78. | 299A, 301L, 307I, 309R | 312K | 79 |
| 79. | 301L, 309R, 310K | 310K, 312K | 80 |
| 80. | 301L | 312K | 81 |
| 81. | 300H, 301L, 309R, 312E, 333K | 333K | 82 |
| 82. | des293-294, 300H, 301L, 309R, 312E, 313K, 333K | 313K, 333K | 83 |
| 83. | 301L, 309K, 312E, 333K | 309K, 333K | 84 |
| 84. | 301L, 306Y, 312E, 324K, 333K | 324K, 333K | 85 |
| 85. | 300H, 301L, 309R, 312E, 314K, 333K | 314K, 333K | 86 |
| 86. | 294W, 301L, 309R, 312E, 333K | 333K | 87 |
| 87. | 301L, 309K, 312E, 328K | 309K, 328K | 88 |
| 88. | 301L, 309K, 312E, 313K | 309K, 313K | 89 |
| 89. | des293, 301L, 309R, 312E, 333K | 333K | 90 |
| 90. | 301L, 309R, 312E, 324K, 328K | 324K, 328K | 91 |
| 91. | 292A, 301L, 309R, 312E, 333K | 333K | 92 |
| 92. | 301L, 306Y, 309R, 312E, 313K, 333K | 313K, 333K | 93 |
| 93. | 301L, 309K, 312E, 332K | 309K, 332K | 94 |
| 94. | 301L, 309R, 312E, 321K, 332K | 321K, 332K | 95 |
| 95. | 300H, 301L, 309R, 312E, 313K, 332K | 313K, 332K | 96 |
| 96. | 301L, 309R, 312E, 313K, 321E, 332K | 313K, 332K | 97 |
| 97. | 301L, 309R, 312E, 313K, 321E, 333K | 313K, 333K | 98 |
| 98. | 301L, 309R, 312E, 313K, 314K | 313K, 314K | 99 |
| 99. | 301L, 309R, 313K | 312K, 313K | 100 |
| 100. | 301L, 309R, 314K | 312K, 314K | 101 |
| 101. | 301L, 309R, 311K, 312E, 313K | 311K, 313K | 102 |
| 102. | 300H, 301L, 309R, 312E, 313K, 321E, 333K | 313K, 333K | 103 |
| 103. | 301L, 309R, 312E, 321E, 328K, 333K | 333K | 104 |
| 104. | 301L, 309R, 312E, 321E, 324K, 333K | 324K, 333K | 105 |
| 105. | 301L, 309K, 312E, 324K | 309K, 324K | 106 |
| 106. | 301L, 309R, 312E | None | 107 |
| 107. | 301L, 309R, 312E, 321E | None | 108 |
| 108. | 301L, 307I, 309R, 312E, 321E | None | 109 |
| 109. | 301L, 306Y, 312E, 321E | None | 110 |
| 110. | 300H, 301L, 309R, 312E, 321E | None | 111 |
| 111. | 301L, 309R, 312E, 313K, 321E | 313K | 112 |
| 112. | 301L, 309R, 312E, 321E, 324K | 324K | 113 |
| 113. | 301L, 309R, 312E, 321E, 328K | 328K | 114 |

Fusion Polypeptide

In one aspect the invention relates to a fusion polypeptide comprising the amino acid sequence of a GLP-1 analogue and the amino acid sequence of a EGF(A) analogue. As previously described herein an analogue of GLP-1 refers to a variant of (7-37) (SEQ ID No: 137) and an analogue of EGF(A) refers to a variant of the EGF(A) domain of LDL-R (293-332) (SEQ ID NO: 1).

The fusion polypeptide may further be considered and intermediate in the preparation of derivatives as described herein below. When referring to derivatives of the invention the fusion polypeptide may be referred to as the back-bone or peptide back-bone.

Preparation of fusion proteins or fusion polypeptides is well known in the art. A recombinant vector for expressing the fusion polypeptide in a suitable host may be prepared and used to produce the fusion protein by heterologous expression according to common general knowledge (Sambrook et al., Molecular Cloning: a laboratory manual, 1989, Cold Spring Harbor Laboratory Press, Cold Spring Harbor, N.Y.). Alternatively shorter polypeptides are frequently produced by solid-phase peptide synthesis and even peptides of extended length may be produced synthetically. Peptide elements may also be produced separately and subsequently subjected to native chemical ligation to produce the complete fusion polypeptide.

When two peptide segments are to be fused the order may influence the functionality of the resulting fusion polypeptide, and compounds comprising it.

In one embodiment according to the invention the order of the GLP-1 analogue and the EGF(A) analogue starting from the N-terminal is the GLP-1 analogue followed by the EGF(A) analogue, optionally separated by a spacer peptide (see below). One may say that the GLP-1 analogue is fused with the EGF(A) analogue via the C-terminal of the GLP-1 analogue.

In an alternative embodiment the GLP-1 analogue is fused with the EGF(A) analogue via the C-terminal of the EGF(A) analogue placing the EGF(A) analogue at the N-terminal. The resulting fusion polypeptide, may be referred to by the term "back-bone" or "peptide back-bone" defining the polypeptide chain comprising both the GLP-1 analogue and the EGF(A) analogue and optionally a spacer peptide as described here blow.

In one embodiment the compounds of the invention, the fusion polypeptide and the derivatives thereof comprise a GLP-1 analogue as herein above defined, including any of the analogues defined by SEQ ID NO.: 138-187.

In one embodiment the compounds of the invention, the fusion polypeptide and the derivatives thereof comprise an EGF(A) analogue as herein above defined, including any of the analogues defined by SEQ ID NO.: 2-114.

Spacer

Frequently, fusion polypeptides include a spacer to ensure that any functionality residing in the ends of the two peptides are not disturbed by the proximity of the other peptides. In one embodiment the spacer is a peptide, which is herein referred to as a spacer peptide or a peptide spacer. Various spacer peptides are known in the art and may be placed between the GLP-1 analogue and the EGF(A) analogue to obtain fusion polypeptides. As described above the resulting fusion polypeptide (comprising a spacer) may be produced either synthetically or by heterologous expression.

The spacer peptides are usual peptide segments of 4-80 amino acids.

Examples of such peptides as used herein are included below.

| Spacer # | SEQ ID | amino acid sequence |
|---|---|---|
| 1 | 115 | GQAP |
| 2 | 116 | GQAPGQAP |
| 3 | 117 | GQAPGQAPGQAP |
| 4 | 118 | GQAPGQAPGQAPGQAPGQAP |
| 5 | 119 | GQAPGQAPGQAPGQAPGQAPGQAPGQAPGQAP |
| 6 | 120 | GQAPGQAPGQAPGQAPGQAPGQAPGQAPGQAPGQAPGQAPGQAPGQAPGQAPGQAPGQAP |

-continued

| Spacer # | SEQ ID | amino acid sequence |
|---|---|---|
| 7 | 121 | KQAPGQAP |
| 8 | 122 | GKAPGQAP |
| 9 | 123 | GQKPGQAP |
| 10 | 124 | GQAKGQAP |
| 11 | 125 | GQAPKQAP |
| 12 | 126 | GQAPGKAP |
| 13 | 127 | GQAPGQKP |
| 14 | 128 | GQAPGQAK |
| 15 | 129 | GAPSGAPS |
| 16 | 130 | GSGSGSGS |
| 17 | 131 | GEGSGEGS |
| 18 | 132 | GGGGGGGG |
| 19 | 133 | GKGGGGGG |
| 20 | 134 | GGGGSGGGS |
| 21 | 135 | GGGGGGES |
| 22 | 136 | GGGGGGGES |

In one embodiment the compounds of the invention, the fusion polypeptide and the derivatives thereof comprise a peptide spacer, wherein the peptide spacer comprises a sequence selected from the peptides identified by SEQ ID NO 115-136.

In one embodiment the compounds of the invention, the fusion polypeptide and the derivatives thereof comprise a peptide spacer selected from the group of peptide spacers identified by SEQ ID NO 115-136.

In one embodiment the compounds of the invention, the fusion polypeptide and the derivatives thereof comprise a peptide spacer comprising one or more segments of GQAP, such as 1-20, such as 1-10, such as 1-6, such as 1, 2, 3, 4 or 5 GQAP segments.

In one embodiment the peptide spacer comprise a peptide spacer selected from the group of peptides identified by SEQ ID NO.: 115-128.

In one embodiment the peptide spacer is selected from the sequences identified by SEQ ID NO.: 115-128.

In one embodiment the peptide spacer does not comprise a Lys residue.

In one embodiment the peptide spacer comprise a Lys residue.

In one embodiment the compounds of the invention, the fusion polypeptide and the derivatives thereof comprise a peptide spacer comprising one or more segments of GQAP wherein a Lys residue is introduce by amino acid substitution. In further such embodiments, the spacer may be selected from the group of sequences identified, by SEQ ID NO.: 121-128.

In one embodiment the compounds of the invention, the fusion polypeptide and the derivatives thereof comprise a peptide spacer that is Glycine rich, such as a peptide spacer wherein at least half of the amino acid residues are Gly, such as at least ¾ of the amino acid residues are Gly. In such embodiments the peptide spacer may be selected from the peptides identified by SEQ ID NO.: 130-136.

In a further embodiment the peptide spacer is selected from the group of peptides identified by SEQ ID NO: 115-117 and 121-136.

In a further embodiment the peptide spacer is selected from the group of peptides identified by SEQ ID NO: 115-117 and 121-128.

In one embodiment the peptide spacer is selected from the sequences identified by SEQ ID NO.: 115-128.

In a further embodiment the peptide spacer is selected from the group of peptides identified by SEQ ID NO: 115-117. In a further embodiment the peptide spacer is identified by SEQ ID NO: 116.

Multiple examples of fusion polypeptides (peptide backbones) according to the invention are provided in the examples showing variability in all elements, i.e. the GLP-1 analogue, the EGF(A) analogue and the peptide spacer.

In one embodiment the fusion polypeptide or the backbone sequence of the derivatives of the invention consists of a GLP-1 analogue, an EGF(A) analogue and a peptide spacer as herein defined.

The examples of the application include a plurality of such fusion polypeptides and derivatives including such fusion polypeptide as peptide back-bone. The identity of the fusion polypeptide may be deduced from the sequence of the individual elements, i.e. the GLP-1 analogue, the EGF(A) analogue and the peptide spacer which together forms the fusion polypeptide which are individually assigned a SEQ ID according to the following table.

| Fusion peptide SEQ ID NO | GLP-1 analogue | GLP-1 SEQ ID | Spacer SEQ ID | EGF(A) analogue | EGF(A) SEQ ID NO |
|---|---|---|---|---|---|
| 188. | 8Aib | 138 | 116 | 301L, 309R, 312E, 321E | 108 |
| 189. | 8Aib, 34R | 139 | 115 | 301L, 309R, 312E, 321E | 108 |
| 190. | 8Aib, 34R | 139 | 116 | 301L, 309R, 312E, 321E, 333K | 19 |
| 191. | 8Aib, 34R | 139 | 116 | 301L, 309R, 312E, 321K | 21 |
| 192. | 8Aib, 34R | 139 | 116 | 301L, 309R, 312E | 107 |
| 193. | 8Aib, 34R | 139 | 116 | 301L, 309R, 312E, 321E | 108 |
| 194. | 8Aib, 34R | 139 | 116 | 301L, 307I, 309R, 312E, 321E | 109 |
| 195. | 8Aib, 34R | 139 | 116 | 301L, 306Y, 312E, 321E | 110 |
| 196. | 8Aib, 34R | 139 | 116 | 300H, 301L, 309R, 312E, 321E | 111 |
| 197. | 8Aib, 34R | 139 | 116 | 301L, 309R, 312E, 313K, 321E | 112 |
| 198. | 8Aib, 34R | 139 | 116 | 301L, 309R, 312E, 321E, 324K | 113 |
| 199. | 8Aib, 34R | 139 | 116 | 301L, 309R, 312E, 321E, 328K | 114 |
| 200. | 8Aib, 34R | 139 | 117 | 301L, 309R, 312E, 321E | 108 |
| 201. | 8Aib, 34R | 139 | 118 | 301L, 309R, 312E, 321E | 108 |
| 202. | 8Aib, 34R | 139 | 119 | 301L, 309R, 312E, 321E | 108 |
| 203. | 8Aib, 34R | 139 | 120 | 301L, 309R, 312E, 321E | 108 |

-continued

| Fusion peptide SEQ ID NO | GLP-1 analogue | GLP-1 SEQ ID | Spacer SEQ ID | EGF(A) analogue | EGF(A) SEQ ID NO |
|---|---|---|---|---|---|
| 204. | 8Aib, 34R | 139 | 121 | 301L, 309R, 312E, 321E | 108 |
| 205. | 8Aib, 34R | 139 | 122 | 301L, 309R, 312E, 321E | 108 |
| 206. | 8Aib, 34R | 139 | 123 | 301L, 309R, 312E, 321E | 108 |
| 207. | 8Aib, 34R | 139 | 124 | 301L, 309R, 312E, 321E | 108 |
| 208. | 8Aib, 34R | 139 | 125 | 301L, 309R, 312E, 321E | 108 |
| 209. | 8Aib, 34R | 139 | 126 | 301L, 309R, 312E, 321E | 108 |
| 210. | 8Aib, 34R | 139 | 127 | 301L, 309R, 312E, 321E | 108 |
| 211. | 8Aib, 34R | 139 | 128 | 301L, 309R, 312E, 321E | 108 |
| 212. | 8Aib, 34R | 139 | 129 | 301L, 309R, 312E, 321E | 108 |
| 213. | 8Aib, 34R | 139 | 130 | 301L, 309R, 312E, 321E | 108 |
| 214. | 8Aib, 34R | 139 | 131 | 301L, 309R, 312E, 321E | 108 |
| 215. | 8Aib, 34R | 139 | 132 | 301L, 309R, 312E, 321E | 108 |
| 216. | 8Aib, 34R | 139 | 134 | 301L, 309R, 312E, 321E | 108 |
| 217. | 8Aib, 34R | 139 | 135 | 301L, 309R, 312E, 321E | 108 |
| 218. | 8Aib, 34R | 139 | 136 | 301L, 309R, 312E, 321E | 108 |
| 219. | 8G, 34R | 140 | 116 | 301L, 309R, 312E, 321E | 108 |
| 220. | 8W, 34R | 141 | 116 | 301L, 309R, 312E, 321E | 108 |
| 221. | 8Aib, 34Q | 142 | 116 | 301L, 309R, 312E, 321E | 108 |
| 222. | 8Aib, des(32-37) | 143 | 116 | 301L, 309R, 312E, 321E | 108 |
| 223. | 8Aib, des(33-37) | 144 | 116 | 301L, 309R, 312E, 321E | 108 |
| 224. | 8Aib, des(34-37) | 145 | 116 | 301L, 309R, 312E, 321E | 108 |
| 225. | 8Aib, 34R, des(35-37) | 146 | 116 | 301L, 309R, 312E, 321E | 108 |
| 226. | 8Aib, 12K, 26R, 34R | 147 | 116 | 301L, 309R, 312E, 321E | 108 |
| 227. | 8Aib, 21K, 26R, 34R | 148 | 116 | 301L, 309R, 312E, 321E | 108 |
| 228. | 8Aib, 24K, 26R, 34R | 149 | 116 | 301L, 309R, 312E, 321E | 108 |
| 229. | 8Aib, 25K, 26R, 34R | 150 | 116 | 301L, 309R, 312E, 321E | 108 |
| 230. | 8Aib, 26R, 27K, 34R | 151 | 116 | 301L, 309R, 312E, 321E | 108 |
| 231. | 8Aib, 26R, 31K, 34R | 152 | 116 | 301L, 309R, 312E, 321E | 108 |
| 232. | 8Aib, 26R, 32K, 34R | 153 | 116 | 301L, 309R, 312E, 321E | 108 |
| 233. | 8Aib, 26R, 34R, 36K | 154 | 116 | 301L, 309R, 312E, 321E | 108 |
| 234. | 8Aib, 21G, 34R | 155 | 116 | 301L, 309R, 312E, 321E, 333K | 19 |
| 235. | 8Aib, 21G, 34R | 155 | 116 | 301L, 309R, 312E, 321K | 21 |
| 236. | 8Aib, 21G, 34R | 155 | 116 | 301L, 309R, 312E, 321E | 108 |
| 237. | 8Aib, 21G, 34R | 155 | 116 | 301L, 309R, 312E, 313K, 321E | 112 |
| 238. | 8Aib, 21G, 34R | 155 | 116 | 301L, 309R, 312E, 321E, 324K | 113 |
| 239. | 8Aib, 21G, 34R | 155 | 116 | 301L, 309R, 312E, 321E, 328K | 114 |
| 240. | 8Aib, 21G, 34R | 155 | 121 | 301L, 309R, 312E, 321E | 108 |
| 241. | 8Aib, 21G, 34R | 155 | 122 | 301L, 309R, 312E, 321E | 108 |
| 242. | 8Aib, 21G, 34R | 155 | 123 | 301L, 309R, 312E, 321E | 108 |
| 243. | 8Aib, 21G, 34R | 155 | 124 | 301L, 309R, 312E, 321E | 108 |
| 244. | 8Aib, 21G, 34R | 155 | 125 | 301L, 309R, 312E, 321E | 108 |
| 245. | 8Aib, 21G, 34R | 155 | 126 | 301L, 309R, 312E, 321E | 108 |
| 246. | 8Aib, 21G, 34R | 155 | 127 | 301L, 309R, 312E, 321E | 108 |
| 247. | 8Aib, 21G, 34R | 155 | 128 | 301L, 309R, 312E, 321E | 108 |
| 248. | 8Aib, 23G, 34R | 156 | 116 | 301L, 309R, 312E, 321E, 333K | 19 |
| 249. | 8Aib, 23G, 34R | 156 | 116 | 301L, 309R, 312E, 321K | 21 |
| 250. | 8Aib, 23G, 34R | 156 | 116 | 301L, 309R, 312E, 321E | 108 |
| 251. | 8Aib, 23G, 34R | 156 | 116 | 301L, 309R, 312E, 313K, 321E | 112 |
| 252. | 8Aib, 23G, 34R | 156 | 116 | 301L, 309R, 312E, 321E, 324K | 113 |
| 253. | 8Aib, 23G, 34R | 156 | 116 | 301L, 309R, 312E, 321E, 328K | 114 |
| 254. | 8Aib, 23G, 34R | 156 | 121 | 301L, 309R, 312E, 321E | 108 |
| 255. | 8Aib, 23G, 34R | 156 | 122 | 301L, 309R, 312E, 321E | 108 |
| 256. | 8Aib, 23G, 34R | 156 | 123 | 301L, 309R, 312E, 321E | 108 |
| 257. | 8Aib, 23G, 34R | 156 | 124 | 301L, 309R, 312E, 321E | 108 |
| 258. | 8Aib, 23G, 34R | 156 | 125 | 301L, 309R, 312E, 321E | 108 |
| 259. | 8Aib, 23G, 34R | 156 | 126 | 301L, 309R, 312E, 321E | 108 |
| 260. | 8Aib, 23G, 34R | 156 | 127 | 301L, 309R, 312E, 321E | 108 |
| 261. | 8Aib, 23G, 34R | 156 | 128 | 301L, 309R, 312E, 321E | 108 |
| 262. | 8Aib, 24G, 34R | 157 | 116 | 301L, 309R, 312E, 321E, 333K | 19 |
| 263. | 8Aib, 24G, 34R | 157 | 116 | 301L, 309R, 312E, 321K | 21 |
| 264. | 8Aib, 24G, 34R | 157 | 116 | 301L, 309R, 312E, 321E | 108 |
| 265. | 8Aib, 24G, 34R | 157 | 116 | 301L, 309R, 312E, 313K, 321E | 112 |
| 266. | 8Aib, 24G, 34R | 157 | 116 | 301L, 309R, 312E, 321E, 324K | 113 |
| 267. | 8Aib, 24G, 34R | 157 | 116 | 301L, 309R, 312E, 321E, 328K | 114 |
| 268. | 8Aib, 24G, 34R | 157 | 121 | 301L, 309R, 312E, 321E | 108 |
| 269. | 8Aib, 24G, 34R | 157 | 122 | 301L, 309R, 312E, 321E | 108 |
| 270. | 8Aib, 24G, 34R | 157 | 123 | 301L, 309R, 312E, 321E | 108 |
| 271. | 8Aib, 24G, 34R | 157 | 124 | 301L, 309R, 312E, 321E | 108 |
| 272. | 8Aib, 24G, 34R | 157 | 125 | 301L, 309R, 312E, 321E | 108 |
| 273. | 8Aib, 24G, 34R | 157 | 126 | 301L, 309R, 312E, 321E | 108 |
| 274. | 8Aib, 24G, 34R | 157 | 127 | 301L, 309R, 312E, 321E | 108 |
| 275. | 8Aib, 24G, 34R | 157 | 128 | 301L, 309R, 312E, 321E | 108 |
| 276. | 8Aib, 24V, 34R | 158 | 116 | 301L, 309R, 312E, 321E | 108 |
| 277. | 8Aib, 25G, 34R | 159 | 116 | 301L, 309R, 312E, 321E, 333K | 19 |
| 278. | 8Aib, 25G, 34R | 159 | 116 | 301L, 309R, 312E, 321K | 21 |

-continued

| Fusion peptide SEQ ID NO | GLP-1 analogue | GLP-1 SEQ ID | Spacer SEQ ID | EGF(A) analogue | EGF(A) SEQ ID NO |
|---|---|---|---|---|---|
| 279. | 8Aib, 25G, 34R | 159 | 116 | 301L, 309R, 312E, 321E | 108 |
| 280. | 8Aib, 25G, 34R | 159 | 116 | 301L, 309R, 312E, 313K, 321E | 112 |
| 281. | 8Aib, 25G, 34R | 159 | 116 | 301L, 309R, 312E, 321E, 324K | 113 |
| 282. | 8Aib, 25G, 34R | 159 | 116 | 301L, 309R, 312E, 321E, 328K | 114 |
| 283. | 8Aib, 25G, 34R | 159 | 121 | 301L, 309R, 312E, 321E | 108 |
| 284. | 8Aib, 25G, 34R | 159 | 122 | 301L, 309R, 312E, 321E | 108 |
| 285. | 8Aib, 25G, 34R | 159 | 123 | 301L, 309R, 312E, 321E | 108 |
| 286. | 8Aib, 25G, 34R | 159 | 124 | 301L, 309R, 312E, 321E | 108 |
| 287. | 8Aib, 25G, 34R | 159 | 125 | 301L, 309R, 312E, 321E | 108 |
| 288. | 8Aib, 25G, 34R | 159 | 126 | 301L, 309R, 312E, 321E | 108 |
| 289. | 8Aib, 25G, 34R | 159 | 127 | 301L, 309R, 312E, 321E | 108 |
| 290. | 8Aib, 25G, 34R | 159 | 128 | 301L, 309R, 312E, 321E | 108 |
| 291. | 8Aib, 25V, 34R | 160 | 116 | 301L, 309R, 312E, 321E | 108 |
| 292. | 8Aib, 27G, 34R | 161 | 116 | 301L, 309R, 312E, 321E, 333K | 19 |
| 293. | 8Aib, 27G, 34R | 161 | 116 | 301L, 309R, 312E, 321K | 21 |
| 294. | 8Aib, 27G, 34R | 161 | 116 | 301L, 309R, 312E, 321E | 108 |
| 295. | 8Aib, 27G, 34R | 161 | 116 | 301L, 309R, 312E, 313K, 321E | 112 |
| 296. | 8Aib, 27G, 34R | 161 | 116 | 301L, 309R, 312E, 321E, 324K | 113 |
| 297. | 8Aib, 27G, 34R | 161 | 116 | 301L, 309R, 312E, 321E, 328K | 114 |
| 298. | 8Aib, 27G, 34R | 161 | 121 | 301L, 309R, 312E, 321E | 108 |
| 299. | 8Aib, 27G, 34R | 161 | 122 | 301L, 309R, 312E, 321E | 108 |
| 300. | 8Aib, 27G, 34R | 161 | 123 | 301L, 309R, 312E, 321E | 108 |
| 301. | 8Aib, 27G, 34R | 161 | 124 | 301L, 309R, 312E, 321E | 108 |
| 302. | 8Aib, 27G, 34R | 161 | 125 | 301L, 309R, 312E, 321E | 108 |
| 303. | 8Aib, 27G, 34R | 161 | 126 | 301L, 309R, 312E, 321E | 108 |
| 304. | 8Aib, 27G, 34R | 161 | 127 | 301L, 309R, 312E, 321E | 108 |
| 305. | 8Aib, 27G, 34R | 161 | 128 | 301L, 309R, 312E, 321E | 108 |
| 306. | 8Aib, 29A, 34R | 162 | 116 | 301L, 309R, 312E, 321E | 108 |
| 307. | 8Aib, 29V, 34R | 163 | 116 | 301L, 309R, 312E, 321E | 108 |
| 308. | 8Aib, 30G, 34R | 164 | 116 | 301L, 309R, 312E, 321E, 333K | 19 |
| 309. | 8Aib, 30G, 34R | 164 | 116 | 301L, 309R, 312E, 321K | 21 |
| 310. | 8Aib, 30G, 34R | 164 | 116 | 301L, 309R, 312E, 321E | 108 |
| 311. | 8Aib, 30G, 34R | 164 | 116 | 301L, 309R, 312E, 313K, 321E | 112 |
| 312. | 8Aib, 30G, 34R | 164 | 116 | 301L, 309R, 312E, 321E, 324K | 113 |
| 313. | 8Aib, 30G, 34R | 164 | 116 | 301L, 309R, 312E, 321E, 328K | 114 |
| 314. | 8Aib, 30G, 34R | 164 | 121 | 301L, 309R, 312E, 321E | 108 |
| 315. | 8Aib, 30G, 34R | 164 | 122 | 301L, 309R, 312E, 321E | 108 |
| 316. | 8Aib, 30G, 34R | 164 | 123 | 301L, 309R, 312E, 321E | 108 |
| 317. | 8Aib, 30G, 34R | 164 | 124 | 301L, 309R, 312E, 321E | 108 |
| 318. | 8Aib, 30G, 34R | 164 | 125 | 301L, 309R, 312E, 321E | 108 |
| 319. | 8Aib, 30G, 34R | 164 | 126 | 301L, 309R, 312E, 321E | 108 |
| 320. | 8Aib, 30G, 34R | 164 | 127 | 301L, 309R, 312E, 321E | 108 |
| 321. | 8Aib, 30G, 34R | 164 | 128 | 301L, 309R, 312E, 321E | 108 |
| 322. | 8Aib, 31G, 34R | 165 | 116 | 301L, 309R, 312E, 321E, 333K | 19 |
| 323. | 8Aib, 31G, 34R | 165 | 116 | 301L, 309R, 312E, 321K | 21 |
| 324. | 8Aib, 31G, 34R | 165 | 116 | 301L, 309R, 312E, 321E | 108 |
| 325. | 8Aib, 31G, 34R | 165 | 116 | 301L, 309R, 312E, 313K, 321E | 112 |
| 326. | 8Aib, 31G, 34R | 165 | 116 | 301L, 309R, 312E, 321E, 324K | 113 |
| 327. | 8Aib, 31G, 34R | 165 | 116 | 301L, 309R, 312E, 321E, 328K | 114 |
| 328. | 8Aib, 31G, 34R | 165 | 121 | 301L, 309R, 312E, 321E | 108 |
| 329. | 8Aib, 31G, 34R | 165 | 122 | 301L, 309R, 312E, 321E | 108 |
| 330. | 8Aib, 31G, 34R | 165 | 123 | 301L, 309R, 312E, 321E | 108 |
| 331. | 8Aib, 31G, 34R | 165 | 124 | 301L, 309R, 312E, 321E | 108 |
| 332. | 8Aib, 31G, 34R | 165 | 125 | 301L, 309R, 312E, 321E | 108 |
| 333. | 8Aib, 31G, 34R | 165 | 126 | 301L, 309R, 312E, 321E | 108 |
| 334. | 8Aib, 31G, 34R | 165 | 127 | 301L, 309R, 312E, 321E | 108 |
| 335. | 8Aib, 31G, 34R | 165 | 128 | 301L, 309R, 312E, 321E | 108 |
| 336. | 8Aib, 32A, 34R | 166 | 116 | 301L, 309R, 312E, 321E | 108 |
| 337. | 8Aib, 32G, 34R | 167 | 116 | 301L, 309R, 312E, 321E, 333K | 19 |
| 338. | 8Aib, 32G, 34R | 167 | 116 | 301L, 309R, 312E, 321K | 21 |
| 339. | 8Aib, 32G, 34R | 167 | 116 | 301L, 309R, 312E, 321E | 108 |
| 340. | 8Aib, 32G, 34R | 167 | 116 | 301L, 309R, 312E, 313K, 321E | 112 |
| 341. | 8Aib, 32G, 34R | 167 | 116 | 301L, 309R, 312E, 321E, 324K | 113 |
| 342. | 8Aib, 32G, 34R | 167 | 116 | 301L, 309R, 312E, 321E, 328K | 114 |
| 343. | 8Aib, 32G, 34R | 167 | 121 | 301L, 309R, 312E, 321E | 108 |
| 344. | 8Aib, 32G, 34R | 167 | 122 | 301L, 309R, 312E, 321E | 108 |
| 345. | 8Aib, 32G, 34R | 167 | 123 | 301L, 309R, 312E, 321E | 108 |
| 346. | 8Aib, 32G, 34R | 167 | 124 | 301L, 309R, 312E, 321E | 108 |
| 347. | 8Aib, 32G, 34R | 167 | 125 | 301L, 309R, 312E, 321E | 108 |
| 348. | 8Aib, 32G, 34R | 167 | 126 | 301L, 309R, 312E, 321E | 108 |
| 349. | 8Aib, 32G, 34R | 167 | 127 | 301L, 309R, 312E, 321E | 108 |
| 350. | 8Aib, 32G, 34R | 167 | 128 | 301L, 309R, 312E, 321E | 108 |
| 351. | 8Aib, 32I, 34R | 168 | 116 | 301L, 309R, 312E, 321E | 108 |
| 352. | 8Aib, 32T, 34R | 169 | 116 | 301L, 309R, 312E, 321E | 108 |
| 353. | 8Aib, 32V, 34R | 170 | 116 | 301L, 309R, 312E, 321E | 108 |

-continued

| Fusion peptide SEQ ID NO | GLP-1 analogue | GLP-1 SEQ ID | Spacer SEQ ID | EGF(A) analogue | EGF(A) SEQ ID NO |
|---|---|---|---|---|---|
| 354. | 8Aib, 33G, 34R | 171 | 116 | 301L, 309R, 312E, 321E, 333K | 19 |
| 355. | 8Aib, 33G, 34R | 171 | 116 | 301L, 309R, 312E, 321K | 21 |
| 356. | 8Aib, 33G, 34R | 171 | 116 | 301L, 309R, 312E, 321E | 108 |
| 357. | 8Aib, 33G, 34R | 171 | 116 | 301L, 309R, 312E, 313K, 321E | 112 |
| 358. | 8Aib, 33G, 34R | 171 | 116 | 301L, 309R, 312E, 321E, 324K | 113 |
| 359. | 8Aib, 33G, 34R | 171 | 116 | 301L, 309R, 312E, 321E, 328K | 114 |
| 360. | 8Aib, 33G, 34R | 171 | 121 | 301L, 309R, 312E, 321E | 108 |
| 361. | 8Aib, 33G, 34R | 171 | 122 | 301L, 309R, 312E, 321E | 108 |
| 362. | 8Aib, 33G, 34R | 171 | 123 | 301L, 309R, 312E, 321E | 108 |
| 363. | 8Aib, 33G, 34R | 171 | 124 | 301L, 309R, 312E, 321E | 108 |
| 364. | 8Aib, 33G, 34R | 171 | 125 | 301L, 309R, 312E, 321E | 108 |
| 365. | 8Aib, 33G, 34R | 171 | 126 | 301L, 309R, 312E, 321E | 108 |
| 366. | 8Aib, 33G, 34R | 171 | 127 | 301L, 309R, 312E, 321E | 108 |
| 367. | 8Aib, 33G, 34R | 171 | 128 | 301L, 309R, 312E, 321E | 108 |
| 368. | 8Aib, 33I, 34R | 172 | 116 | 301L, 309R, 312E, 321E | 108 |
| 369. | 8Aib, 33L, 34R | 173 | 116 | 301L, 309R, 312E, 321E | 108 |
| 370. | 8Aib, 21K, 34R | 174 | 116 | 301L, 309R, 312E, 321E | 108 |
| 371. | 8Aib, 23K, 34R | 175 | 116 | 301L, 309R, 312E, 321E | 108 |
| 372. | 8Aib, 24K, 34R | 176 | 116 | 301L, 309R, 312E, 321E | 108 |
| 373. | 8Aib, 25K, 34R | 177 | 116 | 301L, 309R, 312E, 321E | 108 |
| 374. | 8Aib, 27K, 34R | 178 | 116 | 301L, 309R, 312E, 321E | 108 |
| 375. | 8Aib, 30K, 34R | 179 | 116 | 301L, 309R, 312E, 321E | 108 |
| 376. | 8Aib, 31K, 34R | 180 | 116 | 301L, 309R, 312E, 321E | 108 |
| 377. | 8Aib, 32K, 34R | 181 | 116 | 301L, 309R, 312E, 321E | 108 |
| 378. | 8Aib, 33K, 34R | 182 | 116 | 301L, 309R, 312E, 321E | 108 |
| 379. | 8Aib, 26R, 34R | 183 | 116 | 301L, 309R, 312E, 321E, 333K | 19 |
| 380. | 8Aib, 26R, 34R | 183 | 116 | 301L, 309R, 312E, 313K, 321K | 73 |
| 381. | 8Aib, 26R, 34R | 183 | 122 | 301L, 309R, 312E, 321E | 108 |
| 382. | 8Aib, 23K, 26R, 34R | 184 | 116 | 301L, 309R, 312E, 321E | 108 |
| 383. | 8Aib, 26R, 30K, 34R | 185 | 116 | 301L, 309R, 312E, 321E | 108 |
| 384. | 8Aib, 26R, 33K, 34R | 186 | 116 | 301L, 309R, 312E, 321E | 108 |
| 387. | 8Aib, 30G, 34R | 164 | 116 | 301L, 309R, 312E | 107 |
| 388. | 8Aib, 34R | 139 | 119 | 301L, 309R, 312E | 107 |

Examples with GLP-1 Analogue C-Terminal to the EGF(A) Analogue

| Fusion peptide SEQ ID NO | EGF(A) analogue | EGF(A) SEQ ID | Spacer SEQ ID | GLP-1 analogue | GLP-1 SEQ ID NO |
|---|---|---|---|---|---|
| 385. | 301L, 309R, 312E, 321E | 108 | 116 | 8Aib | 138 |
| 386. | 301L, 309R, 312E, 321E | 108 | 116 | 8Aib, 34R | 139 |

In one embodiment the invention relates to a fusion polypeptide selected from the group of fusion polypeptides defined by SEQ ID NO.: 188-384, 386-387.

In one embodiment the invention relates to a fusion polypeptide selected from the group of fusion polypeptides defined by SEQ ID NO.: 188-384.

In one embodiment the invention relates to a fusion polypeptide selected from the group of fusion polypeptides defined by SEQ ID NO.: 193, 226-233 and 381-384.

In one embodiment the invention relates to a fusion polypeptide selected from the group of fusion polypeptides defined by SEQ ID NO.: 379-380.

In one embodiment the invention relates to a fusion polypeptide selected from the group of fusion polypeptides defined by SEQ ID NO.: 193, 219 and 220.

In one embodiment the invention relates to a fusion polypeptide selected from the group of fusion polypeptides defined by SEQ ID NO.: 189, 193, 200-203 and 212-218.

In one embodiment the invention relates to a fusion polypeptide selected from the group of fusion polypeptides defined by SEQ ID NO.: 222-225.

In one embodiment the invention relates to a fusion polypeptide selected from the group of fusion polypeptides defined by SEQ ID NO.: 224-225.

In one embodiment the invention relates to a fusion polypeptide selected from the group of fusion polypeptides defined by SEQ ID NO.: 192-196.

In one embodiment the invention relates to a fusion polypeptide selected from the group of fusion polypeptides defined by SEQ ID NO.: 221, 236, 250, 264, 276, 279, 291, 294, 306, 307, 310, 324, 336, 339, 351, 352, 353, 356, 368 and 369.

In one embodiment the invention relates to a fusion polypeptide selected from the group of fusion polypeptides defined by SEQ ID NO.: 221, 250, 276, 279, 291, 294, 306, 307, 310, 324, 336, 351, 353, 356, 368 and 369.

In one embodiment the invention relates to a fusion polypeptide selected from the group of fusion polypeptides defined by SEQ ID NO.: 217, 218, 219, 220, 221, 310 and 386. In one embodiment the invention relates to a fusion polypeptide selected from the group of fusion polypeptides defined by SEQ ID NO.: 217, 218, 221, 310 and 386. In one embodiment the invention relates to a fusion polypeptide selected from the group of fusion polypeptides defined by SEQ ID NO.: 217, 218, 310 and 386. In one embodiment the invention relates to a fusion polypeptide selected from the group of fusion polypeptides defined by SEQ ID NO.: 221, 310 and 386. In one embodiment the invention relates to a fusion polypeptide selected from the group of fusion polypeptides defined by SEQ ID NO.: 310 and 386. In one embodiment the invention relates to a fusion polypeptide defined by SEQ ID NO.: 310.

In one embodiment the invention relates to a fusion polypeptide selected from the group of fusion polypeptides defined by SEQ ID NO.: 188 and 370-378.

In one embodiment the invention relates to a fusion polypeptide selected from the group of fusion polypeptides defined by SEQ ID NO.: 190, 191, 197, 198 and 199.

In one embodiment the invention relates to a fusion polypeptide selected from the group of fusion polypeptides defined by SEQ ID NO.: 204-211.

In one embodiment the invention relates to a fusion polypeptide selected from the group of fusion polypeptides defined by SEQ ID NO.: 240-247, 254-261, 268-275, 283-290, 298-305, 314-321, 328-335, 343-350 and 360-367.

In one embodiment the invention relates to a fusion polypeptide selected from the group of fusion polypeptides defined by SEQ ID NO.: 234-235, 237-239, 248-249, 251-253, 262-263, 265-267, 277-278, 280-282, 292-293, 295-297, 308-309, 311-313, 322-323, 325-327, 337-338, 340-342, 354-355 and 357-359.

In one embodiment the invention relates to a fusion polypeptide that comprises exactly one Lys residue.

In one embodiment the invention relates to a fusion polypeptide that comprises up to two Lys residues.

In one embodiment the invention relates to a fusion polypeptide that comprises two Lys residues.

In one embodiment the invention relates to a derivative comprising a fusion polypeptide or peptide back-bone defined by SEQ ID NO.: 188-384, or any of the above defined fusion polypeptide, as further described herein below.

GLP-1 Function

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it.

And a "full" GLP-1 receptor agonist may be defined as a GLP-1 receptor agonist which is capable of eliciting a magnitude of GLP-1 receptor response that is similar to native GLP-1.

In one embodiment the GLP-1 analogues of the invention are a GLP-1 receptor agonist. In some embodiments the GLP-1 analogues of the invention are a full GLP-1 receptor agonist. In some embodiments the bi-functional compounds of the invention are a GLP-1 receptor agonist. In some embodiments the bi-functional compounds of the invention are a full GLP-1 receptor agonist. In some embodiments the derivatives of the invention are a GLP-1 receptor agonist. In some embodiments the derivatives of the invention are a full GLP-1 receptor agonist.

It follows that the GLP-1 receptor agonist should display "GLP-1 activity" which refers to the ability of the compound, i.e. a GLP-1 analogue or a compound comprising a GLP-1 analogue, to bind to the GLP-1 receptor and initiate a signal transduction pathway resulting in insulinotropic action or other physiological effects as is known in the art. For example, the GLP-1 analogues, bi-functional compounds and derivatives thereof can be tested for GLP-1 activity using the GLP-1 potency assay described in Method section C. herein. In one embodiment the GLP-1 analogues or the compounds comprising the GLP-1 analogues, i.e. the GLP-1/EGF(A) fusion polypeptides and derivatives thereof have GLP-1 activity.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the GLP-1 analogues and compounds comprising the GLP-1 analogues may be determined as described above, and the $EC_{50}$ determined. The lower the $EC_{50}$ value, the better the potency.

In one embodiment the GLP-1 analogue or the compound comprising the GLP-1 analogues have an EC50 in the GLP-1 in vitro potency assay described in C1 (without HSA) of up to 50 pM, 50-100 pM, 100-250 pM or 250-1000 pM. In one embodiment the EC50 is at most 500 pM, such as at most 300 pM, such as at most 200 pM. In one embodiment the EC50 is comparable to human GLP-1(7-37), such as at most 50 pM. In a further embodiment the EC50 is at most 40 pM, such as at most 30 pM such as at most 20 pM, such as at most 10 pM. The high potency of compounds with a EC50 of around 10 pM is equivalent to the potency of the semaglutide molecule.

As described elsewhere herein the GLP-1 potency must be balanced with the potency of the EGF(A) analogue and therefore it may in some embodiments be preferred to include a GLP-1 analogue providing a GLP-1 potency that is less than the potency of semaglutide, such that the potency of the GLP-1 analogue or the compound comprising the GLP-1 analogue is reduced at least 2 fold, such as at least 5 fold compared to semaglutide, such as at least 10 fold, such as at least 25 fold, such as at least 50 fold, such as at least 100 fold compared to semaglutide. It may even be preferred that the potency is reduced compared to wt GLP-1.

In one embodiments, the EC50 (measured as described in C1 without HSA) of the GLP-1 analogues or the compound comprising the GLP-1 analogue is at least 25 pM, such as at least 50 pM, such as at least 75 pM, such as at least 100 pM, such as at least 250 pM, or such as at least 500 pM.

In such embodiments, the EC50 measured as described in (C1 without HSA) of the GLP-1 analogues or the compound comprising the GLP-1 analogue is at most 500 pM, such as at most 400 pM, such as at most 300 pM, such as at most 200 pM, such as at most 100 pM, such as at most 50 pM In further embodiments, the EC50 (measured as described in C1 without HSA) of the GLP-1 analogues or the compound comprising the GLP-1 analogue is 20-1000 pM, such as 50-500 pM, such as 100-250 pM, such as 75-100 pM.

In further embodiments, the EC50 (measured as described in C1 without HSA) of the GLP-1 analogues or the compound comprising the GLP-1 analogue is 20-800 pM, such as 20-600 pM, such as 20-400 pM, such as 20-200 pM or such as 20-100 pM Alternatively the EC50 (measured as described in C1 without HSA) of the GLP-1 analogues or the compound comprising the GLP-1 analogue is 200-1000 pM, such as 300-800 pM or such as 400-600 pM or 250-750 pM or 300-500 pM.

The above potency considerations are also relevant when evaluating potency in the presence of HSA.

In one embodiments, the EC50 (measured as described in C1 with 1% HSA) of the GLP-1 analogues or the compound comprising the GLP-1 analogue is at least 500 pM, such as at least 750 pM, such as at least 1000 pM, such as at least 1500 pM, or such as at least 2000 pM.

In such embodiments, the EC50 measured as described in (C1 with 1% HSA) of the GLP-1 analogues or the compound comprising the GLP-1 analogue is at most 2500 pM, such as at most 2000 pM, such as at most 1500 pM, such as at most 1250 pM, or such as at most 1000 pM In further embodiments, the EC50 (measured as described in C1 with 1% HSA) of the GLP-1 analogues or the compound comprising the GLP-1 analogue is 500-2500 pM, such as 500-2000 pM, such as 500-1500 pM, such as 500-1000 pM.

In further embodiments, the EC50 (measured as described in C1 with 1% HSA) of the GLP-1 analogues or the compound comprising the GLP-1 analogue is 750-2500 pM, such as 1000-2500 pM, such as 1500-2500 pM, such as 2000-2500 pM or such as 1800-2500 pM Alternatively the EC50 (measured as described in C1 with 1% HSA) of the GLP-1 analogues or the compound comprising the GLP-1 analogue is 500-2500 pM, such as 750-2000 pM or such as 1000-2000 pM or 1500-2000 pM. The GLP-1 potency may be reduced to allow for full binding to PCSK9 while reducing GLP-1 related side effects, such as, but not limited to nausea.

The in vitro binding affinity of GLP-1 analogues and compounds comprising a GLP-1 analogue may alternatively be tested in the in vitro binding assay described in C2, and the affinity for a compound with functionality equivalent to wt GLP-1 or semaglutide is in the neighbourhood of 1 nM when tested in the presence of low HSA.

In one embodiment the GLP-1 analogue or the compound comprising the GLP-1 analogues have an IC50 in the in vitro binding assay of at most 200 nM, in a further embodiment the IC50 is at most 100 nM, such as at most 75 nM, such as at most 50 nM, such as at most 25 nM, such as at most 10 nM, such as at most 5 nM. In some embodiments it may be preferred to have binding that is less than the binding of semaglutide, such that the binding of the GLP-1 analogue or a compound comprising a GLP-1 analogue is reduced at least 5 fold compared to semaglutide, such as at least 10 fold, such as at least 25 fold, such as at least 50 fold, such as at least 100 fold compared to semaglutide. It may even be preferred that the binding affinity is reduced compared to wt GLP-1.

In one embodiment, the IC50 (measured as described in C2 without HSA) of the GLP-1 analogues or a compound comprising a GLP-1 analogue is at least 1 nM, such as at least 5 nM, such as at least 10 nM, such as at least 25 nM, such as at least 50 nM, such as at least 100 nM.

In such embodiments, the IC50 measured as described in (C2 without HSA) of the GLP-1 analogues or a compound comprising a GLP-1 analogue is at most 200 nM, such as at most 100 nM, such as at most 75 nM, such as at most 50 nM, such as at most 25 nM, such as at most 15 nM, such as at most 10 nM, such as at most 5 nM.

In further embodiments, the IC50 (measured as described in C2 without HSA) of the GLP-1 analogues or a compound comprising a GLP-1 analogue is 0.1-200 nM, such as 1-100 nM, such as 5-75 nM, such as 5-50 nM.

The above considerations are relevant when evaluating binding in the absence of HSA. The GLP-1 binding may be reduced to allow for full binding to PCSK9 while reducing GLP-1 related side effects, such as, but not limited to nausea.

The GLP-1 effect may alternatively or additionally be measured in vivo by measuring the effect of GLP-1 analogues and compounds comprising a GLP-1 analogue on blood glucose and/or body weight. A reduction of blood glucose and/or body weight can be measured in suitable models, such as in db/db mice as described in C7 and in DIO rats as described in C8.

In on embodiment a GLP-1 analogue or compound comprising a GLP-1 analogue has the ability to reduce blood glucose in db/db mice as described in C7 herein. The effect can be estimated based on the area under the curve for delta blood glucose from 0 until 24 hours (AUC $\Delta BG_{24h}$) and the Effective Doses 50% (ED50, dose of GLP-1 derivative that gives a response halfway between baseline and maximal effect) calculated for AUC $\Delta BG_{24h}$.

In an embodiment it is preferred that the GLP-1 analogue or compound comprising a GLP-1 analogue has a EC50 AUC $\Delta BG_{24h}$ of less than 15 nmol/kg. In one embodiment the EC50 AUC $\Delta BG_{24h}$ is between 1-15, such as 2-12 or such as 5-10 nmol/kg.

The ability to reduce body weight may likewise be evaluated using the DIO rats as described in C8.

In one embodiment the GLP-1 analogue or compound comprising a GLP-1 analogue is capable of reducing body weight to at least 95% of baseline BW, when dosed with 300 nmol/kg/day and measured after 21 days.

In one embodiment the GLP-1 analogue or compound comprising a GLP-1 analogue is capable of reducing body weight to at least 90% of baseline BW, when dosed with 300 nmol/kg/day and measured after 21 days.

EGF(A) Function—(PCSK9i)

As described herein the EGF(A) analogue is a variant of the LDL-R(293-332) EGF(A) peptide defined by SEQ ID NO: 1. The EGF(A) analogues are herein defined as peptides comprising an amino acid sequence which is an analogue of SEQ ID NO: 1.

Such EGF(A) analogues preferably have the ability to bind to PCSK9. In a specific embodiment, the EGF(A) analogues have an improved ability to bind to PCSK9, for example compared to native LDL-R(293-332) (native EGF (A)) or to other PCSK9-binding compounds.

EGF(A) analogues may further have the ability to inhibit PCSK9 binding to LDL-R. In one embodiment the EGF(A) analogue is a PCSK9 inhibitor. In one embodiment the EGF(A) analogue inhibits PCSK9 binding to human Low Density Lipoprotein Receptor (LDL-R).

Such binding may be assessed using the assay described in Section C3 herein, which measures the ability of a test compound to competitively inhibit the binding of PCSK9 to human LDLR. Due to their ability to inhibit the interaction of PCSK9 with LDL-R, such compounds are referred to as PCSK9 inhibitors.

In one embodiment the EGF(A) analogues and compounds comprising an EGF(A) analogue (fusion polypeptide or derivatives) of the invention are PCSK9 inhibitor compounds or simply PCSK9 inhibitors. In one embodiment the invention relates to a compound comprising a EGF(A) analogue of SEQ ID NO.:1, wherein the analogue is capable of inhibiting PCSK9 binding to human Low Density Lipoprotein Receptor (LDL-R).

In one embodiment the EGF(A) analogue and compounds comprising said analogue) have an improved ability to bind PCSK9 compared to EGF(A) LDL-R(293-332) (SEQ ID 1). As the wt sequence has a relatively poor inhibitory function comparison may also be made to an EGF(A) analogue. In one embodiment the EGF(A) analogue (and compounds comprising said analogue) have an improved ability to bind PCSK9 compared to [299A, 301L, 307I, 309R, 310K]EGF (A) defined by SEQ ID NO.:2. The potency as measured in the ELISA assay provides an apparent affinity for the EGF (A) analogue or a compound comprising an EGF(A) analogue reported as a $K_i$ and as described in C3, a low Ki is characteristic for compounds with a strong inhibitory function.

In one embodiment the $K_i$ of the EGF(A) analogues and compounds comprising said analogue as measured in the PCSK9-LDL-R binding competitive ELISA assay (Section C3) is below 50 nM, such as below 25 nM or such as below 10 nM. In a further embodiment the $K_i$ of the EGF(A) analogues and compounds comprising said analogue as measured in the PCSK9-LDL-R binding competitive ELISA assay (Section C3) is below 8.0 nM, such as below 5.0 nM, such as below 2.5 nM or even below 2.0 nM. In one embodiment the $K_i$ of the EGF(A) analogues and compounds comprising said analogue as measured in the PCSK9-LDL-R binding competitive ELISA assay (Section C3) is 0.1-10.0 nM, such as 0.1-8.0 nM or 0.1-5.0 nM.

Functionality of EGF(A) analogues and compounds comprising such may be further characterized by their ability to improve LDL uptake, such as described in Section C4 herein.

In one embodiment the EGF(A) analogue and compounds comprising said analogue increases LDL uptake in the presence of PCSK9. In one embodiment the EGF(A) analogue and compounds comprising said are capable of reversing or reducing PCSK9 mediated reduction of LDL uptake.

In one embodiment the EGF(A) analogue and compounds comprising said analogue have a EC50 as measured in the LDL uptake assay below 1500 nM, such as below 1000 nM or such as below 500 nM.

The effect of an EGF(A) analogue and compounds comprising an analogue on blood cholesterol can be evaluated in a suitable model, such as by a study in DIO rats as described in section C8 herein. The study involves several administrations of the test compound and the effect is thus dependent on the dosage and frequency of administration. In the present studies the effect of both low, high and very high dosages was evaluated after 21 days.

In one embodiment the EGF(A) analogue or compound comprising the EGF(A) analogue is capable of reducing cholesterol by at least 0.5 mmol/L when dosed with 30 nmol/kg/day and measured after 21 days. In further embodiments the cholesterol level is reduces at least 0.6 or such as 0.8 mmol/L when dosed with 30 nmol/kg/day and measured after 21 days.

In one embodiment the EGF(A) analogue or compound comprising the EGF(A) analogue is capable of reducing cholesterol by at least 0.8 mmol/L when dosed with 300 nmol/kg/day and measured after 21 days. In further embodiments the cholesterol level is reduces at least 1.0 or such as 1.2 mmol/L when dosed with 300 nmol/kg/day and measured after 21 days.

Bifunctionality

As described herein above, different functionalities are associated with the two analogues, the GLP-1 analogue and the EGF(A) analogue. When combining the two, in compounds of the invention it is preferred that the functionalities of each analogue is maintained i.e. that the GLP-1 analogue has the ability to stimulate the GLP-1 receptor and that the EGF(A) analogue competitively binds PCSK9 and further that the compound comprising both analogues has both functionalities. The functionality of such compound may be tested in the assays described herein for testing GLP-1 and EGF(A) functionality.

In one embodiment the compounds are referred to as bi-functional molecules.

In order to obtain a compound suitable for therapeutic use the functionalities must be balanced to obtain the desired level of activity of both the PCSK9 inhibitor and the GLP-1 receptor agonist. In one embodiment the compound is a GLP-1 receptor agonist as described herein above. In one embodiment the compound is a PCSK9 inhibitor as described herein above. Measurement of GLP-1 receptor potency is described in section C1 and binding affinities for GLP-1 analogues are described in section C2, and these functional requirements are equally relevant for compounds comprising a GLP-1 analogue and an EGF(A) analogue.

Likewise the functionality of EGF(A) analogues have been described in the section on EGF(A) function and assays described in section C3, C4 and C6 herein.

The compounds according to the present invention, comprising a GLP-1 analogue and an EGF(A) analogue, are monovalent with regards to each of the analogues i.e. the compounds comprise one EGF(A) analogue and one GLP-1 analogue. To balance the GLP-1 receptor agonist function and the PCSK9 inhibitor function the analogues may individually be selected to obtain a suitable level of both activities. It is well known that high dosages of GLP-1 receptor agonists may provide side-effects such as nausea and it is therefore preferred to decrease GLP-1 potency while securing good PCSK9 inhibitory function to obtain a proper balance of both activities at the same plasma concentration.

In one embodiment the GLP-1 potency is reduced compared to GLP-1(3-37) or semaglutide as described herein above. In such embodiments, the EC50 measured by the in vitro cre luc assay (section C1 without HSA) is at least 10 pM In one embodiment the apparent $K_i$ measured by competitive ELISA (Section C3) is below 50 nM,)

In one embodiment the ratio of the apparent EGF(A) Ki (C3) and the GLP-1 potency (C1 without HSA) is at most 5000, such as at most 4000, such as at most 3000, such as at most 2000 or such as at most 1000.

In one embodiment the ratio of the apparent EGF(A) Ki (C3) and the GLP-1 potency (C1 without HSA) is at most 1000, such as at most 800, such as at most 600, such as at most 400 or such as at most 200.

In one embodiment the ratio of the apparent EGF(A) Ki (C3) and the GLP-1 potency (C1 without HSA) is at most 200, such as at most 150, such as at most 100, such as at most 50.

In order to confirm that the compound is truly bifunctional it is preferable to evaluate the functionalities which as described herein can be done in the DIO rats as described in section C8 herein, wherein the effect on both body weight and cholesterol can be measured.

In one embodiment the compound is capable of reducing cholesterol and body weight at least equal to GLP-1/EGF(A) Compound #41 in an in vivo rat study as described in section C8 herein.

In one embodiment the compound is capable of reducing cholesterol by at least 0.5 mmol/L when dosed with 30 nmol/kg/day and measured after 21 days.

In further embodiments the cholesterol level is reduces at least 0.6 or such as 0.8 mmol/L when dosed with 30 nmol/kg/day and measured after 21 days.

In one embodiment the compound is capable of reducing cholesterol by at least 0.8 mmol/L when dosed with 300 nmol/kg/day and measured after 21 days.

In further embodiments the cholesterol level is reduces at least 1.0 or such as 1.2 mmol/L when dosed with 300 nmol/kg/day and measured after 21 days.

In one embodiment the compound is capable of reducing body weight to at least 95% of baseline BW, when dosed with 300 nmol/kg/day and measured after 21 days.

In one embodiment the compound is capable of reducing body weight to at least 90% of baseline BW, when dosed with 300 nmol/kg/day and measured after 21 days.

Derivative

The term "derivative" as used herein in the context of a bi-functional compound means a chemically modified bi-functional compound, in which one or more substituents has been covalently attached to the compound.

As described herein above, the substituent is covalently attached to the compounds. Multiple ways of attaching substituents to a polypeptides is known, such as by attaching the substituent via the N-terminal, the C-terminal or an internal amino acid residue.

In one embodiment, the compound may comprise one or more substituents. In one embodiment, the compound comprises one or two substituents. In one embodiment, the compound has one or two substituents. In one embodiment, the compound has one substituent. In one embodiment, the compound has two substituents.

In embodiments where the compound has two substituents it is preferred that the two substituents are identical.

In one embodiment the one or two substituents are attached to nitrogen atoms of the peptide back-bone. In one embodiment the one or two substituents are attached to amino groups of the peptide back-bone. In one embodiment the one or two substituents are attached to the epsilon nitrogen's of one or two Lys residues.

In one embodiment the two substituents are attached to different Lys residues of the peptide back-bone. In one embodiment the two substituents are attached to the epsilon-nitrogens of different Lys residues in the peptide back-bone.

As described herein above the fusion polypeptide or the peptide back-bone of the derivative comprising or consisting of an GLP-1 analogue, a peptide spacer and an EGF(A) analogue may have one or more Lys residues. Various examples of GLP-1 analogues, peptide spacers and EGF(A) analogues with different numbers of Lys residues have been described herein above, and such sequences may be combined to obtain the fusion polypeptide or peptide back-bone having exactly one or two Lys residues.

In one embodiment the peptide back-bone has one or two Lys residues. In one embodiment the peptide back-bone comprise only one Lys residue. In one embodiment the peptide back-bone comprise exactly two Lys residues.

In one embodiment the peptide back-bone comprise a GLP-1 analogue comprising one or two Lys residues. In one embodiment the peptide back-bone comprise a GLP-1 analogue comprising only one Lys residue. In one embodiment the peptide back-bone comprise a GLP-1 analogue comprising exactly two residues.

In one embodiment the peptide back-bone comprise an EGF(A) analogue comprising one or two Lys residues. In one embodiment the peptide back-bone comprise a an EGF(A) analogue comprising only one Lys residue. In one embodiment the peptide back-bone comprises an EGF(A) analogue comprising exactly two Lys residues.

In one embodiment the peptide back-bone comprise a peptide spacer comprising one or two Lys residues. In one embodiment the peptide back-bone comprise a peptide spacer comprising only one Lys residue. In one embodiment the peptide back-bone comprise a peptide spacer comprising exactly two residues.

In an embodiment the substituent is aimed at improving the functionality of the peptides.

In one embodiment the substituent increases half-life of the compound, so that the plasma half-live of a derivative comprising a peptide backbone and a substituent have an increased half-life compared to the half-life of the peptide backbone as illustrated herein (Section C5, table 5).

Methods for determining half-life in different species are well known in the art and exemplified herein for minipigs (Section C5).

In one embodiment the derivative according to the invention has a half-life above 12 hours.

In one embodiment the derivative according to the invention has a half-life above 24 hours, such as above 36 hours or such as above 48 hours in minipigs measured after either subcutaneously or intravenously dosing.

Substituent

The term "substituent" refers to a moiety that is attached to a polypeptide via an amino acid residue, by substituting the atom normally present in the same position. Frequently the substituent replaces a hydrogen atom, such as a hydrogen of an amino group ($-NH_2$). The substituent is thus a moiety covalently attached to a peptide or polypeptide. According to the invention it is preferred that the moiety e.g. the substituent has no or minimal effect on the functionality of the peptide while adding other beneficial properties, such as increase stability or increase half-life.

In one embodiment, a half-life extending substituent is a protein moiety. In a further such embodiment the protein moiety may include human albumin, an Fc-domain or an unstructured protein extension. In a further embodiment the protein moiety may by fused to one of the analogues. In a further embodiment, the protein moiety is an Fc domain and the Fc domain is fused to the GLP-1 analogue or the EGF(A) analogue. When an Fc fusion is prepared the resulting compound will usually be divalent as two Fc-polypeptides will form one Fc-domain.

In one embodiment the substituent is not a protein moiety.

In one embodiment the substituent is not a protein moiety fused to the peptide back-bone.

In another embodiment the substituent is a non-protein moiety.

In a particular embodiment, the substituent is capable of forming non-covalent complexes with albumin, thereby promoting the circulation of the derivative within the blood stream, and also having the effect of protracting the time of action of the derivative. In a particular embodiment, the substituent is capable of protracting the time of action of the derivative without substantially decreasing its binding capacity to PCSK9 and/or the GLP-1 receptor.

In one embodiment the derivative comprises a half-life extending substituent. Various half-life extending substituents are well-known in the art and include in particular albumin binders comprising a fatty acid group as described further below, and such albumin binders are non-protein substituents.

The substituent comprises at least one fatty acid group.

In a particular embodiment, the fatty acid group comprises a carbon chain which contains at least 8 consecutive —$CH_2$— groups. In one embodiment the fatty acid group comprise at least 10 consecutive —$CH_2$— groups, such as least 12 consecutive —$CH_2$— groups, at least 14 consecutive —$CH_2$— groups, at least 16 consecutive —$CH_2$— groups, at least 18 consecutive —$CH_2$— groups.

In one embodiment the fatty acid group comprises 8-20 consecutive —$CH_2$— groups. In one embodiment the fatty acid group comprises 10-18 consecutive —$CH_2$— groups. In one embodiment the fatty acid group comprises 12-18 consecutive —$CH_2$— groups. In one embodiment the fatty acid group comprises 14-18 consecutive —$CH_2$— groups.

In situations where the derivative comprise two substituents, an increased half-life may be obtained with shorter fatty acid groups, thus in an embodiment where the derivate comprise two substituents the fatty acid groups may comprise at least 8 consecutive —$CH_2$— groups, such as least 10 consecutive —$CH_2$— groups, such as least 12 consecutive —$CH_2$— groups, at least 14 consecutive —$CH_2$— groups, at least 16 consecutive —$CH_2$— groups, at least 18 consecutive —$CH_2$— groups.

In a further embodiment where the derivative comprises two substituents, the substituents each comprise a fatty acid group comprising 8-18 consecutive —$CH_2$— groups. In further such embodiments the fatty acid groups comprise 10-18 consecutive —$CH_2$— groups, such as 12-18 consecutive —$CH_2$— groups, such as 14-18 consecutive —$CH_2$— groups. The term "fatty acid group" as used herein may be referred to as chemical group comprising at least one functional group being a Brønsted-Lowry acid with a pKa <7.

In one embodiment the substituent comprises at least eight consecutive —$CH_2$-groups and at least one functional group (FG) with a pKa <7. Non-limiting examples of such functional groups that are Brønsted-Lowry acids include carboxylic acids (including also carboxyphenoxy).

The fatty acid group in one embodiment comprise a carbonyl at the opposite end of the function group (the acid), such fatty acid groups may also be referred to as di-acids.

In one embodiment the term "protractor" may be used to describe the fatty acid group which is the terminal part of the substituent responsible for extending half-life of the compound.

In one embodiment the protractor may be defined by:
Chem. 1: HOOC—$(CH_2)_n$—CO—* wherein n is an integer in the range of 8-20, which may also be referred to as a C(n+2) diacid or as
Chem. 1b:

HO—C(=O)—[CH_2]_n—C(=O)—*, wherein n is an integer in the range of 8-20.

In one embodiment the protractor may be defined by:
Chem. 2: HOOC—$(C_6H_4)$—O—$(CH_2)_m$—CO—* wherein m is an integer in the range of 8-11 or as
Chem. 2b:

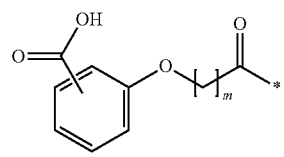

wherein the carboxy group is in position 2, 3 or 4 of the ($C_6H_4$) group of Chem. 3 and wherein m is an integer in the range of 8-11. In one embodiment the protractor may be defined by Chem1, Chem 1b, Chem 2 or Chem 2b as defined above.

Substituents according to the invention in an embodiment comprise one or more linker elements. The linker elements may be linked to each other and the protractor by amide bonds and referred to as "Z" (see further below).

As further defined herein below the number of linker elements may be at most 6, referred to as Z1-Z2-Z3-Z4-Z5-Z6-, where Z1 is connected with the protractor (Pro-) and the last Z element is connected with the peptide, in which case the substituent may be referred to as Pro-Z1-Z2-Z3-Z4-Z5-Z6-. The symbol * above thus indicates the attachment point to Z1, which when bound via an amide bond is a nitrogen. In an embodiment, where Z1 is a bond (see below), the symbol * indicates the attachment point to the nitrogen of the neighbouring Z element.

In one embodiment the substituent is defined by: Pro-Z1-Z2-Z3-Z4-Z5-Z6- wherein Pro- is selected from Chem1, Chem 1b, Chem 2 and Chem 2b and wherein n is an integer in the range of 8-20 and m is an integer in the range of 8-11.

In a particular embodiment, n is 8, 9, 10, 11, 12, 13, 14, 15, 16, 17, 18, 19 or 20 in Chem. 1 or 1b and m is 8, 9, 10 or 11.

The term "bond" as used here means a covalent bond. When a linker element of Z1-Z6 is defined as a bond, it is equivalent to a situation wherein said component is absent. The indication herein below that any of Z1-Z6 is a bond may also be read as any of $Z1-Z_6$ being absent. Logically "a bond" cannot follow "a bond". The indication "a bond" here thus means that the previous Z element is covalently linked to the next Z element that is not "a bond" (or absent).

The linker elements Z1-Z6 are individually selected from chemical moieties capable of forming amide bonds, including amino acid like moieties, such as Glu, γGlu (also termed gamma Glu or gGlu and defined by *—NH—CH—(COOH)—$CH_2$—$CH_2$—CO—*) Gly, Ser, Ala, Thr, Ado, Aeep and Aeeep and further moieties as described below.

In one embodiment the Z1 element is optional, in one such embodiment Z1 is selected from Chem. 3: *—NH—CH$_2$—(C$_6$H$_{10}$)—CO—* or Chem. 3b:

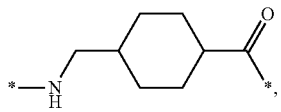

and a bond.

Chem.3 may also be referred to as Trx for Tranexamic acid trans-4-(aminomethyl)cyclohexanecarboxylic acid, where Chem 3. covers the o-(1,2), m-(1,3) and p-(1,4) forms, while Chem 3b.specifies the p-(1,4) form.

In one embodiment Z2 is selected from γGlu, Glu, or a bond. In one embodiment Z2 is γGlu.

In one embodiment Z3, Z4, Z5 and Z6 are selected, independently of each other, from Glu, γGlu, Gly, Ser, Ala, Thr, Ado, Aeep and Aeeep and a bond.

Glu, Gly, Ser, Ala, Thr are amino acid residues well known in the art.

γGlu is defined by Chem. 4: *—NH—CH(COOH)—(CH$_2$)$_2$—CO—* which is the same as Chem. 4b:

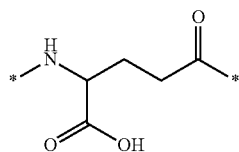 [SMILES: *NC(CCC(*)=O)C(=O)O]

and may also be referred to as γGlu.

Ado is defined by Chem. 5: *—NH—(CH$_2$)$_2$—O—(CH$_2$)$_2$—O—CH$_2$—CO—* may also be referred to as 8-amino-3,6-dioxaoctanoic acid and which is the same as Chem. 5b:

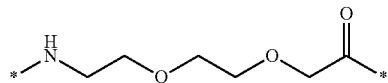 [SMILES: *NCCOCCOCC(*)=O]

Aeep is defined by Chem. 6: *NH—CH$_2$CH$_2$OCH$_2$CH$_2$OCH$_2$CH$_2$C0*, which may also be referred to as Chem. 6b:

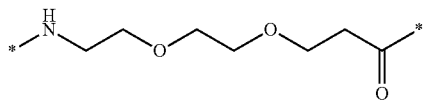 [SMILES: *NCCOCCOCCC(*)=O]

Aeeep is defined of Chem. 7: *NH—CH$_2$CH$_2$OCH$_2$CH$_2$OCH$_2$CH$_2$OCH$_2$CH$_2$CO*, which may also be referred to as Chem. 7b:

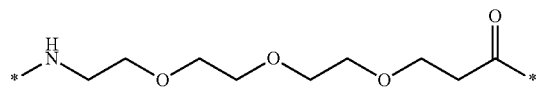 [SMILES: *NCCOCCOCCOCCC(*)=O]

In one embodiment Z$_3$, Z$_4$, Z$_5$ and Z$_6$ are selected, independently of each other, from Glu, γGlu, Gly, Ala, Ado, Aeep and Aeeep and a bond.

In one embodiment Z$_3$, Z$_4$, Z$_5$ and Z$_6$ are selected, independently of each other, from Glu, γGlu, Gly, Ala, Ado and a bond.

In one embodiment Z$_3$, Z$_4$, Z$_5$ and Z$_6$ are selected, independently of each other, from Glu, γGlu, Gly, Ado and a bond.

In one embodiment Z$_3$, Z$_4$, Z$_5$ and Z$_6$ are selected, independently of each other, from γGlu, Gly, Ado and a bond.

In one embodiment Z$_3$, Z$_4$, Z$_5$ and Z$_6$ are selected, independently of each other, from γGlu, Ado and a bond.

In an embodiment the substituent(s) is/are selected from the group of substituents defined by #1 to #14 below.

| Substituent # | Pro Chem 1 or 2 | Z1 Chem3 | Z2 Chem 4 | Z3 Chem 5 | Z4 Chem 4/5 | Z5 Chem 4/5 | Z6 Chem 4/5 |
|---|---|---|---|---|---|---|---|
| 1. | C18 diacid | — | γGlu | Ado | Ado | — | — |
| 2. | C18 diacid | — | γGlu | Ado | Ado | Ado | Ado |
| 3. | C18 diacid | — | γGlu | — | Ado | — | — |
| 4. | C18 diacid | — | γGlu | — | — | — | — |
| 5. | C20 diacid | — | γGlu | Ado | Ado | — | — |
| 6. | C20 diacid | Trx | γGlu | Ado | Ado | — | — |
| 7. | C20 diacid | Trx | γGlu | — | γGlu | γGlu | γGlu |
| 8. | C20 diacid | Trx | γGlu | Ado | Ado | Ado | — |
| 9. | C20 diacid | Trx | γGlu | — | γGlu | — | — |
| 10. | C20 diacid | Trx | γGlu | — | Ado | — | — |
| 11. | C20 diacid | Trx | γGlu | Ado | Ado | Ado | Ado |
| 12. | C20 diacid | Trx | γGlu | — | — | — | — |
| 13. | 4—COOH—PhO—C11 | — | γGlu | Ado | Ado | — | — |
| 14. | C16 diacid | — | γGlu | Ado | Ado | — | — |

Substituent #1 is defined by Chem. 6: HOOC—(CH$_2$)$_{16}$—CO-γGlu-Ado-Ado-* which is the same as Chem. 6b:
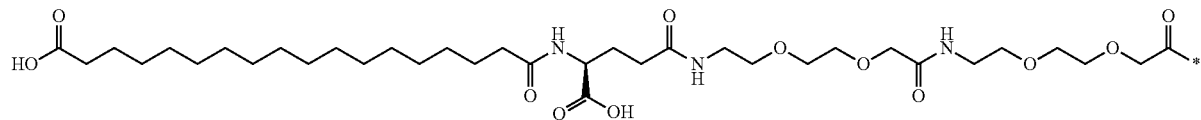 [SMILES: *C(=O)COCCOCCNC(=O)COCCOCCNC(=O)CC[C@H](NC(=O)CCCCCCCCCCCCCCCCC(=O)O)C(=O)O]
Substituent #2 is defined by Chem. 7: HOOC—(CH$_2$)$_{16}$—CO-γGlu-Ado-Ado-Ado-Ado-* which is the same as Chem. 7b:
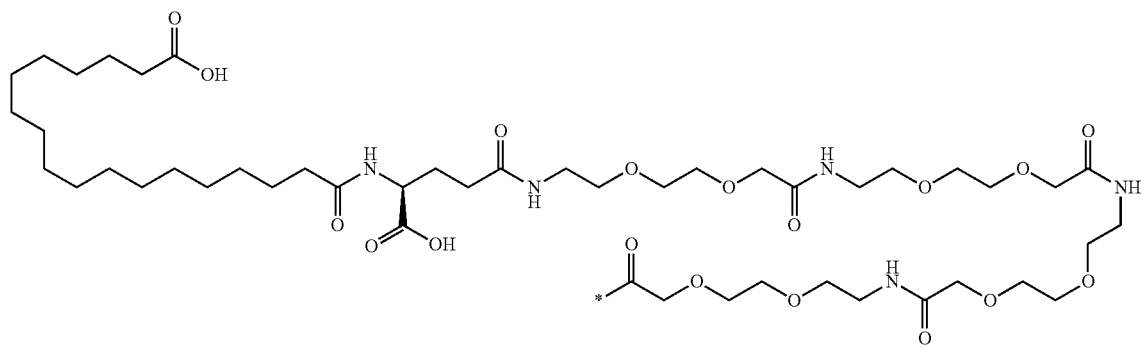 [SMILES: *C(=O)COCCOCCNC(=O)COCCOCCNC(=O)COCCOCCNC(=O)COCCOCCNC(=O)CC[C@H](NC(=O)CCCCCCCCCCCCCCCCC(=O)O)C(=O)O]
Substituent #3 is defined by Chem. 8: HOOC—(CH$_2$)$_{16}$—CO-γGlu-Ado* which is the same as Chem. 8b:
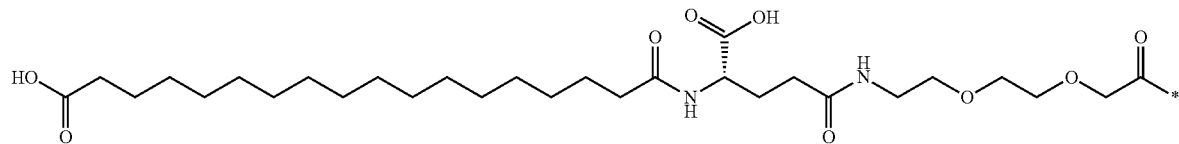 [SMILES: *C(=O)COCCOCCNC(=O)CC[C@H](NC(=O)CCCCCCCCCCCCCCCCC(=O)O)C(=O)O]
Substituent #4 is defined by Chem. 9: HOOC—(CH$_2$)$_{16}$—CO-γGlu-* which is the same as Chem. 9b:
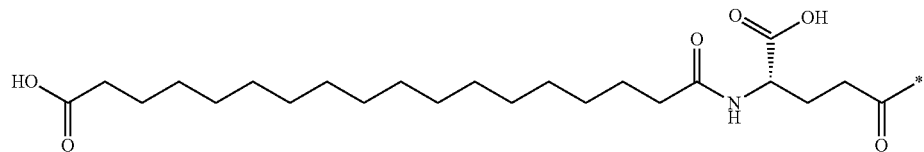 [SMILES: *C(=O)CC[C@H](NC(=O)CCCCCCCCCCCCCCCCC(=O)O)C(=O)O]

Substituent #5 is defined by Chem. 10: HOOC—(CH$_2$)$_{18}$—CO-γGlu-Ado-Ado-* which is the same as Chem. 10b:
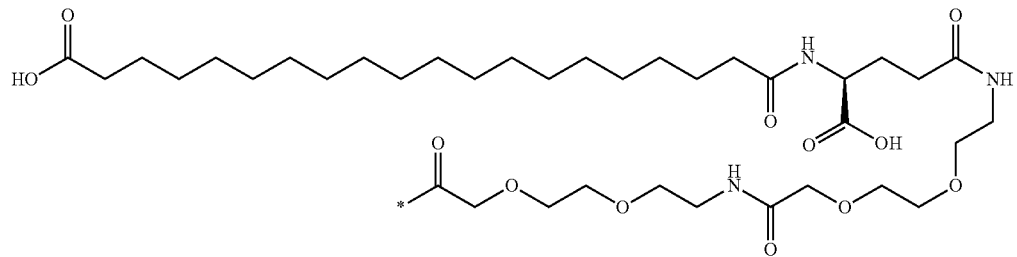 [SMILES: *C(=O)COCCOCCNC(=O)COCCOCCNC(=O)CC[C@H](NC(=O)CCCCCCCCCCCCCCCCCCC(=O)O)C(=O)O]
Substituent #6 is defined by Chem. 11: HOOC—(CH$_2$)$_{18}$—CO-Trx-γGlu-Ado-Ado-* which is specified as Chem. 11b:
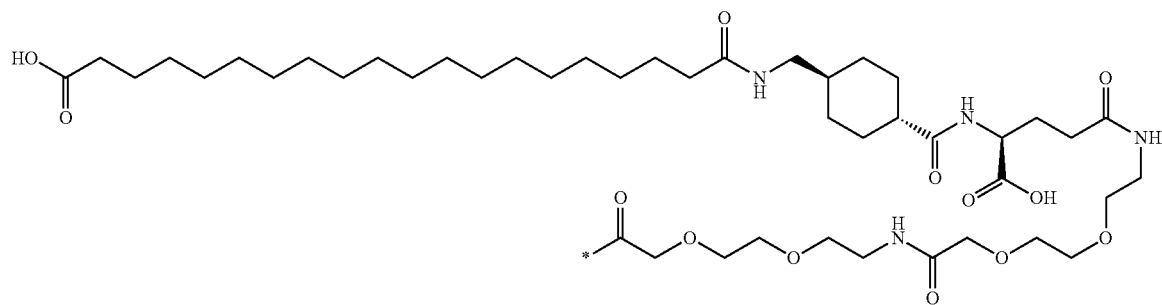 [SMILES: *C(=O)COCCOCCNC(=O)COCCOCCNC(=O)CC[C@H](NC(=O)[C@H]1CC[C@H](CNC(=O)CCCCCCCCCCCCCCCCCCC(=O)O)CC1)C(=O)O]
Substituent #7 is defined by Chem. 12: HOOC—(CH$_2$)$_{18}$—CO-Trx-γGlu-γGlu-γGlu-γGlu-* which is specified as Chem. 12b:
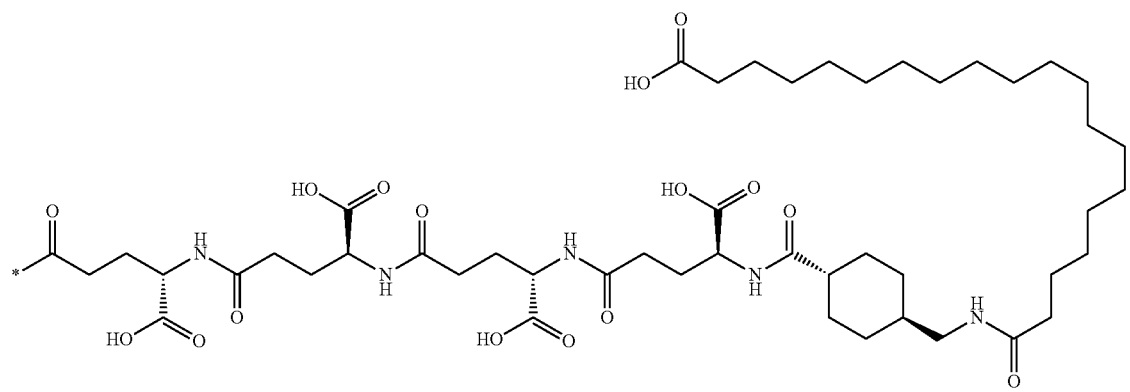 [SMILES: *C(=O)CC[C@H](NC(=O)CC[C@H](NC(=O)CC[C@H](NC(=O)CC[C@H](NC(=O)[C@H]1CC[C@H](CNC(=O)CCCCCCCCCCCCCCCCCCC(=O)O)CC1)C(=O)O)C(=O)O)C(=O)O)C(=O)O]

Substituent #8 is defined by Chem. 13: HOOC—(CH$_2$)$_{18}$—CO-Trx-γGlu-Ado-Ado-Ado-* which is specified as Chem. 13b:
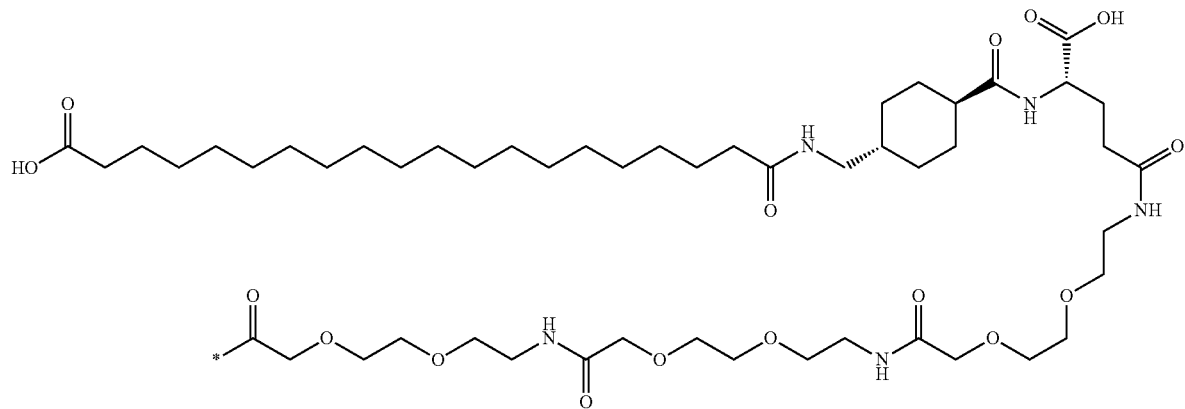 [SMILES: *C(=O)COCCOCCNC(=O)COCCOCCNC(=O)COCCOCCNC(=O)CC[C@H](NC(=O)[C@H]1CC[C@H](CNC(=O)CCCCCCCCCCCCCCCCCCC(=O)O)CC1)C(=O)O]
Substituent #9 is defined by Chem. 14: HOOC—(CH$_2$)$_{18}$—CO-Trx-γGlu-γGlu-* which is specified as Chem. 14b:
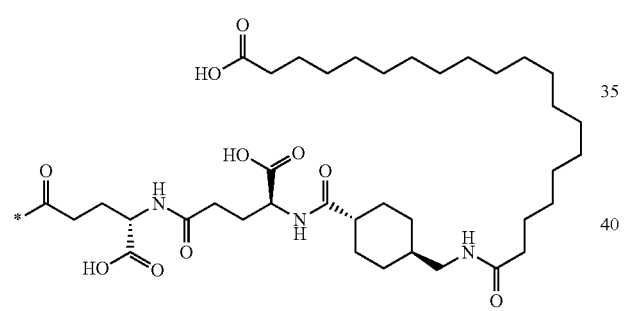
Substituent #10 is defined by Chem. 15: HOOC—(CH$_2$)$_{18}$—CO-Trx-γGlu-Ado-* which is specified as Chem. 15b:
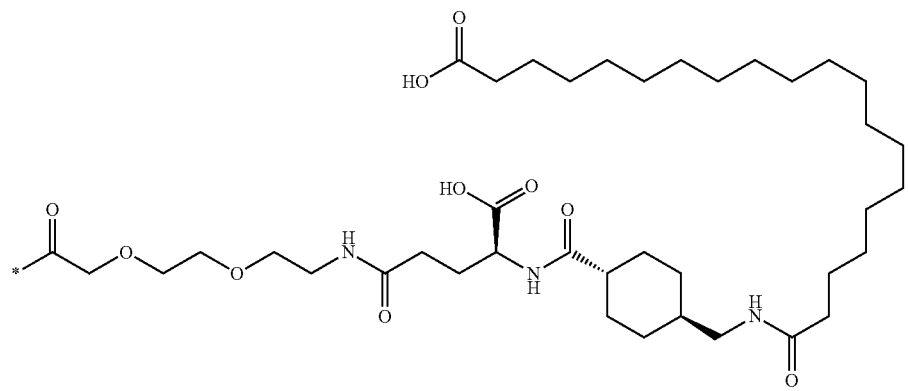 [SMILES: *C(=O)COCCOCCNC(=O)CC[C@H](NC(=O)[C@H]1CC[C@H](CNC(=O)CCCCCCCCCCCCCCCCCCC(=O)O)CC1)C(=O)O]

Substituent #11 is defined by Chem. 16: HOOC—(CH$_2$)$_{18}$—CO-Trx-γGlu-Ado-Ado-Ado-Ado-* which is specified as
Chem. 16b:
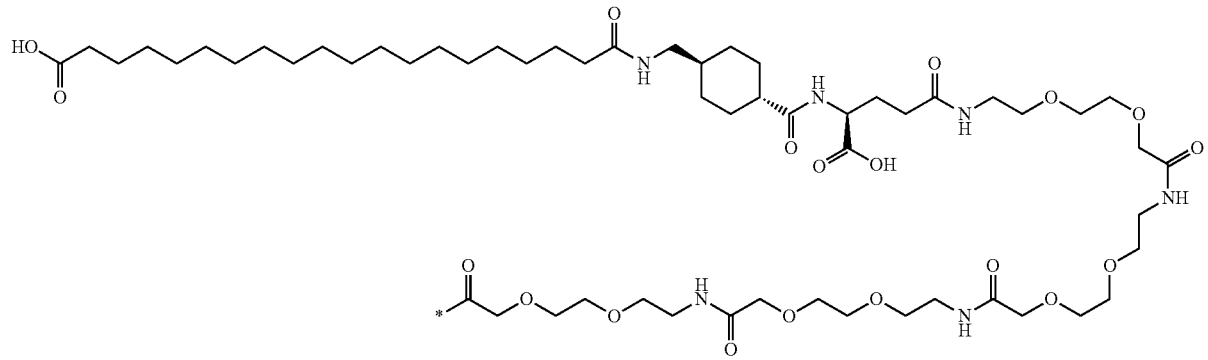 [SMILES: *C(=O)COCCOCCNC(=O)COCCOCCNC(=O)COCCOCCNC(=O)COCCOCCNC(=O)CC[C@H](NC(=O)[C@H]1CC[C@H](CNC(=O)CCCCCCCCCCCCCCCCCCC(=O)O)CC1)C(=O)O]
Substituent #12 is defined by Chem. 17: HOOC—(CH$_2$)$_{18}$—CO-Trx-γGlu-* which is specified as
Chem. 17b:
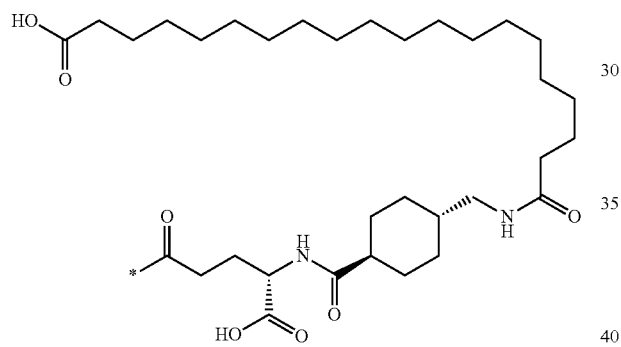
Substituent #13 is defined by Chem. 18: 4-COOH-PhO-C11-γGlu-Ado-Ado-* which is specified as
Chem. 18b:
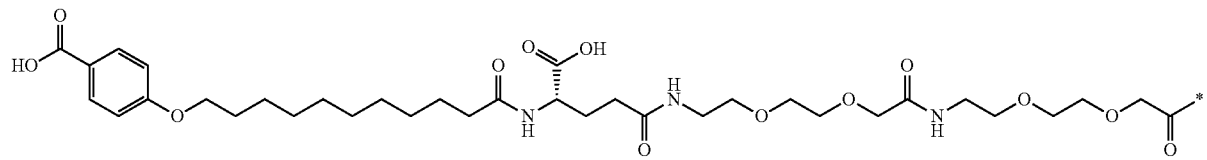 [SMILES: *C(=O)COCCOCCNC(=O)COCCOCCNC(=O)CC[C@H](NC(=O)CCCCCCCCCCOc1ccc(C(=O)O)cc1)C(=O)O]
Substituent #14 is defined by Chem. 19: HOOC—(CH$_2$)$_{14}$—CO-γGlu-Ado-Ado-* which is specified as
Chem. 19b:
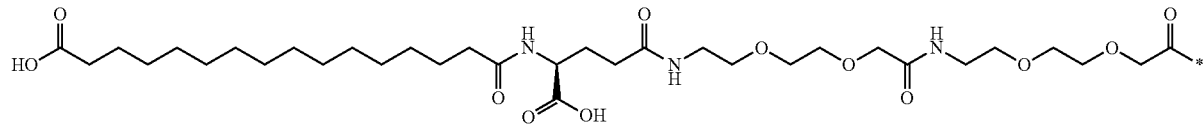 [SMILES: *C(=O)COCCOCCNC(=O)COCCOCCNC(=O)CC[C@H](NC(=O)CCCCCCCCCCCCCCC(=O)O)C(=O)O]

Bifunctional Compounds

Multiple fusion compounds are described herein and as described elsewhere the challenge is to ensure that both functionalities are maintained and balanced. The compounds disclosed include variation in the EGF(A) analogue, the spacer and the GLP-1 analogue and the order of the elements.

In one embodiment the fusion polypeptide comprises the GLP-1 analogue in the N-terminal and the EGF(A) analogue in the C-terminal, which was found to be important to maintain GLP-1 functionality.

In further embodiments the sequence of the EGF(A) analogues should the very least include the 301L mutation, and preferable one or more of 309R and 309I as described in details herein and exemplified by the sequences of the EGF(A) analogue identified by SEQ ID NO.: 107 and 108 which may also include a 312E mutation to remove the wildtype lysine.

In one embodiment the GLP-1 analogue comprises mutations as described herein above, such as a mutation of residue 8, to such as 8Aib, 8G or 8W, and residue 34, to such as 34R, this allows for the substituent to be attached to K26. A further mutation such as 30G may be favourable to reduce the potency of the GLP-1 analogue.

In such embodiments the compound comprises a GLP-1 analogue and an EGF(A) analogue, wherein
i) said GLP-1 analogue is identified by SEQ ID No.: 139, 140, 141, 142 or 164 and
ii) said EGF(A) analogue is identified by SEQ ID No.: 107, 108 109.

In one embodiment the compound comprises a GLP-1 analogue and an EGF(A) analogue, wherein
i) said GLP-1 analogue is identified by SEQ ID No.: 139 or 164 and
ii) said EGF(A) analogue is identified by SEQ ID No.: 107 or 108.

In one embodiment the compound comprises a GLP-1 analogue and an EGF(A) analogue, wherein
i) said GLP-1 analogue is identified by SEQ ID No.: 164 and
ii) said EGF(A) analogue is identified by SEQ ID No.: 108.

In one embodiment the compound is any of the GLP-1/EGF(A) compounds #1-74 and 76-314.

In one embodiment the compound is selected from the group of compounds defined as GLP-1/EGF(A) compounds #1-74, 76-314.

In one embodiment the compound is the GLP-1/EGF(A) compounds #69 and/or #306. In one embodiment the compound is the GLP-1/EGF(A) compound #69. In one embodiment the compound is the GLP-1/EGF(A) compound #306.

In one embodiment the compound is the GLP-1/EGF(A) compounds #41 and/or #48. In one embodiment the compound is the GLP-1/EGF(A) compound #41. In one embodiment the compound is the GLP-1/EGF(A) compound #48.

Methods of Preparation

The compounds described herein may be prepared using common general knowledge. The backbone or fusion polypeptide may be provided either by chemical synthesis (as described in Method section A1) or by heterologous expression. Expression vectors encoding the fusion polypeptide can be prepared by ordinary molecular biology and a suitable host can be selected. Methods may also be combined whereby one part of the back-bone is prepared synthetically while another part of the back-bone is prepared by recombinant technology. The substituent may be attached to the peptide back-bone during chemical synthesis or in a subsequent reaction with the back-bone or part hereof. Independently of the method of preparation the compounds are defined by their elements e.g. a fusion polypeptide (the peptide back-bone) and one or more substituent(s).

An aspect of the invention relates to a method of preparing a fusion polypeptide comprising a GLP-1 analogue and a EGF(A) analogue as described herein.

An aspect of the invention relates to a method of preparing a derivative of a fusion polypeptide comprising a GLP-1 analogue and an EGF(A) analogue further comprising one or more substituents covalently attached to the fusion polypeptide.

Pharmaceutical Composition

The invention also relates to pharmaceutical compositions comprising a compound of the invention (or a pharmaceutically acceptable salt, amide, or ester thereof), and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, diluent, tablet aid, and/or to improve administration, and/or absorption of the active substance. Non-limiting examples of excipients are: solvents, diluents, buffers, preservatives, tonicity regulating agents, chelating agents, and stabilisers. The formulation of pharmaceutically active ingredients with various excipients is known in the art, see e.g. Remington: The Science and Practice of Pharmacy (e.g. 19$^{th}$ edition (1995), and any later editions).

A composition of the invention may be in the form of a liquid formulation, i.e. aqueous formulation comprising water. A liquid formulation may be a solution, or a suspension. Alternatively, it may be a solid formulation, e.g. a freeze-dried or spray-dried composition.

A composition of the invention may be for parenteral administration, e.g. administration is to be performed by subcutaneous, intramuscular, intraperitoneal or intravenous injection by means of a syringe, optionally a pen-like syringe, or by means of an infusion pump.

A pharmaceutical composition of the invention may further comprise a second active ingredient, such as a therapeutic agent, which may simplify administration in case of combination treatments.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0, such as from 7.0 to 9.5, or from 3.0 to 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

The derivative or analogue may be administered in the form of a pharmaceutical composition. It may be administered to a patient in need thereof by various routes known in the art. The route of administration may be, for example, parenteral, epidermal; dermal; transdermal; conjunctival; uretal; vaginal; rectal; and/or ocular, lingual; sublingual; buccal; in the mouth; oral; in the stomach; in the intestine; nasal; pulmonary, such as through the bronchioles, the alveoli, or a combination thereof.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may further be compounded in a drug carrier or drug delivery system, e.g. in order to improve stability, bioavailability, and/or solubility. A composition may also be used in the formulation of controlled, sustained, protracting, retarded, and/or slow release drug delivery systems.

Medical Use

In one aspect the invention relates to the use of a compound according to the invention for use in the manufacture of a medicament.

The invention also relates to a compound of the invention or a pharmaceutical composition thereof for use as a medicament or in the manufacture of a medicament.

In an embodiment, a compound of the invention or a composition thereof may be used for treatment or prevention of cardiovascular diseases and/or cardiovascular risks.

In an embodiment, a compound of the invention or a composition thereof may be used for
i. improving lipid parameters, such as prevention and/or treatment of dyslipidemia, lowering total serum lipids; lowering LDL-C, increasing HDL; lowering small, dense LDL; lowering VLDL; lowering triglycerides; lowering cholesterol; lowering plasma levels of lipoprotein a (Lp(a)); inhibiting generation of apolipoprotein A (apo(A));
ii. the prevention and/or the treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or the reduction of blood pressure, such as reduction of systolic blood pressure; the treatment of cardiovascular disease.

The invention also relates to a method for treatment or prevention of cardiovascular diseases and/or cardiovascular risks The invention further relates to a method for (i) improving lipid parameters, such as prevention and/or treatment of dyslipidemia, lowering total serum lipids; increasing HDL- C; lowering LDL-C, lowering small, dense LDL-C; lowering VLDL-C; lowering triglycerides; lowering cholesterol; lowering plasma levels of lipoprotein a (Lp(a)); inhibiting generation of apolipoprotein A (apo(A)); (ii) prevention and/or treatment of cardiovascular diseases, such as cardiac syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis oblitterens), diastolic dysfunction, and/or systolic dysfunction; and/or reduction of blood pressure, such as reduction of systolic blood pressure; the treatment of cardiovascular disease; wherein a pharmaceutically active amount of a compound according to the invention is administered.

In some embodiments, the compound of the invention may be used for the following medical treatments:

i. prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

ii. delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

iii. improving β-cell function, such as decreasing β-cell apoptosis, increasing β-cell function and/or β-cell mass, and/or for restoring glucose sensitivity to β-cells;

iv. prevention and/or treatment of cognitive disorders and/or neurodegenerative disorders, such as Alzheimer's disease, Parkinson's disease, and/or multiple sclerosis;

v. prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

vi. prevention and/or treatment of diabetic complications, such as angiopathy; neuropathy, including peripheral neuropathy; nephropathy; and/or retinopathy;

vii. improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo (a)) in vitro and/or in vivo;

viii. prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

ix. prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

x. prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

xi. prevention and/or treatment of polycystic ovary syndrome (PCOS);

xii. prevention and/or treatment of cerebral disease, such as cerebral ischemia, cerebral haemorrhage, and/or traumatic brain injury;

xiii. prevention and/or treatment of sleep apnoea; and/or xiv. prevention and/or treatment of abuse, such as alcohol abuse and/or drug abuse.

In some embodiments the indication is selected from the group consisting of (i)-(xiv), such as indications (i)-(viii), (x)-(xiii), and/or (xiv), and relates in one way or the other to diabetes.

In some embodiments, the indication is selected from the group consisting of (i)-(iii) and (v)-(viii), such as indications (i), (ii), and/or (iii); or indication (v), indication (vi), indication (vii), and/or indication (viii).

In some embodiments, the indication is (i). In a further particular embodiment the indication is (v). In a still further particular embodiment the indication is (viii).

In some embodiments the compound of the invention may be used in the treatment and/or prevention of all forms of diabetes including eating disorders, cardiovascular diseases, gastrointestinal diseases, diabetic complications, and/or polycystic ovary syndrome; and/or for improving lipid parameters, improving (3-cell function, and/or for delaying or preventing diabetic disease progression.

The following indications are particularly preferred: Type 2 diabetes and/or obesity. In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the derivative or analogue of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/(height in meters)$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity.

In some embodiments the invention relates to use of the compound of the invention for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the compound of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In further embodiments the invention relates to use of compounds according to the invention in treatment or prevention of diabetes and cardiovascular diseases or cardiovascular risks as mentioned above addressing two diseases or disorders by one drug.

In one embodiment the invention relates to a method of treatment as described above, comprising a step of administering a therapeutically effective dosage of a compound according to the invention to a patient in need thereof.

The dosage to be administered can be determined individually and could be less than 50 mg per week, such as 10-15 mg per week, or 70-100 mg/month depending on the specific drug compound and dosing regimen selected.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

EMBODIMENTS

1. A compound comprising a GLP-1 analogue and an EGF(A) analogue, wherein
   i. said GLP-1 analogue is an analogue of GLP-1(7-37) identified by SEQ ID No: 137 and
   ii. said EGF(A) analogue is an analogue of the EGF(A) domain of LDL-R (293-332) identified by SEQ ID No:1.

2. The compound according to embodiment 1, wherein said compound has at least one Lys residue.
3. The compound according to embodiment 1, wherein said compound has at least two Lys residues.
4. The compound according to embodiment 1, wherein said compound has exactly one or two Lys residue.
5. The compound according to embodiment 1, wherein said compound has exactly one Lys residue.
6. The compound according to embodiment 1, wherein said compound has exactly two Lys residue.
7. The compound according to embodiment 1, wherein said compound comprises a fusion polypeptide.
8. The compound according to embodiment 7, wherein said fusion polypeptide comprise a GLP-1 analogue and a EGF(A) analogue.
9. The compound according to embodiment 8, wherein the GLP-1 analogue is fused to the EGF(A) analogue via the C-terminal amino acid residue of the GLP-1 analogue.
10. The compound according to embodiment 8, wherein the fusion polypeptide comprises the GLP-1 analogue in the N-terminal and the EGF(A) analogue in the C-terminal.
11. The compound according to embodiment 8, wherein EGF(A) analogue is fused to a GLP-1 analogue via the C-terminal amino acid residue of the EGF(A) analogue.
12. The compound according to embodiment 8, wherein the fusion polypeptide comprises the EGF(A) analogue in the N-terminal and the GLP-1 analogue in the C-terminal.
13. The compound according to any of the embodiments 7-12, wherein said fusion polypeptide comprises a peptide spacer.
14. The compound according to embodiment 13, wherein the peptide spacer consists of 4-80 amino acid residues.
15. The compound according to embodiment 14, wherein the peptide spacer consists of 4-20 amino acid residues.
16. The compound according to embodiment 14, wherein the peptide spacer comprises a Lys residue.
17. The compound according to embodiment 14, wherein the peptide spacer does not comprise a Lys residue.
18. The compound according to embodiment 14, wherein the peptide spacer is selected from the group of peptides identified by SEQ ID NO 115-126.
19. The compound according to embodiment 14, wherein the peptide spacer is selected from the group of peptides identified by SEQ ID NO 115-136.
20. The compound according to any of the previous embodiments, wherein the GLP-1 analogue is a GLP-1 receptor agonist.
21. The compound according to any of the previous embodiments, wherein the GLP-1 analogue has an EC50 in the GLP-1 in vitro potency assay described in C1 (without HSA), which is 1-50 pM, 10-100 pM, 50-100 pM, 100-250 pM or 250-1000 pM
22. The compound according to any of the previous embodiments, wherein the GLP-1 analogue is a full GLP-1 receptor agonist.
23. The compound according to any of the previous embodiments, wherein the GLP-1 analogue has an EC50 in the GLP-1 in vitro potency assay described in C1 (without HSA), which is comparable to wt GLP-1.
24. The compound according to embodiment 23, wherein the GLP-1 analogue has an EC50 of at most 50 pM.
25. The compound according to any of the previous embodiments, wherein the GLP-1 analogue has an EC50 in the GLP-1 in vitro potency assay described in C1 (without HSA), which is comparable to semaglutide.
26. The compound according to embodiment 25, wherein the GLP-1 analogue has an EC50 of 5-15 pM.

27. The compound according to any of the previous embodiments, wherein the GLP-1 analogue has an EC50 in the GLP-1 in vitro potency assay described in C1 (with 1% HSA), which is most 2500 pM.
28. The compound according to any of the previous embodiments, wherein the GLP-1 analogue has an EC50 in the GLP-1 in vitro potency assay described in C1 (with 1% HSA), which is a least 500 pM.
29. The compound according to any of the previous embodiments, wherein the GLP-1 analogue has the ability to reduce blood glucose in db/db mice as described in C7.
30. The compound according to any of the previous embodiments, wherein the GLP-1 analogue has the ability to reduce blood glucose in db/db mice as described in C7 and wherein the EC50 AUC $\Delta BG_{24h}$ is less than 15 nmol/kg.
31. The compound according to any of the previous embodiments, wherein the GLP-1 analogue has the ability to reduce body weight in DIO rats as described in C8.
32. The compound according to any of the previous embodiments, wherein the GLP-1 analogue has the ability to reduce body weight in DIO rats as described in C8 and wherein the GLP-1 analogue is capable of reducing body weight to at least 95% of baseline BW, when dosed with 300 nmol/kg/day and measured after 21 days.
33. The compound according to any of the previous embodiments, wherein the GLP-1 analogue has the ability to reduce body weight in DIO rats as described in C8 and wherein the GLP-1 analogue is capable of reducing body weight to at least 90% of baseline BW, when dosed with 300 nmol/kg/day and measured after 21 days.
34. The compound according to any of the previous embodiments, wherein the GLP-1 analogue is at least 80, such as 85, such as 90, such as 95% identical to SEQ ID NO.:137.
35. The compound according to any of the previous embodiments, wherein the GLP-1 analogue comprises at most 6 amino acid substitutions compared to SEQ ID NO.: 137.
36. The compound according to any of the previous embodiments, wherein the GLP-1 analogue comprises an amino acid substitution of 8A.
37. The compound according to any of the previous embodiments, wherein the GLP-1 analogue comprises an amino acid substitution of 8A to G or W
38. The compound according to any of the previous embodiments, wherein the GLP-1 analogue comprises a non-proteogenic amino acid residue in positions 8.
39. The compound according to any of the previous embodiments, wherein the GLP-1 analogue comprises the non-proteogenic amino acid residue Aib in positions 8.
40. The compound according to any of the previous embodiments, wherein the GLP-1 analogue comprises an amino acid substitution of 8A to G, W or the non-proteogenic amino acid residue Aib.
41. The compound according to any of the previous embodiments, wherein the GLP-1 analogue comprises 8Aib.
42. The compound according to any of the previous embodiments, wherein the GLP-1 analogue comprises zero, one or two Lys residues.
43. The compound according to any of the previous embodiments, wherein the GLP-1 analogue comprises one or two Lys residues selected from the group consisting of: 12K, 21K, 23K, 24K, 25K, 26K, 27K, 30K, 31K, 32K, 33K, 34K and 36K.
44. The compound according to any of the previous embodiments, wherein the GLP-1 analogue comprises the Lys residues 26K and 34K.
45. The compound according to any of the previous embodiments, wherein the GLP-1 analogue comprises a substitution or deletion of one or both of 26K and 34K.
46. The compound according to any of the previous embodiments, wherein the GLP-1 analogue does not comprise 26K.
47. The compound according to any of the previous embodiments, wherein the GLP-1 analogue comprises a deletion of 26K.
48. The compound according to any of the previous embodiments, wherein the GLP-1 analogue comprises an amino acid substitution of 26K.
49. The compound according to any of the previous embodiments, wherein the GLP-1 analogue comprises 26R.
50. The compound according to any of the previous embodiments, wherein the GLP-1 analogue comprises an additional Lys residue.
51. The compound according to any of the previous embodiments, wherein the GLP-1 analogue comprises an additional Lys selected from the group of: 12K, 21K, 23K, 24K, 25K, 27K, 30K, 31K, 32K, 33K and 36K.
52. The compound according to any of the previous embodiments, wherein the GLP-1 analogue comprises exactly one Lys residue selected from: 12K, 21K, 23K, 24K, 25K, 26K, 27K, 30K, 31K, 32K, 33K, 34K and 36K.
53. The compound according to any of the previous embodiments, wherein the GLP-1 analogue comprises exactly two lys residues selected from the pairs of:
k) 21K and 26K
l) 23K and 26K
m) 24K and 26K
n) 25K and 26K
o) 27K and 26K
p) 30K and 26K
q) 31K and 26K
r) 32K and 26K
s) 33K and 26K
t) 34K and 26K
54. The compound according to any of the previous embodiments, wherein the GLP-1 analogue does not comprise 34K.
55. The compound according to any of the previous embodiments, wherein the GLP-1 analogue comprises a deletion of 34K.
56. The compound according to any of the previous embodiments, wherein the GLP-1 analogue comprises an amino acid substitution of 34K.
57. The compound according to any of the previous embodiments, wherein the GLP-1 analogue comprises 34R or 34Q.
58. The compound according to any of the previous embodiments, wherein the GLP-1 analogue comprises a deletion of amino acid residues 35-37, 34-37 or 33-37
59. The compound according to any of the previous embodiments, wherein the GLP-1 analogue comprises 33L.
60. The compound according to any of the previous embodiments, wherein the GLP-1 analogue comprises at least 26, such as at least 27 or at least 28 amino acid residues.
61. The compound according to any of the previous embodiments, wherein the GLP-1 analogue comprises an amino acid substitution of one of the amino acid residues 21, 23, 24, 25, 27, 29, 30, 31, 32 and 33.
62. The compound according to any of the previous embodiments, wherein the GLP-1 analogue has the sequence defined as follows: H-$X_8$-E-G-T-$X_{12}$-T-S-D-V-S-S-Y-L-$X_{21}$-G-$X_{23}$-$X_{24}$-$X_{25}$-$X_{26}$-$X_{27}$-F-$X_{29}$-$X_{30}$-$X_{31}$-$X_{32}$-$X_{33}$-$X_{34}$-$X_{35}$-$X_{36}$-$X_{37}$ (SEQ ID NO 187) wherein X₈ is A, G, W or Aib,
X₁₂ is F or K,
X₂₁ is E, G or K,
X₂₃ is Q, G or K,
X₂₄ is A, G, V or K,
X₂₅ is A, G, V or K,
X₂₆ is K or R,
X₂₇ is E, G or K,
X₂₉ is I, A or V,
X₃₀ is A, G or K,
X₃₁ is W, G or K,
X₃₂ is L, G, T, V, I or K,
X₃₃ is V, G, I, L, K or absent,
X₃₄ is K, R, Q or absent,
X₃₅ is G or absent,
X₃₆ is R, K or absent and
X₃₇ is G or is absent.

63. The compound according to any of the previous embodiments, wherein the GLP-1 analogue is selected from the group of GLP-1 analogues identified by SEQ ID NO.: 138 to 186, such as SEQ ID NO.: 139-146, 155-162, 164-173, such as SEQ ID NO.: 139-142, 155-162, 164-173, such as SEQ ID NO.: 139, 142, 155-162, 164-173, such as SEQ ID NO.: 139, 155-162, 164-173, such as SEQ ID NO.: 155-162, 164-173 or such as SEQ ID NO.: 139 and 164.

64. The compound according to any of the previous embodiments, wherein the EGF(A) analogue is a PCSK9 inhibitor.

65. The compound according to any of the previous embodiments, wherein the EGF(A) analogue has increased binding affinity to human PCSK9 compared to the EGF(A) domain of LDL-R (293-332) identified by SEQ ID NO.: 1.

66. The compound according to any of the previous embodiments, wherein the EGF(A) analogue binds PCSK9 with a Ki below 50 nM, such as below 25 nM or such as below 10 nM, when measured in a PCSK9-LDL-R binding competitive ELISA assay as described in Section C3.

67. The compound according to any of the previous embodiments, wherein the EGF(A) analogue binds PCSK9 with a Ki below 5 nM, when measured in the PCSK9-LDL-R binding competitive ELISA assay as described in Section C3.

68. The compound according to any of the previous embodiments, wherein the EGF(A) analogue increases LDL uptake.

69. The compound according to any of the previous embodiments, wherein the EGF(A) analogue increases LDL uptake in the presence of human PCSK9.

70. The compound according to any of the previous embodiments, wherein the EGF(A) analogue has a EC50 below 1000 nM when measured in the LDL uptake assay described in section C4.

71. The compound according to any of the previous embodiments, wherein the EGF(A) analogue has a EC50 below 500 nM when measured in the LDL uptake assay described in section C4.

72. The compound according to any of the previous embodiments, wherein the EGF(A) analogue decreases blood cholesterol.

73. The compound according to any of the previous embodiments, wherein the EGF(A) analogue decreases blood cholesterol in DIO rats when evaluated as described in section C8

74. The compound according to any of the previous embodiments, wherein the EGF(A) analogue reduces blood cholesterol at least 0.5 mmol/L when dosed with 30 nmol/kg/day and measured after 21 days.

75. The compound according to any of the previous embodiments, wherein the EGF(A) analogue reduces blood cholesterol by at least 0.8 mmol/L when dosed with 300 nmol/kg/day and measured after 21 days.

76. The compound according to any of the previous embodiments, wherein the EGF(A) analogue is at least 80, 85, 90 or such as 95% identical to SEQ ID NO.: 1.

77. The compound according to any of the previous embodiments, wherein the EGF(A) analogue comprises 1-15 amino acid substitution(s) compared to SEQ ID NO.: 1.

78. The compound according to any of the previous embodiments, wherein the EGF(A) analogue comprises 301L.

79. The compound according to any of the previous embodiments, wherein the EGF(A) analogue comprises 301L and 309R.

80. The compound according to any of the previous embodiments, wherein the EGF(A) analogue comprises one or more of the (wild-type) amino acid residues 295N (Asn), 296E (Glu), 298L (Leu), 302G (Gly) and 310D (Asp).

81. The compound according to any of the previous embodiments, wherein the EGF(A) analogue does not comprise any K residue.

82. The compound according to any of the previous embodiments, wherein the EGF(A) analogue does not comprise 312K.

83. The compound according to any of the previous embodiments, wherein the EGF(A) analogue comprises 312E, 312D, 312Q or 312R.

84. The compound according to any of the previous embodiments, wherein the EGF(A) analogue comprises 301L, 309R and an amino acid substitution of 312K, such as 312E.

85. The compound according to any of the previous embodiments, wherein the EGF(A) analogue comprises 301L, 310D and an amino acid substitution of 312K, such as 312E.

86. The compound according to any of the previous embodiments, wherein the EGF(A) analogue comprises 301L and 310D and the peptide does not have a substitution of 299D to G, V or H.

87. The compound according to any of the previous embodiments, wherein the EGF(A) analogue comprises 321D or 321E.

88. The compound according to any of the previous embodiments, wherein the EGF(A) analogue comprises 301L, 309R, 312E and 321E.

89. The compound according to any of the previous embodiments, wherein the EGF(A) analogue sequence is defined by any one of SEQ ID NO.: 19, 21, 73, 107, 108, 109, 110, 111, 112, 113 and 114, such as 107, 108, 109, 110 and 111, such as 107 and 108.

90. The compound according to any of the previous embodiments 7-89, wherein the fusion polypeptide comprises a GLP-1 analogue, a spacer peptide and an EGF(A) analogue.

91. The compound according to embodiment 90, wherein the GLP-1 analogue is as defined in any of the embodiments 20-63.

92. The compound according to embodiment 90 or embodiment 91, wherein the EGF(A) analogue is as defined in any of the embodiments 64-89.

93. The compound according to embodiment 90, 91 or 92, wherein spacer peptide is as defined in any of the embodiments 14-19.

94. The compound according to embodiment 90, wherein the fusion polypeptide is selected from the group of sequences identified by SEQ ID NO.:188-384.

95. The compound according to any of the embodiment 90-94, wherein the fusion polypeptide comprises up to two lysine residues.

96. The compound according to any of the previous embodiments, wherein the compound comprise up to two substituents.

97. The compound according to any of the previous embodiments, wherein the compound comprise up to two half-life extending substituents.

98. The compound according to any of the previous embodiments, wherein the compound is a derivative comprising a peptide back-bone and up to two substituents attached hereto.

99. The compound according to embodiment 98, wherein the peptide back-bone is a fusion peptide as defined in any of the embodiments 7-94.

100. The compound according to any of the previous embodiments 96-99, wherein at least one substituent is attached to the GLP-1 analogue, the EGF(A) analogue and/or the spacer.

101. The compound according to embodiment 100, wherein at least one substituent is attached to the GLP-1 analogue.

102. The compound according to embodiment 100, wherein at least one substituent is attached to the EGF(A) analogue.

103. The compound according to embodiment 100, wherein at least one substituent is attached to the spacer.

104. The compound according to embodiment 100, wherein at least one substituent is attached via a Lys/K amino acid residue.

105. The compound according to embodiment 100, wherein at least one substituent is attached to the GLP-1 analogue via a Lys/K amino acid residue.

106. The compound according to embodiment 100, wherein at least one substituent is attached to the GLP-1 analogue via a Lys/K amino acid residue selected from the group consisting of: 12K, 21K, 24K, 25K, 26K, 27K, 31K, 32K and 36K.

107. The compound according to embodiment 100, wherein at least one substituent is attached to the GLP-1 analogue via 26K.

108. The compound according to embodiment 100, wherein at least one substituent is attached to the EGF(A) analogue.

109. The compound according to embodiment 100, wherein at least one substituent is attached to the EGF(A) analogue via 292Lys, 293Lys, 294Lys, 299Lys, 300Lys, 303Lys, 305Lys, 306Lys, 309Lys, 311Lys, 312Lys, 313Lys, 314Lys, 315Lys, 316Lys, 318Lys, 320Lys, 321Lys, 322Lys, 323Lys, 324Lys, 325Lys, 326Lys, 327Lys, 328Lys, 329Lys, 330Lys, 332Lys or 333Lys.

110. The compound according to embodiment 100, wherein at least one substituent is attached to the EGF(A) analogue via 292Lys, 293Lys, 294Lys, 300Lys, 303Lys, 305Lys, 306Lys, 309Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys or 333Lys.

111. The compound according to embodiment 100, wherein at least one substituent is attached to the EGF(A) analogue via 292Lys, 293Lys, 294Lys, 300Lys, 303Lys, 305Lys, 306Lys, 311Lys, 312Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys or 333Lys.

112. The compound according to embodiment 100, wherein at least one substituent is attached to the EGF(A) analogue via 292Lys, 293Lys, 294Lys, 300Lys, 303Lys, 305Lys, 306Lys, 311Lys, 313Lys, 314Lys, 316Lys, 318Lys, 321Lys, 322Lys, 323Lys, 324Lys, 325Lys, 326Lys, 327Lys, 328Lys, 329Lys, 330Lys, 332Lys or 333Lys.

113. The compound according to embodiment 100, wherein at least one substituent is attached to the EGF(A) analogue via 313Lys, 321Lys, 324Lys, 328Lys or 333Lys.

114. The compound according to embodiment 100, wherein at least one substituent is attached to the peptide spacer.

115. The compound according to embodiment 100, wherein at least one substituent is attached to the peptide spacer via a Lys residue.

116. The compound according to embodiment 100, wherein at least one substituent is attached to the peptide spacer via a Lys residue, wherein the spacer is a variant of SEQ ID 116 having a Lys in position 1, 2, 3, 4, 5, 6, 7 or 8.

117. The compound according to any one of the embodiments 96-116, wherein the compound comprises exactly two substituents attached to the fusion peptide.

118. The compound according to embodiment 117, wherein one substituent is attached via the GLP-1 analogue as defined in embodiments 105-107 and one substituent is attached to the spacer as defined in any one of embodiments 115-116.

119. The compound according to embodiment 117, wherein one substituent is attached via the EGF(A) analogue as defined in any one of embodiments 109-113 and one substituent is attached to the peptide spacer as defined in any one of embodiments 115-116.

120. The compound according to embodiment 117, wherein one substituent is attached via the GLP-1 analogue as defined in any one of the embodiments 105-107 and one substituent is attached to the EGF (A) analogue as defined in any one of embodiments 109-113.

121. The compound according to embodiment 117, wherein the two substituents are attached via the GLP-1 analogue as defined in any one of embodiments 105-108.

122. The compound according to embodiment 117, wherein the two substituents are attached via the EGF(A) analogue as defined in any one of embodiments 109-113.

123. The compound according to any of the previous embodiments 96-122, wherein the substituent(s) comprises a fatty acid group (AB).

124. The compound according to embodiment 123, wherein the substituent(s) comprises a fatty acid group selected from the group consisting of Chem 1 —C(=O)—$(CH_2)_n$—COOH wherein n is an integer in the range of 8-20 and Chem 2 —HOOC—$(C_6H_4)$—O—$(CH_2)_m$—CO—* wherein m is an integer in the range of 8-11.

125. The compound according to embodiment 123, wherein the substituent(s) comprises a fatty acid group selected from di-acids —C(=O)—$(CH_2)_n$—COOH wherein n is 14-20.

126. The compound according to embodiment 123, wherein the substituent(s) comprises a fatty acid group selected from di-acids (—HOOC—$(C_6H_4)$—O—$(CH_2)_m$—CO—*) wherein m is an integer in the range of 8-11.

127. The compound according to any of the embodiments 123-126, wherein the at least one substituent further comprises at least one linker element.

128. The compound according to any of the embodiments 123-126, wherein the at least one substituent further comprises at most 6 linker elements referred to as $-Z_1-Z_2-Z_3-Z_4-Z_5-Z_6-$.

129. The compound according to any of the embodiments 123-126, wherein the at least one substituent further comprises at most 6 linker elements referred to as $-Z_1-Z_2-Z_3-Z_4-Z_5-Z_6-$, wherein $Z_1$ is connected with the fatty acid group and the last Z element is connected with the peptide back-bone.

130. The compound according to any of the embodiments 128 and 129, wherein $-Z_1$ is *—NH—CH$_2$—(C$_6$H$_{10}$)—CO—* or a bond.

131. The compound according to any of the embodiments 128 and 130, wherein $-Z_2-$ is γGlu, Glu or a bond.

132. The compound according to any of the embodiments 128 and 130, wherein $-Z_2-$ is γGlu.

133. The compound according to any of the embodiments 128 and 132, wherein $Z_3$, $Z_4$, $Z_5$ and $Z_6$ are selected, independently of each other, from Glu, γGlu, and Ado and a bond.

134. The compound according to any of the embodiments 128 and 132, wherein $Z_3$, $Z_4$, $Z_5$ and $Z_6$ are selected, independently of each other, from γGlu, Ado and a bond.

135. The compound according to any of the embodiments 123-134, wherein the at least one substituent comprises a linker comprising -γGlu-Ado-Ado-.

136. The compound according to any of the embodiments 123, wherein the at least one substituent is selected from the substituents #1-13, such as from substituents #1-4, #5-12, #6-12 or the group of substituents consisting of: substituent #1, #5 and #6.

137. The compound according to any of the previous embodiments, wherein the compound is bi-functional.

138. The compound according to any of the previous embodiments, wherein the compound is a GLP-1 receptor agonist.

139. The compound according to embodiment 137 or embodiment 138, wherein the compound has an EC50 in the GLP-1 in vitro potency assay described in C1 (without HSA), which is 1-50 pM, 10-100 pM, 50-100 pM, 100-250 pM or 250-1000 pM.

140. The compound according to any of the previous embodiments 137-139, wherein the compound is a full GLP-1 receptor agonist.

141. The compound according to any of the previous embodiments 137-139, wherein the compound has an EC50 in the GLP-1 in vitro potency assay described in C1 (without HSA), which is comparable to wt GLP-1.

142. The compound according to any of the previous embodiments 137-139, wherein the compound has an EC50 in the GLP-1 in vitro potency assay described in C1 (without HSA) of at most 50 pM.

143. The compound according to any of the previous embodiments 137-139, wherein the compound has an EC50 in the GLP-1 in vitro potency assay described in C1 (without HSA), which is comparable to semaglutide.

144. The compound according to any of the previous embodiments 137-139, wherein the compound has an EC50 in the GLP-1 in vitro potency assay described in C1 (without HSA) of 5-15 pM.

145. The compound according to any of the previous embodiments 137-139, wherein the compound has an EC50 in the GLP-1 in vitro potency assay described in C1 (with 1% HSA), which is at most 2500 pM.

146. The compound according to any of the previous embodiments 137-139, wherein the compound has an EC50 in the GLP-1 in vitro potency assay described in C1 (with 1% HSA), which is a least 500 pM.

147. The compound according to any of the previous embodiments 137-146, wherein the compound has the ability to reduce blood glucose in db/db mice as described in C7.

148. The compound according to any of the previous embodiments 137-146, wherein the compound has the ability to reduce blood glucose in db/db mice as described in C7 and wherein the EC50 AUC ΔBG$_{24h}$ is less than 15 nmol/kg.

149. The compound according to any of the previous embodiments 137-146, wherein the GLP-1 analogue has the ability to reduce body weight in DIO rats as described in C8.

150. The compound according to any of the previous embodiments 137-146, wherein the compound has the ability to reduce body weight in DIO rats as described in C8 and wherein the GLP-1 analogue is capable of reducing body weight to at least 95% of baseline BW, when dosed with 300 nmol/kg/day and measured after 21 days.

151. The compound according to any of the previous embodiments 137-146, wherein the compound has the ability to reduce body weight in DIO rats as described in C8 and wherein the GLP-1 analogue is capable of reducing body weight to at least 90% of baseline BW, when dosed with 300 nmol/kg/day and measured after 21 days.

152. The compound according to any of the previous embodiments, wherein the compound is a PCSK9 inhibitor.

153. The compound according to any of the previous embodiments 137-145, wherein the compound has increased binding affinity to human PCSK9 compared to the EGF(A) domain of LDL-R (293-332) identified by SEQ ID NO.: 1.

154. The compound according to any of the previous embodiments 137-145, wherein the compound binds PCSK9 with a Ki below 50 nM, such as below 25 nM or such as below 10 nM, when measured in a PCSK9-LDL-R binding competitive ELISA assay as described in Section C3.

155. The compound according to any of the previous embodiments 137-145, wherein the compound binds PCSK9 with a Ki below 5 nM, when measured in the PCSK9-LDL-R binding competitive ELISA assay as described in Section C3.

156. The compound according to any of the previous embodiments 137-145, wherein the compound increases LDL uptake. 157. The compound according to any of the previous embodiments 137-145, wherein the compound increases LDL uptake in the presence of human PCSK9.

158. The compound according to any of the previous embodiments 137-152, wherein the compound has an EC50 below 1000 nM when measured in the LDL uptake assay described in section C4.

159. The compound according to any of the previous embodiment 137-145, wherein the compound has an EC50 below 500 nM when measured in the LDL uptake assay described in section C4.

160. The compound according to any of the previous embodiments, wherein the compound decreases blood cholesterol when evaluated in DIO rats as described in section C8

161. The compound according to embodiment 160, wherein the compound reduces blood cholesterol at least 0.5 mmol/L when dosed with 30 nmol/kg/day and measured after 21 days.

162. The compound according to embodiment 160, wherein the compound reduces blood cholesterol by at least 0.8 mmol/L when dosed with 300 nmol/kg/day and measured after 21 days.
163. The compound according to any of the embodiments, wherein the compound is a GLP-1 receptor agonist as defined in any one of previous embodiments 139-144 and a PCSK9 inhibitor as defined in any one of the previous embodiments 153-159
164. The compound according to embodiment 160, wherein the compound has a ratio of the apparent EGF(A) Ki (C3) and the GLP-1 potency (C1, without HSA) which is at most 5000, such as at most 4000, such as at most 3000, such as at most 2000 or such as at most 1000.
165. The compound according to embodiment 160, wherein the compound has a ratio of the apparent EGF(A) Ki (C3) and the GLP-1 potency (C1, without HSA) which is at most 1000, such as at most 800, such as at most 600, such as at most 400 or such as at most 200.
166. The compound according to embodiment 160, wherein the compound has a ratio of the apparent EGF(A) Ki (C3) and the GLP-1 potency (C1, without HSA) is at most 200, such as at most 150, such as at most 100, such as at most 50, 25 and 10.
167. The compound according to any of the previous embodiments 137-166, wherein the compound is capable of reducing cholesterol and body weight at least equal to GLP-1/EGF(A) Compound #41 in an in vivo rat study as described in section C8 herein.
168. The compound according to embodiment 167, wherein the compound is capable of reducing cholesterol at least 0.5 mmol/L when dosed with 30 nmol/kg/day and measured after 21 days.
169. The compound according to embodiment 167, wherein the compound is capable of reducing cholesterol at least 0.6 such as 0.7 or such as 0.8 mmol/L, when dosed with 30 nmol/kg/day and measured after 21 days.
170. The compound according to embodiment 167, wherein the compound is capable of reducing cholesterol at least 0.8 mmol/L when dosed with 300 nmol/kg/day and measured after 21 days.
171. The compound according to embodiment 167, wherein the compound is capable of reducing cholesterol at least 1.0 or such as 1.2 mmol/L when dosed with 300 nmol/kg/day and measured after 21 days.
172. The compound according to embodiment 167-171, wherein the compound is capable of reducing body weight to at least 95% of baseline BW, when dosed with 300 nmol/kg/day and measured after 21 days.
173. The compound according to embodiment 167-171, wherein the compound is capable of reducing body weight to at least 90% of baseline BW, when dosed with 300 nmol/kg/day and measured after 21 days.
174. The compound according to any of the previous embodiments, wherein the compound is selected from the group of compounds defined as GLP-1/EGF(A) compounds #1 to #314.
175. A compound comprising a GLP-1 receptor agonist and an EGF(A) analogue, wherein said EGF(A) analogue is an analogue of the EGF(A) domain of LDL-R (293-332) identified by SEQ ID No:1.
176. The compound of embodiment 175, wherein the EGF (A) analogue is as defined in any of the previous embodiments 64-89.
177. A compound selected from the group of compounds defined as GLP-1/EGF(A) compounds #1 to #305.
178. A compound selected from the group of compounds defined as GLP-1/EGF(A) compounds #1 to #314.
179. A compound selected from the group of compounds defined as GLP-1/EGF(A) compounds #1, 2, 21, 22, 23, 25, 26, 27, 29, 32, 41, 48, 51, 52, 53, 54, 69, 82, 86, 221, 230, 287, 298 and 306.
180. A compound selected from the group of compounds defined as GLP-1/EGF(A) compounds #1, 2, 21, 22, 23, 25, 26, 27, 29, 32, 48, 52, 53, 54, 69 and 306.
181. A compound selected from the group of compounds defined as GLP-1/EGF(A) compounds #41, #48, #69 and #306, such as #306 and #69, or such as #306 or #69.
182. Use of a compound according to any of the previous embodiments for the preparation of a medicament.
183. A compound according to any of the previous embodiments 1-181 for use in the preparation of a medicament.
184. A compound according to any of the previous embodiments 1-181 for use in a method of treatment.
185. A compound according to any of the previous embodiments 1-181 for use in a method of treatment of diabetes and/or overweight.
186. A compound according to any of the previous embodiments 1-181 for use in a method of treatment or prevention of cardiovascular diseases and/or cardiovascular risks.
187. A compound according to any of the previous embodiments 1-181 for use in a method of treatment for improving lipid parameters.
188. A compound according to any of the previous embodiments 1-181 for use in a method of treatment of diabetes and cardiovascular diseases.
189. A method for treatment of diabetes and/or overweight, said method comprising administering a pharmaceutically active amount of a compound according to any of the previous embodiments 1-181 to a patient in need thereof.
190. A method for treatment or prevention of cardiovascular diseases and/or cardiovascular risks, said method comprising administering a pharmaceutically active amount of a compound according to any of the previous embodiments 1-181 to a patient in need thereof.
191. A method of treatment for improving lipid parameters, said method comprising administering a pharmaceutically active amount of a compound according to any of the previous embodiments 1-181 to a patient in need thereof.
192. A method for treatment of diabetes and cardiovascular diseases, said method comprising administering a pharmaceutically active amount of a compound according to any of the previous embodiments 1-181 to a patient in need thereof.

Further Embodiments

1. A compound comprising a GLP-1 analogue and an EGF(A) analogue, wherein
   i. said GLP-1 analogue is an analogue of GLP-1(7-37) identified by SEQ ID NO: 137 and
   ii. said EGF(A) analogue is an analogue of the EGF(A) domain of LDL-R (293-332) identified by SEQ ID No:1.
2. The compound according to embodiment 1, wherein the compound is bi-functional.
3. The compound according to embodiment 1, wherein the compound comprises a fusion polypeptide comprising the GLP-1 analogue and the EGF(A) analogue.
4. The compound according to embodiment 3, wherein the fusion polypeptide comprises the GLP-1 analogue in the N-terminal and the EGF(A) analogue in the C-terminal.

5. The compound according to embodiment 3 or embodiment 4, wherein the fusion polypeptide comprises a peptide spacer, such as a spacer selected from the group of spacers defined by SEQ ID NO. 115-136.
6. The compound according to any of the previous embodiments, wherein the compound comprises one or two Lys residues.
7. The compound according to any of the previous embodiments, wherein the GLP-1 analogue is selected from the group of GLP-1 analogues defined by SEQ ID NO's 138 to 187, such as SEQ ID NO.: 139-146, 155-162 and 164-173, such as SEQ ID NO.: 139-142, 155-162 and 164-173, such as SEQ ID NO.: 139, 142, 155-162 and 164-173, such as SEQ ID NO.: 139, 155-162 and 164-173, such as SEQ ID NO.: 155-162 and 164-173, such as SEQ ID NO.: 139 and 164 or such as SEQ ID NO.: 139 or 164.
8. The compound according to any of the previous embodiments, wherein the EGF(A) analogue is selected from the group of EGF(A) analogues defined by SEQ ID NO's 2 to 114, such as by SEQ ID NO.s 2-4, 6-19, 21-44, 46, 47, 49-53, 55 and 58-114, such as by SEQ ID NOs: 19, 21, 73, 107, 108, 109, 110, 111, 112, 113 and 114, such as by SEQ ID NOs: 107 and 108 or such as SEQ ID NO.: 108.
9. The compound according to any of the previous embodiments, wherein the fusion polypeptide is selected from the group of sequences defined by SEQ ID NOs 188-384 and 387-388.
10. The compound according to any of the previous embodiments, wherein the compound comprises at least one half-life extending substituent.
11. The compound according to any of the previous embodiments, wherein the compound comprises at least one substituent comprising a fatty acid group and a linker.
12. The compound according to embodiment 11 or embodiment 12, wherein the at least one substituent is attached via lys residue(s).
13. A compound selected from the group of compounds defined as GLP-1/EGF(A) compounds #41, #48, #69 and #306, such as #306 and #69, or such as #306 or #69.
14. A compound according to any of the previous embodiments for use in a method of treatment of diabetes, over-weight and/or cardiovascular diseases.
15. A method of treatment of diabetes, over-weight and/or cardiovascular diseases comprising administering a pharmaceutically effective dosage of a compound according to any of embodiments 1-14 to a patient in need thereof.

METHODS AND EXAMPLES

List of Abbreviations

Aib: α-aminoisobutyric acid (2-Aminoisobutyric acid)
AcOH: acetic acid
Ado: 8-amino-3,6-dioxaoctanoic acid
API: Active Pharmaceutical Ingredient
AUC: Area Under the Curve
BG: Blood Glucose
BHK: Baby Hamster Kidney
BW: Body Weight
Boc: t-butyloxycarbonyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (imidazopropionic acid or 3-(Imidazol-5-yl)propanoic acid), Imp)
DIC: diisopropylcarbodiimide
DIPEA: diisopropylethylamine
DMEM: Dulbecco's Modified Eagle's Medium (DMEM)
DooaSuc: 8-amino-3,6-dioxaoctyl succinamic acid
DTT: 1,4-dithiothreitol
EDTA: ethylenediaminetetraacetic acid
EGF: Epidermal growth factor-like
EGF(A): Epidermal growth factor-like domain A
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP: 1,1,1,3,3,3-hexafluoro-2-propanol or hexafluoroisopropanol
HOAt: 1-hydroxy-7-azabenzotriazole
HOBt: 1-hydroxybenzotriazole hPCSK9: human PCSK9
HPLC: High Performance Liquid Chromatography
HSA: Human Serum Albumin
IBMX: 3-isobutyl-1-methylxanthine
$IC_{50}$: half maximum inhibitory concentration
Imp: Imidazopropionic acid or 3-(Imidazol-5-yl)propanoic acid) (also referred to as des-amino histidine, DesH)
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LDL-R or LDLr: LDL receptor
LDL: low density lipoprotein
LDL-C: LDL cholesterol
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
MRT: Mean residence time
Mtt: 4-methyltrityl
NMP: N-methyl pyrrolidone
ND: not determined
OBz: benzoyl ester
OEG: 8-amino-3,6-dioxaoctanoic acid (also termed Ado)
OPfp: pentafluorophenoxy
OPnp: para-nitrophenoxy
OSu: O-succinimidyl esters (hydroxysuccinimide esters)
OtBu: tert butyl ester
OXYMA PURE®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
QC: Quality control
RP: Reverse Phase
RP-HPLC: Reverse Phase High Performance Liquid Chromatography
RT: Room Temperature Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS or TIPS: triisopropylsilane
Tos: tosylate (or pare-toluenesulfonyl)
TotaGlyc: 13-amino-4,7,10-trioxatridecayl diglycolamic acid
Tris: tris(hydroxymethyl)aminomethane or 2-amino-2-hydroxymethyl-propane-1,3-diol
Trt: triphenylmethyl (trityl)
Trx: tranexamic acid
TtdSuc: 13-amino-4,7,10-trioxatridecayl succinamic acid
UPLC: Ultra Performance Liquid Chromatography
Special Materials
Eicosanedioic acid mono-tert-butyl ester
Docosanedioic acid mono-tert-butyl ester
4-(10-Carboxydecyloxy) benzoic acid tert-butyl ester
Fmoc-8-amino-3,6-dioxaoctanoic acid
Fmoc-tranexamic acid
Fmoc-Lys(Mtt)-OH
Boc-His(Trt)-OH
Fmoc-Aib-OH The preparation of eicosanedioic acid mono-tert-butyl ester, docosanedioic acid mono-tert-butyl ester, and 4-(10-carboxydecyloxy) benzoic acid tert-butyl ester are described in section 2 below, and the five last-mentioned materials are commercially available.

Methods

This section is divided in three: Section A relating to general methods of preparation of compounds of the invention, section B relating to the preparation of a number of specific compounds of the invention, and section C relating to methods of characterisation of compounds of the invention including also the results for a number of specific example compounds.

A1. General Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS and UPLC methods).

The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used are the standard recommended: Fmoc-Ala-OH, Fmoc-Arg(Pbf)-OH, Fmoc-Asn(Trt)-OH, Fmoc-Asp(OtBu)-OH, Fmoc-Cys (Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid is Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-isonipecotic acid, Fmoc-Glu-OtBu and hexadecanoic acid mono-tert-butyl ester are supplied from e.g. Anaspec, Bachem, Iris Biotech, or Novabiochem. Eicosanedioic acid mono-tert-butyl ester, docosanedioic acid mono-tert-butyl ester and 4-(10-carboxydecyloxy) benzoic acid tert-butyl ester can be prepared as described below. All operations stated below are performed at 400-µmol or 450-µmol synthesis scale.

1. Synthesis of Resin Bound Protected Peptide Hydrazides
Method: SPPS_P

SPPS_P is performed on a Prelude or SymphonyX Solid Phase Peptide Synthesizer from Protein Technologies (Tucson, Ariz. 85714 U.S.A.) at 400-µmol or 450-µmol scale using five fold excess of Fmoc-amino acids (300 mM in DMF with 300 mM OXYMA PURE®) relative to resin loading, e.g. 0.49 mmol/g of Fmoc-hydrazono-pyruvyl-aminomethylpolystyrene resin (PYV1000 from Iris Biotech, 95615 Marktredwitz, Germany). Fmoc-deprotection is performed using 20% piperidine in DMF or 20% piperidine in DMF with 0.1 M OXYMA PURE®. Coupling is performed using 5:5:5:5 amino acid/OXYMA PURE®/DIC/collidine in DMF. DMF top washes (6 cycles of 9 ml) are performed between deprotection and coupling steps. Coupling times are generally 120 minutes. Some amino acids including, but not limited to Fmoc-Arg(Pbf)-OH, Fmoc-Aib-OH or Boc-His(Trt)-OH are "double coupled", meaning that after the first coupling (e.g. 60 min), the resin is drained and more reagents are added (amino acid, OXYMA PURE®, DIC, and collidine), and the mixture allowed to react again (e.g. 60 min).

2. Synthesis of Resin Bound Protected Cys-Peptide Acids

SPPS_P is performed as described above using a low load Fmoc-Glu(OtBu)-Wang (0.32 mmol/g) resin using the same coupling procedures.

3. Synthesis of Albumin Binder

Eicosanedioic acid mono-tert-butyl ester can be prepared as is known in the art, e.g. as described in WO 2010102886 A1.

Docosanedioic acid mono-tert-butyl ester can be prepared as is known in the art, e.g. as described in WO2015000942 A1.

4-(10-Carboxydecyloxy) benzoic acid tert-butyl ester can be prepared as is known in the art, e.g. as described in WO2006082204 A1

4. Attachment of Side Chains to Resin Bound Protected Peptide Backbone

When an acylation is present on a lysine side chain, the epsilon amino group of lysine to be acylated is protected with Mtt. Removal of Mtt is performed using hexafluoroisopropanol/DCM (75:25, 3×10 ml, 5 min, 25 min and 25 min, respectively) followed by wash of the resin with DCM (4× 10 ml), DMF (2× 9 ml), 20% piperidine in DMF with 0.1 M OXYMA PURE® (1× 9 ml), DMF (4× 9 ml). The protracting moiety and/or linker can be attached to the peptide either by acylation of the resin bound peptide or by acylation in solution of the unprotected peptide (as described in WO2010029159 A1). In case of attachment of the protracting moiety and/or linker to the protected peptidyl resin the attachment can be modular using SPPS and suitably protected building blocks.

Method: SC_P

The N-ε-lysine protection group is removed as described above and the chemical modification of the lysine is performed by one or more automated steps on the Prelude or SymphonyX peptide synthesiser using suitably protected building blocks as described above. Double couplings are performed as described in SPPS_P with 1 hour per coupling or single couplings with 2 hour per coupling.

5. Cleavage of Resin Bound Peptide with or without Attached Side Chains and Purification Method: CP_M1

After synthesis the resin is washed with DCM, and the peptide is cleaved from the resin by a 2-3 hour treatment with TFA/TIS/water/DTT (92.5/2.5/2.5/2.5 or 90/5/2.5/2.5) followed by precipitation with diethyl ether. The peptide is dissolved in a suitable solvent (such as water/acetonitrile) and purified by standard RP-HPLC on a C18, 5 μm column, using acetonitrile/water/TFA. The fractions are analysed by a combination of UPLC and LCMS methods, and the appropriate fractions are pooled and lyophilised.

If desired the peptide counter ion can be exchanged to sodium using methods known in the art. As an example a 5 gram Sep-pak C18 column is washed with 50 ml 2-propanol, 50 ml acetonitrile and 50 ml water. A solution of approximate 70 mg protein in 21 ml 50 mM HEPES-buffer (pH 7.2) is loaded onto the Sep-pak column, which is washed with 50 ml water, 50 ml 0.1 M sodium chloride(aq) and 50 ml water. The sodium salt of the protein is eluted with 100 ml water/acetonitrile (30:70) and lyophilised.

6. Native Chemical Ligation of Peptide Hydrazide with Cys-Peptide and Purification Method: NCL_M1

The peptide hydrazide (1.0 eq) is dissolved in 0.2 M disodium phosphate/6.0 M guanidine hydrochloride (aq, pH 3.0) to a final concentration of 4.0 mM and cooled to −10° C. Sodium nitrite (0.2 M in water, 5 eq) is added, and the mixture is stirred for 20 minutes at −10° C. A solution of 0.2 M 4-mercaptophenylacetic acid (50 eq) in 0.2 M disodium phosphate/6.0 M guanidine hydrochloride (pH adjusted to 7.0) is added to the solution, followed by addition of the Cys-peptide (1.1 eq). pH of the solution is adjusted to 6.7 with sodium hydroxide (1.0 M, aq) and the mixture is stirred 16 hours at 25° C. 1,4-Dithiothreitol (100 eq) is added to the reaction mixture and stirred for 30 minutes before the pH is adjusted to 3.0 with concentrated hydrochloric acid (aq). The reaction mixture is concentrated by ultrafiltration using an Amicon Ultra-15 centrifugal filter unit with Ultracel-3 membrane from EMD Millipore (Billerica, Mass. 01821 U.S.A.). The concentrated solution is diluted with 0.05 M disodium phosphate/6.0 M guanidine hydrochloride (aq, pH 3.0) and concentrated by ultrafiltration again. This is repeated until the concentration of 4-mercaptophenylacetic acid is below 0.1 mM (which corresponded to >1000-fold dilution). The concentrated solution is added dropwise to a stirred solution of 50 mM tris(hydroxymethyl)aminomethane, 5 mM calcium chloride, 3 mM cysteine, 0.3 mM cystine, (aq, pH 8.2), resulting in a protein concentration of app. 0.1 mg/ml. The solution is stirred for 16 hours at 25° C. pH of the folding mixture is adjusted to app. 3 with concentrated hydrochloric acid (aq) before being purified by standard RP-HPLC on a C18, 5 μm column, using acetonitrile/water/TFA. The fractions are analysed by a combination of UPLC and LCMS methods, and the appropriate fractions are pooled and lyophilised.

7. Recombinant Expression of Fusion Protein

The fusion protein of interest is provided by heterologous expression using a suitable host. Expression plasmids are constructed using known technologies and the fusion protein expressed and purified by methods known to the person skilled in the art. In short cells are harvested and lysed in 1×PBS buffer at pH7 by cell disruptor. The insoluble fraction, containing the fusion protein, is collected and washed in the same buffer twice (6,000 g/20 min). 20 mM ethanolamine, 2M urea, pH 10.5 is then used to solubilize the inclusion bodies to a concentration of 10 mg/mL at room temperature (22-26° C.). After one hour, the solution is diluted 3 times by demineralized water, and the pH is adjusted to 8.5. Enterokinase cleavage is carried out at the same temperature for 20 hours at the ratio of 1:1,000. Following that, a final concentration of 10 mM $CaCl_2$) and 5 mM cysteine are added for refolding. After adjusting the pH to 3.0, the protein is captured from SP fast flow sepharose. The captured sample is applied onto reverse phase FeF column at pH7.5. Source 30Q column (20 mM Tris, 5 mM $CaCl_2$), pH 9.0) is selected as the final polishing step.

8. Incorporation of Non-Proteogenic Amino Acid in Recombinant Protein

The N-terminal His-Aib dipeptide can be introduced by acylation in solution with Fmoc-His-Aib-OH followed by removal of the Fmoc-protecting group (as described in WO2013098191 A1).

A2. General Methods for Detection and Characterisation

1. LC-MS methods

Method: LCMS01

LCMS01 is performed on a setup consisting of Waters Acquity UPLC system and LCT Premier XE mass spectrometer from Micromass. Eluents: A: 0.1% Formic acid in water; B: 0.1% Formic acid in acetonitrile. The analysis is performed at RT by injecting an appropriate volume of the sample (preferably 2-100) onto the column which is eluted with a gradient of A and B. The UPLC conditions, detector settings and mass spectrometer settings are: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

Method: LCMS34

LCMS34 is performed on a setup consisting of Waters Acquity UPLC system and Xevo G2-XS Qtof mass spectrometer. Eluents: A: 0.1% Formic acid in water; B: 0.1% Formic acid in acetonitrile. The analysis is performed at RT by injecting an appropriate volume of the sample (preferably 2-10 μl) onto the column which is eluted with a gradient of A and B. The UPLC conditions, detector settings and mass spectrometer settings are: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

Method: LCMS27

LCMS27 is performed on a setup consisting of Agilent 1290 infinity series and an Agilent Technologies LC/MSD TOF 6230 (G6230A) detector with Agilent Jet Stream source ionization. Eluents: A: 0.02% TFA in water; B: 0.02% TFA in acetonitrile. The analysis is performed at RT by injecting an appropriate volume of the sample (preferably 2-10 μl) onto the column which is eluted with a gradient of A and B. The UPLC conditions, detector settings and mass spectrometer settings are: Column: Aeris Widepore, C-18, 3.6 μm, 2.1 mm×50 mm. Gradient: Linear 5%-95% acetonitrile during 4.0 min at 0.4 ml/min. Detection: 214 nm (analogue output from TUV (Tunable UV detector)). Scan: 100-3200 amu.

2. UPLC method
Method: UPLC01
The RP-analysis is performed using a Waters UPLC system fitted with a dual band detector. UV detections at 214 nm and 254 nm are collected using an ACQUITY UPLC BEH130, C18, 130 Å, 1.7 um, 2.1 mm×150 mm column, 40° C. The UPLC system is connected to two eluent reservoirs containing: A: 99.95% H$_2$O, 0.05% TFA; B: 99.95% CH$_3$CN, 0.05% TFA. The following linear gradient is used: 95% A, 5% B to 40% A, 60% B over 16 minutes at a flow-rate of 0.40 ml/min.

Method: UPLC02
The RP-analysis is performed using a Waters UPLC system fitted with a dual band detector. UV detections at 214 nm and 254 nm are collected using an ACQUITY UPLC BEH130, C18, 130 Å, 1.7 um, 2.1 mm×150 mm column, 40° C. The UPLC system is connected to two eluent reservoirs containing: A: 99.95% H$_2$O, 0.05% TFA; B: 99.95% CH$_3$CN, 0.05% TFA. The following linear gradient is used: 95% A, 5% B to 5% A, 95% B over 16 minutes at a flow-rate of 0.40 ml/min.

A3. Characterization of Selected Intermediates
Peptide Hydrazide:

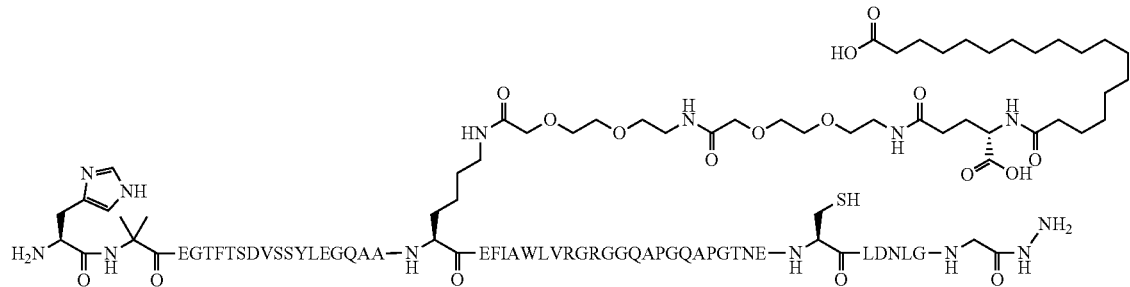

[8Aib, 34R]GLP-1(7-37)-GQAPGQAP-[30IL]EGF(A)(293-303) (amino acid 1-50 of SEQ ID NO: 193) hydrazide with substituent #1 (HOOC—(CH$_2$)$_{16}$—CO-γGlu-Ado-Ado) attached via (the epsilon nitrogen of) 26K of [8Aib, 34R]GLP-1(7-37) (SEQ ID NO: 139).
Preparation method: SPPS_P; CP_M1
LCMS34: m/3=1970.3, m/4=1478.0, m/5=1182.6
UPLC02: Rt=9.3 min
Cys-peptide:

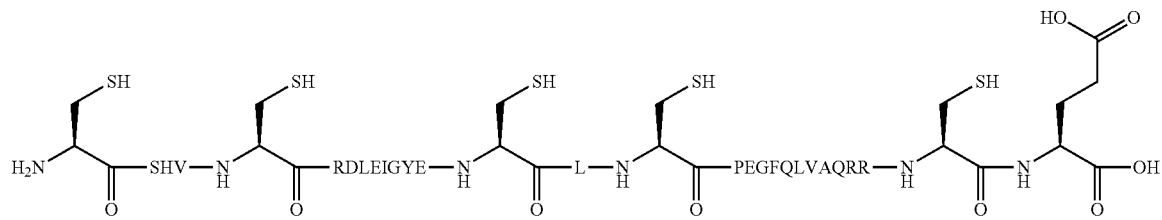

[309R, 312E, 321E]EGF(A)(304-332) (amino acid 51-79 of SEQ ID NO: 193)
Preparation method: SPPS_P; CP_M1
LCMS01: m/3=1119.8, m/4=840.1, m/5=672.3
UPLC02: Rt=8.4 min B1. Specific Compounds—EGF(A) Analogues and Derivatives
Summary Table of EGF(A) Analogues and Derivatives (EGF(A) Compounds 1-159)

| EGF(A) compound # | EGF(A) analogue | Substituent | Attachment sites |
|---|---|---|---|
| 1 | 299A, 301L, 307I, 309R, 310K | HOOC—(CH$_2$)$_{16}$—CO-gGlu-2xADO-NH—CH$_2$—(C$_6$H$_4$)—CH$_2$— | N-terminal |
| 2 | 301L, 309R | HOOC—(CH$_2$)$_{16}$—CO-gGlu-2xADO-NH—CH$_2$—(C$_6$H$_4$)—CH$_2$— | N-terminal |
| 3 | 301L, 309R, 312E, 333K | HOOC—(CH$_2$)$_{16}$—CO-gGlu-2xADO | 333K |
| 4 | 301L, 309R | HOOC—(CH$_2$)$_{16}$—CO-gGlu-2xADO | 312K |
| 5 | 301L, 309R, 312E | HOOC—(CH$_2$)$_{16}$—CO-gGlu-2xADO-NH—CH$_2$—(C$_6$H$_4$)—CH$_2$— | N-terminal |
| 6 | 299K, 301L, 309R, 312E | HOOC—(CH$_2$)$_{16}$—CO-gGlu-2xADO | 299K |
| 7 | 301L, 309R, 312E, 330K | HOOC—(CH$_2$)$_{16}$—CO-gGlu-2xADO | 330K |
| 8 | 301L, 309R, 312E | HOS(O)2-(CH2)15-CO—gGlu-2xADO-NH—CH$_2$—(C$_6$H$_4$)—CH$_2$— | N-terminal |
| 9 | 301L, 309R, 312E, 330K | HOOC—(CH$_2$)$_{16}$—CO-gGlu-2xADO | N-terminal, 330K |
| 10 | 301L, 309R, 312E, 332K | HOOC—(CH$_2$)$_{16}$—CO-gGlu-2xADO | 332K |
| 11 | 293K, 301L, 309R, 312E | HOOC—(CH$_2$)$_{16}$—CO-gGlu-2xADO | 293K |
| 12 | 293K, 301L, 309R, 312E, 333K | HOOC—(CH$_2$)$_{16}$—CO-gGlu-2xADO | 293K, 333K |
| 13 | 293K, 301L, 309R, 312E, 333K | 4-HOOC—(C$_6$H$_4$)—O—(CH$_2$)$_{10}$—CO-gGlu-2xADO | 293K, 333K |
| 14 | 301L, 309R, 312E, 332K, 333K | 4-HOOC—(C$_6$H$_4$)—O—(CH$_2$)$_{10}$—CO-gGlu-2xADO | 332K, 333K |
| 15 | 301L, 309R, 312E, 330K, 333K | 4-HOOC—(C$_6$H$_4$)—O—(CH$_2$)$_{10}$—CO-gGlu-2xADO | 330K, 333K |
| 16 | 301L, 309R, 312E, 321K, 333K | 4-HOOC—(C$_6$H$_4$)—O—(CH$_2$)$_{10}$—CO-gGlu-2xADO | 321K, 333K |
| 17 | 301L, 309R, 333K | 4-HOOC—(C$_6$H$_4$)—O—(CH$_2$)$_{10}$—CO-gGlu-2xADO | 312K, 333K |
| 18 | 301L, 309R, 312E, 321E, 333K | HOOC—(CH$_2$)$_{16}$—CO-gGlu-2xADO | 333K |
| 19 | 301L, 309R, 312E | HOOC—(CH$_2$)$_{16}$—CO-gGlu-2xADO | N-terminal |
| 20 | 301L, 309R, 312E, 321K | HOOC—(CH$_2$)$_{16}$—CO-gGlu-2xADO | 321K |
| 21 | 301L, 309R, 312E, 324K | HOOC—(CH$_2$)$_{16}$—CO-gGlu-2xADO | 324K |
| 22 | 301L, 309R, 312Q | HOOC—(CH$_2$)$_{16}$—CO-gGlu-2xADO | N-terminal |
| 23 | 301L, 309R, 312E, 321E, 332K | HOOC—(CH$_2$)$_{16}$—CO-gGlu-2xADO | 332K |
| 24 | 293K, 301L, 309R, 312E, 321E | HOOC—(CH$_2$)$_{16}$—CO-gGlu-2xADO | 293K |
| 25 | 293K, 301L, 309R, 312E | HOOC—(CH$_2$)$_{16}$—CO-gGlu-2xADO | N-terminal, 293K |
| 26 | 300K, 301L, 309R, 312E | HOOC—(CH$_2$)$_{16}$—CO-gGlu-2xADO | 300K |
| 27 | 293K, 294K, 301L, 309R, 312E | 4-HOOC—(C$_6$H$_4$)—O—(CH$_2$)$_{10}$—CO-gGlu-2xADO | 293K, 294K |
| 28 | 293K, 301L, 309R | 4-HOOC—(C$_6$H$_4$)—O—(CH$_2$)$_{10}$—CO-gGlu-2xADO | 293K, 312K |
| 29 | 301L, 309K, 312E | HOOC—(CH$_2$)$_{16}$—CO-gGlu-2xADO | 309K |
| 30 | 301L, 309R, 312E, 318K | HOOC—(CH$_2$)$_{16}$—CO-gGlu-2xADO | 318K |
| 31 | 301L, 309R, 312E, 313K, 333K | 4-HOOC—(C$_6$H$_4$)—O—(CH$_2$)$_{10}$—CO-gGlu-2xADO | 313K, 333K |
| 32 | 301L, 309R, 312E, 326K | HOOC—(CH$_2$)$_{16}$—CO-gGlu-2xADO | 326K |
| 33 | 301L, 309R, 312E, 325K | HOOC—(CH$_2$)$_{16}$—CO-gGlu-2xADO | 325K |
| 34 | 301L, 309R, 312E, 323K | HOOC—(CH$_2$)$_{16}$—CO-gGlu-2xADO | 323K |
| 35 | 301L, 309R, 312E, 322K | HOOC—(CH$_2$)$_{16}$—CO-gGlu-2xADO | 322K |
| 36 | 301L, 309R, 312E, 320K | HOOC—(CH$_2$)$_{16}$—CO-gGlu-2xADO | 320K |
| 37 | 301L, 309R, 312E, 329K | HOOC—(CH$_2$)$_{16}$—CO-gGlu-2xADO | 329K |
| 38 | 301L, 309R, 312E, 313K | HOOC—(CH$_2$)$_{16}$—CO-gGlu-2xADO | 313K |
| 39 | 301L, 309R, 312E, 328K | HOOC—(CH$_2$)$_{16}$—CO-gGlu-2xADO | 328K |
| 40 | 301L, 309R, 312E, 316K | HOOC—(CH$_2$)$_{16}$—CO-gGlu-2xADO | 316K |
| 41 | 301L, 309R, 312E, 315K | HOOC—(CH$_2$)$_{16}$—CO-gGlu-2xADO | 315K |

-continued

| EGF(A) compound # | EGF(A) analogue | Substituent | Attachment sites |
|---|---|---|---|
| 42 | 300H, 301L, 309R, 312R, 333K | HOOC—(CH$_2$)$_{16}$—CO-gGlu-2xADO | 333K |
| 43 | 301L, 309R, 312E, 314K | HOOC—(CH$_2$)$_{16}$—CO-gGlu-2xADO | 314K |
| 44 | 301L, 309R, 311K, 312E | HOOC—(CH$_2$)$_{16}$—CO-gGlu-2xADO | 311K |
| 45 | 301L, 307K, 309R, 312E | HOOC—(CH$_2$)$_{16}$—CO-gGlu-2xADO | 307K |
| 46 | 301L, 309S, 312R, 333K | HOOC—(CH$_2$)$_{16}$—CO-gGlu-2xADO | 333K |
| 47 | 301L, 309S, 312E, 333K | HOOC—(CH$_2$)$_{16}$—CO-gGlu-2xADO | 333K |
| 48 | 299A, 301L, 307I, 309R, 310K | | |
| 49 | 301L, 309R | | |
| 50 | 301L, 309R, 312E | | |
| 51 | 301L, 306Y, 309S, 312E | HOOC—(CH$_2$)$_{16}$—CO-gGlu-2xADO | N-terminal |
| 52 | 293N, 301L, 309S, 312E | HOOC—(CH$_2$)$_{16}$—CO-gGlu-2xADO | N-terminal |
| 53 | 301L, 306K, 309R, 312E | HOOC—(CH$_2$)$_{16}$—CO-gGlu-2xADO | 306K |
| 54 | 301L, 305K, 309R, 312E | HOOC—(CH$_2$)$_{16}$—CO-gGlu-2xADO | 305K |
| 55 | 301L, 303K, 309R, 312E | HOOC—(CH$_2$)$_{16}$—CO-gGlu-2xADO | 303K |
| 56 | 301L, 302K, 309R, 312E | HOOC—(CH$_2$)$_{16}$—CO-gGlu-2xADO | 302K |
| 57 | 293N, 300H, 301L, 309R, 312R, 333K | HOOC—(CH$_2$)$_{16}$—CO-gGlu-2xADO | 333K |
| 58 | 301K, 309R, 312E | HOOC—(CH$_2$)$_{16}$—CO-gGlu-2xADO | 301K |
| 59 | 298K, 301L, 309R, 312E | HOOC—(CH$_2$)$_{16}$—CO-gGlu-2xADO | 298K |
| 60 | 293N, 301L, 309R, 312R, 333K | HOOC—(CH$_2$)$_{16}$—CO-gGlu-2xADO | 333K |
| 61 | 301L, 307I, 332K | HOOC—(CH$_2$)$_{16}$—CO-gGlu-2xADO | 332K |
| 62 | 301L, 306Y, 312E, 332K | HOOC—(CH$_2$)$_{16}$—CO-gGlu-2xADO | 332K |
| 63 | 301L, 307I, 312E, 332K | HOOC—(CH$_2$)$_{16}$—CO-gGlu-2xADO | 332K |
| 64 | 300H, 301L, 309R | HOOC—(CH$_2$)$_{16}$—CO-gGlu-2xADO-NH—CH2-(C6H4)-CH2- | N-terminal |
| 65 | 300P, 301L, 307I, 309R, 312E | HOOC—(CH$_2$)$_{16}$—CO-gGlu-2xADO | N-terminal |
| 66 | 293N, 301L, 307I, 309R, 312D, 333K | HOOC—(CH$_2$)$_{16}$—CO-gGlu-2xADO | 333K |
| 67 | 293N, 301L, 309R, 312D, 333K | HOOC—(CH$_2$)$_{16}$—CO-gGlu-2xADO | 333K |
| 68 | 301L, 309R, 312E | Tetrazolyl-(CH$_2$)$_{15}$—CO—NH—SO$_2$—(CH$_2$)$_3$—CO-ADO-ADO-NH—CH$_2$—(C$_6$H$_4$)—CH$_2$— | N-terminal |
| 69 | 301L, 309R, 312E, 328K, 329H | HOOC—(CH$_2$)$_{16}$—CO-gGlu-2xADO | 328K |
| 70 | 295D, 301L, 309R, 312E, 332K | HOOC—(CH$_2$)$_{16}$—CO-gGlu-2xADO | 332K |
| 71 | 300H, 301L, 309R | HOOC—(CH$_2$)$_{16}$—CO-gGlu-2xADO | 312K |
| 72 | 300H, 301L, 307I, 309R, 312E | HOOC—(CH$_2$)$_{16}$—CO-gGlu-2xADO | N-terminal |
| 73 | 296K, 301L, 309R, 312E | HOOC—(CH$_2$)$_{16}$—CO-gGlu-2xADO | 296K |
| 74 | 294K, 301L, 309R, 312E | HOOC—(CH$_2$)$_{16}$—CO-gGlu-2xADO | 294K |
| 75 | 292K, 301L, 309R, 312E | HOOC—(CH$_2$)$_{16}$—CO-gGlu-2xADO | 292K |
| 76 | des293, 294G, 301L, 309R, 312E, 328K | HOOC—(CH$_2$)$_{16}$—CO-gGlu-2xADO | 328K |
| 77 | 301L, 306D, 309R, 312E, 324G, 333K | HOOC—(CH$_2$)$_{16}$—CO-gGlu-2xADO | 333K |
| 78 | 301L, 306D, 309R, 312E, 333K | 4-HOOC—(C$_6$H$_4$)—O—(CH$_2$)$_{10}$—CO-gGlu-3xADO and 4-HOOC—(C$_6$H$_4$)—O—(CH$_2$)$_{10}$—CO-gGlu-2xADO | N-terminal, 333K |
| 79 | 301L, 309R, 312E, 321K, 333K | 4-HOOC—(C$_6$H$_4$)—O—(CH$_2$)$_9$—CO-gGlu-2xADO | 321K, 333K |

-continued

| EGF(A) compound # | EGF(A) analogue | Substituent | Attachment sites |
|---|---|---|---|
| 80 | 301L, 309R, 312E, 333K | HOOC—$(CH_2)_{14}$—CO-gGlu-2xADO | 333K |
| 81 | 301L, 309R, 312E, 333K | HOOC—$(CH_2)_{18}$—CO-gGlu-2xADO | 333K |
| 82 | 301L, 309R, 312E, 333K | HOOC—$(CH_2)_{16}$—CO-gGlu | 333K |
| 83 | 301L, 309R, 312E, 321K, 333K | HOOC—$(CH_2)_{12}$—CO-gGlu-2xADO | 321K, 333K |
| 84 | 301L, 309R, 312E, 321K, 333K | HOOC—$(CH_2)_{14}$—CO-gGlu-2xADO | 321K, 333K |
| 85 | 300H, 301L, 309R, 312E, 313K, 333K | 4-HOOC—$(C_6H_4)$—O—$(CH_2)_9$—CO-gGlu-2xADO | 313K, 333K |
| 86 | 301L, 309R, 312E, 313K, 328K | 4-HOOC—$(C_6H_4)$—O—$(CH_2)_{10}$—CO-gGlu-2xADO | 313K, 328K |
| 87 | 301L, 309R, 312E, 313K, 324K | 4-HOOC—$(C_6H_4)$—O—$(CH_2)_{10}$—CO-gGlu-2xADO | 313K, 324K |
| 88 | 301L, 309R, 312E, 313K | 4-HOOC—$(C_6H_4)$—O—$(CH_2)_{10}$—CO-gGlu-2xADO | N-terminal, 313K |
| 89 | 301L, 309R, 312E, 324K, 333K | 4-HOOC—$(C_6H_4)$—O—$(CH_2)_{10}$—CO-gGlu-2xADO | 324K, 333K |
| 90 | 301L, 309R, 312E, 313K, 321K | 4-HOOC—$(C_6H_4)$—O—$(CH_2)_{10}$—CO-gGlu-2xADO | 313K, 321K |
| 91 | des293, 300H, 301L, 309R, 312E, 313K, 333K | 4-HOOC—$(C_6H_4)$—O—$(CH_2)_9$—CO-gGlu-2xADO | 313K, 333K |
| 92 | 300H, 301L, 309R, 312E, 313K, 333K | 4-HOOC—$(C_6H_4)$—O—$(CH_2)_{10}$—CO-gGlu-2xADO | 313K, 333K |
| 93 | 292A, 301L, 309R, 312E, 313K | 4-HOOC—$(C_6H_4)$—O—$(CH_2)_{10}$—CO-gGlu-2xADO | N-terminal, 313K |
| 94 | des293, 301L, 309R, 312E, 313K | 4-HOOC—$(C_6H_4)$—O—$(CH_2)_{10}$—CO-gGlu-2xADO | N-terminal, 313K |
| 95 | des293, 301L, 309R, 312E, 313K | HOOC—$(CH_2)_{16}$—CO-gGlu-2xADO | 313K |
| 96 | 301L, 309R, 312E, 313K, 332K | 4-HOOC—$(C_6H_4)$—O—$(CH_2)_{10}$—CO-gGlu-2xADO | 313K, 332K |
| 97 | 301L, 309R, 312E, 328K, 333K | 4-HOOC—$(C_6H_4)$—O—$(CH_2)_{10}$—CO-gGlu-2xADO | 328K, 333K |
| 98 | 301L, 309R, 312E, 313K, 333K | 4-HOOC—$(C_6H_4)$—O—$(CH_2)_{10}$—CO-gGlu | 313K, 333K |
| 99 | 301L, 309R, 312E, 313K, 333K | 4-HOOC—$(C_6H_4)$—O—$(CH_2)_{10}$—CO-2xgGlu | 313K, 333K |
| 100 | 301L, 309R, 312E, 313K, 333K | 4-HOOC—$(C_6H_4)$—O—$(CH_2)_{10}$—CO-gGlu-3xGly | 313K, 333K |
| 101 | 301L, 309R, 312E, 313K, 333K | 4-HOOC—$(C_6H_4)$—O—$(CH_2)_{10}$—CO-2xgGlu-2xADO | 313K, 333K |
| 102 | 301L, 309R, 312E, 313K, 333K | 3-HOOC—$(C_6H_4)$—O—$(CH_2)_9$—CO-gGlu-2xADO | 313K, 333K |
| 103 | 299A, 301L, 307I, 309R | | |
| 104 | 301L, 309R, 310K | | |
| 105 | 301L | | |
| 106 | 300H, 301L, 309R, 312E, 333K | HOOC—$(CH_2)_{16}$—CO-gGlu-2xADO | 333K |
| 107 | 301L, 309R, 312E, 333K | 4-HOOC—$(C_6H_4)$—O—$(CH_2)_{10}$—CO-gGlu-2xADO | N-terminal, 333K |
| 108 | des293-294, 300H, 301L, 309R, 312E, 313K, 333K | 4-HOOC—$(C_6H_4)$—O—$(CH_2)_9$—CO-gGlu-2xADO | 313K, 333K |
| 109 | 300H, 301L, 309R, 312E, 313K, 333K | 3-HO-Isoxazole-$(CH_2)_{12}$—CO-gGlu-2xADO | 313K, 333K |
| 110 | 301L, 309R, 312E, 313K, 333K | 3-HO-Isoxazole-$(CH_2)_{12}$—CO-gGlu-2xADO | 313K, 333K |
| 111 | 301L, 309K, 312E, 333K | 4-HOOC—$(C_6H_4)$—O—$(CH_2)_{10}$—CO-gGlu-2xADO | 309K, 333K |
| 112 | 301L, 306Y, 312E, 324K, 333K | 4-HOOC—$(C_6H_4)$—O—$(CH_2)_{10}$—CO-gGlu-2xADO | 324K, 333K |
| 113 | 300H, 301L, 309R, 312E, 314K, 333K | 4-HOOC—$(C_6H_4)$—O—$(CH_2)_{10}$—CO-gGlu-2xADO | 314K, 333K |
| 114 | 294W, 301L, 309R, 312E, 333K | 4-HOOC—$(C_6H_4)$—O—$(CH_2)_{10}$—CO-gGlu-2xADO | N-terminal, 333K |

| EGF(A) compound # | EGF(A) analogue | Substituent | Attachment sites |
|---|---|---|---|
| 115 | 301L, 309K, 312E, 328K | 4-HOOC—(C$_6$H$_4$)—O—(CH$_2$)$_{10}$—CO-gGlu-2xADO | 309K, 328K |
| 116 | 301L, 309K, 312E, 313K | 4-HOOC—(C$_6$H$_4$)—O—(CH$_2$)$_{10}$—CO-gGlu-2xADO | 309K, 313K |
| 117 | des293, 301L, 309R, 312E, 333K | 4-HOOC—(C$_6$H$_4$)—O—(CH$_2$)$_{10}$—CO-gGlu-2xADO | N-terminal, 333K |
| 118 | 301L, 309R, 312E, 324K, 328K | 4-HOOC—(C$_6$H$_4$)—O—(CH$_2$)$_{10}$—CO-gGlu-2xADO | 324K, 328K |
| 119 | 292A, 301L, 309R, 312E, 333K | 4-HOOC—(C$_6$H$_4$)—O—(CH$_2$)$_{10}$—CO-gGlu-2xADO | N-terminal, 333K |
| 120 | 301L, 306Y, 309R, 312E, 313K, 333K | 4-HOOC—(C$_6$H$_4$)—O—(CH$_2$)$_{10}$—CO-gGlu-2xADO | 313K, 333K |
| 121 | 301L, 309R, 312E, 332K | 4-HOOC—(C$_6$H$_4$)—O—(CH$_2$)$_{10}$—CO-gGlu-2xADO | N-terminal, 332K |
| 122 | 301L, 309R, 312E, 328K | 4-HOOC—(C$_6$H$_4$)—O—(CH$_2$)$_{10}$—CO-gGlu-2xADO | N-terminal, 328K |
| 123 | 301L, 309R, 312E, 324K | 4-HOOC—(C$_6$H$_4$)—O—(CH$_2$)$_{10}$—CO-gGlu-2xADO | N-terminal, 324K |
| 124 | 301L, 309K, 312E, 332K | 4-HOOC—(C$_6$H$_4$)—O—(CH$_2$)$_{10}$—CO-gGlu-2xADO | 309K, 332K |
| 125 | 301L, 309K, 312E, 324K | 4-HOOC—(C$_6$H$_4$)—O—(CH$_2$)$_{10}$—CO-gGlu-2xADO | 309K, 324K |
| 126 | 301L, 309K, 312E | 4-HOOC—(C$_6$H$_4$)—O—(CH$_2$)$_{10}$—CO-gGlu-2xADO | N-terminal, 309K |
| 127 | 301L, 309R, 312E, 321K, 332K | 4-HOOC—(C$_6$H$_4$)—O—(CH$_2$)$_{10}$—CO-gGlu-2xADO | 321K, 332K |
| 128 | 301L, 309R, 312E, 313K, 333K | HOOC—(CH$_2$)$_{14}$—CO-gGlu-2xADO | 313K, 333K |
| 129 | 301L, 309R, 312E, 313K, 333K | HOOC—(CH2)14-CO-gGlu | 313K, 333K |
| 130 | 300H, 301L, 309R, 312E, 313K, 332K | 4-HOOC—(C$_6$H$_4$)—O—(CH$_2$)$_{10}$—CO-gGlu-2xADO | 313K, 332K |
| 131 | 301L, 309R, 312E, 313K, 333K | 4-HOOC—(C$_6$H$_4$)—O—(CH$_2$)$_{10}$—CO-gGlu-TtdSuc | 313K, 333K |
| 132 | 301L, 309R, 312E, 313K, 321E, 332K | 4-HOOC—(C$_6$H$_4$)—O—(CH$_2$)$_{10}$—CO-gGlu-TtdSuc | 313K, 332K |
| 133 | 301L, 309R, 312E, 313K, 321E, 333K | 4-HOOC—(C$_6$H$_4$)—O—(CH$_2$)$_{10}$—CO-gGlu-2xADO | 313K, 333K |
| 134 | 301L, 309R, 312E, 321E, 333K | HOOC—(CH$_2$)$_{18}$—CO-gGlu-2xADO | 333K |
| 135 | 301L, 309R, 312E, 313K, 314K | 4-HOOC—(C$_6$H$_4$)—O—(CH$_2$)$_{10}$—CO-gGlu-2xADO | 313K, 314K |
| 136 | 301L, 309R, 313K | 4-HOOC—(C$_6$H$_4$)—O—(CH$_2$)$_{10}$—CO-gGlu-2xADO | 312K, 313K |
| 137 | 301L, 309R, 314K | 4-HOOC—(C$_6$H$_4$)—O—(CH$_2$)$_{10}$—CO-gGlu-2xADO | 312K, 314K |
| 138 | 301L, 309R, 311K, 312E, 313K | 4-HOOC—(C$_6$H$_4$)—O—(CH$_2$)$_{10}$—CO-gGlu-2xADO | 311K, 313K |
| 139 | 300H, 301L, 309R, 312E, 313K, 333K | 4-HOOC—(C$_6$H$_4$)—O—(CH$_2$)$_9$—CO | 313K, 333K |
| 140 | 301L, 309R, 312E, 313K, 333K | Tetrazolyl-(CH$_2$)$_{12}$—CO-gGlu-2xADO | 313K, 333K |
| 141 | 301L, 309R, 312E, 313K, 333K | HOS(O)$_2$—(CH$_2$)$_{13}$—CO-gGlu-2xADO | 313K, 333K |
| 142 | 301L, 309R, 312E, 313K, 333K | MeS(O)$_2$NH(CO)NH—(CH$_2$)$_{12}$—CO-gGlu-2xADO | 313K, 333K |
| 143 | 301L, 309R, 312E, 313K, 321E, 333K | 4-HOOC—(C$_6$H$_4$)—O—(CH$_2$)$_{10}$—CO-gGlu | 313K, 333K |
| 144 | 301L, 309R, 312E, 313K, 321E, 333K | HOOC—(CH$_2$)$_{14}$—CO-gGlu-2xADO | 313K, 333K |
| 145 | 301L, 309R, 312E, 313K, 333K | Tetrazolyl-(CH$_2$)$_{15}$—CO-gGlu-2xADO | 313K, 333K |
| 146 | 301L, 309R, 312E, 313K, 321E, 333K | HOOC—(CH$_2$)$_{14}$—CO-gGlu | 313K, 333K |
| 147 | 300H, 301L, 309R, 312E, 313K, 321E, 333K | 4-HOOC—(C$_6$H$_4$)—O—(CH$_2$)$_{10}$—CO-gGlu-2xADO | 313K, 333K |

-continued

| EGF(A) compound # | EGF(A) analogue | Substituent | Attachment sites |
|---|---|---|---|
| 148 | 301L, 309R, 312E, 313K, 333K | 4-HOOC—($C_6H_4$)—O—$(CH_2)_{10}$—CO-gGlu-4xADO | 313K, 333K |
| 149 | des293, 300H, 301L, 309R, 312E, 313K, 333K | 4-HOOC—($C_6H_4$)—O—$(CH_2)_{10}$—CO-gGlu-2xADO | 313K, 333K |
| 150 | 301L, 309R, 312E, 328K, 333K | HOOC—$(CH_2)_{14}$—CO-gGlu-2xADO | 328K, 333K |
| 151 | 301L, 309R, 312E, 321E, 328K, 333K | HOOC—$(CH_2)_{14}$—CO-gGlu-2xADO | 328K, 333K |
| 152 | 301L, 309R, 312E, 324K, 333K | HOOC—$(CH_2)_{14}$—CO-gGlu-2xADO | 324K, 333K |
| 153 | 301L, 309R, 312E, 321E, 324K, 333K | HOOC—$(CH_2)_{14}$—CO-gGlu-2xADO | 324K, 333K |
| 154 | 301L, 309R, 312E, 321E, 328K, 333K | HOOC—$(CH_2)_{16}$—CO-gGlu-2xADO | 328K, 333K |
| 155 | 301L, 309R, 312E, 313K, 321K | HOOC—$(CH_2)_{14}$—CO-gGlu-2xADO | 313K, 321K |
| 156 | 301L, 309R, 312E, 313K, 333K | 4-HOOC—($C_6H_4$)—O—$(CH_2)_{10}$—CO-Trx-gGlu-2xADO | 313K, 333K |
| 157 | 301L, 309R, 312E, 313K, 321E, 333K | 4-HOOC—($C_6H_4$)—O—$(CH_2)_{10}$—CO-Trx-gGlu-2xADO | 313K, 333K |
| 158 | 301L, 309R, 312E, 321E, 333K | HOOC—$(CH_2)_{18}$—CO-Trx-gGlu-2xADO | 333K |
| 159 | 301L, 309R, 312E, 321E, 333K | HOOC—$(CH_2)_{16}$—CO-Trx-gGlu-2xADO | 333K |

B2. Specific Compounds—GLP-1/EGF(A) Compounds

Preparation of compounds was performed as described above. The identity of the compounds is provided by reference to the amino acid sequence of each element as provided elsewhere herein, the substituent(s) and the specific attachment point of the one or two substituents. A few examples are shown below and a summary table is provided below.

GLP-1/EGF(A) Compound # 1

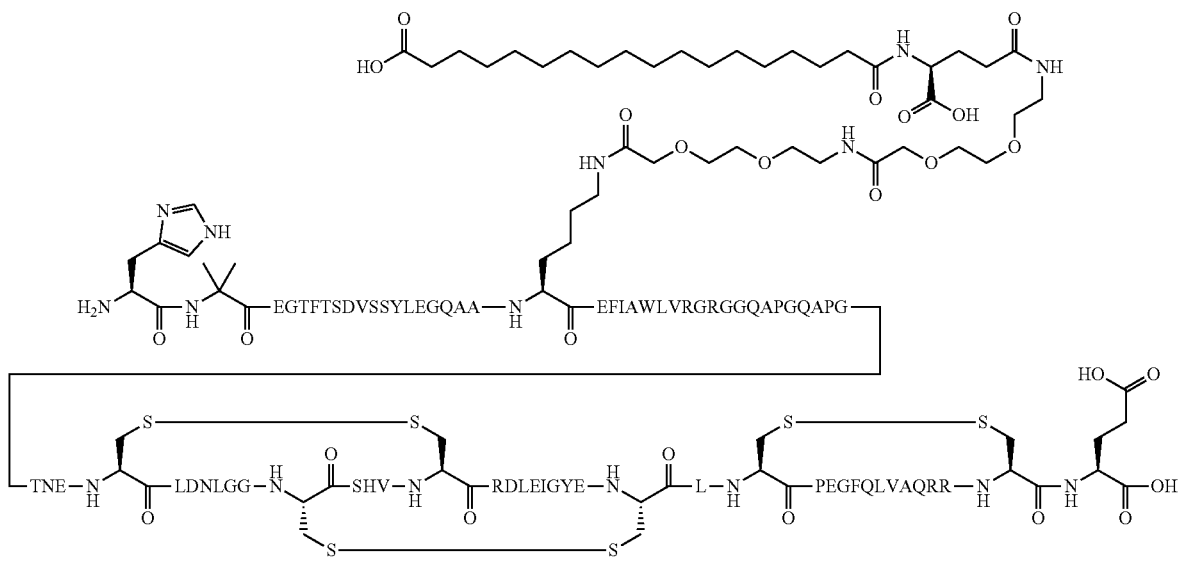

which may also be described as:
[8Aib, 34R]GLP-1(7-37)-GQAPGQAP-[301L, 309R, 312E, 321E]EGF(A) (SEQ ID NO: 193) with substituent #1

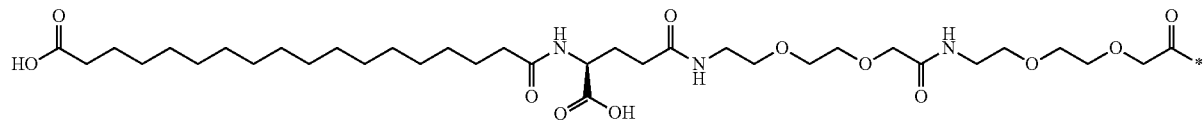 [SMILES: *C(=O)COCCOCCNC(=O)COCCOCCNC(=O)CC[C@H](NC(=O)CCCCCCCCCCCCCCCCC(=O)O)C(=O)O]

attached via (the epsilon nitrogen of) 26K of [8Aib, 34R]GLP-1(7-37) (SEQ ID NO: 139).
or
[8Aib, 34R]GLP-1(7-37)-GQAPGQAP-[301L, 309R, 312E, 321E]EGF(A) (SEQ ID NO:193) with substituent #1 (HOOC—(CH$_2$)$_{16}$—CO-γGlu-Ado-Ado) attached via (the epsilon nitrogen of) 26K of [8Aib, 34R]GLP-1(7-37) (SEQ ID NO: 139).
or
SEQ ID 193 with substituent #1 attached via (the epsilon nitrogen of) Lysine (K) in position 20 of SEQ ID 193 (equal to 26K of [8Aib, 34R]GLP-1(7-37) (SEQ ID NO: 139).

GLP-1/EGF(A) Compound # 23

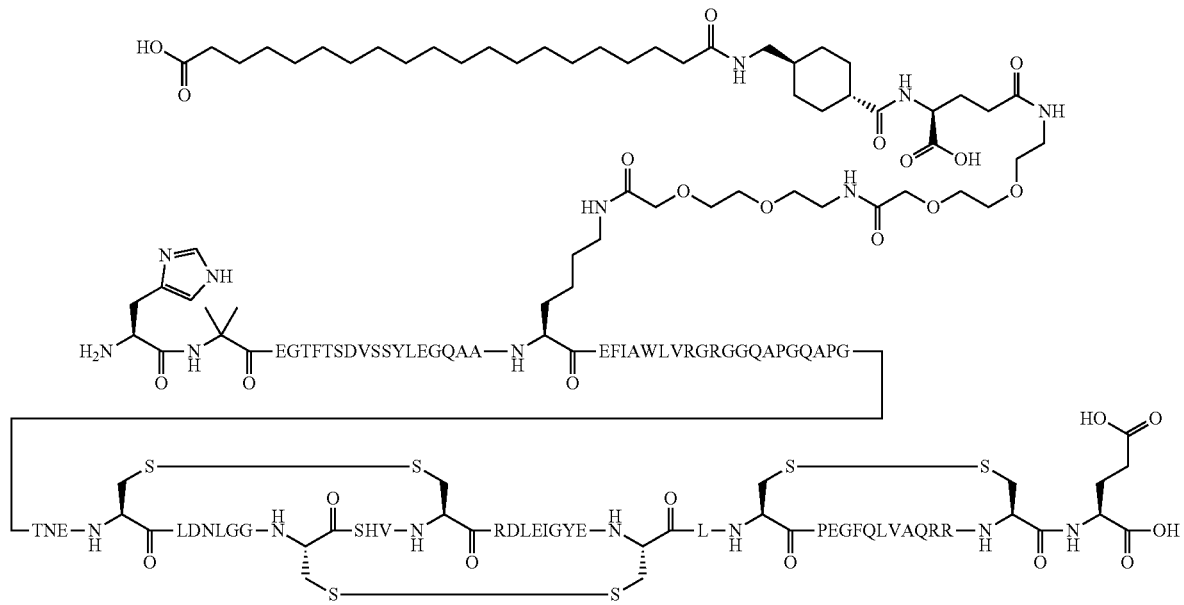

which may also be described as:
[8Aib, 34R]GLP-1(7-37)-GQAPGQAP-[301L, 309R, 312E, 321E]EGF(A) (SEQ ID NO:193) with substituent #6

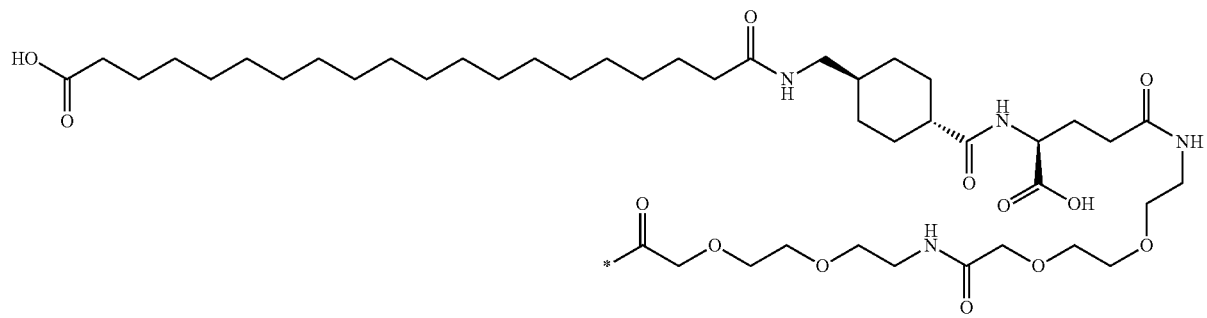 [SMILES: *C(=O)COCCOCCNC(=O)COCCOCCNC(=O)CC[C@H](NC(=O)[C@H]1CC[C@H](CNC(=O)CCCCCCCCCCCCCCCCCCC(=O)O)CC1)C(=O)O]

attached via (the epsilon nitrogen of) 26K of [8Aib, 34R] GLP-1(7-37) (SEQ ID NO: 139).
or
[8Aib, 34R]GLP-1(7-37)-GQAPGQAP-[301L, 309R, 312E, 321E]EGF(A) (SEQ ID NO: 193) with substituent #6 (HOOC—$(CH_2)_{18}$—CO-Trx-γGlu-Ado-Ado) attached via (the epsilon nitrogen of) 26K of [8Aib, 34R]GLP-1(7-37). (SEQ ID NO: 139)
or
SEQ ID 193 with substituent #6 attached via Lysine (K) in position 20 of SEQ ID 193.

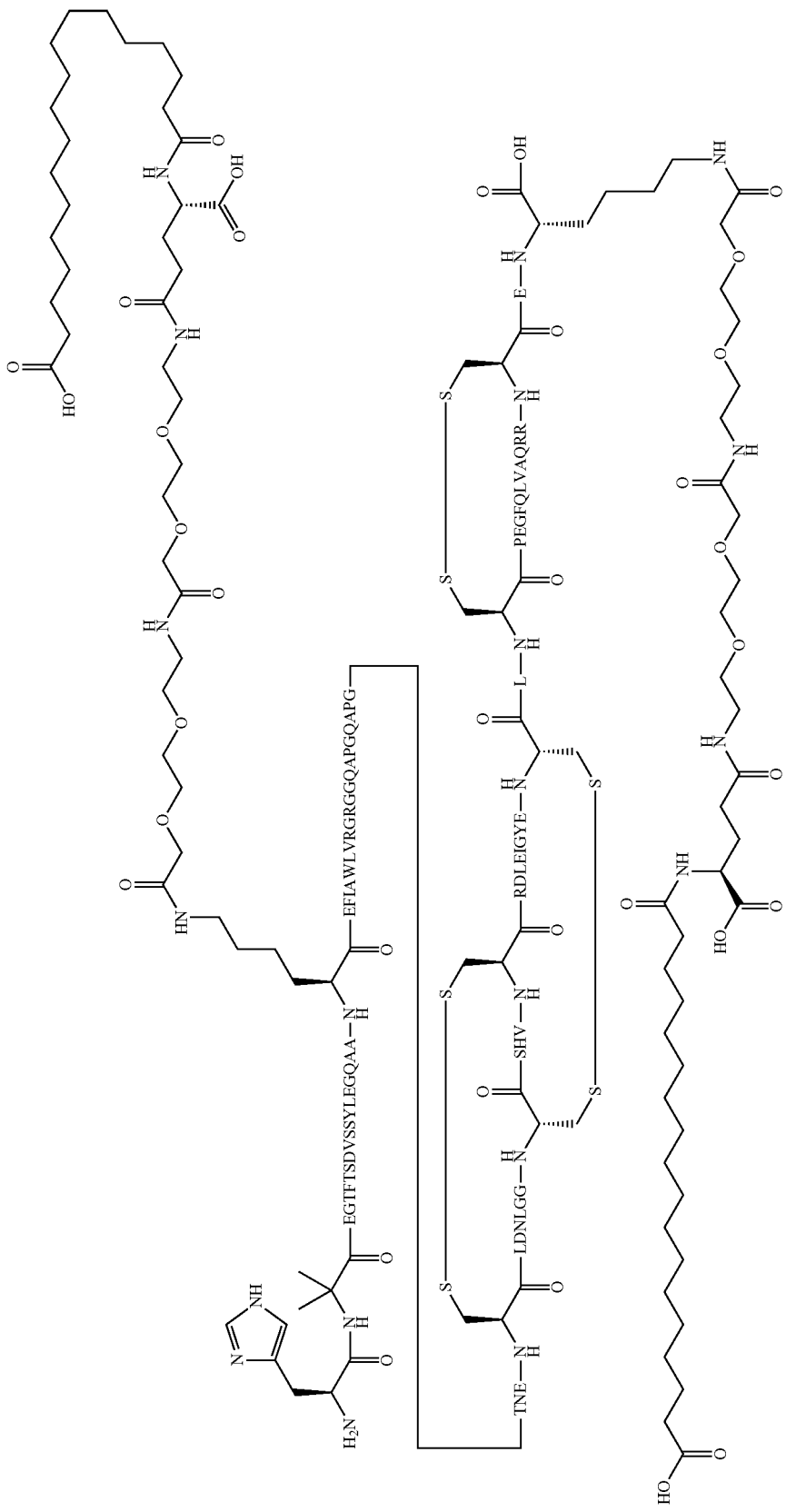

which may also be described as
[8Aib, 34R]GLP-1(7-37)-GQAPGQAP-[301L, 309R, 312E, 321E]EGF(A) (SEQ ID NO: 190) with substituent #1

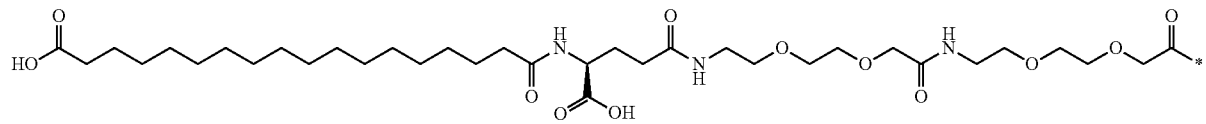 [SMILES: *C(=O)COCCOCCNC(=O)COCCOCCNC(=O)CC[C@H](NC(=O)CCCCCCCCCCCCCCCCC(=O)O)C(=O)O]

attached via (the epsilon nitrogen of) 26K [8Aib, 34R] GLP-1 (SEQ ID NO: 139) and (the epsilon nitrogen of) 333K of [301L, 309R, 312E, 321E, 333K]EGF(A) (SEQ ID NO: 19)

or

[8Aib, 34R]GLP-1(7-37)-GQAPGQAP-[301L, 309R, 312E, 321E, 333K]EGF(A) (SEQ ID NO: 190) with substituent #1 (HOOC—(CH$_2$)$_{16}$—CO-γGlu-Ado-Ado) attached via (the epsilon nitrogen of) 26K [8Aib, 34R]GLP-1 (SEQ ID NO: 139) and (the epsilon nitrogen of) 333K of [301L, 309R, 312E, 321E, 333K]EGF(A) (SEQ ID NO: 19)

or

SEQ ID 190 with substituent #1 (HOOC—(CH$_2$)$_{16}$—CO-γGlu-Ado-Ado) attached via (the epsilon nitrogen of) 26K [8Aib, 34R]GLP-1 (SEQ ID NO: 139) and (the epsilon nitrogen of) 333K of [301L, 309R, 312E, 321E, 333K]EGF(A) (SEQ ID NO: 19)

or

SEQ ID 190 with substituent #1 (HOOC—(CH$_2$)$_{16}$—CO-γGlu-Ado-Ado) attached via Lys in positions 20 and 80.

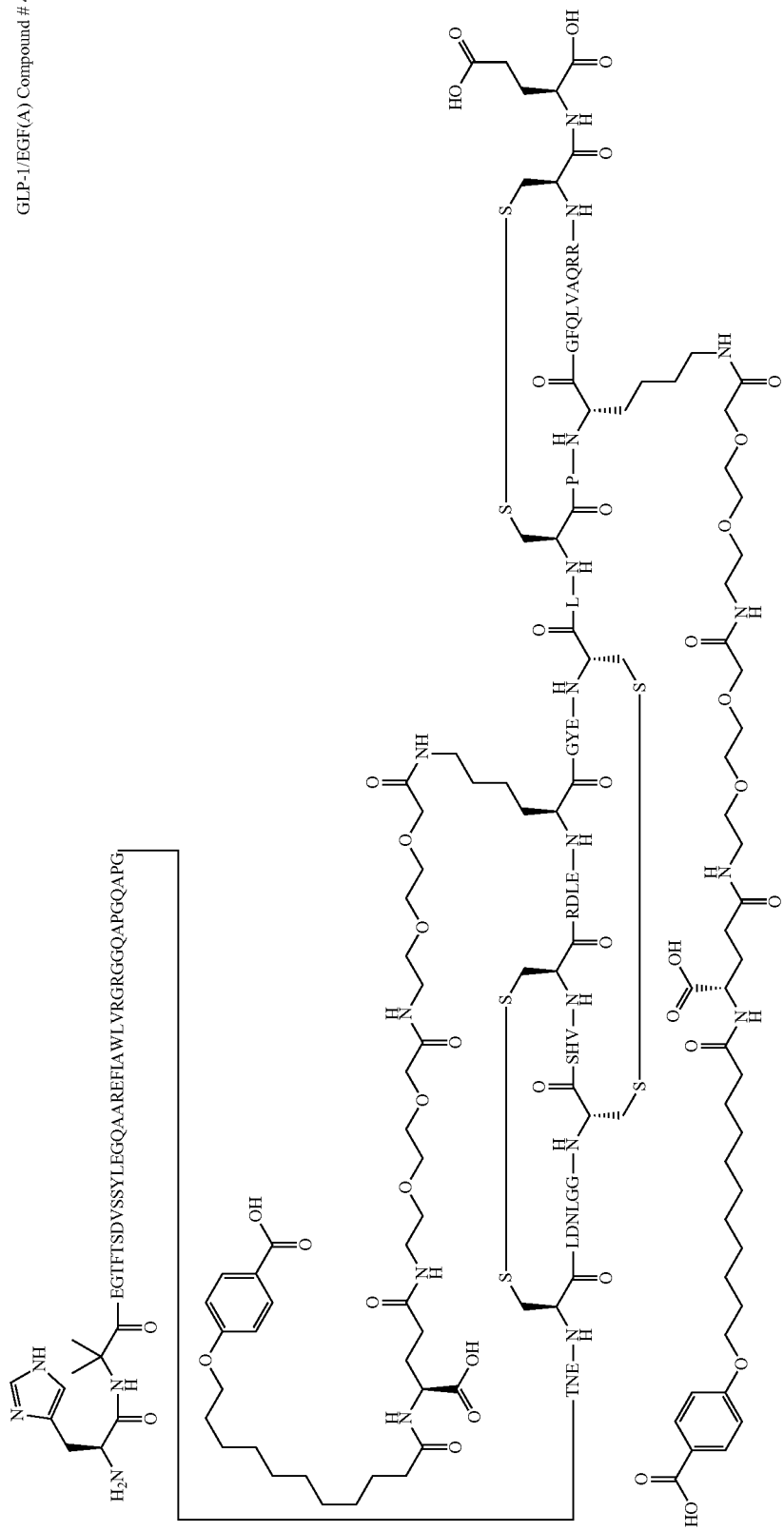
GLP-1/EGF(A) Compound # 42 which may be described as
[8Aib, 26R, 34R]GLP-1(7-37)-GQAPGQAP-[301L, 309R, 312E, 313K, 321K]EGF(A) (SEQ ID NO: 380) with substituent #13

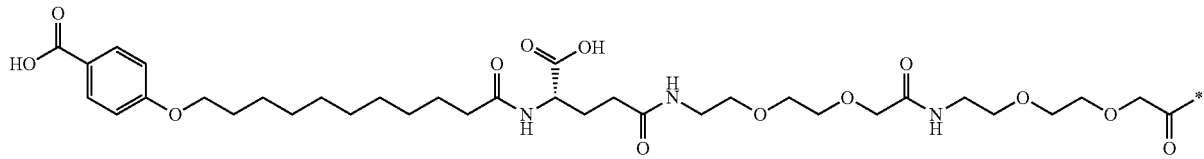 [SMILES: *C(=O)COCCOCCNC(=O)COCCOCCNC(=O)CC[C@H](NC(=O)CCCCCCCCCCOc1ccc(C(=O)O)cc1)C(=O)O]

attached via (the epsilon nitrogen of) 313K and 321K of [301L, 309R, 312E, 313K, 321K]EGF(A) (SEQ ID NO: 73).
or
[8Aib, 26R, 34R]GLP-1(7-37)-GQAPGQAP-[301L, 309R, 312E, 313K, 321K]EGF(A) (SEQ ID NO: 380) with substituent #13 (4-COOH-PhO-C11-γGlu-Ado-Ado) attached via (the epsilon nitrogen of) 313K and 321K of [301L, 309R, 312E, 313K, 321K]EGF(A) (SEQ ID NO: 73)
or
SEQ ID 380 with substituent #13 (4-COOH-PhO-C11-γGlu-Ado-Ado) attached via (the epsilon nitrogen of) 313K and 321K of [301L, 309R, 312E, 313K, 321K]EGF(A) (SEQ ID NO: 73)
or
SEQ ID 380 with substituent #13 attached via Lys in positions 60 and 68 of SEQ ID 380.

GLP-1/EGF(A) Compound # 75

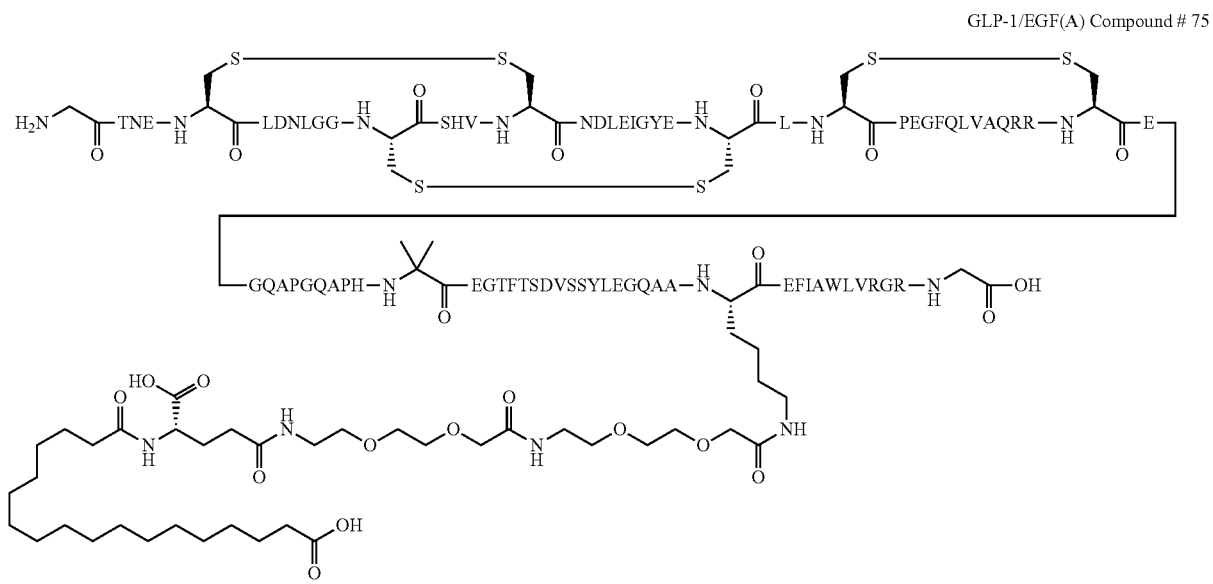

which may also be described as
[301L, 309R, 312E, 321E]EGF(A)-GQAPGQAP-[8Aib, 34R]GLP-1(7-37) (SEQ ID NO: 386) with substituent #1

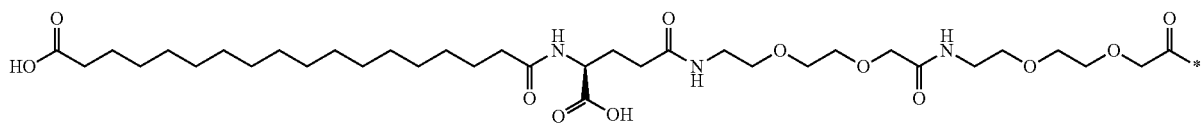 [SMILES: *C(=O)COCCOCCNC(=O)COCCOCCNC(=O)CC[C@H](NC(=O)CCCCCCCCCCCCCCCCC(=O)O)C(=O)O]

attached via (the epsilon nitrogen of) 26K of [8Aib, 34R] GLP-1(7-37) (SEQ ID NO: 139)
or
[301L, 309R, 312E, 321E]EGF(A)-GQAPGQAP-[8Aib, 34R]GLP-1(7-37) (SEQ ID NO: 386) with substituent #1 (HOOC—(CH$_2$)$_{16}$—CO-γGlu-Ado-Ado) attached via (the epsilon nitrogen of) 26K of [8Aib, 34R]GLP-1(7-37) (SEQ ID NO: 139)
or
SEQ ID 386 with substituent #1 (HOOC—(CH$_2$)$_{16}$—CO-γGlu-Ado-Ado) attached via (the epsilon nitrogen of) 26K of [8Aib, 34R]GLP-1(7-37) (SEQ ID NO: 139)
or
SEQ ID 386 with substituent #1 attached via Lys in position 68 of SEQ ID 386.(7-37).

The identity of the further compounds is provided by reference to the amino acid sequence of each element, as provided elsewhere herein, the substituent(s) and the specific attachment point of the one or two substituents.

Summary Tables of Derivatives Comprising a GLP-1 Analogue and an EGF(A) Analogue (GLP-1/EGF(A) Compounds)

The attachment of the substituent is indicated by reference to the GLP-1 and EGF(A) analogues respectively. As noted above 26K equals position 20 in the GLP-1(7-37) sequence and 324K of an EGF(A) analogue is an amino substitution in position 32 of an EGF(A) domain of LDL-R (293-332) analogue. The specific position for other attachment sites can be deduced in a similar manner. The specific position(s) of the substituent(s) in relation to the peptide back-bone will vary depending on the length of the spacer and possible truncations of the GLP-1 and EGF(A) analogues.

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 1 | 139 | 116 | 108 | 193 | 26K of SEQ ID NO. 139 | 1 |
| 2 | 150 | 116 | 108 | 229 | 25K of SEQ ID NO. 150 | 1 |
| 3 | 140 | 116 | 108 | 219 | 26K of SEQ ID NO. 140 | 1 |
| 4 | 151 | 116 | 108 | 230 | 27K of SEQ ID NO. 151 | 1 |
| 5 | 154 | 116 | 108 | 233 | 36K of SEQ ID NO. 154 | 1 |
| 6 | 146 | 116 | 108 | 225 | 26K of SEQ ID NO. 146 | 1 |
| 7 | 144 | 116 | 108 | 223 | 26K of SEQ ID NO. 144 | 1 |
| 8 | 145 | 116 | 108 | 224 | 26K of SEQ ID NO. 145 | 1 |
| 9 | 153 | 116 | 108 | 232 | 32K of SEQ ID NO. 153 | 1 |
| 10 | 148 | 116 | 108 | 227 | 21K of SEQ ID NO. 148 | 1 |
| 11 | 147 | 116 | 108 | 226 | 12K of SEQ ID NO. 147 | 1 |
| 12 | 149 | 116 | 108 | 228 | 24K of SEQ ID NO. 149 | 1 |
| 13 | 162 | 116 | 108 | 306 | 26K of SEQ ID NO. 162 | 1 |
| 14 | 166 | 116 | 108 | 336 | 26K of SEQ ID NO. 166 | 1 |
| 15 | 139 | 129 | 108 | 212 | 26K of SEQ ID NO. 139 | 1 |
| 16 | 139 | 130 | 108 | 213 | 26K of SEQ ID NO. 139 | 1 |
| 17 | 139 | 131 | 108 | 214 | 26K of SEQ ID NO. 139 | 1 |
| 18 | 144 | 116 | 108 | 223 | 26K of SEQ ID NO. 144 | 5 |
| 19 | 145 | 116 | 108 | 224 | 26K of SEQ ID NO. 145 | 5 |
| 20 | 146 | 116 | 108 | 225 | 26K of SEQ ID NO. 146 | 5 |
| 21 | 140 | 116 | 108 | 219 | 26K of SEQ ID NO. 140 | 5 |
| 22 | 139 | 116 | 108 | 193 | 26K of SEQ ID NO. 139 | 5 |
| 23 | 139 | 116 | 108 | 193 | 26K of SEQ ID NO. 139 | 6 |
| 24 | 139 | 132 | 108 | 215 | 26K of SEQ ID NO. 139 | 5 |
| 25 | 142 | 116 | 108 | 221 | 26K of SEQ ID NO. 142 | 5 |
| 26 | 184 | 116 | 108 | 381 | 2K of SEQ ID NO. 116 | 5 |
| 27 | 141 | 116 | 108 | 220 | 26K of SEQ ID NO. 141 | 1 |
| 28 | 140 | 116 | 108 | 219 | 26K of SEQ ID NO. 140 | 6 |
| 29 | 139 | 116 | 108 | 193 | 26K of SEQ ID NO. 139 | 2 |
| 30 | 139 | 134 | 108 | 216 | 26K of SEQ ID NO. 139 | 1 |
| 31 | 142 | 116 | 108 | 221 | 26K of SEQ ID NO. 142 | 1 |
| 32 | 152 | 116 | 108 | 231 | 31K of SEQ ID NO. 152 | 1 |
| 33 | 143 | 116 | 108 | 222 | 26K of SEQ ID NO. 143 | 1 |
| 34 | 141 | 116 | 108 | 220 | 26K of SEQ ID NO. 141 | 6 |
| 35 | 139 | 116 | 107 | 192 | 26K of SEQ ID NO. 139 | 1 |
| 36 | 139 | 116 | 109 | 194 | 26K of SEQ ID NO. 139 | 1 |
| 37 | 139 | 116 | 110 | 195 | 26K of SEQ ID NO. 139 | 1 |
| 38 | 139 | 116 | 111 | 196 | 26K of SEQ ID NO. 139 | 1 |
| 39 | 139 | 134 | 108 | 216 | 26K of SEQ ID NO. 139 | 6 |
| 40 | 183 | 116 | 19 | 379 | 333K of SEQ ID NO. 183 | 1 |
| 41 | 139 | 116 | 19 | 190 | 26K of SEQ ID NO. 139 and 333K of SEQ ID NO. 19 | 1 |
| 42 | 183 | 116 | 73 | 380 | 313K and 321K of SEQ ID NO. 73 | 13 |
| 43 | 139 | 119 | 108 | 202 | 26K of SEQ ID NO. 139 | 1 |
| 44 | 139 | 115 | 108 | 189 | 26K of SEQ ID NO. 139 | 1 |
| 45 | 139 | 117 | 108 | 200 | 26K of SEQ ID NO. 139 | 1 |
| 46 | 139 | 135 | 108 | 217 | 26K of SEQ ID NO. 139 | 1 |
| 47 | 139 | 136 | 108 | 218 | 26K of SEQ ID NO. 139 | 1 |
| 48 | 139 | 119 | 108 | 202 | 26K of SEQ ID NO. 139 | 6 |
| 49 | 166 | 116 | 108 | 336 | 26K of SEQ ID NO. 166 | 6 |
| 50 | 170 | 116 | 108 | 353 | 26K of SEQ ID NO. 170 | 6 |
| 51 | 168 | 116 | 108 | 351 | 26K of SEQ ID NO. 168 | 6 |
| 52 | 173 | 116 | 108 | 369 | 26K of SEQ ID NO. 173 | 6 |
| 53 | 160 | 116 | 108 | 291 | 26K of SEQ ID NO. 160 | 6 |
| 54 | 158 | 116 | 108 | 276 | 26K of SEQ ID NO. 158 | 6 |

-continued

| GLP-1/EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 55 | 159 | 116 | 108 | 279 | 26K of SEQ ID NO. 159 | 6 |
| 56 | 139 | 116 | 108 | 193 | 26K of SEQ ID NO. 139 | 3 |
| 57 | 139 | 116 | 108 | 193 | 26K of SEQ ID NO. 139 | 4 |
| 58 | 167 | 116 | 108 | 339 | 26K of SEQ ID NO. 167 | 6 |
| 59 | 169 | 116 | 108 | 352 | 26K of SEQ ID NO. 169 | 6 |
| 60 | 172 | 116 | 108 | 368 | 26K of SEQ ID NO. 172 | 6 |
| 61 | 150 | 116 | 108 | 229 | 25K of SEQ ID NO. 150 | 6 |
| 62 | 139 | 122 | 108 | 205 | 26K of SEQ ID NO. 139 and 2K of SEQ ID NO. 122 | 1 |
| 63 | 139 | 127 | 108 | 210 | 26K of SEQ ID NO. 139 and 7K of SEQ ID NO. 127 | 1 |
| 64 | 139 | 124 | 108 | 207 | 26K of SEQ ID NO. 139 and 4K of SEQ ID NO. 124 | 1 |
| 65 | 155 | 116 | 108 | 236 | 26K of SEQ ID NO. 155 | 6 |
| 66 | 156 | 116 | 108 | 250 | 26K of SEQ ID NO. 156 | 6 |
| 67 | 157 | 116 | 108 | 264 | 26K of SEQ ID NO. 157 | 6 |
| 68 | 161 | 116 | 108 | 294 | 26K of SEQ ID NO. 161 | 6 |
| 69 | 164 | 116 | 108 | 310 | 26K of SEQ ID NO. 164 | 6 |
| 70 | 165 | 116 | 108 | 324 | 26K of SEQ ID NO. 165 | 6 |
| 71 | 171 | 116 | 108 | 356 | 26K of SEQ ID NO. 171 | 6 |
| 72 | 165 | 116 | 108 | 324 | 26K of SEQ ID NO. 165 | 1 |
| 73 | 167 | 116 | 108 | 339 | 26K of SEQ ID NO. 167 | 1 |
| 74 | 171 | 116 | 108 | 356 | 26K of SEQ ID NO. 171 | 1 |
| 76 | 139 | 116 | 108 | 193 | 26K of SEQ ID NO. 139 | 7 |
| 77 | 139 | 116 | 108 | 193 | 26K of SEQ ID NO. 139 | 8 |
| 78 | 139 | 116 | 108 | 193 | 26K of SEQ ID NO. 139 | 9 |
| 79 | 139 | 116 | 108 | 193 | 26K of SEQ ID NO. 139 | 10 |
| 80 | 139 | 116 | 108 | 193 | 26K of SEQ ID NO. 139 | 11 |
| 81 | 139 | 116 | 108 | 193 | 26K of SEQ ID NO. 139 | 12 |
| 82 | 139 | 121 | 108 | 204 | 26K of SEQ ID NO. 139 and 1K of SEQ ID NO. 121 | 1 |
| 83 | 139 | 123 | 108 | 206 | 26K of SEQ ID NO. 139 and 3K of SEQ ID NO. 123 | 1 |
| 84 | 139 | 125 | 108 | 208 | 26K of SEQ ID NO. 139 and 5K of SEQ ID NO. 125 | 1 |
| 85 | 139 | 126 | 108 | 209 | 26K of SEQ ID NO. 139 and 6K of SEQ ID NO. 126 | 1 |
| 86 | 139 | 128 | 108 | 211 | 26K of SEQ ID NO. 139 and 8K of SEQ ID NO. 128 | 1 |
| 87 | 139 | 121 | 108 | 204 | 26K of SEQ ID NO. 139 and 1K of SEQ ID NO. 121 | 5 |
| 88 | 139 | 122 | 108 | 205 | 26K of SEQ ID NO. 139 and 2K of SEQ ID NO. 122 | 5 |
| 89 | 139 | 123 | 108 | 206 | 26K of SEQ ID NO. 139 and 3K of SEQ ID NO. 123 | 5 |
| 90 | 139 | 124 | 108 | 207 | 26K of SEQ ID NO. 139 and 4K of SEQ ID NO. 124 | 5 |
| 91 | 139 | 125 | 108 | 208 | 26K of SEQ ID NO. 139 and 5K of SEQ ID NO. 125 | 5 |
| 92 | 139 | 126 | 108 | 209 | 26K of SEQ ID NO. 139 and 6K of SEQ ID NO. 126 | 5 |
| 93 | 139 | 127 | 108 | 210 | 26K of SEQ ID NO. 139 and 7K of SEQ ID NO. 127 | 5 |
| 94 | 139 | 128 | 108 | 211 | 26K of SEQ ID NO. 139 and 8K of SEQ ID NO. 128 | 5 |
| 95 | 139 | 121 | 108 | 204 | 26K of SEQ ID NO. 139 and 1K of SEQ ID NO. 121 | 6 |
| 96 | 139 | 122 | 108 | 205 | 26K of SEQ ID NO. 139 and 2K of SEQ ID NO. 122 | 6 |
| 97 | 139 | 123 | 108 | 206 | 26K of SEQ ID NO. 139 and 3K of SEQ ID NO. 123 | 6 |
| 98 | 139 | 124 | 108 | 207 | 26K of SEQ ID NO. 139 and 4K of SEQ ID NO. 124 | 6 |
| 99 | 139 | 125 | 108 | 208 | 26K of SEQ ID NO. 139 and 5K of SEQ ID NO. 125 | 6 |
| 100 | 139 | 126 | 108 | 209 | 26K of SEQ ID NO. 139 and 6K of SEQ ID NO. 126 | 6 |
| 101 | 139 | 127 | 108 | 210 | 26K of SEQ ID NO. 139 and 7K of SEQ ID NO. 127 | 6 |
| 102 | 139 | 128 | 108 | 211 | 26K of SEQ ID NO. 139 and 8K of SEQ ID NO. 128 | 6 |
| 103 | 184 | 116 | 108 | 382 | 23K of SEQ ID NO. 184 | 6 |
| 104 | 185 | 116 | 108 | 383 | 30K of SEQ ID NO. 185 | 6 |
| 105 | 186 | 116 | 108 | 384 | 33K of SEQ ID NO. 186 | 6 |
| 106 | 147 | 116 | 108 | 226 | 12K of SEQ ID NO. 147 | 6 |

-continued

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 107 | 148 | 116 | 108 | 227 | 21K of SEQ ID NO. 148 | 6 |
| 108 | 149 | 116 | 108 | 228 | 24K of SEQ ID NO. 149 | 6 |
| 109 | 151 | 116 | 108 | 230 | 27K of SEQ ID NO. 151 | 6 |
| 110 | 152 | 116 | 108 | 231 | 31K of SEQ ID NO. 152 | 6 |
| 111 | 153 | 116 | 108 | 232 | 32K of SEQ ID NO. 153 | 6 |
| 112 | 154 | 116 | 108 | 233 | 36K of SEQ ID NO. 154 | 6 |
| 113 | 155 | 116 | 108 | 236 | 26K of SEQ ID NO. 155 | 1 |
| 114 | 156 | 116 | 108 | 250 | 26K of SEQ ID NO. 156 | 1 |
| 115 | 157 | 116 | 108 | 264 | 26K of SEQ ID NO. 157 | 1 |
| 116 | 159 | 116 | 108 | 279 | 26K of SEQ ID NO. 159 | 1 |
| 117 | 161 | 116 | 108 | 294 | 26K of SEQ ID NO. 161 | 1 |
| 118 | 164 | 116 | 108 | 310 | 26K of SEQ ID NO. 164 | 1 |
| 119 | 174 | 116 | 108 | 370 | 21K and 26K of SEQ ID NO. 174 | 1 |
| 120 | 175 | 116 | 108 | 371 | 23K and 26K of SEQ ID NO. 175 | 1 |
| 121 | 176 | 116 | 108 | 372 | 24K and 26K of SEQ ID NO. 176 | 1 |
| 122 | 177 | 116 | 108 | 373 | 25K and 26K of SEQ ID NO. 177 | 1 |
| 123 | 178 | 116 | 108 | 374 | 27K and 26K of SEQ ID NO. 178 | 1 |
| 124 | 179 | 116 | 108 | 375 | 30K and 26K of SEQ ID NO. 179 | 1 |
| 125 | 180 | 116 | 108 | 376 | 31K and 26K of SEQ ID NO. 180 | 1 |
| 126 | 181 | 116 | 108 | 377 | 32K and 26K of SEQ ID NO. 181 | 1 |
| 127 | 182 | 116 | 108 | 378 | 33K and 26K of SEQ ID NO. 182 | 1 |
| 128 | 138 | 116 | 108 | 188 | 34K and 26K of SEQ ID NO. 138 | 1 |
| 129 | 174 | 116 | 108 | 370 | 21K and 26K of SEQ ID NO. 174 | 5 |
| 130 | 175 | 116 | 108 | 371 | 23K and 26K of SEQ ID NO. 175 | 5 |
| 131 | 176 | 116 | 108 | 372 | 24K and 26K of SEQ ID NO. 176 | 5 |
| 132 | 177 | 116 | 108 | 373 | 25K and 26K of SEQ ID NO. 177 | 5 |
| 133 | 178 | 116 | 108 | 374 | 27K and 26K of SEQ ID NO. 178 | 5 |
| 134 | 179 | 116 | 108 | 375 | 30K and 26K of SEQ ID NO. 179 | 5 |
| 135 | 180 | 116 | 108 | 376 | 31K and 26K of SEQ ID NO. 180 | 5 |
| 136 | 181 | 116 | 108 | 377 | 32K and 26K of SEQ ID NO. 181 | 5 |
| 137 | 182 | 116 | 108 | 378 | 33K and 26K of SEQ ID NO. 182 | 5 |
| 138 | 138 | 116 | 108 | 188 | 34K and 26K of SEQ ID NO. 138 | 5 |
| 139 | 174 | 116 | 108 | 370 | 21K and 26K of SEQ ID NO. 174 | 6 |
| 140 | 175 | 116 | 108 | 371 | 23K and 26K of SEQ ID NO. 175 | 6 |
| 141 | 176 | 116 | 108 | 372 | 24K and 26K of SEQ ID NO. 176 | 6 |
| 142 | 177 | 116 | 108 | 373 | 25K and 26K of SEQ ID NO. 177 | 6 |
| 143 | 178 | 116 | 108 | 374 | 27K and 26K of SEQ ID NO. 178 | 6 |
| 144 | 179 | 116 | 108 | 375 | 30K and 26K of SEQ ID NO. 179 | 6 |
| 145 | 180 | 116 | 108 | 376 | 31K and 26K of SEQ ID NO. 180 | 6 |
| 146 | 181 | 116 | 108 | 377 | 32K and 26K of SEQ ID NO. 181 | 6 |
| 147 | 182 | 116 | 108 | 378 | 33K and 26K of SEQ ID NO. 182 | 6 |
| 148 | 138 | 116 | 108 | 188 | 34K and 26K of SEQ ID NO. 138 | 6 |
| 149 | 155 | 121 | 108 | 240 | 26K of SEQ ID NO. 155 and 1K of SEQ ID NO. 121 | 1 |

-continued

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 150 | 156 | 121 | 108 | 254 | 26K of SEQ ID NO. 156 and 1K of SEQ ID NO. 121 | 1 |
| 151 | 157 | 121 | 108 | 268 | 26K of SEQ ID NO. 157 and 1K of SEQ ID NO. 121 | 1 |
| 152 | 159 | 121 | 108 | 283 | 26K of SEQ ID NO. 159 and 1K of SEQ ID NO. 121 | 1 |
| 153 | 161 | 121 | 108 | 298 | 26K of SEQ ID NO. 161 and 1K of SEQ ID NO. 121 | 1 |
| 154 | 164 | 121 | 108 | 314 | 26K of SEQ ID NO. 164 and 1K of SEQ ID NO. 121 | 1 |
| 155 | 165 | 121 | 108 | 328 | 26K of SEQ ID NO. 165 and 1K of SEQ ID NO. 121 | 1 |
| 156 | 167 | 121 | 108 | 343 | 26K of SEQ ID NO. 167 and 1K of SEQ ID NO. 121 | 1 |
| 157 | 171 | 121 | 108 | 360 | 26K of SEQ ID NO. 171 and 1K of SEQ ID NO. 121 | 1 |
| 158 | 155 | 122 | 108 | 241 | 26K of SEQ ID NO. 155 and 2K of SEQ ID NO. 122 | 1 |
| 159 | 156 | 122 | 108 | 255 | 26K of SEQ ID NO. 156 and 2K of SEQ ID NO. 122 | 1 |
| 160 | 157 | 122 | 108 | 269 | 26K of SEQ ID NO. 157 and 2K of SEQ ID NO. 122 | 1 |
| 161 | 159 | 122 | 108 | 284 | 26K of SEQ ID NO. 159 and 2K of SEQ ID NO. 122 | 1 |
| 162 | 161 | 122 | 108 | 299 | 26K of SEQ ID NO. 161 and 2K of SEQ ID NO. 122 | 1 |
| 163 | 164 | 122 | 108 | 315 | 26K of SEQ ID NO. 164 and 2K of SEQ ID NO. 122 | 1 |
| 164 | 165 | 122 | 108 | 329 | 26K of SEQ ID NO. 165 and 2K of SEQ ID NO. 122 | 1 |
| 165 | 167 | 122 | 108 | 344 | 26K of SEQ ID NO. 167 and 2K of SEQ ID NO. 122 | 1 |
| 166 | 171 | 122 | 108 | 361 | 26K of SEQ ID NO. 171 and 2K of SEQ ID NO. 122 | 1 |
| 167 | 155 | 123 | 108 | 242 | 26K of SEQ ID NO. 155 and 3K of SEQ ID NO. 123 | 1 |
| 168 | 156 | 123 | 108 | 256 | 26K of SEQ ID NO. 156 and 3K of SEQ ID NO. 123 | 1 |
| 169 | 157 | 123 | 108 | 270 | 26K of SEQ ID NO. 157 and 3K of SEQ ID NO. 123 | 1 |
| 170 | 159 | 123 | 108 | 285 | 26K of SEQ ID NO. 159 and 3K of SEQ ID NO. 123 | 1 |
| 171 | 161 | 123 | 108 | 300 | 26K of SEQ ID NO. 161 and 3K of SEQ ID NO. 123 | 1 |
| 172 | 164 | 123 | 108 | 316 | 26K of SEQ ID NO. 164 and 3K of SEQ ID NO. 123 | 1 |
| 173 | 165 | 123 | 108 | 330 | 26K of SEQ ID NO. 165 and 3K of SEQ ID NO. 123 | 1 |
| 174 | 167 | 123 | 108 | 345 | 26K of SEQ ID NO. 167 and 3K of SEQ ID NO. 123 | 1 |
| 175 | 171 | 123 | 108 | 362 | 26K of SEQ ID NO. 171 and 3K of SEQ ID NO. 123 | 1 |
| 176 | 155 | 124 | 108 | 243 | 26K of SEQ ID NO. 155 and 4K of SEQ ID NO. 124 | 1 |
| 177 | 156 | 124 | 108 | 257 | 26K of SEQ ID NO. 156 and 4K of SEQ ID NO. 124 | 1 |
| 178 | 157 | 124 | 108 | 271 | 26K of SEQ ID NO. 157 and 4K of SEQ ID NO. 124 | 1 |
| 179 | 159 | 124 | 108 | 286 | 26K of SEQ ID NO. 159 and 4K of SEQ ID NO. 124 | 1 |
| 180 | 161 | 124 | 108 | 301 | 26K of SEQ ID NO. 161 and 4K of SEQ ID NO. 124 | 1 |
| 181 | 164 | 124 | 108 | 317 | 26K of SEQ ID NO. 164 and 4K of SEQ ID NO. 124 | 1 |
| 182 | 165 | 124 | 108 | 331 | 26K of SEQ ID NO. 165 and 4K of SEQ ID NO. 124 | 1 |
| 183 | 167 | 124 | 108 | 346 | 26K of SEQ ID NO. 167 and 4K of SEQ ID NO. 124 | 1 |
| 184 | 171 | 124 | 108 | 363 | 26K of SEQ ID NO. 171 and 4K of SEQ ID NO. 124 | 1 |
| 185 | 155 | 125 | 108 | 244 | 26K of SEQ ID NO. 155 and 5K of SEQ ID NO. 125 | 1 |
| 186 | 156 | 125 | 108 | 258 | 26K of SEQ ID NO. 156 and 5K of SEQ ID NO. 125 | 1 |

-continued

| GLP-1/EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 187 | 157 | 125 | 108 | 272 | 26K of SEQ ID NO. 157 and 5K of SEQ ID NO. 125 | 1 |
| 188 | 159 | 125 | 108 | 287 | 26K of SEQ ID NO. 159 and 5K of SEQ ID NO. 125 | 1 |
| 189 | 161 | 125 | 108 | 302 | 26K of SEQ ID NO. 161 and 5K of SEQ ID NO. 125 | 1 |
| 190 | 164 | 125 | 108 | 318 | 26K of SEQ ID NO. 164 and 5K of SEQ ID NO. 125 | 1 |
| 191 | 165 | 125 | 108 | 332 | 26K of SEQ ID NO. 165 and 5K of SEQ ID NO. 125 | 1 |
| 192 | 167 | 125 | 108 | 347 | 26K of SEQ ID NO. 167 and 5K of SEQ ID NO. 125 | 1 |
| 193 | 171 | 125 | 108 | 364 | 26K of SEQ ID NO. 171 and 5K of SEQ ID NO. 125 | 1 |
| 194 | 155 | 126 | 108 | 245 | 26K of SEQ ID NO. 155 and 6K of SEQ ID NO. 126 | 1 |
| 195 | 156 | 126 | 108 | 259 | 26K of SEQ ID NO. 156 and 6K of SEQ ID NO. 126 | 1 |
| 196 | 157 | 126 | 108 | 273 | 26K of SEQ ID NO. 157 and 6K of SEQ ID NO. 126 | 1 |
| 197 | 159 | 126 | 108 | 288 | 26K of SEQ ID NO. 159 and 6K of SEQ ID NO. 126 | 1 |
| 198 | 161 | 126 | 108 | 303 | 26K of SEQ ID NO. 161 and 6K of SEQ ID NO. 126 | 1 |
| 199 | 164 | 126 | 108 | 319 | 26K of SEQ ID NO. 164 and 6K of SEQ ID NO. 126 | 1 |
| 200 | 165 | 126 | 108 | 333 | 26K of SEQ ID NO. 165 and 6K of SEQ ID NO. 126 | 1 |
| 201 | 167 | 126 | 108 | 348 | 26K of SEQ ID NO. 167 and 6K of SEQ ID NO. 126 | 1 |
| 202 | 171 | 126 | 108 | 365 | 26K of SEQ ID NO. 171 and 6K of SEQ ID NO. 126 | 1 |
| 203 | 155 | 127 | 108 | 246 | 26K of SEQ ID NO. 155 and 7K of SEQ ID NO. 127 | 1 |
| 204 | 156 | 127 | 108 | 260 | 26K of SEQ ID NO. 156 and 7K of SEQ ID NO. 127 | 1 |
| 205 | 157 | 127 | 108 | 274 | 26K of SEQ ID NO. 157 and 7K of SEQ ID NO. 127 | 1 |
| 206 | 159 | 127 | 108 | 289 | 26K of SEQ ID NO. 159 and 7K of SEQ ID NO. 127 | 1 |
| 207 | 161 | 127 | 108 | 304 | 26K of SEQ ID NO. 161 and 7K of SEQ ID NO. 127 | 1 |
| 208 | 164 | 127 | 108 | 320 | 26K of SEQ ID NO. 164 and 7K of SEQ ID NO. 127 | 1 |
| 209 | 165 | 127 | 108 | 334 | 26K of SEQ ID NO. 165 and 7K of SEQ ID NO. 127 | 1 |
| 210 | 167 | 127 | 108 | 349 | 26K of SEQ ID NO. 167 and 7K of SEQ ID NO. 127 | 1 |
| 211 | 171 | 127 | 108 | 366 | 26K of SEQ ID NO. 171 and 7K of SEQ ID NO. 127 | 1 |
| 212 | 155 | 128 | 108 | 247 | 26K of SEQ ID NO. 155 and 8K of SEQ ID NO. 128 | 1 |
| 213 | 156 | 128 | 108 | 261 | 26K of SEQ ID NO. 156 and 8K of SEQ ID NO. 128 | 1 |
| 214 | 157 | 128 | 108 | 275 | 26K of SEQ ID NO. 157 and 8K of SEQ ID NO. 128 | 1 |
| 215 | 159 | 128 | 108 | 290 | 26K of SEQ ID NO. 159 and 8K of SEQ ID NO. 128 | 1 |
| 216 | 161 | 128 | 108 | 305 | 26K of SEQ ID NO. 161 and 8K of SEQ ID NO. 128 | 1 |
| 217 | 164 | 128 | 108 | 321 | 26K of SEQ ID NO. 164 and 8K of SEQ ID NO. 128 | 1 |
| 218 | 165 | 128 | 108 | 335 | 26K of SEQ ID NO. 165 and 8K of SEQ ID NO. 128 | 1 |
| 219 | 167 | 128 | 108 | 350 | 26K of SEQ ID NO. 167 and 8K of SEQ ID NO. 128 | 1 |
| 220 | 171 | 128 | 108 | 367 | 26K of SEQ ID NO. 171 and 8K of SEQ ID NO. 128 | 1 |
| 221 | 139 | 116 | 21 | 191 | 26K of SEQ ID NO. 139 and 321K of SEQ ID NO. 21 | 1 |
| 222 | 139 | 116 | 112 | 197 | 26K of SEQ ID NO. 139 and 313K of SEQ ID NO. 112 | 1 |
| 223 | 139 | 116 | 113 | 198 | 26K of SEQ ID NO. 139 and 324K of SEQ ID NO. 113 | 1 |

-continued

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 224 | 139 | 116 | 114 | 199 | 26K of SEQ ID NO. 139 and 328K of SEQ ID NO. 114 | 1 |
| 225 | 139 | 116 | 19 | 190 | 26K of SEQ ID NO. 139 and 333K of SEQ ID NO. 19 | 5 |
| 226 | 139 | 116 | 21 | 191 | 26K of SEQ ID NO. 139 and 321K of SEQ ID NO. 21 | 5 |
| 227 | 139 | 116 | 112 | 197 | 26K of SEQ ID NO. 139 and 313K of SEQ ID NO. 112 | 5 |
| 228 | 139 | 116 | 113 | 198 | 26K of SEQ ID NO. 139 and 324K of SEQ ID NO. 113 | 5 |
| 229 | 139 | 116 | 114 | 199 | 26K of SEQ ID NO. 139 and 328K of SEQ ID NO. 114 | 5 |
| 230 | 139 | 116 | 19 | 190 | 26K of SEQ ID NO. 139 and 333K of SEQ ID NO. 19 | 6 |
| 231 | 139 | 116 | 21 | 191 | 26K of SEQ ID NO. 139 and 321K of SEQ ID NO. 21 | 6 |
| 232 | 139 | 116 | 112 | 197 | 26K of SEQ ID NO. 139 and 313K of SEQ ID NO. 112 | 6 |
| 233 | 139 | 116 | 113 | 198 | 26K of SEQ ID NO. 139 and 324K of SEQ ID NO. 113 | 6 |
| 234 | 139 | 116 | 114 | 199 | 26K of SEQ ID NO. 139 and 328K of SEQ ID NO. 114 | 6 |
| 235 | 155 | 116 | 19 | 234 | 26K of SEQ ID NO. 155 and 333K of SEQ ID NO. 19 | 1 |
| 236 | 155 | 116 | 21 | 235 | 26K of SEQ ID NO. 155 and 321K of SEQ ID NO. 21 | 1 |
| 237 | 155 | 116 | 112 | 237 | 26K of SEQ ID NO. 155 and 313K of SEQ ID NO. 112 | 1 |
| 238 | 155 | 116 | 113 | 238 | 26K of SEQ ID NO. 155 and 324K of SEQ ID NO. 113 | 1 |
| 239 | 155 | 116 | 114 | 239 | 26K of SEQ ID NO. 155 and 328K of SEQ ID NO. 114 | 1 |
| 240 | 156 | 116 | 19 | 248 | 26K of SEQ ID NO. 156 and 333K of SEQ ID NO. 19 | 1 |
| 241 | 156 | 116 | 21 | 249 | 26K of SEQ ID NO. 156 and 321K of SEQ ID NO. 21 | 1 |
| 242 | 156 | 116 | 112 | 251 | 26K of SEQ ID NO. 156 and 313K of SEQ ID NO. 112 | 1 |
| 243 | 156 | 116 | 113 | 252 | 26K of SEQ ID NO. 156 and 324K of SEQ ID NO. 113 | 1 |
| 244 | 156 | 116 | 114 | 253 | 26K of SEQ ID NO. 156 and 328K of SEQ ID NO. 114 | 1 |
| 245 | 157 | 116 | 19 | 262 | 26K of SEQ ID NO. 157 and 333K of SEQ ID NO. 19 | 1 |
| 246 | 157 | 116 | 21 | 263 | 26K of SEQ ID NO. 157 and 321K of SEQ ID NO. 21 | 1 |
| 247 | 157 | 116 | 112 | 265 | 26K of SEQ ID NO. 157 and 313K of SEQ ID NO. 112 | 1 |
| 248 | 157 | 116 | 113 | 266 | 26K of SEQ ID NO. 157 and 324K of SEQ ID NO. 113 | 1 |
| 249 | 157 | 116 | 114 | 267 | 26K of SEQ ID NO. 157 and 328K of SEQ ID NO. 114 | 1 |
| 250 | 159 | 116 | 19 | 277 | 26K of SEQ ID NO. 159 and 333K of SEQ ID NO. 19 | 1 |
| 251 | 159 | 116 | 21 | 278 | 26K of SEQ ID NO. 159 and 321K of SEQ ID NO. 21 | 1 |
| 252 | 159 | 116 | 112 | 280 | 26K of SEQ ID NO. 159 and 313K of SEQ ID NO. 112 | 1 |
| 253 | 159 | 116 | 113 | 281 | 26K of SEQ ID NO. 159 and 324K of SEQ ID NO. 113 | 1 |
| 254 | 159 | 116 | 114 | 282 | 26K of SEQ ID NO. 159 and 328K of SEQ ID NO. 114 | 1 |
| 255 | 161 | 116 | 19 | 292 | 26K of SEQ ID NO. 161 and 333K of SEQ ID NO. 19 | 1 |
| 256 | 161 | 116 | 21 | 293 | 26K of SEQ ID NO. 161 and 321K of SEQ ID NO. 21 | 1 |
| 257 | 161 | 116 | 112 | 295 | 26K of SEQ ID NO. 161 and 313K of SEQ ID NO. 112 | 1 |
| 258 | 161 | 116 | 113 | 296 | 26K of SEQ ID NO. 161 and 324K of SEQ ID NO. 113 | 1 |
| 259 | 161 | 116 | 114 | 297 | 26K of SEQ ID NO. 161 and 328K of SEQ ID NO. 114 | 1 |
| 260 | 164 | 116 | 19 | 308 | 26K of SEQ ID NO. 164 and 333K of SEQ ID NO. 19 | 1 |

-continued

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 261 | 164 | 116 | 21 | 309 | 26K of SEQ ID NO. 164 and 321K of SEQ ID NO. 21 | 1 |
| 262 | 164 | 116 | 112 | 311 | 26K of SEQ ID NO. 164 and 313K of SEQ ID NO. 112 | 1 |
| 263 | 164 | 116 | 113 | 312 | 26K of SEQ ID NO. 164 and 324K of SEQ ID NO. 113 | 1 |
| 264 | 164 | 116 | 114 | 313 | 26K of SEQ ID NO. 164 and 328K of SEQ ID NO. 114 | 1 |
| 265 | 165 | 116 | 19 | 322 | 26K of SEQ ID NO. 165 and 333K of SEQ ID NO. 19 | 1 |
| 266 | 165 | 116 | 21 | 323 | 26K of SEQ ID NO. 165 and 321K of SEQ ID NO. 21 | 1 |
| 267 | 165 | 116 | 112 | 325 | 26K of SEQ ID NO. 165 and 313K of SEQ ID NO. 112 | 1 |
| 268 | 165 | 116 | 113 | 326 | 26K of SEQ ID NO. 165 and 324K of SEQ ID NO. 113 | 1 |
| 269 | 165 | 116 | 114 | 327 | 26K of SEQ ID NO. 165 and 328K of SEQ ID NO. 114 | 1 |
| 270 | 167 | 116 | 19 | 337 | 26K of SEQ ID NO. 167 and 333K of SEQ ID NO. 19 | 1 |
| 271 | 167 | 116 | 21 | 338 | 26K of SEQ ID NO. 167 and 321K of SEQ ID NO. 21 | 1 |
| 272 | 167 | 116 | 112 | 340 | 26K of SEQ ID NO. 167 and 313K of SEQ ID NO. 112 | 1 |
| 273 | 167 | 116 | 113 | 341 | 26K of SEQ ID NO. 167 and 324K of SEQ ID NO. 113 | 1 |
| 274 | 167 | 116 | 114 | 342 | 26K of SEQ ID NO. 167 and 328K of SEQ ID NO. 114 | 1 |
| 275 | 171 | 116 | 19 | 354 | 26K of SEQ ID NO. 171 and 333K of SEQ ID NO. 19 | 1 |
| 276 | 171 | 116 | 21 | 355 | 26K of SEQ ID NO. 171 and 321K of SEQ ID NO. 21 | 1 |
| 277 | 171 | 116 | 112 | 357 | 26K of SEQ ID NO. 171 and 313K of SEQ ID NO. 112 | 1 |
| 278 | 171 | 116 | 113 | 358 | 26K of SEQ ID NO. 171 and 324K of SEQ ID NO. 113 | 1 |
| 279 | 171 | 116 | 114 | 359 | 26K of SEQ ID NO. 171 and 328K of SEQ ID NO. 114 | 1 |
| 280 | 144 | 116 | 108 | 223 | 26K of SEQ ID NO. 144 | 6 |
| 281 | 145 | 116 | 108 | 224 | 26K of SEQ ID NO. 145 | 6 |
| 282 | 146 | 116 | 108 | 225 | 26K of SEQ ID NO. 146 | 6 |
| 283 | 174 | 116 | 108 | 370 | 21K and 26K of SEQ ID NO. 174 | 14 |
| 284 | 175 | 116 | 108 | 371 | 23K and 26K of SEQ ID NO. 175 | 14 |
| 285 | 176 | 116 | 108 | 372 | 24K and 26K of SEQ ID NO. 176 | 14 |
| 286 | 177 | 116 | 108 | 373 | 25K and 26K of SEQ ID NO. 177 | 14 |
| 287 | 178 | 116 | 108 | 374 | 27K and 26K of SEQ ID NO. 178 | 14 |
| 288 | 179 | 116 | 108 | 375 | 30K and 26K of SEQ ID NO. 179 | 14 |
| 289 | 180 | 116 | 108 | 376 | 31K and 26K of SEQ ID NO. 180 | 14 |
| 290 | 181 | 116 | 108 | 377 | 32K and 26K of SEQ ID NO. 181 | 14 |
| 291 | 182 | 116 | 108 | 378 | 33K and 26K of SEQ ID NO. 182 | 14 |
| 292 | 138 | 116 | 108 | 188 | 34K and 26K of SEQ ID NO. 138 | 14 |
| 293 | 139 | 116 | 112 | 197 | 26K of SEQ ID NO. 139 and 313K of SEQ ID NO. 112 | 14 |
| 294 | 139 | 116 | 21 | 191 | 26K of SEQ ID NO. 139 and 321K of SEQ ID NO. 21 | 14 |
| 295 | 139 | 116 | 113 | 198 | 26K of SEQ ID NO. 139 and 324K of SEQ ID NO. 113 | 14 |
| 296 | 139 | 116 | 114 | 199 | 26K of SEQ ID NO. 139 and 328K of SEQ ID NO. 114 | 14 |
| 297 | 139 | 116 | 19 | 190 | 26K of SEQ ID NO. 139 and 333K of SEQ ID NO. 19 | 14 |
| 298 | 139 | 121 | 108 | 204 | 26K of SEQ ID NO. 139 and 1K of SEQ ID NO. 121 | 14 |
| 299 | 139 | 122 | 108 | 205 | 26K of SEQ ID NO. 139 and 2K of SEQ ID NO. 122 | 14 |

-continued

| GLP-1/ EGF(A) Compound # | GLP-1 analogue (SEQ ID) | Spacer (SEQ ID) | EGF(A) analogue (SEQ ID) | Fusion peptide (SEQ ID) | Attachment | Substituent # |
|---|---|---|---|---|---|---|
| 300 | 139 | 123 | 108 | 206 | 26K of SEQ ID NO. 139 and 3K of SEQ ID NO. 123 | 14 |
| 301 | 139 | 124 | 108 | 207 | 26K of SEQ ID NO. 139 and 4K of SEQ ID NO. 124 | 14 |
| 302 | 139 | 125 | 108 | 208 | 26K of SEQ ID NO. 139 and 5K of SEQ ID NO. 125 | 14 |
| 303 | 139 | 126 | 108 | 209 | 26K of SEQ ID NO. 139 and 6K of SEQ ID NO. 126 | 14 |
| 304 | 139 | 127 | 108 | 210 | 26K of SEQ ID NO. 139 and 7K of SEQ ID NO. 127 | 14 |
| 305 | 139 | 128 | 108 | 211 | 26K of SEQ ID NO. 139 and 8K of SEQ ID NO. 128 | 14 |
| 306 | 164 | 116 | 108 | 310 | 26K of SEQ ID NO. 164 | 5 |
| 307 | 139 | 119 | 108 | 202 | 26K of SEQ ID NO. 139 | 5 |
| 308 | 175 | 116 | 108 | 371 | 23K and 26K of SEQ ID NO. 175 | 2 |
| 309 | 138 | 116 | 108 | 188 | 34K and 26K of SEQ ID NO. 138 | 2 |
| 310 | 139 | 124 | 108 | 207 | 26K of SEQ ID NO. 139 and 4K of SEQ ID NO. 124 | 2 |
| 311 | 176 | 116 | 108 | 372 | 24K and 26K of SEQ ID NO. 176 | 2 |
| 312 | 182 | 116 | 108 | 378 | 33K and 26K of SEQ ID NO. 182 | 2 |
| 313 | 164 | 116 | 107 | 387 | 26K of SEQ ID NO. 164 | 6 |
| 314 | 139 | 119 | 107 | 388 | 26K of SEQ ID NO. 139 | 6 |

Compounds with an EGF(A) Analogue in the N-Terminal

| GLP-1/EGF(A) Compound # | EGF(A) analogue (SEQ ID) | Spacer (SEQ ID) | GLP-1 analogue (SEQ ID) | Fusion peptide (SEQ ID) | Attachment | Substituent # |
|---|---|---|---|---|---|---|
| 75 | 108 | 116 | 139 | 386 | 26K of SEQ ID NO. 139 | 1 |

Analytical data for a selection of compounds are provided in below table.

Table with Analytical Data for GLP-1/EGF(A) Compounds

| GLP-1/EGF(A) Compound no. | Rt (min, UPLC02) | LCMS method | Calc. molweight | found (m + 4)/4 | found (m + 5)/5 | found (m + 6)/6 | found (m + 7)/7 | found (m + 8)/8 |
|---|---|---|---|---|---|---|---|---|
| 1 | 8.8 | LCMS34 | 9228.2 | 2308.1 | 1846.6 | 1539.1 | 1319.5 | 1154.6 |
| 2 | 8.4 | LCMS34 | 9313.3 |  | 1863.7 | 1553.2 | 1331.5 | 1165.2 |
| 3 | 7.8 | LCMS01 | 9200.2 |  | 1841.1 | 1534.4 | 1315.1 | 1150.8 |
| 4 | 8.6 | LCMS34 | 9255.3 | 2314.8 | 1852.0 | 1543.5 | 1323.2 | 1157.9 |
| 5 | 8.9 | LCMS34 | 9228.2 | 2307.8 | 1846.4 | 1538.9 | 1319.2 | 1154.5 |
| 6 | 9.1 | LCMS34 | 8957.9 | 2240.1 | 1792.3 | 1493.8 | 1280.5 | 1120.6 |
| 7 | 9.1 | LCMS34 | 8702.6 | 2176.3 | 1741.3 | 1451.3 | 1244.1 | 1088.7 |
| 8 | 9.5 | LCMS34 | 8801.8 | 2201.3 | 1761.2 | 1468.0 | 1258.3 | 1101.2 |
| 9 | 8.1 | LCMS34 | 9271.3 | 2318.8 | 1855.1 | 1546.2 | 1325.3 | 1159.8 |
| 10 | 8.6 | LCMS34 | 9255.3 | 2314.9 | 1851.9 | 1543.6 | 1323.1 | 1157.8 |
| 11 | 8.4 | LCMS34 | 9237.2 | 2310.3 | 1848.3 | 1540.6 | 1320.5 | 1155.6 |
| 12 | 8.4 | LCMS34 | 9313.3 | 2329.4 | 1863.5 | 1553.2 | 1331.5 | 1165.1 |
| 14 | 8.4 | LCMS34 | 9186.1 | 2297.1 | 1837.9 | 1532.0 | 1313.1 | 1149.1 |
| 15 | 8.8 | LCMS34 | 9146.1 | 2287.2 | 1829.9 | 1525.1 | 1307.6 | 1144.1 |
| 16 | 8.7 | LCMS34 | 9098.0 | 2275.1 | 1820.3 | 1517.1 | 1300.6 | 1138.1 |
| 17 | 8.7 | LCMS34 | 9182.1 | 2296.4 | 1837.1 | 1531.1 | 1312.7 | 1148.6 |
| 18 | 8.9 | LCMS34 | 8730.7 | 2183.3 | 1746.9 | 1455.9 | 1248.1 | 1092.2 |
| 19 | 9.2 | LCMS34 | 8829.8 | 2208.1 | 1766.7 | 1472.4 | 1262.4 | 1104.6 |
| 20 | 8.8 | LCMS34 | 8986.0 | 2247.1 | 1798.1 | 1498.5 | 1284.5 | 1124.1 |
| 21 | 8.5 | LCMS34 | 9228.2 | 2307.7 | 1846.4 | 1538.8 | 1319.1 | 1154.5 |
| 22 | 8.5 | LCMS34 | 9256.3 | 2314.9 | 1851.9 | 1543.6 | 1323.1 | 1157.9 |
| 23 | 8.7 | LCMS34 | 9395.5 | 2349.9 | 1880.1 | 1566.8 | 1343.2 | 1175.3 |
| 24 | 8.4 | LCMS34 | 9005.9 | 2252.1 | 1801.9 | 1501.8 | 1287.4 | 1126.6 |
| 25 | 8.7 | LCMS34 | 9228.2 | 2307.6 | 1846.3 | 1539.0 | 1319.1 | 1154.4 |
| 26 | 9.0 | LCMS34 | 9284.3 | 2322.0 | 1857.6 | 1548.2 | 1327.3 | 1161.5 |

Table with analytical data for GLP-1/EGF(A) compounds

| GLP-1/EGF(A) Compound no. | Rt (min, UPLC02) | LCMS method | Calc. molweight | found (m + 4)/4 | found (m + 5)/5 | found (m + 6)/6 | found (m + 7)/7 | found (m + 8)/8 |
|---|---|---|---|---|---|---|---|---|
| 27 | 8.8 | LCMS34 | 9329.3 | 2333.0 | 1866.6 | 1555.8 | 1333.6 | 1167.1 |
| 28 | 9.6 | LCMS34 | 9367.4 | 2342.2 | 1874.6 | 1562.3 | 1339.3 | 1172.0 |
| 29 | 8.0 | LCMS34 | 9518.5 | 2380.9 | 1904.9 | 1587.4 | 1360.9 | 1191.0 |
| 30 | 8.0 | LCMS34 | 9152.0 | 2289.0 | 1831.6 | 1526.6 | 1308.5 | 1145.1 |
| 31 |  | LCMS34 | 9200.2 | 2301.3 | 1841.1 | 1534.6 | 1315.5 | 1150.9 |
| 32 | 7.0 | LCMS34 | 9198.2 | 2300.6 | 1840.7 | 1534.1 | 1315.1 | 1150.8 |
| 33 | 8.1 | LCMS34 | 8589.5 | 2148.4 | 1718.9 | 1432.6 | 1228.1 |  |
| 34 | 9.0 | LCMS34 | 9496.6 | 2375.0 | 1900.2 | 1583.5 | 1357.6 | 1187.9 |
| 35 | 8.6 | LCMS34 | 9214.2 | 2304.6 | 1843.9 | 1536.7 | 1317.3 | 1152.8 |
| 36 | 8.6 | LCMS34 | 9242.3 | 2311.6 | 1849.5 | 1541.6 | 1321.4 | 1156.3 |
| 37 | 8.9 | LCMS34 | 9212.2 | 2303.9 | 1843.2 | 1536.3 | 1316.9 | 1152.4 |
| 38 | 8.5 | LCMS34 | 9251.3 | 2313.8 | 1851.0 | 1542.7 | 1322.5 | 1157.3 |
| 39 | 9.0 | LCMS34 | 9319.3 | 2330.5 | 1864.8 | 1554.2 | 1332.2 | 1165.8 |
| 40 | 8.2 | LCMS34 | 9384.4 | 2347.2 | 1877.8 | 1565.0 | 1341.6 | 1174.1 |
| 41 | 9.2 | LCMS34 | 10072.3 | 2518.9 | 2015.3 | 1679.6 | 1439.8 | 1259.8 |
| 42 | 8.3 | LCMS34 | 10002.1 | 2501.3 | 2001.3 | 1667.9 | 1429.8 | 1251.2 |
| 43 | 7.9 | LCMS34 | 12055.2 | 3014.7 | 2412.0 | 2010.1 | 1723.3 | 1507.9 |
| 44 | 8.6 | LCMS34 | 8874.9 | 2219.4 | 1775.8 | 1480.0 | 1268.7 | 1110.2 |
| 45 | 8.6 | LCMS34 | 9581.6 | 2396.2 | 1917.2 | 1598.0 | 1369.7 | 1198.5 |
| 46 | 8.6 | LCMS34 | 9080.0 | 2270.7 | 1817.0 | 1514.3 | 1298.0 | 1135.9 |
| 47 | 8.6 | LCMS34 | 9194.1 | 2299.4 | 1839.6 | 1533.1 | 1314.3 | 1150.1 |
| 48 | 8.4 | LCMS34 | 12222.5 | 3056.5 | 2445.4 | 2038.0 | 1747.0 | 1528.8 |
| 49 | 8.4 | LCMS34 | 9353.4 | 2339.3 | 1871.4 | 1559.9 | 1337.0 | 1170.2 |
| 50 | 8.5 | LCMS34 | 9381.4 | 2346.3 | 1877.3 | 1564.7 | 1341.2 | 1173.7 |
| 51 | 8.6 | LCMS34 | 9395.5 | 2349.8 | 1879.9 | 1566.7 | 1343.2 | 1175.4 |
| 52 | 8.8 | LCMS34 | 9409.5 | 2353.3 | 1882.7 | 1569.1 | 1345.2 | 1177.2 |
| 53 | 9.8 | LCMS34 | 9423.5 | 2356.6 | 1885.5 | 1571.5 | 1347.1 | 1178.9 |
| 54 | 9.8 | LCMS34 | 9423.5 | 2356.4 | 1885.3 | 1571.3 | 1347.1 | 1178.7 |
| 55 | 9.4 | LCMS34 | 9381.4 | 2346.1 | 1877.1 | 1564.3 | 1341.1 | 1173.4 |
| 56 | 9.0 | LCMS34 | 9083.1 | 2271.3 | 1817.5 | 1514.6 | 1298.4 | 1136.2 |
| 57 | 9.1 | LCMS34 | 8937.9 | 2235.0 | 1788.3 | 1490.4 | 1277.6 | 1118.1 |
| 58 | 8.1 | LCMS34 | 9339.4 | 2335.3 | 1868.5 | 1557.3 | 1335.1 | 1168.2 |
| 59 | 8.2 | LCMS34 | 9383.4 | 2346.6 | 1877.5 | 1564.6 | 1341.3 | 1173.7 |
| 60 | 8.7 | LCMS34 | 9409.5 | 2353.1 | 1882.5 | 1569.3 | 1345.0 | 1177.0 |
| 61 | 8.2 | LCMS34 | 9480.6 | 2370.9 | 1896.7 | 1581.0 | 1355.3 | 1185.9 |
| 62 | 9.0 | LCMS34 | 9944.1 | 2486.7 | 1989.6 | 1658.2 | 1421.4 | 1243.8 |
| 63 | 8.9 | LCMS34 | 10001.2 | 2500.9 | 2001.1 | 1667.7 | 1429.6 | 1251.0 |
| 64 | 8.9 | LCMS34 | 9975.2 | 2494.4 | 1995.8 | 1663.3 | 1425.9 | 1247.8 |
| 65 | 9.8 | LCMS34 | 9323.4 | 2331.9 | 1865.7 | 1554.9 | 1332.8 | 1166.4 |
| 66 | 9.7 | LCMS34 | 9324.4 | 2332.1 | 1865.9 | 1555.1 | 1333.1 | 1166.4 |
| 67 | 9.6 | LCMS34 | 9381.4 | 2346.4 | 1877.1 | 1564.6 | 1341.2 | 1173.6 |
| 68 | 9.6 | LCMS34 | 9323.4 | 2331.8 | 1865.7 | 1554.9 | 1332.8 | 1166.4 |
| 69 | 9.6 | LCMS34 | 9381.4 | 2346.4 | 1877.1 | 1564.6 | 1341.2 | 1173.6 |
| 70 | 9.3 | LCMS34 | 9266.3 | 2317.6 | 1854.3 | 1545.4 | 1324.8 | 1159.2 |
| 71 | 9.5 | LCMS34 | 9353.4 | 2339.4 | 1871.7 | 1559.8 | 1337.2 | 1170.2 |
| 72 | 8.7 | LCMS34 | 9099.1 | 2275.6 | 1820.7 | 1517.4 | 1300.8 | 1138.3 |
| 73 | 8.5 | LCMS34 | 9172.1 | 2293.8 | 1835.2 | 1529.4 | 1311.1 | 1147.3 |
| 74 | 8.8 | LCMS34 | 9186.1 | 2297.1 | 1837.9 | 1531.8 | 1313.1 | 1149.1 |
| 75 | 8.9 | LCMS34 | 9186.1 | 2297.7 | 1838.1 | 1532.1 | 1313.4 | 1149.2 |
| 77 | 8.2 | LCMS34 | 9540.6 | 2386.2 | 1909.1 | 1591.1 | 1363.9 | 1193.6 |
| 78 | 8.2 | LCMS34 | 9234.3 | 2309.6 | 1847.9 | 1540.1 | 1320.2 | 1155.3 |
| 79 | 8.2 | LCMS34 | 9250.3 | 2313.6 | 1851.1 | 1542.7 | 1322.5 | 1157.3 |
| 80 | 8.1 | LCMS34 | 9685.8 | 2422.5 | 1938.2 | 1615.3 | 1384.7 | 1211.7 |
| 81 | 8.3 | LCMS34 | 9105.2 | 2277.3 | 1822.0 | 1518.5 | 1301.7 | 1139.2 |
| 82 | 9.9 | LCMS34 | 10015.2 | 2504.7 | 2004.0 | 1670.2 | 1431.7 | 1252.9 |
| 83 | 9.9 | LCMS34 | 10001.2 | 2501.2 | 2001.1 | 1667.8 | 1429.6 | 1250.9 |
| 84 | 9.9 | LCMS34 | 10015.2 | 2504.7 | 2004.0 | 1670.2 | 1431.8 | 1252.9 |
| 85 | 9.9 | LCMS34 | 9944.1 | 2487.0 | 1989.8 | 1658.3 | 1421.4 | 1244.0 |
| 86 | 9.0 | LCMS34 | 9975.2 | 2494.8 | 1996.0 | 1663.5 | 1426.0 | 1247.9 |
| 87 | 10.7 | LCMS27 | 10071.3 | 2518.8 | 2015.3 | 1679.6 | 1439.8 | 1259.9 |
| 91 | 10.6 | LCMS27 | 10071.3 | 2518.8 | 2015.3 | 1679.6 | 1439.8 | 1259.9 |
| 92 | 10.6 | LCMS27 | 10000.2 | 2501.1 | 2001.0 | 1667.7 | 1429.6 | 1251.0 |
| 95 | 11.9 | LCMS27 | 10349.7 | 2588.4 | 2070.9 | 1726.0 | 1479.5 | 1294.7 |
| 99 | 10.9 | LCMS27 | 10349.7 | 2588.4 | 2070.9 | 1726.0 | 1479.5 | 1294.7 |
| 100 | 11.0 | LCMS27 | 10278.6 | 2570.7 | 2056.7 | 1714.1 | 1469.4 | 1285.8 |
| 103 | 9.4 | LCMS34 | 9423.5 | 2356.9 | 1885.7 | 1571.6 | 1347.2 | 1178.9 |
| 104 | 9.3 | LCMS34 | 9480.6 | 2371.1 | 1897.1 | 1581.1 | 1355.4 | 1186.1 |
| 105 | 9.2 | LCMS34 | 9452.5 | 2364.1 | 1891.5 | 1576.4 | 1351.4 | 1182.6 |
| 106 | 9.3 | LCMS34 | 9404.5 | 2352.1 | 1881.9 | 1568.4 | 1344.5 | 1176.6 |
| 107 | 9.3 | LCMS34 | 9422.5 | 2356.6 | 1885.5 | 1571.4 | 1347.1 | 1178.8 |
| 108 | 9.1 | LCMS34 | 9480.6 | 2371.1 | 1897.1 | 1581.1 | 1355.4 | 1186.1 |
| 109 | 9.3 | LCMS34 | 9422.5 | 2356.6 | 1885.5 | 1571.4 | 1347.1 | 1178.8 |
| 110 | 9.1 | LCMS34 | 9365.4 | 2342.4 | 1874.1 | 1561.9 | 1338.9 | 1171.7 |
| 111 | 9.0 | LCMS34 | 9438.5 | 2360.6 | 1888.7 | 1574.1 | 1349.4 | 1180.8 |

Table with analytical data for GLP-1/EGF(A) compounds

| GLP-1/EGF(A) Compound no. | Rt (min, UPLC02) | LCMS method | Calc. molweight | found (m + 4)/4 | found (m + 5)/5 | found (m + 6)/6 | found (m + 7)/7 | found (m + 8)/8 |
|---|---|---|---|---|---|---|---|---|
| 112 | 9.6 | LCMS34 | 9395.5 | 2349.9 | 1880.1 | 1566.9 | 1343.2 | 1175.4 |
| 113 | 9.2 | LCMS34 | 9156.2 | 2290.0 | 1832.2 | 1527.0 | 1309.0 | 1145.5 |
| 114 | 9.2 | LCMS34 | 9157.1 | 2290.3 | 1832.4 | 1527.2 | 1309.2 | 1145.6 |
| 115 | 8.9 | LCMS34 | 9214.2 | 2304.5 | 1843.8 | 1536.7 | 1317.3 | 1152.8 |
| 116 | 8.8 | LCMS34 | 9214.2 | 2304.5 | 1843.8 | 1536.7 | 1317.3 | 1152.8 |
| 117 | 9.0 | LCMS34 | 9156.2 | 2290.0 | 1832.2 | 1527.0 | 1309.0 | 1145.5 |
| 118 | 9.0 | LCMS34 | 9214.2 | 2304.5 | 1843.8 | 1536.7 | 1317.3 | 1152.8 |
| 119 | 10.1 | LCMS34 | 9943.2 | 2486.8 | 1989.6 | 1658.2 | 1421.5 | 1243.9 |
| 120 | 9.9 | LCMS34 | 9944.1 | 2487.0 | 1989.8 | 1658.4 | 1421.6 | 1244.0 |
| 123 | 9.8 | LCMS34 | 9943.2 | 2486.8 | 1989.6 | 1658.2 | 1421.5 | 1243.9 |
| 124 | 9.9 | LCMS34 | 10001.2 | 2501.3 | 2001.2 | 1667.9 | 1429.7 | 1251.1 |
| 128 | 10.1 | LCMS34 | 9916.1 | 2480.0 | 1984.2 | 1653.7 | 1417.6 | 1240.5 |
| 221 | 9.1 | LCMS34 | 9943.2 | 2486.8 | 1989.6 | 1658.2 | 1421.5 | 1243.9 |
| 222 | 9.9 | LCMS34 | 9959.1 | 2490.8 | 1992.8 | 1660.9 | 1423.7 | 1245.9 |
| 223 | 8.6 | LCMS34 | 9944.1 | 2487.0 | 1989.8 | 1658.4 | 1421.6 | 1244.0 |
| 224 | 10.0 | LCMS34 | 9944.1 | 2487.0 | 1989.8 | 1658.4 | 1421.6 | 1244.0 |
| 225 | 9.4 | LCMS34 | 10128.4 | 2533.1 | 2026.7 | 1689.1 | 1447.9 | 1267.0 |
| 226 | 10.5 | LCMS34 | 9999.3 | 2500.8 | 2000.9 | 1667.5 | 1429.5 | 1250.9 |
| 227 | 10.4 | LCMS34 | 10015.2 | 2504.8 | 2004.0 | 1670.2 | 1431.7 | 1252.9 |
| 229 | 10.6 | LCMS34 | 10000.2 | 2501.1 | 2001.0 | 1667.7 | 1429.6 | 1251.0 |
| 230 | 10.8 | LCMS34 | 10406.8 | 2602.7 | 2082.4 | 1735.5 | 1487.7 | 1301.8 |
| 281 | 9.1 | LCMS34 | 8969.0 | 2243.2 | 1794.8 | 1495.8 | 1282.3 | 1122.1 |
| 283 | 9.4 | LCMS34 | 9887.0 | 2472.8 | 1978.4 | 1648.8 | 1413.4 | 1236.9 |
| 284 | 9.6 | LCMS34 | 9888.0 | 2473.0 | 1978.6 | 1649.0 | 1413.6 | 1237.0 |
| 285 | 9.4 | LCMS34 | 9945.1 | 2487.3 | 1990.0 | 1658.5 | 1421.7 | 1244.1 |
| 286 | 9.1 | LCMS34 | 9945.1 | 2487.3 | 1990.0 | 1658.5 | 1421.7 | 1244.1 |
| 287 | 9.4 | LCMS34 | 9887.0 | 2472.8 | 1978.4 | 1648.8 | 1413.4 | 1236.9 |
| 288 | 9.7 | LCMS34 | 9945.1 | 2487.3 | 1990.0 | 1658.5 | 1421.7 | 1244.1 |
| 289 | 9.5 | LCMS34 | 9830.0 | 2458.5 | 1967.0 | 1639.3 | 1405.3 | 1229.7 |
| 290 | 9.2 | LCMS34 | 9903.0 | 2476.8 | 1981.6 | 1651.5 | 1415.7 | 1238.9 |
| 291 | 9.7 | LCMS34 | 9917.0 | 2480.3 | 1984.4 | 1653.8 | 1417.7 | 1240.6 |
| 292 | 9.9 | LCMS34 | 9860.0 | 2466.0 | 1973.0 | 1644.3 | 1409.6 | 1233.5 |
| 293 | 9.3 | LCMS34 | 9903.0 | 2476.8 | 1981.6 | 1651.5 | 1415.7 | 1238.9 |
| 294 | 8.6 | LCMS34 | 9887.0 | 2472.8 | 1978.4 | 1648.8 | 1413.4 | 1236.9 |
| 295 | 8.0 | LCMS34 | 9888.0 | 2473.0 | 1978.6 | 1649.0 | 1413.6 | 1237.0 |
| 296 | 9.3 | LCMS34 | 9888.0 | 2473.0 | 1978.6 | 1649.0 | 1413.6 | 1237.0 |
| 297 | 8.4 | LCMS34 | 10016.2 | 2505.0 | 2004.2 | 1670.4 | 1431.9 | 1253.0 |
| 298 | 8.3 | LCMS34 | 9959.1 | 2490.8 | 1992.8 | 1660.9 | 1423.7 | 1245.9 |
| 299 | 8.3 | LCMS34 | 9888.0 | 2473.0 | 1978.6 | 1649.0 | 1413.6 | 1237.0 |
| 300 | 8.3 | LCMS34 | 9945.1 | 2487.3 | 1990.0 | 1658.5 | 1421.7 | 1244.1 |
| 301 | 8.3 | LCMS34 | 9919.0 | 2480.8 | 1984.8 | 1654.2 | 1418.0 | 1240.9 |
| 302 | 8.3 | LCMS34 | 9959.1 | 2490.8 | 1992.8 | 1660.9 | 1423.7 | 1245.9 |
| 303 | 8.3 | LCMS34 | 9888.0 | 2473.0 | 1978.6 | 1649.0 | 1413.6 | 1237.0 |
| 304 | 8.3 | LCMS34 | 9945.1 | 2487.3 | 1990.0 | 1658.5 | 1421.7 | 1244.1 |
| 305 | 8.2 | LCMS34 | 9919.0 | 2480.8 | 1984.8 | 1654.2 | 1418.0 | 1240.9 |
| 306 | 8.4 | LCMS34 | 9242.3 | 2311.6 | 1849.5 | 1541.4 | 1321.3 | 1156.3 |
| 307 | 8.4 | LCMS34 | 12083.3 | 3021.8 | 2417.7 | 2014.9 | 1727.2 | 1511.4 |
| 308 | 9.7 | LCMS34 | 10524.8 | 2632.2 | 2106.0 | 1755.1 | 1504.5 | 1316.6 |
| 309 | 9.9 | LCMS34 | 10496.7 | 2625.2 | 2100.3 | 1750.5 | 1500.5 | 1313.1 |
| 310 | 9.6 | LCMS34 | 10555.8 | 2640.0 | 2112.2 | 1760.3 | 1509.0 | 1320.5 |
| 311 | 9.3 | LCMS34 | 10581.8 | 2646.5 | 2117.4 | 1764.6 | 1512.7 | 1323.7 |
| 312 | 9.4 | LCMS34 | 10553.8 | 2639.5 | 2111.8 | 1760.0 | 1508.7 | 1320.2 |
| 313 | 9.7 | LCMS34 | 9367.4 | 2342.6 | 1874.5 | 1562.3 | 1339.2 | 1171.8 |
| 314 | 9.6 | LCMS34 | 12208.4 |  | 2442.4 | 2035.6 | 1744.8 | 1527.0 |

C. General Methods for Characterisation

In order to characterise the compounds the functionality may be tested in various assays.

C1—GLP-1 In-Vitro Potency

The purpose of this assay is to test the GLP-1 activity (or potency), of a compound, such as a derivative comprising a GLP-1 analogue in vitro. The in vitro potency is the measure of human GLP-1 receptor activation in a whole cell assay.

The potencies of the derivatives of GLP-1/EGF(A) compounds were determined as described below and data for GLP-1 (7-37) and semaglutide is included for comparison.

Principle

In vitro potency is determined by measuring the response of the human GLP-1 receptor in a reporter gene assay. The assay is performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) are BHK cells with BHKTS13 as a parent cell line. The cells are derived from a clone (FCW467-12A) that expresses the human GLP-1 receptor and established by further transfection with CRE luciferase to obtain the current clone.

The cells are cultured at 5% $CO_2$ in Cell Culture Medium. They are aliquoted and stored in liquid nitrogen. Before each assay an aliquot is taken up and washed twice in PBS before being suspended at the desired concentration in the assay specific buffer. For 96-well plates the suspension is made to give a final concentration of $5\times10^3$ cells/well.

Materials

The following chemicals are used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell Culture Medium is DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium is DMEM w/o phenol red, 10 mM Hepes and 1× Glutamax. The Assay Buffer consisted of 2% ovalbumin and 0.2% Pluronic F-68 in Assay Medium.

Procedure

1) Cell stocks are thawed in a 37° C. water bath.
2) Cells are washed three times in PBS.
3) The cells are counted and adjusted to $5\times10^3$ cells/50 μl ($1\times10^5$ cells/ml) in Assay Medium. A 50 μl aliquot of cells is transferred to each well in the assay plate.
4) Stocks of the test compounds and reference compounds are diluted to a concentration of 0.2 μM in Assay Buffer. Compounds are diluted 10-fold to give the following concentrations: $2\times10^{-7}$ M, $2\times10^{-8}$ M; $2\times10^{-9}$ M, $2\times10^{-10}$ M, $2\times10^{-11}$ M, $2\times10^{-12}$ M, $2\times10^{-13}$ M, and $2\times10^{-14}$ M.
5) A 50 μl aliquot of compound or blank is transferred from the dilution plate to the assay plate. Compounds are tested at the following final concentrations: $1\times10^{-7}$ M, $1\times10^{-8}$ M; $1\times10^{-9}$ M, $1\times10^{-10}$ M, $1\times10^{-11}$ M, $1\times10^{-12}$ M, $1\times10^{-13}$ M, and $1\times10^{-14}$ M.
6) The assay plate is incubated for 3 h in a 5% $CO_2$ incubator at 37° C.
7) The assay plate is removed from the incubator and allowed to stand at room temperature for 15 min.
8) A 100 μl aliquot of steadylite plus reagent is added to each well of the assay plate (reagent is light sensitive).
9) Each assay plate is covered with aluminum foil to protect it from light and shaken for 30 min at room temperature.
10) Each assay plate is read in a Packard TopCount NXT instrument.

Calculations and Results

The in vitro potency assay as described above was performed on a series of compounds with and without HSA included. The data from the TopCount instrument are transferred to GraphPad Prism software. The software performs a non-linear regression (log(agonist) vs response). $EC_{50}$ values which are calculated by the software and reported in pM are shown in Table 1 below.

A minimum of two replicates was measured for each sample. The reported values are averages of the replicates.

TABLE 1

In vitro potency for GLP-I/EGF(A) compounds (i.e. the derivatives comprising a GLP-1 analogue and an EGF(A) analogue).

| Compound no. | $EC_{50}$ (pM) 0% HSA | $EC_{50}$ (pM) 1% HSA |
|---|---|---|
| GLP-1 (7-37) | 13.2 | 4.1 |
| Semaglutide | 7.3 | 210 |
| 1 | 36.7 | 271 |
| 2 | 65.8 | 287 |
| 3 | 224.8 | 1119 |
| 4 | 6.2 | 71 |
| 5 | 13.1 | 83 |
| 6 | 63.4 | 516 |
| 7 | 2718.8 | 9003 |
| 8 | 23.3 | 253 |
| 9 | 421.0 | 2827 |
| 10 | 687.0 | 2658 |
| 11 | 164.7 | 1210 |
| 12 | 18.9 | 109 |
| 13 | 3278.0 | >10000 |
| 14 | 378.7 | 1937 |
| 15 | 19.6 | 215 |
| 16 | 27.7 | 286 |
| 17 | 26.2 | 281 |
| 18 | 657.0 | 10000 |
| 19 | 18.6 | 737 |
| 20 | 31.5 | 770 |
| 21 | 138.0 | 2019 |
| 22 | 20.4 | 453 |
| 23 | 26.2 | 689 |
| 24 | 15.0 | 309 |
| 25 | 13.0 | 538 |
| 26 | 5.7 | 198 |
| 27 | 101.8 | 931 |
| 28 | 203.3 | 4059 |
| 29 | 80.5 | 597 |
| 30 | 27.4 | 271 |
| 31 | 23.6 | 187 |
| 32 | 27.2 | 395 |
| 33 | >10000 | >10000 |
| 34 | 110.6 | 2155 |
| 35 | 59.2 | 520 |
| 36 | 51.5 | 597 |
| 37 | 18.6 | 205 |
| 38 | 31.8 | 283 |
| 39 | 28.1 | 672 |
| 40 | 16.6 | 72 |
| 41 | 81.2 | 2322 |
| 42 | 19.9 | 66 |
| 43 | 28.3 | 272 |
| 44 | 22.5 | 192 |
| 45 | 26.2 | 270 |
| 46 | 28.3 | 301 |
| 47 | 23.2 | 230 |
| 48 | 18.1 | 997 |
| 49 | 108.0 | 4520 |
| 50 | 55.1 | 1390 |
| 51 | 48.5 | 1222 |
| 52 | 41.2 | 705 |
| 53 | 21.3 | 530 |
| 54 | 27.5 | 925 |
| 55 | 214.0 | 3723 |
| 56 | 20.0 | 188 |
| 57 | 27.2 | 293 |
| 58 | 9245.0 | >10000 |
| 59 | 315.0 | >10000 |
| 60 | 25.4 | 599 |
| 61 | 22.1 | 626 |
| 62 | 165.5 | >10000 |
| 63 | 145.5 | 7974 |
| 64 | 145.0 | 9610 |
| 65 | 856.0 | 7831 |
| 66 | 149.0 | 2974 |
| 67 | 416.0 | 6518 |
| 68 | 21.8 | 783 |
| 69 | 30.2 | 1631 |
| 70 | 116.0 | 5852 |
| 71 | 501.0 | >10000 |
| 72 | 276.0 | 1331 |

TABLE 1-continued

In vitro potency for GLP-I/EGF(A) compounds (i.e. the derivatives comprising a GLP-1 analogue and an EGF(A) analogue).

| Compound no. | $EC_{50}$ (pM) 0% HSA | $EC_{50}$ (pM) 1% HSA |
|---|---|---|
| 73 | >10000 | >10000 |
| 74 | 940.0 | 5123 |
| 75 | 1597.0 | 19375 |
| 77 | 11.4 | 710 |
| 78 | 11.2 | 485 |
| 79 | 8.4 | 252 |
| 80 | 16.7 | 1054 |
| 81 | 15.9 | 570 |
| 82 | 136.0 | 2086 |
| 83 | 191.0 | 3628 |
| 84 | 153.4 | 583 |
| 85 | 172.7 | 2316 |
| 86 | 49.5 | 480 |
| 87 | 113.0 | >10000 |
| 91 | 160.0 | 3802 |
| 92 | 116.0 | >10000 |
| 95 | 294.0 | >10000 |
| 99 | 190.0 | 3481 |
| 100 | 261.0 | >10000 |
| 103 | 5.4 | 138 |
| 104 | 8.3 | 93 |
| 105 | 3.1 | 109 |
| 106 | 52.6 | 818 |
| 107 | 609.0 | 2607 |
| 108 | 14.1 | 279 |
| 109 | 6.6 | 115 |
| 110 | 6.3 | 399 |
| 111 | 68.6 | 3078 |
| 112 | 3.0 | 122 |
| 113 | 379.3 | 566 |
| 114 | 74.8 | 385 |
| 115 | 234.7 | 484 |
| 116 | 75.7 | 259 |
| 117 | 8.3 | 121 |
| 118 | 20.0 | 222 |
| 119 | 1200.5 | 361 |
| 120 | 90.5 | 5318 |
| 123 | 20.8 | 176 |
| 124 | 119.0 | 5487 |
| 128 | 95.9 | 8923 |
| 221 | 102.7 | 3259 |
| 222 | 75.2 | 357 |
| 223 | 55.6 | 2174 |
| 224 | 80.7 | 1228 |
| 225 | 86.4 | 4276 |
| 226 | 124.0 | 4880 |
| 227 | 131.0 | 1434 |
| 229 | 138.3 | 6460 |
| 230 | 68.1 | 934 |
| 281 | 14.2 | 530 |
| 283 | 1749.7 | 536 |
| 284 | 108.0 | 1378 |
| 285 | 213.0 | 320 |
| 286 | 971.0 | 266 |
| 287 | 41.8 | 377 |
| 288 | 154.0 | 572 |
| 289 | 1159.0 | 1197 |
| 290 | 881.3 | 210 |
| 291 | 554.0 | 2481 |
| 292 | 194.5 | 2884 |
| 293 | 36.0 | 506 |
| 294 | 39.7 | 730 |
| 295 | 31.2 | 977 |
| 296 | 36.6 | 539 |
| 297 | 35.4 | 730 |
| 298 | 37.2 | 993 |
| 299 | 55.0 | 1258 |
| 300 | 69.2 | 1105 |
| 301 | 53.0 | 1268 |
| 302 | 87.9 | 722 |
| 303 | 53.3 | 1287 |
| 304 | 69.7 | 1269 |
| 305 | 48.4 | 1088 |
| 306 | 21.2 | 684 |
| 307 | 17.8 | 622 |
| 308 | 452.0 | 5234 |
| 309 | 323.0 | 4104 |
| 310 | 237.0 | 3990 |
| 311 | 277.0 | 1648 |
| 312 | 272.0 | 367 |
| 313 | 65.7 | 1245 |
| 314 | 54.9 | 673 |

The majority of the GLP-1/EGF(A) compounds show GLP-1 activity. The specific potency (both in the absence and presence of HSA) is influence by amino acid variations in the analogues and the identity of the spacer as well as the substituent. The data above demonstrate that compounds with a potency comparable or reduced relatively to GLP-1 (7-37) and Semaglutide can be obtained.

Furthermore, a significant loss of GLP-1 potency is observed when the EGF(A) analogue is attached to the N-terminal of the GLP-1 analogue (compound 75, SEQ ID 386) instead of the C-terminal of the GLP-1 analogue (compound 1, SEQ ID 193).

C2—GLP-1—In Vitro Receptor Binding

The purpose of this example is to test the receptor binding of the GLP-1 derivatives in vitro. The receptor binding is a measure of affinity of a derivative for the human GLP-1 receptor.

Principle

The receptor binding to the human GLP-1 receptor is measured in a competitive binding assay. In this type of assay a labelled ligand (in this case $^{125}$I-GLP-1) is bound to the receptor. Each derivative/compound is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. GLP-1 (7-37) and Semaglutide are included as comparative compound.

Materials

The following chemicals are used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36)$NH_2$ (produced in-house), OPTIPLATE™-96 (Packard 6005290).

Buffer 1 consists of 20 mM Na-HEPES plus 10 mM EDTA and pH is adjusted to 7.4. Buffer 2 consists of 20 mM Na-HEPES plus 0.1 mM EDTA and pH is adjusted to 7.4. Assay buffer consists of 50 mM HEPES supplemented with 5 mM EGTA, 5 mM $MgCl_2$, 0.005% Tween 20 and pH is adjusted to 7.4. An 8% albumin stock consists of HSA dissolved at 8% (w/v) in assay buffer. An 0.02% albumin stock consists of HSA dissolved at 0.02% (w/v) in assay buffer.

Cell Culture and Membrane Preparation

The cells used in this assay (clone FCW467-12A) are BHK cells with BHKTS13 as a parent cell line. The cells express the human GLP-1 receptor.

The cells are grown at 5% $CO_2$ in DMEM, 10% fetal calf serum, 1% Pen/Strep (Penicillin/Streptomycin) and 1.0 mg/ml of the selection marker G418. To make a membrane preparation the cells are grown to approximately 80% confluence. The cells are washed twice in phosphate-buffered saline and harvested. The cells are pelleted using a brief centrifugation and the cell pellet is kept on ice. The cell pellet is homogenised with ULTRA-THURRAX™ dispersing instrument for 20-30 seconds in a suitable amount of buffer 1 (e.g., 10 ml). The homogenate is centrifuged for 15 minutes. The pellet is re-suspended (homogenised) in 10 ml buffer 2 and centrifuged. This step is repeated once more. The resulting pellet is re-suspended in buffer 2 and the protein concentration is determined. The membranes are aliquoted and stored at minus 80° C.

Procedure

1) For the receptor binding assay in the presence of low HSA (0.005%) 50 µl of the assay buffer is added to each well of an assay plate.
2) Test compounds are serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl are added to appropriate wells in the assay plate.
3) Cell membrane aliquots are thawed and diluted to their working concentration. Fifty µl are added to each well in the assay plate.
4) WGA SPA beads are suspended in assay buffer at 20 mg/ml. The suspension is diluted to 10 mg/ml in assay buffer just prior to addition to the assay plate. Fifty µl are added to each well in the assay plate.
5) The incubation is started by adding 25 µl of 480 pM solution of [$^{125}$I]-GLP-1]-(7-36)$NH_2$ to each well of the assay plate. A 25 µl aliquot is reserved for measuring total counts/well.
6) The assay plate is incubated for 2 h at 30° C.
7) The assay plate is centrifuged for 10 min.
8) The assay plate is read in a Packard TopCount NXT instrument.

Calculations

The data from the TopCount instrument are transferred to GraphPad Prism software. The software performed a non-linear regression. $IC_{50}$ values are calculated by the software and reported in nM.

Results

The following results were obtained:

TABLE 2

GLP-1 receptor binding for GLP-1/EGF(A) compounds

| GLP-1/EGF(A) Compound no. | Low HSA $IC_{50}$ (nM) |
|---|---|
| GLP-1 (3-37) | 0.5 |
| Semaglutide | 0.6 |
| 1 | 14.5 |
| 2 | 14.8 |
| 3 | 57.4 |
| 4 | 0.4 |
| 5 | 4.9 |
| 6 | 49.8 |
| 7 | 699.9 |
| 8 | 23.8 |
| 9 | 163.4 |
| 10 | 93.1 |
| 11 | 46.1 |
| 12 | 5.8 |
| 13 | 1000.0 |
| 14 | 232.2 |
| 15 | 15.1 |
| 16 | 11.4 |
| 17 | 23.4 |
| 18 | 213.6 |
| 19 | 12.1 |
| 20 | 17.8 |
| 21 | 47.8 |
| 22 | 6.7 |
| 23 | 4.3 |
| 24 | 5.8 |
| 25 | 9.2 |
| 26 | 0.8 |
| 27 | 24.7 |
| 28 | 29.4 |
| 29 | 27.8 |
| 30 | 11.4 |
| 31 | 14.3 |
| 32 | 11.3 |
| 33 | >1000 |
| 34 | 15.1 |
| 35 | 19.9 |
| 36 | 22.4 |
| 37 | 5.0 |
| 38 | 13.8 |
| 39 | 5.5 |
| 40 | 1.6 |
| 41 | 19.1 |
| 42 | 2.2 |
| 43 | 12.0 |
| 44 | 9.3 |
| 45 | 31.4 |
| 46 | 13.6 |
| 47 | 13.4 |
| 48 | 5.6 |
| 49 | 33.1 |
| 50 | 14.5 |
| 51 | 17.7 |
| 52 | 14.6 |
| 53 | 1.8 |
| 54 | 4.1 |
| 55 | 21.9 |
| 56 | 4.7 |
| 57 | 4.6 |
| 58 | >1000 |
| 59 | 66.1 |
| 60 | 3.2 |
| 61 | 2.2 |
| 62 | 57.9 |
| 63 | 50.3 |
| 64 | 156.4 |
| 65 | 204.9 |
| 66 | 26.7 |
| 67 | 84.4 |
| 68 | 2.2 |
| 69 | 11.4 |
| 70 | 57.3 |
| 71 | 122 |
| 72 | 208.3 |
| 73 | 167.7 |
| 74 | 347.6 |
| 75 | 609.0 |
| 77 | 6.8 |
| 78 | 3.6 |
| 79 | 3.9 |
| 80 | 8.5 |
| 81 | 3.1 |
| 82 | 56 |
| 83 | 62.5 |
| 84 | 34.5 |
| 85 | 64.9 |

TABLE 2-continued

GLP-1 receptor binding for GLP-1/EGF(A) compounds

| GLP-1/EGF(A) Compound no. | Low HSA IC$_{50}$ (nM) |
|---|---|
| 86 | 31.7 |
| 87 | 39.7 |
| 91 | 23.8 |
| 92 | 38.7 |
| 95 | 42.6 |
| 99 | 38.3 |
| 100 | 33.8 |
| 103 | 0.9 |
| 104 | 1.4 |
| 105 | 3.1 |
| 106 | 75.1 |
| 107 | 59.8 |
| 108 | 5.1 |
| 109 | 1.2 |
| 110 | 4.3 |
| 111 | 45.6 |
| 112 | 2.8 |
| 113 | 310.8 |
| 114 | 132.9 |
| 115 | 233.8 |
| 116 | 89.7 |
| 117 | 11 |
| 118 | 33.1 |
| 119 | 551.6 |
| 120 | 52.4 |
| 123 | 5.3 |
| 124 | 124.9 |
| 128 | 122.1 |
| 221 | 35.2 |
| 222 | 39.1 |
| 223 | 33 |
| 224 | 58.5 |
| 225 | 21.6 |
| 226 | 25.3 |
| 227 | 19.5 |
| 229 | 32.8 |
| 230 | 18.4 |
| 281 | 10.6 |
| 283 | 576.3 |
| 284 | 105.7 |
| 285 | 288.1 |
| 286 | 425.8 |
| 287 | 51.7 |
| 288 | 184.6 |
| 289 | 456.9 |
| 290 | 489.7 |
| 291 | 859.4 |
| 292 | 321.8 |
| 293 | 83.1 |
| 294 | 45.8 |
| 295 | 58.9 |
| 296 | 73.7 |
| 297 | 52.3 |
| 298 | 50.9 |
| 299 | 95 |
| 300 | 90.5 |
| 301 | 103.3 |
| 302 | 71.9 |
| 303 | 102.5 |
| 304 | 92.7 |
| 305 | 74 |
| 306 | 10 |
| 307 | 6.1 |
| 308 | 185.2 |
| 309 | 112.6 |
| 310 | 32.6 |
| 311 | 38.9 |
| 312 | 51 |
| 313 | 15.2 |
| 314 | 6.7 |

The data above demonstrate that the GLP-1 binding depends on the specific sequence and substituent and that various levels of GLP-1 binding activity can be obtained in order to prepare a compound with receptor binding comparable or reduced relative to GLP-1 (7-37) or semaglutide. Again, a significant loss of GLP-1 binding was observed when the EGF(A) analogue was attached to the N-terminal of the GLP-1 analogue (compound 75, SEQ ID 386) instead of the C-terminal of the GLP-1 analogue (compound 1, SEQ ID 193).

C3—PCSK9-LDL-R Binding—Competitive (ELISA)

This assay measures the apparent binding affinity to PCSK9 in competition with LDL-R. In particular the assay is used to evaluate the apparent binding affinity of EGF(A) analogue and compounds comprising an EGF(A) analogue, such as GLP-1/EGF(A) compounds, to PCSK9.

The assay is performed as follows. The day before the experiment, recombinant human Low Density Lipoprotein Receptor (rhLDL-R; NSO-derived; R & D systems #2148-LD) is dissolved at 1 µg/ml in 50 mM sodium carbonate, pH 9.6, and then 100 µl of the solution is added to each well of the assay plates (Maxisorp 96, NUNC #439454) and coated overnight at 4° C. On the day of the experiments, 8 point concentration curves of the EGF(A) compounds containing Biotinylated PCSK9 (0.5 ug/ml, BioSite/BPSBioscience cat #71304) are made in duplicate. Test compound and biotinylated PCSK9 mixtures are prepared an incubated for 1 hour at room temperature in assay buffer containing 25 mM Hepes, pH 7.2 (15630-056, 100 ml, 1M), 150 mM NaCl (Emsure 1.06404.1000) 1% HSA (Sigma A1887-25G) 0.05% Tween 20(Calbiochem 655205) 2 mM CaCl$_2$) (Sigma 223506-500G). The coated assay plates are then washed 4× in 2000 assay buffer, and then 100 µl of the mixture of test compounds and biotinylated PCSK9 is added to the plates and incubated 2 h at room temperature. The plates are washed 4× in 2000 assay buffer and then incubated with Streptavidin-HRP (25 ng/ml; VWR #14-30-00) for 1 h at room temperature. The reaction is detected by adding 50 µl TMB-on (KEM-EN-TEC) and incubated 10 min in the dark. Then the reaction is stopped by adding 50 µl 4 M H$_3$PO$_4$ to the mixture, added by electronic multi pipetting. The plates are then read in a Spectramax at 450 and 620 nm within 1 h. The 620 nm read is used for background subtraction. IC50 values are calculated using Graphpad Prism, by nonlinear regression log(inhibitor) vs. response-variable slope (four parameters), and converted into Ki values using the following formula: Ki=IC50/(1+(Biotin-PCSK9)/(kd(Biotin-PCSK9))), where Kd of the biotin-PCSK9 is 1.096727714 µg/ml and [Biotin-PCSK9]=0.5 (µg/ml).

The results are shown in Table 3.1 to 3.6 below. Higher Ki values reflects lower apparent binding affinities to PCSK9 and vice versa. It is noticed that few of the compounds display a Ki which is substantially higher than the value measured for EGF66, such as a value above 500 nM, which indicate that the observed binding is not specific. Both the amino acid substitutions of the peptide and/or the one or more side-chain derivation may contribute to the loss of binding to LDL-R. In general a large number of the tested EGF(A) compounds displayed the ability to inhibit PCSK9 in binding to the hLDL-R.

PCSK9 Inhibitors

Initially a group of EGF(A) analogues including various amino acids substitutions were tested as described above and the results are shown in table 3.1.

TABLE 3.1

| Apparent binding affinity (Ki) for selected EGF(A) analogues | | |
|---|---|---|
| EGF(A) compound # | EGF(A) analogue | Ki (nM) |
| WT | — | — |
| 48 | 299A, 301L, 307I, 309R, 310K | 9.4 |
| 103 | 299A, 301L, 307I, 309R | 0.9 |
| 104 | 301L, 309R, 310K | 7.3 |
| 49 | 301L, 309R | 1.2 |
| 105 | 301L | 2.8 |
| 50 | 301L, 309R, 312E | 1.1 |

EGF66 (EGF(A) compound #48) identified as the most potent peptide variant in WO 2012177741, has 5 mutations. It was found that several of these mutations were not of great importance for the Ki value determined in the assay described C3. In particular it was found that compounds including the wild type residue Asp (D) in position 310 had higher potencies than compounds with 310K. It also appeared that the key amino substitution is 301L preferably in combination with 309R. Finally 307I and 299A contributed only modestly to the affinity of the EGF(A) analogues.

N-Terminal Attachment of Substituent

In a subsequent experiment it was tested if attachment of a half-life protractor e.g. a substituent to the peptides influences the Ki as determined by the assay described in C3. As described herein a substituent may be attached by different technologies and the substituent was initially attached to the nitrogen atom of the N-terminal amino acid of the peptides by acylation or alkylation.

As seen in Table 3.2 all the tested compounds have an Ki value below 3.0 nM suggesting that the various protractor and linker elements are well tolerated. This was unusual as potency is usually negatively influence by attachment of a side chain as previously observer for peptides like GLP-1.

TABLE 3.2

| Apparent Ki for N-terminal substituted EGF(A) analogues | | | |
|---|---|---|---|
| EGF(A) compound # | EGF(A) analogue | Attachment | Ki (nM) |
| 1. | 299A, 301L, 307I, 309R, 310K | Alkylation | nd |
| 2 | 301L, 309R | Alkylation | 1.7 |
| 64 | 300H, 301L, 309R | Alkylation | 0.7 |
| 5 | 301L, 309R, 312E | Alkylation | 1.3 |
| 8 | 301L, 309R, 312E | Alkylation | 1.2 |
| 19 | 301L, 309R, 312E | Acylation | 1.7 |
| 68 | 301L, 309R, 312E | Alkylation | 0.8 |
| 22 | 301L, 309R, 312Q | Acylation | 2.6 |
| 51 | 301L, 306Y, 309S, 312E | Acylation | 1.6 |
| 52 | 293N, 301L, 309S, 312E | Acylation | 2.1 |
| 65 | 300P, 301L, 307I, 309R, 312E | Acylation | >1000 |
| 72 | 300H, 301L, 307I, 309R, 312E | Acylation | 2.8 |

Lys Attachment of Substituent

In order to evaluate alternative positions for linkage of a substituent to a PCSK9 inhibitor peptide a series of compounds were prepared. A back-bone peptide including three amino acid substitutions; N301L, N309R and K312E were used except in EGF(A) compound #58, 29 and 4 in combination with a Lys substitution at various positions. All compounds tested included the 6 cysteine amino acids in positions 297, 304, 308, 317, 319, 331 which are usually engaged in cysteine disulfide bridges. The 312E was included to ensure site specific substitution except in EGF (A) compound #4 where attachment to wt 312K is obtained.

Extension of the peptide with one Lys is also tested (EGF(A) compound 75 and 3). The same substituent as described above including a C18 diacid protractor and a γGlu-2×Ado linker was used in all compounds and attached via acylation. The results are included in Table 3.3.

TABLE 3.3

| Apparent Ki for EGF(A) analogue with a substituent attached via a Lys residue | | | |
|---|---|---|---|
| EGF(A) compound # | Peptide variant | Attachment site | Ki (nM) |
| 75 | 292K, 301L, 309R, 312E | 292K | 1.5 |
| 11 | 293K, 301L, 309R, 312E | 293K | 2.4 |
| 74 | 294K, 301L, 309R, 312E | 294K | 1.4 |
| 73 | 296K, 301L, 309R, 312E | 296K | 8.9 |
| 59 | 298K, 301L, 309R, 312E | 298K | 610.7 |
| 6 | 299K, 301L, 309R, 312E | 299K | 3.3 |
| 26 | 300K, 301L, 309R, 312E | 300K | 1.3 |
| 58 | 301K, 309R, 312E | 301K | 1000.0 |
| 56 | 301L, 302K, 309R, 312E | 302K | 1032.0 |
| 55 | 301L, 303K, 309R, 312E | 303K | 1.7 |
| 54 | 301L, 305K, 309R, 312E | 305K | 2.1 |
| 53 | 301L, 306K, 309R, 312E | 306K | 1.7 |
| 45 | 301L, 307K, 309R, 312E | 307K | 1000.0 |
| 29 | 301L, 309K, 312E | 309K | 0.8 |
| 44 | 301L, 309R, 311K, 312E | 311K | 1.0 |
| 4 | 301L, 309R | 312K | 1.2 |
| 38 | 301L, 309R, 312E, 313K | 313K | 0.8 |
| 43 | 301L, 309R, 312E, 314K | 314K | 0.9 |
| 41 | 301L, 309R, 312E, 315K | 315K | 3.0 |
| 40 | 301L, 309R, 312E, 316K | 316K | 1.6 |
| 30 | 301L, 309R, 312E, 318K | 318K | 2.0 |
| 36 | 301L, 309R, 312E, 320K | 320K | 5.5 |
| 20 | 301L, 309R, 312E, 321K | 321K | 2.0 |
| 35 | 301L, 309R, 312E, 322K | 322K | 1.5 |
| 34 | 301L, 309R, 312E, 323K | 323K | 1.7 |
| 21 | 301L, 309R, 312E, 324K | 324K | 0.9 |
| 33 | 301L, 309R, 312E, 325K | 325K | 1.4 |
| 32 | 301L, 309R, 312E, 326K | 326K | 1.4 |
| 39 | 301L, 309R, 312E, 328K | 328K | 0.9 |
| 37 | 301L, 309R, 312E, 329K | 329K | 1.0 |
| 7 | 301L, 309R, 312E, 330K | 330K | 1.4 |
| 10 | 301L, 309R, 312E, 332K | 332K | 1.1 |
| 3 | 301L, 309R, 312E, 333K | 333K | 0.8 |

The analysis showed that the majority of the PCSK9 inhibitor peptide maintain functionality. The exceptions were Lys substitution and derivation in either of position 298, 301, 302 and 307 which gave rise to non-functional peptides. It was also observed that Lys introduction and substitution in position 296, 299, 315 and 320K reduced the apparent affinity.

The data thus also confirm the result from table 3.1 indicating that the amino acid substitution of Asn(N) 301 to Leu (L) is essential for the binding.

No data was observed for Lys introduction and substitution in position 295 and 310. As described above it was previously found that maintenance of Asp in 310 was preferred above the 310K substitution. As seen below it was also found that binding is abolished by introduction of Asp (D) in position 295 (EGF(A) example compound 70).

In summary it was concluded that compounds which do not comprise a substituent attached in any of the positions 295, 298, 302, 307 and 310 or in any of the positions 295, 296, 298, 299, 302, 307, 310, 315 and 320 of the PCSK9 peptide are generally functional. It was further concluded that an amino acid substitution in any of the positions 295, 298, 302, and 310 is generally not attractive. As seen from table 3.1 and 3.2 the V307I mutation none the less seem to be acceptable or even attractive in combination with 301Leu.

It is further considered that peptides with amino acid substitution in one of the positions 295, 296, 298, 302, 310 are likely to have a lower functionality, while substitutions in 299, 315 and 320 only seems to lower functionality slightly. This on the other hand also suggests that a high degree of flexibility may exist for the remaining amino acid residues as Lys substitution and attachment of a sidechain will influence the peptides as much as most other amino acid substitutions.

PCSK9 Inhibitors with Two Substituents

A series of compound with two substituents were prepared. Double substitution may be obtained by acylation, alkylation or a combination at the N-terminal or at Lys (K) residues. Again the N-terminal may be amino acid 293G or a variant amino acid residue such as 292A, 293G, 293K and 294T (in cases where 293G is deleted). The compounds were prepared with different substituents, although the two substituents on the individual compounds are identical. The back-bone used in this study again included the N301L amino acid substitution in combination with N309R and various N-terminal and/or Lys substitutions as required to obtain the specific acylation/alkylation.

TABLE 3.4

Apparent Ki for double substituted EGF(A) analogues

| EGF(A) compound # | Variant 301L, 309R, + | Attachment sites | Ki (nM) |
|---|---|---|---|
| 9 | 312E, 330K | N-terminal, 330K | 2.7 |
| 12 | 293K, 312E, 333K | 293K, 333K | 2.7 |
| 13 | 293K, 312E, 333K | 293K, 333K | 2.1 |
| 14 | 312E, 332K, 333K | 332K, 333K | 1.2 |
| 15 | 312E, 330K, 333K | 330K, 333K | 1.5 |
| 16 | 312E, 321K, 333K | 321K, 333K | 1.1 |
| 17 | 333K | 312E, 333K | 1.8 |
| 25 | 293K, 312E | N-terminal, 293K | 2.0 |
| 27 | 293K, 294K, 312E | 293K, 294K | 0.9 |
| 28 | 293K | 293K, 312K | 0.8 |
| 31 | 312E, 313K, 333K | 313K, 333K | 0.5 |
| 78 | 306D, 312E, 333K | N-terminal, 333K | 2.3 |
| 79 | 312E, 321K, 333K | 321K, 333K | 1.5 |
| 83 | 312E, 321K, 333K | 321K, 333K | 1.5 |
| 84 | 312E, 321K, 333K | 321K, 333K | 1.8 |
| 85 | 300H, 312E, 313K, 333K | 313K, 333K | 0.9 |
| 86 | 312E, 313K, 328K | 313K, 328K | 1.1 |
| 87 | 312E, 313K, 324K | 313K, 324K | 1.0 |
| 88 | 312E, 313K | N-terminal, 313K | 1.2 |
| 89 | 312E, 324K, 333K | 324K, 333K | 1.0 |
| 90 | 312E, 313K, 321K | 313K, 321K | 1.6 |
| 91 | des293, 300H, 312E, 313K, 333K | 313K, 333K | 0.9 |
| 92 | 300H, 312E, 313K, 333K | 313K, 333K | 1.0 |
| 93 | 292A, 312E, 313K | N-terminal (292A), 313K | 1.2 |
| 94 | des293, 312E, 313K | N-terminal (294T), 313K | 0.9 |
| 96 | 312E, 313K, 332K | 313K, 332K | 1.2 |
| 97 | 312E, 328K, 333K | 328K, 333K | 1.2 |
| 98 | 312E, 313K, 333K | 313K, 333K | 0.9 |
| 99 | 312E, 313K, 333K | 313K, 333K | 1.3 |
| 100 | 312E, 313K, 333K | 313K, 333K | 1.4 |
| 101 | 312E, 313K, 333K | 313K, 333K | 0.6 |
| 102 | 312E, 313K, 333K | 313K, 333K | 0.8 |
| 107 | 312E, 333K | N-terminal, 333K | 2.6 |
| 108 | des293-294, 300H, 312E, 313K, 333K | 313K, 333K | 3.8 |
| 109 | 300H, 312E, 313K, 333K | 313K, 333K | 1.0 |
| 110 | 312E, 313K, 333K | 313K, 333K | 1.7 |
| 113 | 300H, 312E, 314K, 333K | 314K, 333K | 1.6 |
| 114 | 294W, 312E, 333K | N-terminal, 333K | 3.1 |
| 117 | des293, 312E, 333K | N-terminal, 333K | 2.5 |
| 118 | 312E, 324K, 328K | 324K, 328K | 1.2 |
| 119 | 292A, 312E, 333K | N-terminal, 333K | 2.1 |

TABLE 3.4-continued

Apparent Ki for double substituted EGF(A) analogues

| | | | |
|---|---|---|---|
| 120 | 306Y, 312E, 313K, 333K | 313K, 333K | 1.6 |
| 121 | 312E, 332K | N-terminal, 332K | 2.1 |
| 122 | 312E, 328K | N-terminal, 328K | 2.2 |
| 123 | 312E, 324K | N-terminal, 324K | 2.0 |
| 127 | 312E, 321K, 332K | 321K, 332K | 2.4 |
| 128 | 312E, 313K, 333K | 313K, 333K | 1.0 |
| 129 | 312E, 313K, 333K | 313K, 333K | 2.6 |
| 130. | 300H, 312E, 313K, 332K | 313K, 332K | 1.8 |
| 131. | 312E, 313K, 333K | 313K, 333K | 2.6 |
| 132. | 312E, 313K, 321E, 332K | 313K, 332K | 1.9 |
| 133. | 301L, 309R, 312E, 313K, 321E, 333K | 313K, 333K | 1.6 |
| 134. | 312E, 321E, 333K | 333K | 1.9 |
| 135. | 312E, 313K, 314K | 313K, 314K | 3.6 |
| 136. | 313K | 312K, 313K | 2.8 |
| 137. | 314K | 312K, 314K | 4.7 |
| 138. | 311K, 312E, 313K | 311K, 313K | 2.5 |
| 139. | 300H, 312E, 313K, 333K | 313K, 333K | 3.3 |
| 140. | 312E, 313K, 333K | 313K, 333K | 1.7 |
| 141. | 312E, 313K, 333K | 313K, 333K | 2.2 |
| 142. | 312E, 313K, 333K | 313K, 333K | 1.7 |
| 143. | 312E, 313K, 321E, 333K | 313K, 333K | 1.9 |
| 144. | 312E, 313K, 321E, 333K | 313K, 333K | 2.09 |
| 145. | 312E, 313K, 333K | 313K, 333K | 2.6 |
| 146. | 312E, 313K, 321E, 333K | 313K, 333K | 3.0 |
| 147. | 300H, 312E, 313K, 321E, 333K | 313K, 333K | 1.5 |
| 148. | 312E, 313K, 333K | 313K, 333K | 2.5 |
| 149. | des293, 300H, 312E, 313K, 333K | 313K, 333K | 1.9 |
| 150. | 312E, 328K, 333K | 328K, 333K | 2.3 |
| 151. | 312E, 321E, 328K, 333K | 328K, 333K | 1.8 |
| 152. | 312E, 324K, 333K | 324K, 333K | 1.9 |
| 153. | 312E, 321E, 324K, 333K | 324K, 333K | 2.0 |
| 154. | 312E, 321E, 328K, 333K | 328K, 333K | 1.8 |
| 155. | 312E, 313K, 321K | 313K, 321K | 1.4 |
| 156. | 312E, 313K, 333K | 313K, 333K | 1.2 |
| 157. | 312E, 313K, 321E, 333K | 313K, 333K | 1.3 |

| Example No. | Variant 301L+ | Attachment sites | Ki (nM) |
|---|---|---|---|
| 111 | 309K, 312E, 333K | 309K, 333K | 1.6 |
| 112 | 306Y, 312E, 324K, 333K | 324K, 333K | 1.5 |
| 115 | 309K, 312E, 328K | 309K, 328K | 1.0 |
| 116 | 309K, 312E, 313K | 309K, 313K | 1.1 |
| 124 | 309K, 312E, 332K | 309K, 332K | 1.2 |
| 125 | 309K, 312E, 324K | 309K, 324K | 1.4 |
| 126 | 309K, 312E | N-terminal, 309K | 2.8 |

Again the inventors concluded that the substituents are very well tolerated in a variety of positions and combinations.

Further EGF(A) Derivatives

To explore further the role of various amino acid substitutions in the EGF(A) sequence further compounds were prepared and tested as shown in table 3.5 All compounds include one substituent which is attached via a Lys residue introduced by amino acid substitution or extension with 333K. The back-bone peptides all include the N301L amino acid substitution and optionally one or more of N309R and I312E. The substituents all includes a fatty diacid comprising 16-20 carbon atoms and a linker which is either γGlu alone or extended with Ado-Ado and/or a tranexamic acid (Trx) moiety.

TABLE 3.5

Apparent Ki for further EGF(A) analogue with a substituent attached via a Lys residue.

| EGF(A) compound # | Variant 301L, 309R, 312E+ | Attachment sites | Ki (nM) |
|---|---|---|---|
| 18 | 321E, 333K | 333K | 1.5 |
| 23 | 321E, 332K | 332K | 0.9 |
| 24 | 293K, 321E | 293K | 1.8 |
| 69 | 328K, 329H | 328K | 1.3 |
| 70 | 295D, 332K | 332K | 1325 |
| 76 | des293, 294G, 328K | 328K | 1.3 |
| 77 | 306D, 324G, 333K | 333K | 2.2 |
| 80 | 333K | 333K | 1.9 |
| 81 | 333K | 333K | 1.4 |
| 82 | 333K | 333K | 1.9 |
| 106 | 300H, 333K | 333K | 1.0 |
| 134 | 321E, 333K | 333K | 1.9 |
| 158 | 321E, 333K | 333K | 2.3 |
| 159 | 321E, 333K | 333K | 1.9 |

| EGF(A) compound # | Variant 301L, 309R, + | Attachment site | Ki |
|---|---|---|---|
| 22 | 312Q | N-term | 2.6 |
| 42 | 300H, 312R, 333K | 333K | 0.7 |
| 57 | 293N, 300H, 312R, 333K | 333K | 0.5 |
| 60 | 293N, 312R, 333K | 333K | 1.0 |
| 66 | 293N, 307I, 312D, 333K | 333K | 2.1 |
| 67 | 293N, 312D, 333K | 333K | 2.0 |
| 71 | 300H | 312K | 0.9 |

| EGF(A) compound # | Variant 301L, 312E, + | Attachment site | Ki |
|---|---|---|---|
| 47 | 309S, 333K | 333K | 2.7 |
| 62 | 306Y, 332K | 332K | 0.6 |
| 63 | 307I, 332K | 332K | 1.4 |

| EGF(A) compound # | Variant 301L, + | Attachment site | Ki |
|---|---|---|---|
| 46 | 309S, 312R, 333K | 333K | 1.3 |
| 61 | 307I, 332K | 332K | 0.7 |

The results in table 3.5 above shows that the internal wt lysine in position 312 can be substituted with Glu (E) as well as Gln (Q), Arg (R) or Asp (D). Based on this variation it is contemplated that a broad range of amino acid residues will be tolerated in position 312 without interfering with the inhibitory function of the peptide.

Several other amino acid substitutions were also proven to be well tolerated including G293N, T294G, D299A, N300H, H306Y, H306D, N3095, Q324G and R329H, while as mentioned above N295D and N300P are none attractive amino acid substitutions. PCSK9 binding of comprising a GLP-1 analogue and an EGF(A) analogues To further explore if the PCSK9 binding functionality could be combined with GLP-1 receptor agonist activity, compounds comprising a GLP-1 analogue and an EGF(A) analogue were tested in the same assay and the results included in table 3.6 below.

TABLE 3.6

Apparent Ki for compounds comprising a GLP-1 analogue and an EGF(A) analogues

| GLP-1/EGF(A) Compound no. | PCSK9 binding, 1% HSA Ki (nM) |
|---|---|
| 1 | 4.9 |
| 2 | 3.2 |
| 3 | 2.2 |
| 4 | 3.0 |
| 5 | 2.9 |
| 6 | 2.5 |
| 7 | 2.8 |
| 8 | 3.5 |
| 9 | 2.3 |
| 10 | 2.1 |
| 11 | 2.8 |
| 12 | 2.4 |
| 13 | 2.5 |
| 14 | 2.4 |
| 15 | 2.4 |
| 16 | 3.4 |
| 17 | 2.7 |
| 18 | 1.9 |
| 19 | 2.2 |
| 20 | 1.7 |
| 21 | 1.6 |
| 22 | 1.7 |
| 23 | 2.5 |
| 24 | 1.6 |
| 25 | 1.3 |
| 26 | 2.5 |
| 27 | 2.4 |
| 28 | 3.3 |
| 29 | 2.8 |
| 30 | 2.9 |
| 31 | 5.1 |
| 32 | 6.1 |
| 33 | 4.7 |
| 34 | 3.3 |
| 35 | 3.1 |
| 36 | 2.5 |
| 37 | 5.2 |
| 38 | 4.1 |
| 39 | 3.8 |
| 40 | 3.6 |
| 41 | 6.8 |
| 42 | 8.3 |
| 43 | 3.2 |
| 44 | 6.5 |
| 45 | 6.6 |
| 46 | 6.2 |
| 47 | 5.6 |
| 48 | 3.1 |
| 49 | 5.2 |
| 50 | 3.9 |
| 51 | 4.4 |
| 52 | 4.6 |
| 53 | 4.6 |
| 54 | 5.1 |
| 55 | 4.8 |
| 56 | 5.3 |
| 57 | 5.0 |
| 58 | 6.0 |
| 59 | 6.9 |
| 60 | 5.9 |
| 61 | 5.5 |
| 62 | 6.5 |
| 63 | 7.0 |
| 64 | 7.1 |
| 65 | 3.9 |
| 66 | 4.3 |
| 67 | 3.7 |
| 68 | 3.2 |
| 69 | 2.8 |
| 70 | 4.0 |
| 71 | 3.7 |
| 72 | 4.6 |
| 73 | 4.8 |
| 74 | 4.6 |

TABLE 3.6-continued

Apparent Ki for compounds comprising a
GLP-1 analogue and an EGF(A) analogues

| GLP-1/EGF(A) Compound no. | PCSK9 binding, 1% HSA Ki (nM) |
|---|---|
| 75 | 4.9 |
| 77 | 2.6 |
| 78 | 2.4 |
| 79 | 2.4 |
| 80 | 2.5 |
| 81 | 2.9 |
| 82 | 3.7 |
| 83 | 5.9 |
| 84 | 5.3 |
| 85 | 4.2 |
| 86 | 4.0 |
| 87 | 3.0 |
| 91 | 3.8 |
| 92 | 2.9 |
| 95 | 3.1 |
| 99 | 3.6 |
| 100 | 3.2 |
| 103 | 2.4 |
| 104 | 2.9 |
| 105 | 2.4 |
| 106 | 1.9 |
| 107 | 2.3 |
| 108 | 2.8 |
| 109 | 2.7 |
| 110 | 2.9 |
| 111 | 3.0 |
| 112 | 2.7 |
| 113 | 2.9 |
| 114 | 3.1 |
| 115 | 2.5 |
| 116 | 2.6 |
| 117 | 2.4 |
| 118 | 3.2 |
| 119 | 2.6 |
| 120 | 3.4 |
| 123 | 4.4 |
| 124 | 3.1 |
| 128 | 3.6 |
| 221 | 3.4 |
| 222 | 2.0 |
| 223 | 2.0 |
| 224 | 1.9 |
| 225 | 2.2 |
| 226 | 3.5 |
| 227 | n.d. |
| 229 | 2.1 |
| 230 | 2.7 |
| 281 | 3.1 |
| 283 | 2.5 |
| 284 | 3.8 |
| 285 | 4.4 |
| 286 | 4.2 |
| 287 | 4.3 |
| 288 | 4.0 |
| 289 | 4.6 |
| 290 | 3.8 |
| 291 | 3.2 |
| 292 | 3.7 |
| 293 | 2.1 |
| 294 | 2.9 |
| 295 | 2.2 |
| 296 | 2.0 |
| 297 | 3.6 |
| 298 | 3.6 |
| 299 | 4.5 |
| 300 | 5.8 |
| 301 | 3.9 |
| 302 | 4.6 |
| 303 | 4.0 |
| 304 | 3.7 |
| 305 | 3.8 |
| 306 | 2.6 |
| 307 | 2.3 |
| 308 | 4.8 |

TABLE 3.6-continued

Apparent Ki for compounds comprising a
GLP-1 analogue and an EGF(A) analogues

| GLP-1/EGF(A) Compound no. | PCSK9 binding, 1% HSA Ki (nM) |
|---|---|
| 309 | 3.8 |
| 310 | 3.8 |
| 311 | 4.2 |
| 312 | 5.2 |
| 313 | 4.5 |
| 314 | 7.9 |

The data shows that the compounds comprising a GLP-1 analogue and an EGF(A) analogue maintain the PCSK9 binding activities associate with the EGF(A) analogue of the compound. The data also shows that there is only very modest variation and that the orientation of the GLP-1 analogue and the EGF(A) analogue does not influence PCSK9 binding.

C4—LDL Uptake Assay in HepG2 Cells

An alternative assay to determine the inhibitory potency of the PCSK9 peptides and derivatives thereof is to measure uptake of LDL in HepG2 cells.

Assay Principle: LDL uptake is primarily mediated by the endogenously expressed hLDLRs, and thus LDL uptake capacity is an indirect measure of LDLR expression. The hLDLRs can be down-regulated by incubation with exogenous PCSK9 in a dose dependent fashion. Thus PCSK9 incubation will decrease the ability of cells to take up LDL molecules. This down-regulation of LDL uptake can then be antagonized by the addition of compounds neutralizing or inhibiting the PCSK9/LDLR binding. Consequently PCSK9 inhibitors can be characterized based on their capacity to increase LDL uptake in the presence of PCSK9 and e.g. counter act the PCSK9 mediated hLDLR down-regulation.

The assay is performed using HepG2 cells (Sigma Aldrich ECACC: Acc no. 85011430) grown in 10% Lipoprotein deficient Foetal Calf Serum (Sigma Aldrich #S5394) and the capacity of the cells to take up BODIPY fluorescently labelled LDL particles (Life technologies Europe BV #L3483) is measured.

Assay protocol: The 96 well plates (Perkin Elmer, ViewPlate-96 Black #60005182) are coated with Poly-D-Lysine (10 mg/L, Sigma Aldrich #P6407 dissolved in PBS Gibco #14190-094) for 1 hour at 37° C. in incubator. Then the plates are washed 2× in 100 µl PBS (Gibco #14190-094). Test compositions for 8 point concentration curves of the EGF(A) compounds are prepared all containing PCSK9 (10 ug/ml) diluted in Assay medium (DMEM (Gibco #31966-021), 10% Lipoprotein deficient Foetal Calf Serum (Sigma Aldrich #S5394) and 1% Pen Strep (Cambrex #DE17-602E)), and added on to the plates in a volume of 50 ul/well.

After 30-60 minutes 50.000 HepG2 cells (Sigma-Aldrich: ECACC: Atcc no. 85011430 lot: 13B023), diluted in Assay medium are added in a volume of 500/well, and the plates are incubated 20 hours (at 37° C., 5% CO2) in CO2 permeable plastic bags (Antalis Team, LDPE bag 120/35× 300×0,025 mm #281604). Hereafter, the plates are emptied and immediately hereafter 50 µl FL-LDL (Life technologies Europe BV #L3483) in a concentration of 10 µg/ml in Assay Medium as added to each well, and the plates are incubated for 2 hours (at 37° C., 5% CO2) in CO2 permeable plastic bag using the black cover on the lid to protect from light. The plates are emptied and washed 2 times with 100 µl of PBS (Gibco #14190-094). Then 100 µl of PBS (Gibco #14190-094) is added and within 15 min hereafter, the plates are read (bottom read) using the following filters Ex (515 nm)/Em (520 nm) on a SpecktraMax M4 (Molecular Probes, Invitrogen Detection Technologies). EC50 values are calculated using GraphPad Prism, nonlinear regression curve fit, sigmoidal dose-response (variable slope).

Results

The LDL uptake assay in HepG2 cells was performed as described above for a series of compounds.

The results are shown in Table 4.1 below. Lower EC50 values reflects higher capacity to reverse the PCSK9 mediated down-regulation of LDL uptake, and inversely a high EC50 value is indicative for a compound with low capacity to inhibit the PCSK9 mediated down-regulation of LDL uptake.

As can be seen most compounds display an EC50 in the LDL uptake assay of 100-500 nM which is indicative of compounds with a high capacity to reverse the PCSK9 mediated down-regulation of LDL uptake and i.e. to increase LDL uptake.

TABLE 4.1

LDL uptake data in HepG2 cells
($EC_{50}$) - (EGF(A) analogues and derivatives

| EGF(A) compound # | LDL uptake $EC_{50}$ (nM) |
|---|---|
| 1. | ND |
| 2. | 255 |
| 3. | 168 |
| 4. | 302 |
| 5. | 220 |
| 6. | 413 |
| 7. | 304 |
| 8. | 130 |
| 9. | ND |
| 10. | 199 |
| 11. | 401 |
| 12. | ND |
| 13. | 280 |
| 14. | 161 |
| 15. | 211 |
| 16. | 144 |
| 17. | 199 |
| 18. | 172 |
| 19. | 206 |
| 20. | 198 |
| 21. | 174 |
| 22. | 357 |
| 23. | 143 |
| 24. | 160 |
| 25. | ND |
| 26. | 358 |
| 27. | ND |
| 28. | ND |
| 29. | 163 |
| 30. | 182 |
| 31. | 170 |
| 32. | 224 |
| 33. | 245 |
| 34. | 232 |
| 35. | 252 |
| 36. | ND |
| 37. | 188 |
| 38. | 149 |
| 39. | 156 |
| 40. | 231 |
| 41. | ND |
| 42. | 324 |
| 43. | 499 |
| 44. | 237 |
| 45. | ND |
| 46. | ND |
| 47. | 1102 |
| 48. | 1278 |
| 49. | 398 |
| 50. | 164 |
| 51. | ND |
| 52. | ND |
| 53. | ND |
| 54. | 526 |
| 55. | ND |
| 56. | ND |
| 57. | 438 |
| 58. | ND |
| 59. | ND |
| 60. | 261 |
| 61. | 347 |
| 62. | 411 |
| 63. | 197 |
| 64. | 590 |
| 65. | 10000 |
| 66. | 248 |
| 67. | 384 |
| 68. | 124 |
| 69. | 311 |
| 70. | ND |
| 71. | 217 |
| 72. | 222 |
| 73. | ND |
| 74. | 123 |
| 75. | 239 |
| 76. | 272 |
| 77. | 2044 |
| 78. | 546 |
| 79. | ND |
| 80. | 248 |
| 81. | 617 |
| 82. | 203 |
| 83. | 165 |
| 84. | 337 |
| 85. | 157 |
| 86. | 248 |
| 87. | 185 |
| 88. | 298 |
| 89. | 139 |
| 90. | 380 |
| 91. | 114 |
| 92. | 147 |
| 93. | 267 |
| 94. | 375 |
| 95. | 257 |
| 96. | 261 |
| 97. | 138 |
| 98. | 203 |
| 99. | 167 |
| 100. | 174 |
| 101. | 129 |
| 102. | 112 |
| 103. | ND |
| 104. | ND |
| 105. | ND |
| 106. | 195 |
| 107. | 486 |
| 108. | 2555 |
| 109. | 572 |
| 110. | 465 |
| 111. | 316 |
| 112. | 539 |
| 113. | 1383 |
| 114. | 739 |
| 115. | 247 |
| 116. | 330 |
| 117. | 316 |
| 118. | 191 |
| 119. | 327 |
| 120. | 300 |
| 121. | 201 |
| 122. | 241 |
| 123. | 351 |
| 124. | 264 |
| 125. | 334 |

TABLE 4.1-continued

LDL uptake data in HepG2 cells
($EC_{50}$) - (EGF(A) analogues and derivatives

| EGF(A) compound # | LDL uptake $EC_{50}$ (nM) |
|---|---|
| 126. | 489 |
| 127. | 245 |
| 128. | 351 |
| 129. | 892 |
| 130. | 259 |
| 131. | 218 |
| 132. | 195 |
| 133. | 220 |
| 134. | 180 |
| 135. | 1505 |
| 136. | 455 |
| 137. | 2070 |
| 138. | 480 |
| 139. | 546 |
| 140. | 226 |
| 141. | 210 |
| 142. | 126 |
| 143. | 299 |
| 144. | 484 |
| 145. | 329 |
| 146. | 718 |
| 147. | 246 |
| 148. | 204 |
| 149. | 233 |
| 150. | ND |
| 151. | ND |
| 152. | ND |
| 153. | ND |
| 154. | 148 |
| 155. | 391 |
| 156. | 167 |
| 157. | ND |
| 158. | 303 |
| 159. | 178 |

The LDL uptake was further evaluated for GLP-1/EGF (A) compounds comprising a GLP-1 analogue and a EGF (A) analogue and it was again confirmed that the linkage with a GLP-1 analogue did not interfere with the functionality of the EGF(A) analogue (see Table 4.2).

TABLE 4.2

LDL uptake data in HepG2 cells ($EC_{50}$)for compounds comprising a GLP-1 analogue and a EGF(A) analogue

| GLP-1/EGF(A) Compound no. | LDL uptake $EC_{50}$ (nM) |
|---|---|
| 1 | 242 |
| 2 | 262 |
| 16 | 160 |
| 19 | 284 |
| 22 | 241 |
| 23 | 241 |
| 26 | 254 |
| 27 | 224 |
| 28 | 161 |
| 29 | 298 |
| 30 | 201 |
| 31 | 302 |
| 32 | 333 |
| 33 | 234 |
| 34 | 214 |
| 41 | 237 |
| 48 | 136 |
| 69 | 138 |
| 82 | 284 |
| 85 | 412 |
| 221 | 357 |
| 222 | 207 |
| 223 | 254 |
| 224 | 201 |

C5—Pharmacokinetic (PK) in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

Female Göttingen minipigs are obtained from Ellegaard Gottingen Minipigs (Dalmose, Denmark) approximately 8-12 months of age and weighing approximately 20-30 kg are used in the studies. The minipigs are housed individually (pigs with permanent catheters) in pens with straw as bedding and fed restrictedly once daily with Altromin 9030 minipig diet (Altromin Spezialfutter GmbH & Co. KG).

After three weeks of acclimatisation two permanent central venous catheters are implanted in vena cava caudalis in each animal. The animals are allowed 1 week recovery after the surgery, and are then used for repeated pharmacokinetic studies with a suitable wash-out period between successive dosing.

The derivatives are dissolved in a buffer containing 50 mM phosphate, 70 nM sodium chloride and 0.05% polysorbate 80, pH 7.4.

Intravenous injections (the volume corresponding to 0.05 ml/kg and dose of 2 nmol/kg) of the derivatives are given through one catheter, and blood is sampled at predefined time points for up till 14 days post dosing (preferably from the other catheter).

Blood samples (for example 0.8 ml) are collected in EDTA (8 mM) coated tubes and then centrifuged at 4° C. and 1942 g for 10 minutes.

Plasma is pipetted into Micronic tubes on dry ice, and kept at −20° C. until analysis for plasma concentration of the derivatives using LOCI. Individual plasma concentration-time profiles are analysed by a non-compartmental pharmacokinetic method in Phoenix v. 6.4 (Pharsight Inc., Mountain View, Calif., USA), and the resulting terminal half-lives (harmonic mean) determined.

Results

A pharmacokinetic study was performed using minipigs as described above. The following results on terminal half-lives were obtained:

TABLE 5

Pharmacokinetic study in minipigs (i.v.)

| GLP/EGF(A) - Compound no. | Terminal half-live (h) |
|---|---|
| GLP-1 (7-37) | <1 |
| 1 | 42 |
| 2 | 56 |
| 5 | 26 |
| 21 | 2 |
| 23 | 44 |
| 25 | 45 |
| 26 | 33 |

TABLE 5-continued

Pharmacokinetic study in minipigs (i.v.)

| GLP/EGF(A) - Compound no. | Terminal half-live (h) |
|---|---|
| 29 | 31 |
| 30 | 31 |

The tested compounds all have an increased terminal half-lives compared to human GLP-1 (7-37).

Compound 21 comprising a GLP-1 analogue with G in position 8 has a terminal half-life of 2 hours which is a 10-25 fold shorter than the half-life of the other compounds which has an non-natural amino acid; Aib in position 8.

C6—hPCSK9 Challenge Model

The aim of this study is to show the change in the LDL receptor expression level in mouse liver in response to inhibiting the action of intravenously injected hPCSK9 with an EGF(A) analogue or a compound comprising an EGF(A) analogue as described herein.

Method

Healthy male B alBC or NMRI mice (Charles River, Germany) are injected with an EGF(A) analogue (or a compound comprising an EGF(A) analogue), either s.c. or i.v. 15-120 minutes before injecting hPCSK9 (Sino Biologicals, China) intravenously in the tail vein at a dose of 0.4 mg/kg. Sixty minutes after the injection of hPCSK9, the animals are anaesthetised in isoflurane and euthanised by cervical dislocation. The liver is then quickly excised and snapfrozen in liquid nitrogen. The livers are kept at −80° C. until analysis.

LDL-R Western Blotting:

Liver tissue samples (100 mg) are homogenized in 500 µl lysis buffer (Life Technology, FNN0011) containing phosphatase inhibitor cocktail; PhosStop (Roche, 04 906 837 001) and protease inhibitor cocktail; compelate (Roche, 04 693 159 001). After adding 1 steel bead tissues are homogenized for 2.5 min at 30 Hz. After centrifugation at 5000×g for 5 min, total protein content is determined using BCA Protein Assay Kit (Pierce, 23225). Equal amounts of proteins (60 µg) in sample buffer (Life Technology, NP0007) are boiled for 10 min and spun for 2 min at 14000 rpm before loaded onto Criterion XT 3-8% Tris-Acetate gels (BioRad #345-0131) and subjected to SDS-PAGE. The proteins are transferred to nitrocellulose membranes (iBlot 2 NC Regular stacks, novex #IB23001) according to manufacturer's instructions (Life Technology). Equal protein transfer is confirmed by Ponceau S (Sigma, P7170) staining of the membranes and the membranes are further blocked in blocking buffer (TBS-T, 2% Tween). LDL-r proteins are detected with Primary rabbit anti LDLr antibody (Cayman Chemical Company #10012422), whereas beta-actin proteins are detected using Primary rabbit anti beta-actin antibody (abcam #ab6276). Both proteins are further visualized with peroxidase-conjugated goat anti-rabbit secondary antibodies (Biorad #170-6516) using the WesternBright Quantum Chemiluminscent (Advansta #K-12042-D10) and imaged using a CCD camera (LAS3000, FujiFilm). Quantitative analysis of chemiluminescent signals from Western blots is done with MultiGauge software (Fujifilm).

Results

The LDL-R expression levels were measured by Western Blot, and the expression levels compared. The expression is decreased by "vehicle-hPCSK9" which represent the group injected with hPCSK9 alone. Groups injected with EGF(A) compound -hPCSK9" showed that expression of LDL-R was normalized as expression returned to at least 90%.

The results show that hPCSK9 decreases the expression level of LDL-R and that this effect is inhibited by the EGF(A) compounds tested. Data are summarized in Table 6.1 and 6.2 presented as percentage change in relation to the window between baseline level in healthy control animals (set to 100%) and the level after down regulation by hPCSK9 alone (set to 0%). The 6 tested EGF(A) compounds are able to inhibit the action of hPCSK9 on the LDL-R expression level and the level of inhibition observed is similar to the level of inhibition observed using the control molecule Alirocumab.

TABLE 6.1

| Group/Test group | Percentage of baseline (%) | Dose of inhibitor (nmol/kg) |
|---|---|---|
| Vehicle-Vehicle | 100 | 0 |
| Vehicle-hPCSK9 | 0 | 0 |
| EGF(A) compound # 2-hPCSK9 | 110 | 300 |
| EGF(A) compound # 3-hPCSK9 | 113 | 300 |
| EGF(A) compound # 5-hPCSK9 | 123 | 300 |
| EGF(A) compound # 6-hPCSK9 | 96 | 300 |
| EGF(A) compound # 13-hPCSK9 | 175 | 300 |
| EGF(A) compound # 19-hPCSK9 | 190 | 300 |
| Alirocumab-hPCSK9 | 157 | 22 |

TABLE 6.2

| Group/Compound no. | Percentage of baseline (%) Mean ± SEM | Dose of compound (nmol/kg) |
|---|---|---|
| Vehicle-Vehicle | 100 | 0 |
| Vehicle-hPCSK9 | 0 | 0 |
| GLP-1/EGF(A) # 1-hPCSK9 | 91 ± 12 | 30 |
| GLP-1/EGF(A) # 2-hPCSK9 | 118 ± 17 | 30 |
| GLP-1/EGF(A) # 19-hPCSK9 | 73 ± 5 | 30 |
| GLP-1/EGF(A) # 21-hPCSK9 | 130 ± 24 | 30 |
| GLP-1/EGF(A) # 22-hPCSK9 | 61 ± 6 | 30 |
| GLP-1/EGF(A) # 23-hPCSK9 | 118 ± 13 | 30 |
| GLP-1/EGF(A) # 41-hPCSK9 | 65 ± 12 | 30 |
| GLP-1/EGF(A) # 48-hPCSK9 | 95 ± 14 | 30 |
| GLP-1/EGF(A) # 69-hPCSK9 | 99 ± 13 | 30 |
| Alirocumab | 100 ± 13 | 30 |

CONCLUSION

Several compound examples have shown efficacy in inhibiting the down-regulation of the LDL-R expression levels by hPCSK9.

C7—Pharmacodynamic Study in db/db Mice

The purpose of this assay is to verify the acute effect on blood glucose (BG) and body weight (BW) in a diabetic setting.

The compounds are tested in a single dose study in an obese, diabetic mouse model (db/db mice) as described in the following. The derivatives are tested at different doses, namely 0.3, 1.0, 3.0, 10, 30 and 100 nmol/kg or 1.0, 3.0, 10, 30, 100 and 300 nmol/kg The mice (from Taconic, Denmark), fed from birth with the diet NIH31 (NIH 31M Rodent Diet, commercially available from Taconic Farms, Inc., US, see www.taconic.com), are enrolled for the study at the age of approximately 10 weeks. Upon arrival at the animal unit, mice are given free access to standard chow (e.g. Altromin 1324, Brogaarden, Gentofte, Denmark) and tap water and kept at 24° C. After 1-2 weeks of acclimatisation, the basal blood glucose are assessed twice on one day. Only mice with a baseline bloodglucose level >15 mM are included. The mice are allocated to treatment groups based on matching blood glucose levels and body weights (N=5-7 per group).

The animals are grouped to receive treatment as follows: Vehicle, subcutaneously or GLP-1/PCSK9i derivative (0.3, 1.0, 3.0, 10, 30 or 100 nmol/kg or 1.0, 3.0, 10, 30, 100 and 300 nmol/kg), subcutaneously, where vehicle is 50 mM sodium phosphate, 70 mM sodium chloride, 0.05% polysorbate 80, pH 7.4.

The GLP-1/EGF(A) compound is dissolved in the vehicle, to dosing concentrations of 0.05, 0.17, 0.5, 1.7, 5.0 or 17 nmol/ml or 0.17, 0.5, 1.7, 5.0, 17 or 50 nmol/ml. Animals are dosed once, at the start of the experiment, s.c. with a dose-volume of 6 ml/kg (i.e. 300 µl per 50 g mouse).

On the day of dosing, blood glucose is assessed in the morning at time −½ h, the mice are weighed after this. The GLP-1/EGF(A) compound is dosed at approximately time 0. On the day of dosing, blood glucose is assessed at times 1, 2, 4 and 8 h after dosing.

On the following days, the blood glucose is assessed at time 24 h, 48 h, 72 h, and 96 h. On each day, the mice are weighed following blood glucose sampling.

The mice are weighed individually on a digital weighing scale.

Samples for the measurement of blood glucose are obtained from the tail tip capillary of conscious mice. Blood, 5 µl, is collected into heparinised capillaries and transferred to 250 µl glucose buffer (EKF system solution, Eppendorf, Germany). The glucose concentration is measured using the glucose oxidase method (glucose analyser Biosen 5040, EKF Diagnostic, GmbH, Barleben, Germany). The samples are kept at room temperature for up to 1 h or a at 4° C. for a maximum of 24 h until analysis.

Baseline subtracted blood glucose and baseline subtracted body weight are calculated in mice.

Results

GLP-1/EGF(A) compounds 1, 2, 21, 22, 23, 25, 26, 27, 29 and 32 were tested in a single dose study as described above. The derivatives were tested at different doses, namely 0.3, 1.0, 3.0, 10, 30 and 100 nmol/kg (compound 2, 21, 22, 23, 25 and 26) or 1.0, 3.0, 10, 30, 100 and 300 nmol/kg (compound 1, 27, 29 and 32).

Table 7.1 gives an overview of the maximal effect (Emax) of the highest dose on delta blood glucose and delta body weight 24 hours after dosing. If the two highest dose levels did not give a similar effect, and hence the true Emax might not have been reached yet, values are marked with an asterisk (*).

TABLE 7.1

Emax values for the effects on blood glucose and body weight in db/db mice

| GLP-1/EGF(A) Compound no. | Emax ΔBG$_{24\,h}$ (mM) Mean ± SEM | Emax ΔBW$_{24\,h}$ (grams) Mean ± SEM |
|---|---|---|
| 1 | −12.7 ± 1.0 | −4.0 ± 0.2 |
| 2 | −10.7 ± 1.7 | −3.4 ± 0.1 |
| 21 | −10.4 ± 1.0 | −3.3 ± 0.2 |
| 22 | −10.9 ± 0.8 | −3.4 ± 0.1 |
| 23 | −11.9 ± 0.5 | −3.8 ± 0.2 |
| 25 | −9.1 ± 0.8 | −4.1 ± 0.6 |
| 26 | −14.5 ± 1.0 | −4.1 ± 0.1 |
| 27 | −13.2 ± 0.7 | −3.9 ± 0.1 |
| 29 | −11.7 ± 0.6 | −3.5 ± 0.2 |
| 32 | −17.3 ± 0.4 | −3.3 ± 0.2 |
| 41 | −13.7 ± 0.9 | −3.2 ± 0.3 |
| 48 | −12.2 ± 1.3 | −2.6 ± 0.2 |
| 51 | −15.3 ± 0.8 | −3.1 ± 0.1 |
| 52 | −14.2 ± 0.5 | −3.1 ± 0.1 |
| 53 | −14.1 ± 1.5 | −2.9 ± 0.2 |
| 54 | −11.5 ± 1.0 | −3.5 ± 0.3 |
| 69 | −11.7 ± 0.6 | −2.8 ± 0.2 |
| 82 | −11.1 ± 0.6 | −2.3 ± 0.1 |
| 86 | −12.0 ± 1.0 | −2.7 ± 0.1 |
| 221 | −10.7 ± 1.1 | −2.4 ± 0.1 |
| 230 | −11.1 ± 0.4 | −2.4 ± 0.2 |
| 287 | −16.4 ± 0.6 | −3.6 ± 0.2 |
| 298 | −13.7 ± 0.5 | −2.5 ± 0.2 |
| 306 | −13.7 ± 1.0 | −2.9 ± 0.2 |

To get an indication of the effect of the GLP-1/PCSK9i derivatives on blood glucose and body weight, the area under the curve for delta blood glucose from 0 until 24 hours (AUC ΔBG$_{24h}$) and delta body weight gain at 24 hours post dosing (ΔBW$_{24h}$) were calculated. Based on the dose response curves for these parameters, the Effective Doses 50% (ED50, dose of GLP-1 derivative that gives a response halfway between baseline and maximal effect) were calculated for AUC ΔBG$_{24h}$ and ΔBW$_{24h}$. The ED50 can be used as an estimate of the potency of the GLP-1/PCSK9i derivatives. The following results were obtained (averages of all individual determinations).

TABLE 7.2

ED50 values for the effects on blood glucose and body weight in db/db mice

| GLP-1/EGF(A) Compound no | ED50 AUC ΔBG$_{24\,h}$ (nmol/kg) Mean ± SEM | ED50 ΔBW$_{24\,h}$ (nmol/kg) Mean ± SEM |
|---|---|---|
| 1 | 2.2 ± 1.3 | 21.3 ± 1.3 |
| 2 | 1.9 ± 1.7 | 27.2 ± 1.4 |
| 21 | 12.5 ± 1.4 | 40.7 ± 1.6 |
| 22 | 6.1 ± 1.5 | 8.5 ± 1.5 |
| 23 | 4.1 ± 1.8 | 18.5 ± 1.6 |
| 25 | 3.1 ± 1.6 | 22.1 ± 1.5 |
| 26 | 3.9 ± 1.3 | 8.8 ± 1.3 |
| 27 | 9.2 ± 1.3 | 78.1 ± 1.5 |
| 29 | 7.9 ± 1.4 | 54.2 ± 1.5 |
| 32 | 2.4 ± 1.2 | 30.0 ± 1.5 |
| 41 | 16.0 ± 1.4 | 289.8 ± 2.2 |
| 48 | 9.6 ± 1.4 | 12.7 ± 1.3 |
| 51 | 18.0 ± 1.2 | 25.7 ± 2.2 |
| 52 | 11.3 ± 1.3 | 22.6 ± 1.3 |
| 53 | 11.5 ± 1.3 | 11.0 ± 1.4 |
| 54 | 6.0 ± 1.4 | 37.2 ± 1.4 |
| 69 | 8.3 ± 1.3 | 19.2 ± 1.2 |
| 82 | 31.1 ± 1.3 | 76.3 ± 2.2 |
| 86 | 32.2 ± 1.3 | 1133 ± 2.9 |
| 221 | 50.3 ± 1.3 | 148.8 ± 1.5 |
| 230 | 115.5 ± 1.5 | 208.7 ± 1.5 |
| 287 | 20.4 ± 1.2 | 60.2 ± 1.3 |
| 298 | 23.9 ± 1.3 | 76.5 ± 1.4 |
| 306 | 9.9 ± 1.3 | 19.5 ± 1.3 |

The tested compounds showed an effect in vivo by dose dependently decreasing blood glucose as well as body weight.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

C8—Pharmacodynamic Study in DIO Rats

The purpose of this assay is to verify the subchronic effect on body weight (BW) and total cholesterol levels in an obese setting. The compounds are tested in a subchronic dose study for 21 days in a diet-induced obesity (DIO) rat model as described in the following. The derivatives are tested at different doses, namely 30 and 300 nmol/kg, and in some instances the 300 nmol/kg group was given a higher dose of 900 nmol/kg for the time indicated.

The Sprague Dawley rats (from Charles River, France), fed from 6 weeks of age with a 60% High Fat Diet (D12492, commercially available from Research Diets, Inc), arrive at our animal unit at 22 weeks of age. Upon arrival at the animal unit, rats are given free access to a 45% High Fat Diet (D12451, commercially available from Research Diets, Inc), and tap water and rats are under controlled lighting (12 h:12 h light/dark cycle; lights on 06:00-18:00) and temperature ($22\pm2°$ C.) conditions. After 2-3 weeks of acclimatisation, rats are allocated to treatment groups based on matching body weights and fat percentages (N=10 per group).

The animals are grouped to receive treatment as follows: Vehicle, subcutaneously or GLP-1/EGF(A) compound (30 or 300 nmol/kg, in some instances rats from the 300 nmol/kg group receive 900 nmol/kg for the indicated number of days), subcutaneously, where vehicle is 50 mM phosphate, 70 mM sodium chloride, 0.007% polysorbate 20, pH 7.4. The GLP-1/EGF(A) compound is dissolved in the vehicle, to dosing concentrations of 15 (for uptitration), 50 (for uptitration), 150, 500 (for uptitration) or 1500 nmol/ml.

Animals are dosed subcutaneously once daily in the morning for 22 days with a dosing volume of 0.2 ml/kg. The doses are slowly uptitrated, so that rats receive 3 nmol/kg on the first day, 10 nmol/kg on the second day, 30 nmol/kg on the third day, and if applicable 100 nmol/kg on the fourth day and 300 nmol/kg on the fifth day. The 30 nmol/kg groups receive the full dose from the third day until the end of the experiment. The 300 nmol/kg groups receive the full dose from the fifth day until the end of the experiment. Rats dosed with 300 nmol/kg of GLP-1/EGF(A) compound 41 receive 900 nmol/kg from day 16 until the end of the experiment. Rats dosed with 300 nmol/kg of GLP-1/EGF(A) compound 48 receive 900 nmol/kg from day 20 until the end of the experiment. The 900 nmol/kg dose is achieved by increasing the dosing volume of the 1500 nmol/ml solution to 0.6 ml/kg.

Rats are weighed daily on a digital weighing scale just before dosing. The weight of the food container is weighed daily as well in order to calculate food consumption. Body composition is assessed by MR scanning 3 to 4 days before the onset of dosing and on day 20 or 21 (Echo MRI 700, Houston, Tex. USA). A sublingual blood sample is taken from conscious rats 5 days before the onset of dosing and at the end of the study. Blood samples are collected in EDTA tubes and mixed thoroughly by inversion. EDTA tubes are placed on ice immediately subsequent to collection. EDTA blood samples are centrifuged at 6000 G×5 min at 4° C., and the plasma samples are stored at −80° C. until analysis. Samples are analysed for total cholesterol levels on a Cobas analyser (Cobas6000, Roche Diagnistics, USA).

Baseline subtracted body weight and baseline subtracted total cholesterol levels are calculated for each rat and averaged per group.

Results

GLP-1/EGF(A) compounds 41, 48 and 69 were tested in a subchronic dose study as described above. The derivatives were tested at different doses, namely 30 and 300 nmol/kg (GLP-1/EGF(A) compound 69) or 30 and 300 nmol/kg with an increase in dose to 900 nmol/kg for the last 2 days (GLP-1/EGF(A) compound 41) or the last 7 days (GLP-1/EGF(A) compound 48).

Table 8.1 gives an overview of the average body weight as a percentage compared to baseline body weight (mean±SEM) and the average delta in plasma total cholesterol levels compared to baseline levels (mean±SEM) per group.

TABLE 8.1

Average body weight as a percentage compared to baseline body weight and average change in plasma total cholesterol levels compared to baseline levels after 21 days

| GLP-1/EGF(A) Compound no. | Dose (nmol/kg/day) | Body weight (% of baseline BW) | Δ total cholesterol (mmol/l) |
| --- | --- | --- | --- |
| 41 | 30 | 102.6 ± 0.73 | −0.63 ± 0.11 |
| 41 | 300 → 900 | 91.5 ± 0.69 | −0.97 ± 0.13 |
| 48 | 30 | 95.3 ± 0.87 | −0.45 ± 0.11 |
| 48 | 300 → 900 | 85.6 ± 1.03 | −1.74 ± 0.11 |
| 69 | 30 | 96.5 ± 0.62 | −1.00 ± 0.11 |
| 69 | 300 | 85.7 ± 0.82 | −1.42 ± 0.22 |

C9—Chemical Stability

Formulations are prepared of GLP-1/EGF(A) compound 69 and 313 to investigate the potential stabilizing effect (reduction of isomer formation) of the EGF(A) analogue where 321D is substituted with 321E. The compound concentration is 2 mg/mL in a formulation consisting of 20 mM Tris, pH 7.4, 18.4 mg/ml propylene glycol, 0.43 mM $CaCl_2$. The formulations are prepared by solubilizing freeze-dried material into MQ water containing Tris, propylene glycol, and $CaCl_2$ at final concentrations. pH is adjusted using 0.1N HCl(aq) and 0.1N NaOH(aq). Each formulation is sterile filtered and filled on HPLC glass vials and stored quiescently in a temperature controlled cabinet at 37° C. Upon selected time points (time 0, 1 week, 2 weeks, 4 weeks), samples are drawn from the HPLC vials and frozen for subsequent UPLC-MS analysis.

A stability indicating purity method based on a BEH C4 column (300 Å, 1.7 um, 1.0×150 mm, Waters) and a 0.1% formic acid in water (eluent A)/0.1% formic acid in acetonitrile (eluent B) solvent system is used to evaluate purity loss of heat-stressed formulations. The following conditions are used: Column temperature: 50° C.; flow rate: 0.30 mL/min; wavelength of UV detector: 215 nm. The gradient is from 31% to 39% B over 41 minutes. The LC flow is on-line line infused to an Orbitrap Fusion Lumos mass spectrometer (Thermo Fischer Scientific) equipped with an electrospray interface operated in positive ion mode. The purity method is shown to be compatible with the aforementioned formulations, and no content/analogue loss is observed. The amount of isomer formed is determined from mass-based extraction on the total ion chromatogram of the various samples i.e. time 0 and samples incubated for 2 and 4 weeks at 37° C., and the percentage of isomers in each sample is calculated from integration of isomer peak areas against the main peak (API) area.

TABLE 9.1

Amount of isomer in formulation samples determined by
mass-based extraction of the total ion chromatograms

| GLP-1/EGF(A) Compound no. | Isomers at day 0 (%) | Isomers after 2 weeks (%) | Isomers after 4 weeks (%) | Isomer increase after 4 weeks (%) |
|---|---|---|---|---|
| 69 (with 321E) | 1.6 | 3.8 | 5.7 | 4.2 |
| 313 (with 321D) | 1.1 | 6.0 | 21.3 | 20.2 |

The results in table 9.1 show that replacing 321D with 321E reduces the amount of isomer formation significantly from 20.2% to 4.2% after 4 weeks of incubation at 37° C.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compound comprising a GLP-1 analogue and an EGF(A) analogue, wherein
   i. said GLP-1 analogue has at most 6 amino acid substitutions compared to GLP-1(7-37) identified by SEQ ID NO: 137 and
   ii. said EGF(A) analogue has 1-8 amino acid substitutions compared to the EGF(A) domain of LDL-R (293-332) identified by SEQ ID NO:1, and comprises 301Leu and wherein the compound is a GLP-1 agonist.

2. The compound according to claim 1, wherein the compound comprises a fusion polypeptide comprising the GLP-1 analogue and the EGF(A) analogue.

3. The compound according to claim 2, wherein the GLP-1 analogue is located N-terminally with respect to EGF(A) analogue.

4. The compound according to claim 1, wherein the GLP-1 analogue comprises one or two Lys residues selected from the group consisting of: 12K, 21K, 23K, 24K, 25K, 26K, 27K, 30K, 31K, 32K, 33K, 34K and 36K.

5. The compound according to claim 1, wherein the GLP-1 analogue is selected from the group consisting of GLP-1 analogues defined by SEQ ID NOs: 138 to 187.

6. The compound according to claim 1, wherein the GLP-1 analogue comprises 8Aib.

7. The compound according to claim 1, wherein the GLP-1 analogue comprises 34R or 34Q.

8. The compound according to claim 1, wherein GLP-1 analogue comprises 8Aib and 34R.

9. The compound according to claim 1, wherein the GLP-1 analogue is selected from the group consisting of GLP-1 analogues defined by SEQ ID NOs: 139, 147-154 and 184-186.

10. The compound according to claim 1, wherein the GLP-1 analogue is defined by SEQ ID NO: 139.

11. The compound according to claim 1, wherein the EGF(A) analogue comprises 309R.

12. The compound according to claim 1, wherein the EGF(A) analogue comprises 321D or 321E.

13. The compound according to claim 1, wherein the EGF(A) analogue comprises 312E, 312D, 312Q or 312R.

14. The compound according to claim 1, wherein the EGF(A) analogue is selected from the group consisting of EGF(A) analogues defined by SEQ ID NOs: 19, 21, 73, 107, 108, 109, 110, 111, 112, 113 and 114.

15. The compound according to claim 1, wherein the EGF(A) analogue is defined by SEQ ID NO: 107.

16. The compound according to claim 1, wherein the EGF(A) analogue is defined by SEQ ID NO: 108.

17. The compound according to claim 2, wherein the fusion polypeptide comprises a peptide spacer selected from the group of consisting of spacers defined by SEQ ID NOs: 115-136.

18. The compound according to claim 2, wherein the fusion polypeptide comprises a peptide spacer, wherein the peptide spacer is defined by SEQ ID NO: 116 or SEQ ID NO: 119.

19. The compound according to claim 1, wherein the compound comprises at least one half-life extending substituent, selected from the group consisting of: substituent #1 defined by Chem 6b, Chem 6b

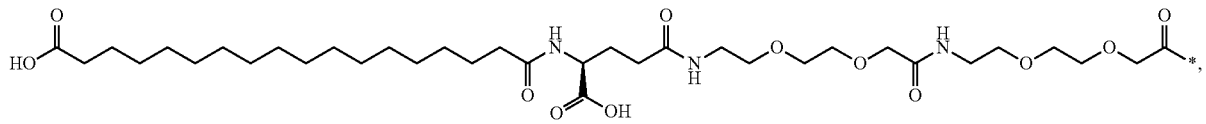

substituent #2 defined by Chem 7b,
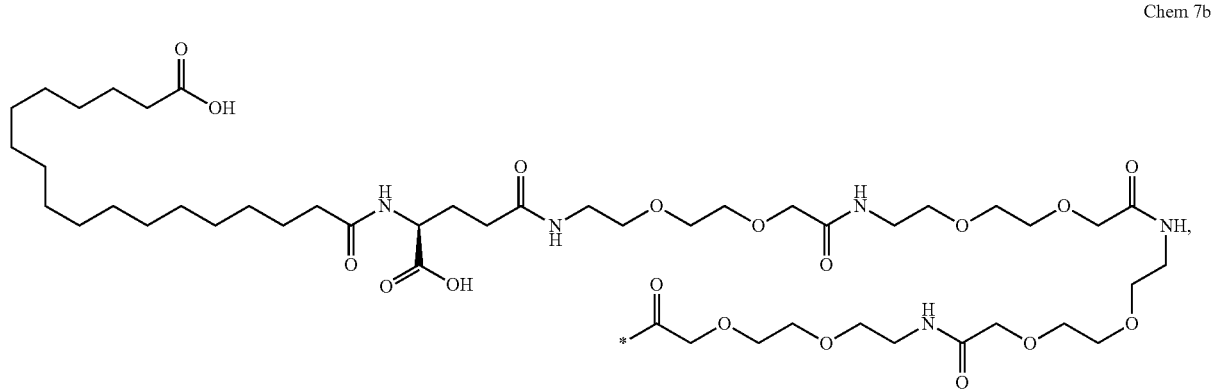 [SMILES: *C(=O)COCCOCCNC(=O)COCCOCCNC(=O)COCCOCCNC(=O)COCCOCCNC(=O)CC[C@H](NC(=O)CCCCCCCCCCCCCCCCC(=O)O)C(=O)O]
substituent #3 defined by Chem 8b,
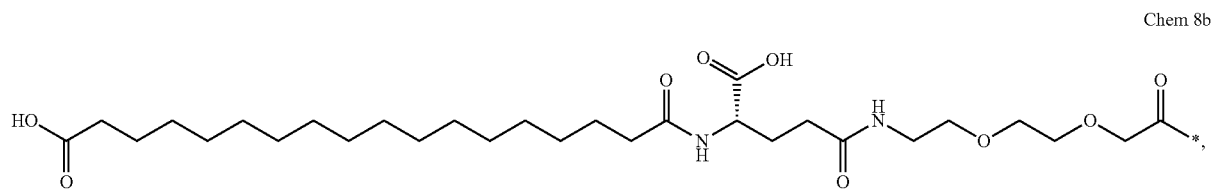
substituent #4 defined by Chem 9b,
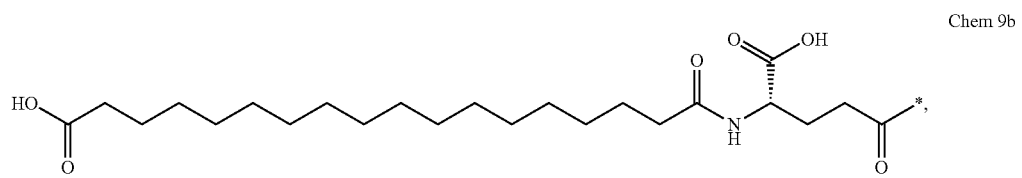
substituent #5 defined by Chem 10b,
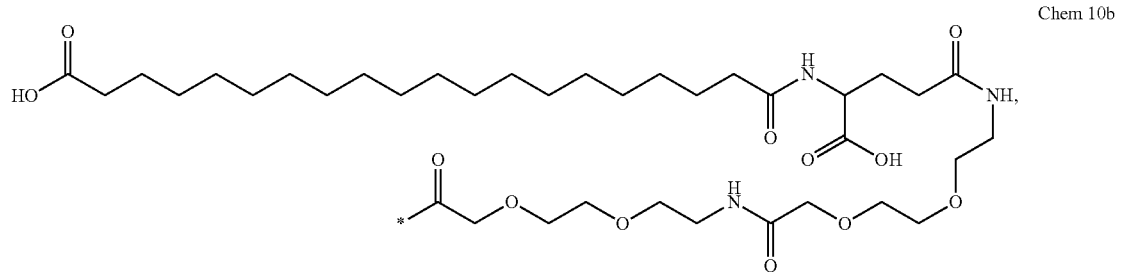 [SMILES: *C(=O)COCCOCCNC(=O)COCCOCCNC(=O)CCC(NC(=O)CCCCCCCCCCCCCCCCCCC(=O)O)C(=O)O]

substituent #6 defined by Chem 11b,
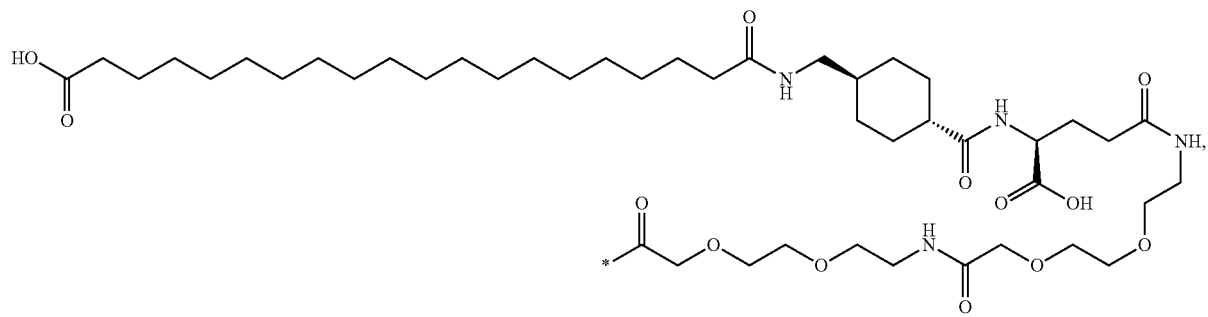
Chem 11b
substituent #7 defined by Chem 12b,
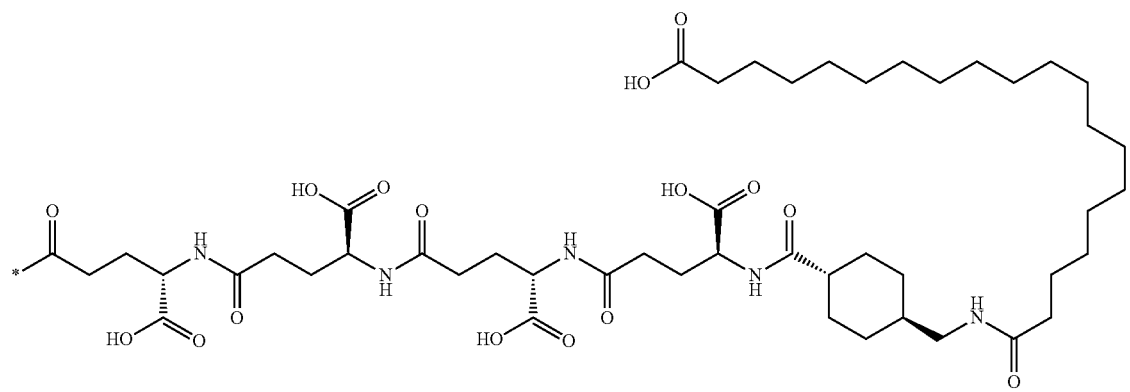
Chem 12b
substituent #8 defined by Chem 13b,
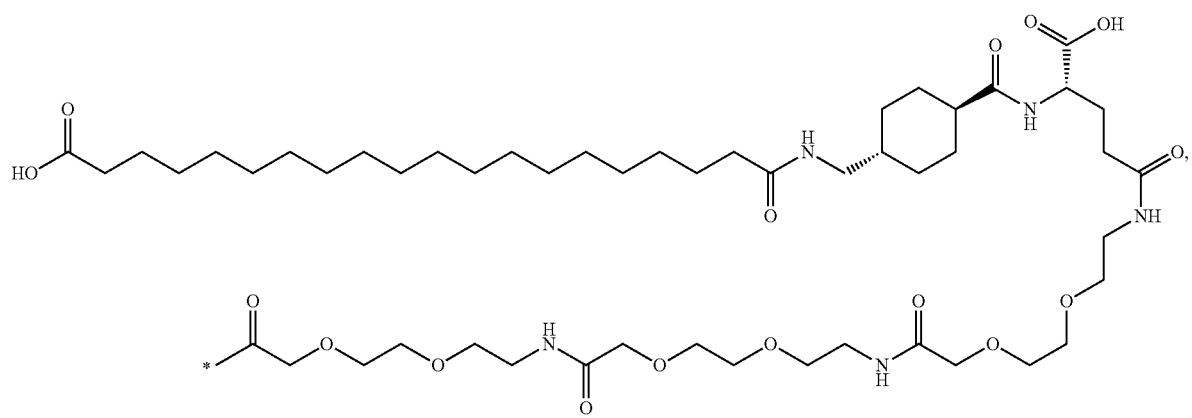
Chem 13b substituent #9 defined by Chem 14b,
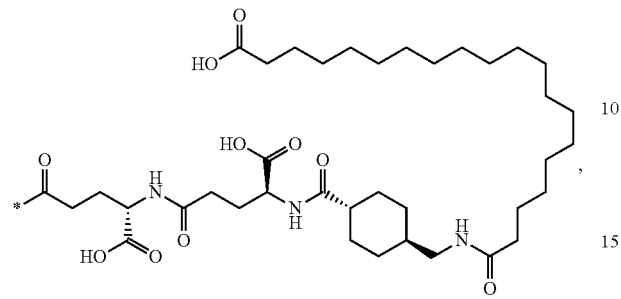
Chem 14b
substituent #10 defined by Chem 15b,
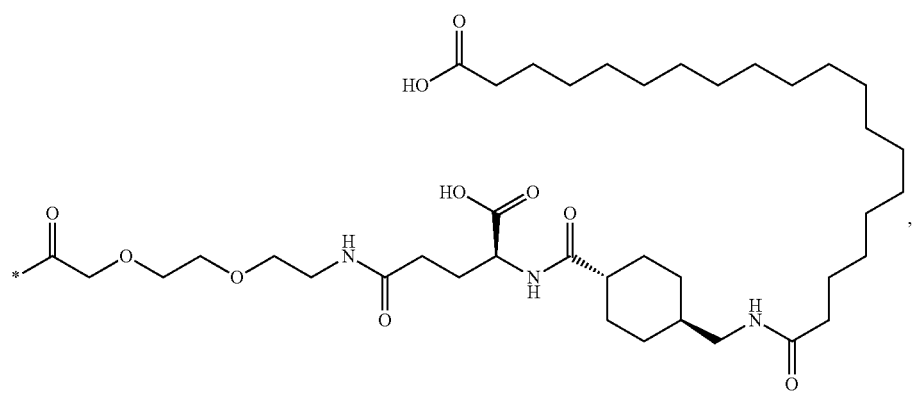
Chem 15b
substituent #11 defined by Chem 16b,
Chem 16b
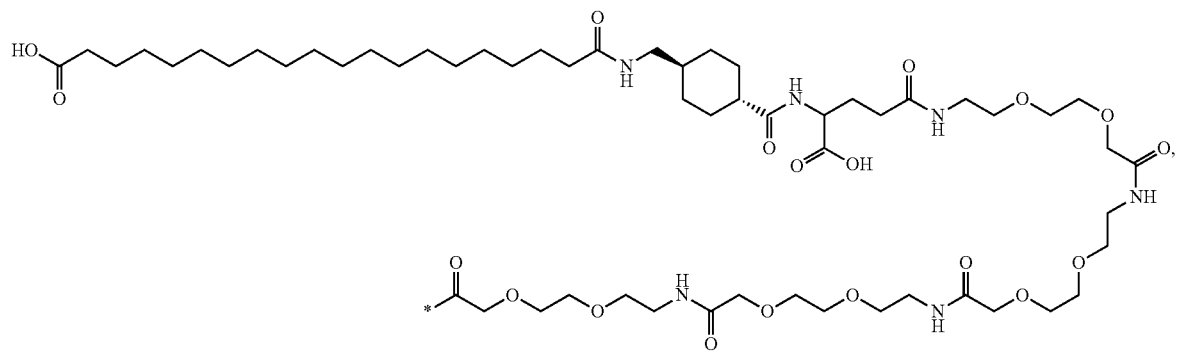

substituent #12 defined by Chem 17b,

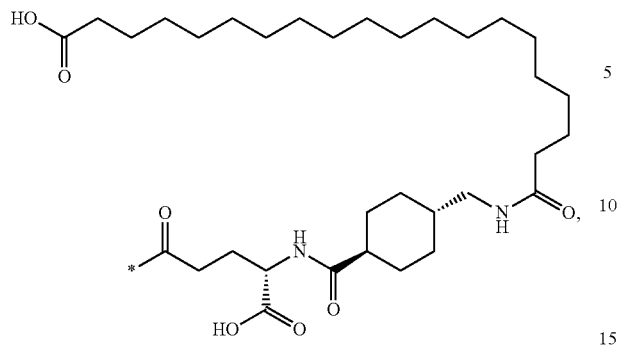

Chem 17b substituent #13 defined by Chem 18b,

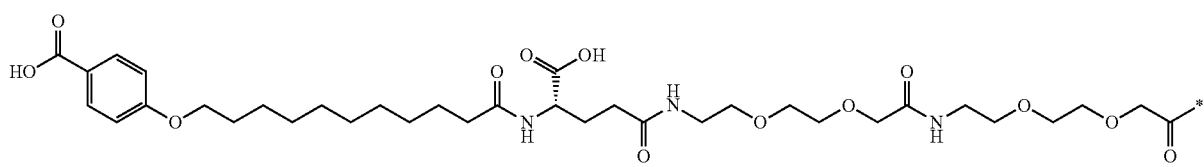

Chem 18b and substituent #14 defined by Chem 19b,

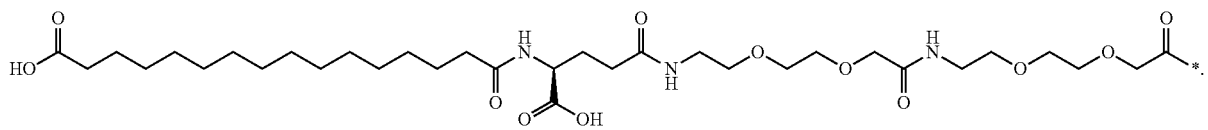

Chem 19b

20. A compound selected from the group consisting of compounds #41, #48, #69 and #306, wherein compound #41 comprises a fusion peptide defined by SEQ ID NO: 190 consisting of the GLP-1 analogue [8Aib, 34R]GLP-1(7-37) defined by SEQ ID NO: 139, the Spacer defined by SEQ ID NO: 116, and the EGF(A) analogue [301L, 309R, 312E, 321E, 333K] EGF(A) defined by SEQ ID NO: 19 and two substituents defined by Chem 6b

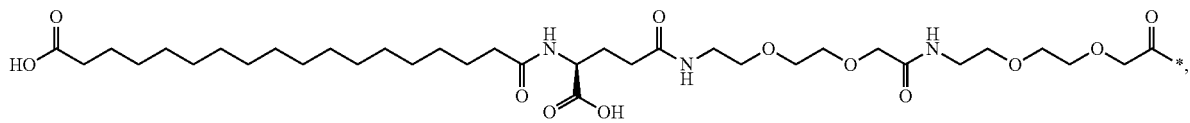

Chem 6b attached to amino acid residues 26K of [8Aib, 34R]GLP-1 (7-37) and 333K of [301L, 309R, 312E, 321E, 333K]EGF (A), compound #48 comprises a fusion peptide defined by SEQ ID NO: 202 consisting of the GLP-1 analogue [8Aib, 34R]GLP-1(7-37) defined by SEQ ID NO: 139, the Spacer defined by SEQ ID NO: 119, and the EGF(A) analogue defined by SEQ ID NO: 108 and one substituent defined by Chem 11b Chem 11b

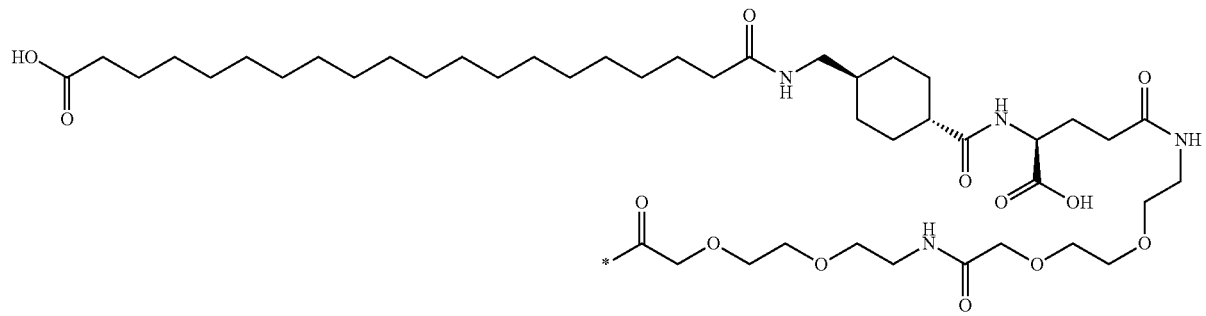

attached to amino acid 26K of [8Aib, 34R]GLP-1(7-37),
compound #69 comprises a fusion peptide defined by SEQ ID NO: 310 consisting of the GLP-1 analogue [8Aib, 30G, 34R]GLP-1(7-37) defined by SEQ ID NO: 164, the Spacer defined by SEQ ID NO: 116, and the EGF(A) analogue defined by SEQ ID NO: 108 and one substituent defined by Chem 11b Chem 11b

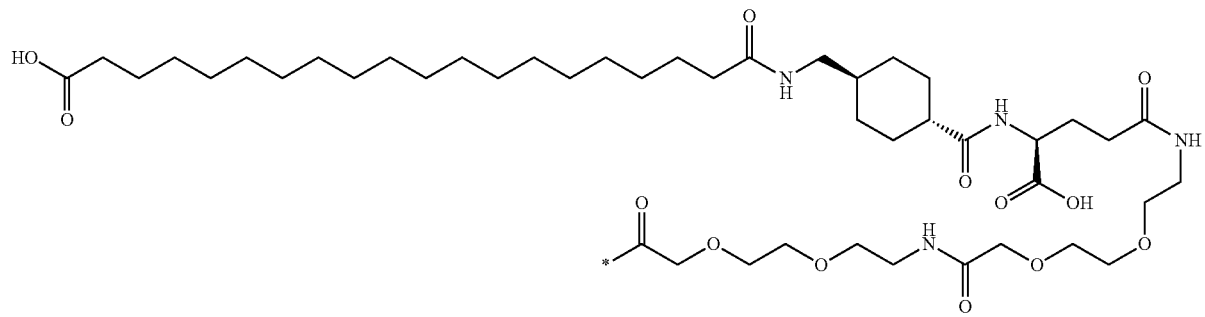

attached to amino acid 26K of [8Aib, 30G, 34R]GLP-1(7-37),
compound #306 comprises a fusion peptide defined by SEQ ID NO: 310 consisting of the GLP-1 analogue [8Aib, 30G, 34R]GLP-1(7-37) defined by SEQ ID NO: 164, the Spacer defined by SEQ ID NO: 116, and the EGF(A) analogue defined by SEQ ID NO: 108 and one substituent defined by Chem 10b Chem 10b

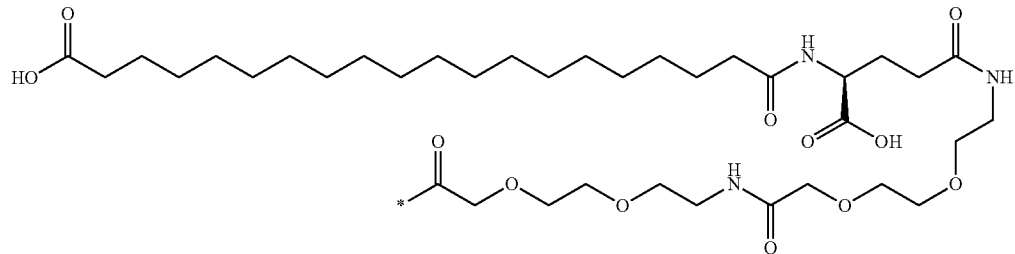

attached to amino acid 26K of [8Aib, 30G, 34R]GLP-1(7-37).

21. A compound of #69, wherein compound #69 comprises a fusion peptide defined by SEQ ID NO: 310 consisting of the GLP-1 analogue [8Aib, 30G, 34R]GLP-1(7-37) defined by SEQ ID NO: 164, the Spacer defined by SEQ ID NO: 116, and the EGF(A) analogue defined by SEQ ID NO: 108 and one substituent defined by Chem 11b

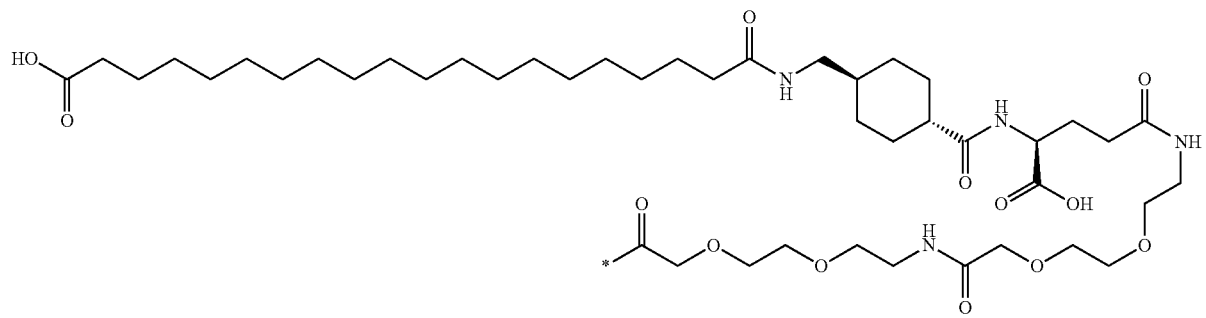

Chem 11b attached to amino acid 26K of [8Aib, 30G, 34R]GLP-1(7-37).

22. A compound of #306, wherein compound #306 comprises a fusion peptide defined by SEQ ID NO: 310 consisting of the GLP-1 analogue [8Aib, 30G, 34R]GLP-1(7-37) defined by SEQ ID NO: 164, the Spacer defined by SEQ ID NO: 116, and the EGF(A) analogue defined by SEQ ID NO: 108 and one substituent defined by Chem 10b

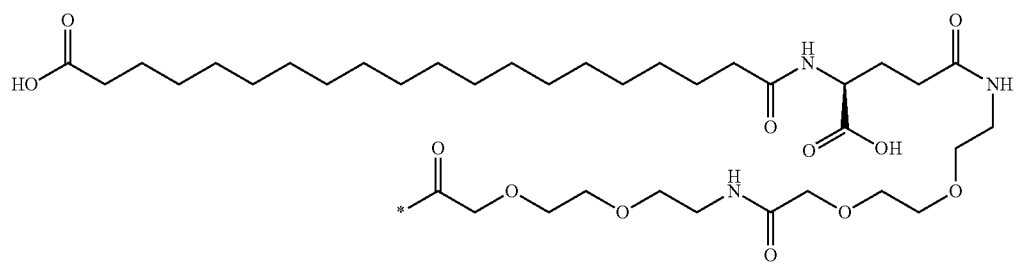

Chem 10b attached to amino acid 26K of [8Aib, 30G, 34R]GLP-1(7-37).

23. A compound according to claim 1, wherein the compound is a GLP-1/EGF(A) compound wherein the GLP-1 analogue is defined by SEQ ID NO: 139 and the EGF(A) analogue is defined by SEQ ID NO: 108.

24. A GLP-1/EGF(A) compound, wherein the compound comprises a fusion peptide defined by SEQ ID NO: 193 and one substituent defined by Chem 6b

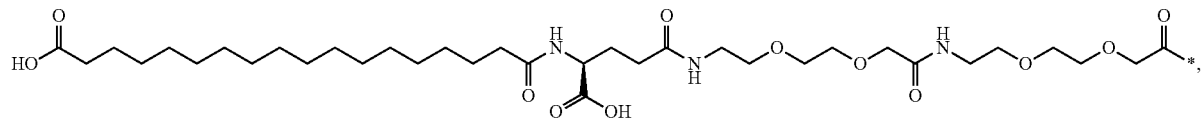

Chem 6b attached via Lysine (K) in position 20 of SEQ ID 193 (equal to amino acid 26K of [8Aib, 34R]GLP-1(7-37)).

25. A method of treatment of diabetes, over-weight or a cardiovascular disease comprising administering a pharmaceutically effective dosage of a compound according to claim 1 to a patient in need thereof.

* * * * *